US010800839B2

(12) United States Patent
Richards et al.

(10) Patent No.: US 10,800,839 B2
(45) Date of Patent: Oct. 13, 2020

(54) DKK1 ANTIBODIES AND METHODS OF USE

(71) Applicant: Amgen Inc., Thousand Oaks, CA (US)

(72) Inventors: William Gleason Richards, Thousand Oaks, CA (US); Hsieng Sen Lu, Westlake Village, CA (US); Hua Zhu Ke, Newbury Park, CA (US); Chaoyang Li, Newbury Park, CA (US); Frederick W. Jacobsen, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 213 days.

(21) Appl. No.: 15/841,065

(22) Filed: Dec. 13, 2017

(65) Prior Publication Data

US 2018/0111985 A1 Apr. 26, 2018

Related U.S. Application Data

(63) Continuation of application No. 13/878,619, filed as application No. PCT/US2011/058025 on Oct. 27, 2011, now Pat. No. 9,879,072.

(60) Provisional application No. 61/407,128, filed on Oct. 27, 2010.

(51) Int. Cl.
*C07K 16/18* (2006.01)
*C07K 16/22* (2006.01)
*A61K 39/395* (2006.01)
*A61K 39/00* (2006.01)

(52) U.S. Cl.
CPC .......... *C07K 16/18* (2013.01); *A61K 39/3955* (2013.01); *C07K 16/22* (2013.01); *A61K 2039/505* (2013.01); *A61K 2039/507* (2013.01); *C07K 2317/21* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,399,216 A | 8/1983 | Axel et al. |
| 4,619,794 A | 10/1986 | Hauser |
| 4,740,461 A | 4/1988 | Kaufman |
| 4,751,180 A | 6/1988 | Cousens et al. |
| 4,816,567 A | 3/1989 | Cabilly et al. |
| 4,881,175 A | 11/1989 | Ladner |
| 4,912,040 A | 3/1990 | Kaufman |
| 4,935,233 A | 6/1990 | Bell et al. |
| 4,946,778 A | 8/1990 | Ladner et al. |
| 4,959,455 A | 9/1990 | Clark et al. |
| 5,011,912 A | 4/1991 | Hopp et al. |
| 5,013,653 A | 5/1991 | Huston et al. |
| 5,091,513 A | 2/1992 | Huston et al. |
| 5,132,405 A | 7/1992 | Huston et al. |
| 5,258,498 A | 11/1993 | Huston et al. |
| 5,260,203 A | 11/1993 | Ladner et al. |
| 5,262,522 A | 11/1993 | Gearing |
| 5,426,048 A | 6/1995 | Gearing et al. |
| 5,455,030 A | 10/1995 | Ladner et al. |
| 5,457,035 A | 10/1995 | Baum et al. |
| 5,476,786 A | 12/1995 | Huston et al. |
| 5,482,858 A | 1/1996 | Huston et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,761 A | 12/1997 | Queen et al. |
| 5,693,762 A | 12/1997 | Queen et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 6,162,963 A | 12/2000 | Kucherlapati et al. |
| 6,180,370 B1 | 1/2001 | Queen et al. |
| 6,255,458 B1 | 7/2001 | Lonberg et al. |
| 6,270,964 B1 | 8/2001 | Michnick et al. |
| 6,300,129 B1 | 10/2001 | Lonberg et al. |
| 6,344,541 B1 | 2/2002 | Bass et al. |

(Continued)

FOREIGN PATENT DOCUMENTS

| | | |
|---|---|---|
| EP | 0088046 A2 | 9/1983 |
| EP | 0143949 A1 | 10/1984 |

(Continued)

OTHER PUBLICATIONS

Winkler, "Changing the antigen binding specificity by single point mutations of an anti-p24 (HIV-1) antibody"; Journal of Immunology, 165, 8, pp. 4505-4514; 2000.

Brown, "Tolerance to single, but not multiple, amino acid replacements in antibody V-H CDR2: A means of minimizing B cell wastage from somatic hypermutation?" Journal of Immunology; 156, 9, pp. 3285-3291; 1996.

Gershoni, "Epitope mapping—The first step in developing epitope-based vaccines", Biod, Adis Intl LTD; 21, 3; pp. 145-156; 2007.

Adams et al., "The c-myc oncogene driven by immunoglobulin enhancers induces lymphoid malignancy in transgenic mice," *Nature*, 318:533-38 (1985).

Alexander et al., "Expression of the c-myc Oncogene under Control of an Immunoglobulin Enhancer in Eμ-myc Transgenic Mice," *Molecular and Cellular Biology*, 7(4):1436-44 (1987).

(Continued)

*Primary Examiner* — Sharon X Wen

(57) ABSTRACT

The present invention provides antibodies and immunologically functional fragments thereof that specifically bind DKK1 polypeptides. Methods for preparing such antibodies or fragments thereof as well as physiologically acceptable compositions containing the antibodies or fragments are also provided. Use of the antibodies and fragments to treat various diseases are also disclosed.

8 Claims, 7 Drawing Sheets

Specification includes a Sequence Listing.

(56) References Cited

U.S. PATENT DOCUMENTS

| | | | |
|---|---|---|---|
| 6,673,986 | B1 | 1/2004 | Kucherlapati et al. |
| 6,713,610 | B1 | 3/2004 | Kucherlapati et al. |
| 7,435,871 | B2 | 10/2008 | Green et al. |
| 7,709,611 | B2 | 5/2010 | Li et al. |
| 7,994,293 | B2 | 8/2011 | An et al. |
| 2007/0128187 | A1 | 6/2007 | Allen et al. |
| 2008/0193449 | A1 | 8/2008 | An et al. |
| 2010/0076178 | A1 | 3/2010 | Ghayur et al. |
| 2012/0276591 | A1 | 11/2012 | Kneissel et al. |

FOREIGN PATENT DOCUMENTS

| | | |
|---|---|---|
| EP | 0133988 A2 | 3/1985 |
| EP | 0058481 B1 | 10/1986 |
| EP | 0036676 B2 | 9/1990 |
| EP | 0546073 B1 | 10/1997 |
| TW | 200922621 A1 | 6/2009 |
| WO | 9004036 A1 | 4/1990 |
| WO | 9110741 A1 | 7/1991 |
| WO | 9203918 A1 | 3/1992 |
| WO | 9222646 A1 | 12/1992 |
| WO | 9301227 A1 | 1/1993 |
| WO | 9310151 A1 | 5/1993 |
| WO | 9315722 A1 | 8/1993 |
| WO | 9402602 A1 | 2/1994 |
| WO | 9410308 A1 | 5/1994 |
| WO | 9420069 A1 | 9/1994 |
| WO | 9633735 A1 | 10/1996 |
| WO | 9824893 A1 | 6/1998 |
| WO | 9910494 A2 | 3/1999 |
| WO | 0009560 A2 | 2/2000 |
| WO | 2006015373 A2 | 2/2006 |
| WO | 2012/118903 A2 | 1/2007 |
| WO | 2009047356 A1 | 4/2009 |
| WO | 2010/032059 A2 | 3/2010 |
| WO | 2010131185 A1 | 11/2010 |

OTHER PUBLICATIONS

*Antibodies: A Laboratory Manual*, Harlow and Lane (eds.), Cold Spring Harbor Laboratory.Press, Cold Spring Harbor, N.Y. (1988) (Table of Contents Only).
Aravind, A. and Koonin, E.V., "A colipase fold in the carboxy-terminal domain of the Wnt antagonists—the Dickkopfs," *Current Biology*, 8(14):R477-R479 (1998).
Ashkenazi et al., "Protection against endotoxic shock by a tumor necrosis factor receptor immunoadhesin," *Proc. Natl. Acad. Sci. USA*, 88:10535-10539 (1991).
Ausubel et al., *Current Protocols in Molecular Biology*, Greene Publishing Associates.(1992) (Table of Contents Only).
Bafico et al., "Novel mechanism of Wnt signaling inhibition mediated by Dickkopf-1 intraction with LRP6/Arrow," *Nature Cell Biol* 3:683-686 (2001).
Bajada et al., "Decreased osteogenesis, increased cell senescence and elevated Dickkopf-1 secretion in human fracture non union stromal cells," *Bone*, 45(4):726-735 (2009).
Balemans et al., "Increased bone density in sclerosteosis is due to the deficiency of a novel secreted protein (SOST)," *Human Molecular Genetics*, 10(5):537-543 (2001).
Baum et al., "Molecular characterization of murine and human OX40/OX40 ligand systems: identification of a human OX40 ligand as the HTLV-1-regulated protein gp34," *The EMBO Journal* 13(17):3992-4001 (1994).
Bemoist and Chambon, "In vivo sequence requirements of the SV40 early promoter region," *Nature*, 290: 304-10 (1981).
Bianchi and McGrew, "High-Level Expression of Full-Length Antibodies Using Trans-Complementing Expression Vectors," *Biotechnology and Bioengineering* 84(4):439-44 (2003).
Bird et al., "Single-Chain Antigen-Binding Proteins," *Science*, 242:423 (1988).
Bloom et al., "Intrachain disulfide bond in the core hinge region of human IgG4," *Protein Science* 6:407-415 (1997).
Bonnarens F. et al., "Production of a Standard Closed Fracture in Laboratory Animal Bone," *Journal of Orthopaedic Research*, 2: 97-101 (1984).
Bowie et al., "A Method to Identify Protein Sequences That Fold into a Known Three-Dimensional Structure," *Science*, 253:164-170 (1991).
Boyden et al., "High Bone Density Due to a Mutation in LDL-Receptor-Related Protein 5," *New England Journal of Medicine*, 346(20):1513-1521, 2002.
(Branden and Tooze, eds.), *Introduction to Protein Structure*, New York: Garland Publishing (1991) (Table of Contents Only).
Brennan et al., "Preparation of Bispecific Antibodies by Chemical Tecomnication of Monoclonal Immunoglobulin G$ {1}$ Fragments," *Science*, 229(4708):81-83 (1985).
Brenner et al., "Population statistics of protein structures: lessons from structural classifications," *Current Opinion in Structural Biology*, 7:369-376 (1997).
Brinster et al., "Regulation of metallothionein-thymidine kinase fusion plasmids injected into mouse eggs," *Nature*, 296: 39-42 (1982).
Bruggermann et al., "Designer Mice: The Production of Human Antibody Repertoires in Transgenic Annimals," *Year in Immunol.*, 7:33-40 (1993).
Brunkow et al., "Bone Dysplasia Sclerosteosis Results from Loss of the SOST Gene Product, a Novel Cystine Knot—Containing Protein," *Am. J. Hum. Genet.*, 68:577-589 (2001).
Byrn et al., "Biological properties of a CD4 immunoadhesin," *Nature*, 344:677 (1990).
Casset et al. "A peptide mimetic of an anti-CD4 monoclonal antibody by rational design," *BBRC*, 307:198-205, (2003).
Chen et al. "Selection and Analysis of an Optimized Anti-VEGF Antibody: Crystal Structure of an Affinity-matured Fab in Complex with Antigen," *J. Mol. Biol.*, 293: 865-881 (1999).
Chen et al., "Immunoglobulin gene rearrangement in B cell deficient mice generated by targeted deletion of the JH locus," *International Immunology*, 5(6): 647-656 (1993).
Cheung, et al., "Epitope-Specific Antibody Response to the Surface Antigen of Duck Hepatitis B Virus in Infected Ducks," *Virology*, 176:546-552 (1990).
Chothia et al., "Conformations of immunoglobulin hypervariable regions," *Nature*, 342: 877-883 (1989).
Chothia et al., "Canonical Structures for the Hypervariable Regions of Immunoglobulin," *J. Mol. Biol.* 196: 901-917 (1987).
Chou et al., "Prediction of Protein Conformation," *Biochemistry*, 13(2):222-245 (1974).
Chou et al., "Conformational Parameters for Amino Acids in Helical, β-Sheet, and Random Coil Regions Calculated from Proteins," *Biochemistry*, 13(2):211-222 (1974).
Chou et al., "Prediction of the Secondary Structure of Proteins from Their Amino Acid Sequence," *Advances in Enzymology and Related Areas of Molecular Biology*, 47:45-148 (1978).
Chou et al., "Empirical Predictions of Protein Conformation," *Ann. Rev. Biochem.* 47:251-276 (1978).
Chou et al., "Prediction of β-Turns," *Biophys. J.*, 26:367-384 (1979).
Chu et al., "SVO40 DNA transfection of cells in suspension: analysis of the efficiency of transcription and translation of T-antigen," *Gene* 13:197-202 (1981).
(Creighton, Ed.), *Proteins, Structures and Molecular Principles*, 1984, W. H. New York: Freeman and Company (Table of Contents Only).
Database Geneseq [Online], "Human erythropoietin (EPO) receptor VL protein, SEQ:53.," XP002668779, retrieved from EBI accession No. GSP: AXR46256, Database accession No. AXR46256, (Nov. 26, 2009).
Davis et al., *Basic Methods in Molecular Biology*, Elsevier (1986) (Table of Contents Only).
DeBoer et al., "The tac promoter: A functional hybrid derived from the trp and lac promoters," *Proc. Natl. Acad. Sci. U.S.A.*, 80: 21-25 (1983).

(56) References Cited

OTHER PUBLICATIONS

De Graaf et al., "Expression of scFvs and scFv Fusion Proteins in Eukaryotic Cells," *Methods in Molecular Biology*, 178:379-87 (2002).
Deal, Chad, "Future therapeutic targets in osteoporosis," Current Opinion in Rheumatology, Current Science, London, GB, 21(4): 380-385 (Jul. 1, 2009).
Delmas et al., "The Use of Biochemical Markers of Bone Turnover in Osteoporosis," *Osteoporos Int., Suppl.* 6:S2-17 (2000).
Dempster et al., "Anabolic Actions of Parathyroid Hormone on Bone," *Endocrine Reviews*, 14(6):690-709 (1993).
Eppstein et al., "Biological activity of liposome-encapsulated murine interferon γ is mediated by a cell membrane receptor," *Proc. Natl. Acad. Sci. USA*, 82: 3688-3692 (1985).
Evans et al., "Design of Nonpeptidal Ligands for a Peptide Receptor: Cholecystokinin Antagonists," *J. Med. Chem.* 30: 1229-1239 (1987).
Fanslow et al., "Structural characteristics of CD40 ligand that determine biological function," *Seminars in Immunology*, 6:267-78 (1994).
Fauchere, "Elements for the Rational Design of Peptide Drugs," *Advances in Drug Research*, 15: 29-69 (1986).
Fedi et al., "Isolation and Biochemical Characterization of the Human DKK-1 Homologue, a Novel Inhibitor of Mammalian Wnt Signaling," *The Journal of Biological Chemistry*, 274(27):19465-19472 (1999).
Fishwild et al., "High-avidity human IgGk monoclonal antibodies from a novel strain of minilocus transgenic mice," *Nature Biotechnology*, 14: 845-851 (1996).
Frost and Jee, "On the rat model of human osteopenias and osteoporosis," *Bone and Mineral*, 18:227-236 (1992).
Du Pasquier, "Evolution of the Immune System," *Fundamental Immunology*, 2nd ed., Ch. 7 (Paul, W., ed.), New York: Raven Press (1989).
Glantschnig et al. "Fully Human anti-DKK1 Antibodies Increase Bone Formation and Resolve Osteopenia in Mouse Models of Estrogen-Deficiency Induced Bone Loss," *J Bone Mineral Res.*, Suppl. 1, S60-S61 (2008).
Glantschnig et al. "Generation and Selection of Novel Fully Human Monoclonal Antibodies That Neutralize Dickkopf-1 (DKK1) Inhibitory Function in Vitro and Increase Bone Mass in Vivo," *J Biol Chem*, 285(51): 40135-40147 (2010).
Glennie et al., "Preparation and performance of bispecific F(ab' gamma)2 antibody containing thioether-linked Fab' gamma fragments," *The Journal of Immunology*, 139: 2367-2375 (1987).
Glinka et al., "Dickkopf-1 is a member of a new family of secreted proteins and functions in head induction," *Nature*, 391:357-62 (1998).
(E. S. Golub and D. R. Gren, eds.), *Immunology—A Synthesis*, 2nd Edition, Sinauer Associates: Sunderland, Mass. (1991) (Table of Contents Only).
Gong et al., "LDL Receptor-Related Protein 5 (LRP5) Affects Bone Accrual and Eye Development," *Cell*, 107:513-23 (2001).
Graham et al., "A New Technique for the Assay of Inefectivity of Human Adenovirus 5 DNA," *Virology*, 52:456-467 (1973).
Gribskov et al., "Profile analysis: Detection of distantly related proteins," *Proc. Nat. Acad. Sci.*, 84:4355-4358 (1987).
Gribskov et al., "Profile Analysis," *Metods in. Enzymology*, 183:146-159 (1990).
Grisanti et al., "Dkk-1 Inhibition Increase Bone Mineral Density in Rodents," *J Bone Mineral Res.*, Suppl. 1, 21(1), S25 (2006).
Grosschedl et al., "Introduction of a μ Immunoglobulin Gene into the Mouse Germ Line: Specific Expression in Lymphoid Cells and Synthesis of Functional Antibody," *Cell*, 38: 647-58 (1984).
Gunness-Hey, "Increased Trabecular Bone Mass in Rats Treated with Human Synthetic Parathyroid Hormone," *Metab. Bone Dis. & Rel. Res.*, 5:177-181 (1984).
Hammer et al., "Diversity of Alpha-Fetoprotein Gene Expression in Mice is Generated by a Combination of Separate Enhancer Elements," *Science*, 235: 53-58 (1987).
Hanahan, "Heritable formation of pancreatic β-cell tumours in transgenic mice expressing recombinant insulin/simian virus 40 oncogenes," *Nature*, 315: 115-22 (1985).
Harding et al., "Class Switching in Human Immunoglobulin Transgenic Mice," Ann. N.Y *Acad. Sci.*, 764: 536-546 (1995).
Heath, et al., "Inhibiting Dickkopf-1 (Dkk1) Removes Suppression of Bone Formation and Prevents the Development of Osteolytic Bone Disease in Multiple Myeloma," *Journal of Bone and Mineral Research*, 24(3): 425-436 (2009).
Hollenbaugh et al., "Construction of Immunoglobulin Fusion Proteins," *Current Protocols in Immunology*, Suppl. 4, pp. 10.19.1-10.19.11 (1992).
Holm et al., "Protein folds and families: sequence and structure alignments," *Nucleic Acids Research*, 27(1):244-247 (1999).
Hoogenboom et al., "By-passing Immunisation Human Antibodies from Synthetic Repertoires of Germline VH Gene Segments Rearranged in Vitro," *J. Mol. Biol.*, 227:381-388 (1991).
Hopp et al., "A Short Polypeptide Marker Sequence Useful for Recombinant Protein Identification and Purification," *Bio/Technology*, 6:1204-1210 (1988).
Hoppe et al., "A parallel three stranded α-helical bundle at the nucleation site of collagen triple-helix formation," *FEBS Letters*, 344:191-195 (1994).
Huston et al., "Protein engineering of antibody binding sites: Recovery of specific activity in an anti-digoxin single-chain Fv analogue produced in *Escherichia coli,"* *Proc. Natl. Acad. Sci. USA*, 85:5879-5883 (1988).
Jakobovits et al., "Germ-line transmission and expression of a human-derived yeast artificial chromosome," *Nature*, 362:255-258 (1993).
Jakobovits et al., "Analysis of homozygous mutant chimeric mice: Deletion of the immunoglobulin heavy-chain joining region blocks B-cell development and antibody production," *Proc. Natl. Acad. Sci. USA*, 90:2551-2555 (1993).
Jee and Yao, "Overview: animal models of osteopenia and osteoporosis," *J. Musculoskel Neuron. Interact.*, 1(3):193-207 (2001).
Jolette et al., "Sclerostin Monoclonal Antibody Stimulates Bone Formation and Improves the Strength and Density of the Fracture Callus and Lumbar Spine in a Primate Fibular Osteotomy Model," ASBMR 31st Annual Meeting, Presentation No. 1290 (2009).
Jones et al., "Replacing the complementarity-determining regions in a human antibody with those from a mouse," *Nature*, 321:522-25 (1986).
Jones, "Progress in protein structure prediction," *Curr. Opin. Struct. Biol.* 7:377-87 (1997).
Kabat et al. In Sequences of Proteins of Immunological Interest, 5th Ed., US Dept. of Health and Human Services, PHS, NIH, NIH Publication No. 91-3242, 1991 (Table of Contents Only).
Kalu, "The Ovariectomized rat model of postmenopausal bone loss," *Bone and Mineral*, 15:175-192 (1991).
Karpovsky et al., "Production of Target-Specific Effector Cells Using Hetero-Cross-Linked Aggregates Containing Anti-Target Cell and Anti-Fcγ Receptor Antibodies," *J. Exp. Med.* 160:1686-1701 (1984).
Ke et al., "Inhibition of Sclerostin by Systemic Treatment with a Sclerostin Monoclonal Antibody Enhances Fracture Healing in Mice and Rats," *Trans ORS*, 34:22 (2009).
Kearney et al, "A New Mouse Myeloma Cell Line That Has Lost Immunoglobulin Expression But Permits the Construction of Antibody-Secreting Hybrid Cell Lines," The *Journal of Immunology*, 123(4): 1548-1550 (1979).
Kelsey et al., "Species- and tissue-specific expression of human α1-antitrypsin in transgenic mice," *Genes and Development*, 1: 161-71 (1987).
Kennet et al. (eds.), Monoclonal Antibodies, Hybridomas: A New Dimension in Biological Analyses, Plenum Press, New York (1980) (Table of Contents Only).
Khosla and Riggs, "Concise Review for Primary-Care Physicians," *Mayo Clin. Proc.*, 70:978-982 (1995).
Kirkland et al., "Analysis of the Fine Specificity and Cross-Reactivity of Monoclonal Anti-Lipid a Antibodies," The *Journal of Immunology*, 137:3614-3619 (1986).

(56) References Cited

OTHER PUBLICATIONS

Kohler and Milstein, "Continuous cultures of fused cells secreting antibody of predefined specificity," Nature, 256: 495-497 (1975).
Kollias et al., "Regulated Expression of Human Aγ-, β-, and Hybrid γβ-Globin Genes in Transgenic Mice: Manipulation of the Developmental Expression Patterns," Cell, 46: 89-94 (1986).
Komatsu, David E. et al., "Modulation of Wnt Signaling Influence Fracture Repair," Journal of Orthopaedic Research, 28(7): 928-936 (Jul. 2010).
Kortt et al., "Single-chain Fv fragments of anti-neuraminidase antibody NC10 containing five- and ten-residue linkers form dimers and with zero-residue linker a trimer," Protein Engineering, 10(4):423 (1997).
Kortt et al., "Dimeric and trimeric antibodies: high avidity scFvs for cancer targeting," Biomolecular Engineering, 18:95-108 (2001).
Kostelny et al., "Formation of a Bispecific Antibody by the Use of Leucine Zipper," The Journal of Immunology, 148:1547-1553 (1992).
Kriangkum et al., "Bispecific and bifunctional single chain recombinant antibodies," Biomolecular Engineering, 18:31-40 (2001).
Krumlauf et al., "Development Regulation of α-Fetoprotein Genes in Transgenic Mice," Molecular Cellular Biology, 5(7): 1639-48 (1985).
Krupnik et al., "Functional and structural diversity of the human Dickkopf gene family," Gene, 238: 301-313 (1999).
Kyte et al., "A Simple Method for Displaying the Hydropathic Character of a Protein," J. Mol. Biol., 157:105-132 (1982).
Lamminmaki et al., "Crystal Structure of a Recombinant Antiestradiol Fab Fragment in Complex with 17 β-Estradiol," The Journal of Biological Chemistry, 276(39): 36687-36694 (2001).
Landschulz et al., "The Leucine Zipper: A Hypothetical Structure Common to a New Class of DNA Binding Proteins," Science, 240:1759 (1988).
Langer et al., "Biocompability of polymeric delivery systems for macromolecules," Journal of Biomedical Materials Research, 15: 267-277 (1981).
Langer, "Controlled release of macromolecules," Chem Tech, 12: 98-105 (1982).
Lantto et al., "Chain Shuffling to Modify Properties of Recombinant Immunoglobulins," Methods of Molecular Biology, 178:303-16 (2002).
Leder et al., "Consequences of Widespread Deregulation of the c-myc Gene in Transgenic Mice: Multiple Neoplasms and Normal Development," Cell, 45: 485-495 (1986).
Li et al., "Sclerostin Antibody Treatment Increases Bone Formation, Bone Mass, and Bone Strength in a Rat Model of Postmenopausal Osteoporosis," Journal of Bone and Mineral Research, 24(4):578-588 (2009).
Little et al., "A Mutation in the LDL Receptor-Related Protein 5 Gene Results in the Autosomal Dominant High-Bone-Mass Trait," Am. J. Hum. Genet., 70(1):11-19 (2002).
Liu, MA et al., "Heteroantibody duplexes target cells for lysis by cytotoxic T lymphocytes," Proc. Natl. Acad. Sci. USA, 82:8648-8652 (1985).
Lonberg, "Transgenic Approaches to Human Monoclonal Antibodies," Handbook of Exp. Pharmacology, 113: 49-101 (1994).
Lonberg et al., "Antigen-specific human antibodies from mice comprising four distinct genetic modifications," Letters to Nature, 368: 856-859 (1994).
Lonberg et al., "Human Antibodies from Transgenic Mice," Intern. Rev. Immunol., 13: 65-93 (1995).
MacCallum et al., "Antibody-antigen Interactions: Contact Analysis and Binding Site Topography," J. Mol. Biol., 262:732-745 (1996).
MacDonald, "Expression of Pancreatic Elastase I Gene in Transgenic Mice," Hepatology, 7(1): 425-515 (1987).
Maniatis et al., "Regulation of Inducible and Tissue-Specific Gene Expression," Science, 236:1237-1244 (1987).
Magram et al., "Developmental regulation of a cloned adult β-globin gene in transgenic mice," Nature, 315: 338-340 (1985).
Mao et al., "LDL-receptor-related protein 6 is a receptor for Dickkopf proteins," Nature 411:321-325 (2001).
Mao et al., "Kremen proteins are Dickkopf receptors that regulate Wnt/β-catenin signaling," Nature, 417:664-667 (2002).
Marks et al., "By-passing Immunication Human Antibodies from V-gene Libraries Displayed on Phage," J. Mol. Biol., 222:581-597 (1991).
Marks et al., "By-Passing Immunization: Building High Affinity Human Antibodies by Chain Shuffling," BioTechnology, 10:779-783 (1992).
Mason et al., "The Hypogonadal Mouse: Reproductive Functions Restored by Gene Therapy," Science, 234: 1372-1378 (1986).
Mendez et al., "Functional transplant of megabase human immunoglobulin loci recapitulates human antibody response in mice," Nature Genetics, 15: 146-156 (1997).
Methods Enzymology, vol. 185, Gene Expression Technology (D. V. Goeddel, ed.), New York: Academic Press (1990) (Table of Contents Only).
Moldenhauer et al., "Identity of HML-1 Antigen on Intestinal Intraepithelial T Cells and of B-ly7 Antigen on Hairy Cell Leukaemia," Scand. J. Immunol. 32:77-82 (1990).
Morel et al., "Monoclonal Antibodies to Bovine Serum Albumin: Affinity and Specificity Determinations," Molecular Immunology, 25(1):7-15 (1988).
Morrison et al., "Chimeric human antibody molecules: Mouse antigen-binding domains with human constant region domains," Proc. Natl. Acad. Sci. USA, 81:6851-6855 (1985).
Moult, "The current state of the art in protein structure prediction," Curr. Op. in Biotech. 7:422-427 (1996).
Needleman et al., "A General Method Applicable to the Search for Similarities in the Amino Acid Sequence of Two Proteins," J. Mol. Biol., 48:443-453 (1970).
Niu et al., "Increased Modeling-Based Bone Formation by Sclerostin Antibody Was Not Altered by Co-Treatment with Alendronate in Ovariectomized Rats," ASBMR 31$^{st}$ Annual Meeting, Presentation No. 1174 (2009).
Ornitz et al., "Elastase I Promoter Directs Expression of Human Growth Hormone and SV40 T Antigen Genes to Pancreatic Acinar Cells in Transgenic Mice," Cold Spring Harbor Symp. Quant. Biol. 50: 399-409 (1986).
Padlan et al., "Structure of an antibody-antigen complex: Crystal structure of the HyHEL-10 Fab-lysozyme complex," Proc. Natl. Acad. Sci., 86:5938-5942 (1989).
Padhi et al., "Single-Dose, Placebo-Controlled, Randomized Study of AMG 785, a Sclerostin Monoclonal Antibody," Journal of Bone and Mineral Research, 26(1): 19-26 (2010).
Pascalis et al. "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, 169: 3076-3084, (2002).
Patel et al., "Regulation of Bone Formation and Vision by LRP5," The New England Journal of Medicine, 346(20):1572-1574 (2002).
Paulus, "Preparation and Biomedical Applications of Bispecific Antibodies," Behring Inst. Mitt., No. 78: 118-132 (1985).
Pinkert et al., "An albumin enhancer located 10 kb upstream functions along with its promoter to direct efficient, liver-specific expression in transgenic mice," Genes & Development 1: 268-276 (1987).
Power, Jon et al., "Sclerostin and the Regulation of Bone Formation: Effects in Hip Osteoarthritis and Femoral Neck Fracture," Journal of Bone and Mineral Research, 25(8): 1867-1876 (Aug. 2010).
Readhead et al., "Expression of a Myelin Basic Protein Gene in Transgenic Shiverer Mice: Correction of the Dysmyelinating Phenotype," Cell, 48: 703-12 (1987).
Remington's Pharmaceutical Sciences, 18th Edition, (A. R. Gennaro, ed.), 1990, Mack Publishing Company (Table of Contents Only).
Riechmann et al., "Reshaping human antibodies for therapy," Nature, 332: 323-327 (1988).
Riggs, "Overview of Osteoporosis," West J. Med. 154:63-77 (1991).
Rizo and Gierasch, "Constrained Peptides: Models of Bioactive Peptides and Protein Substructures," Annu. Rev. Biochem., 61: 387-418 (1992).
Rudikoff, et al., "Single amino acid substitution altering antigen-binding specificity," PNAS, 79(6): 1979-1983 (Mar. 1982).

(56) References Cited

OTHER PUBLICATIONS

Sambrook et al. Molecular Cloning: A Laboratory Manual, 2d ed., Cold Spring Harbor Laboratory Press, Cold Spring Harbor, N.Y. (1989).
Sambrook et al., Molecular Cloning: A Laboratory Manual, Id. (2001).
Shani, "Tissue-specific expression of rat myosin light-chain 2 gene in transgenic mice," Nature 314: 283-86 (1985).
Semenov et al., "Head inducer Dickkopf-1 is a ligan for Wnt coreceptor LRP6," Curr Biol 11:951-961 (2001).
Sidman et al., "Controlled Release of Macromolecules and Pharmaceuticals from Synthetic Polypeptides Based on Glutamic Acid," *Biopolymers*, 22: 547-556 (1983).
Sippl et al., "Threading thrills and threats," *Structure*, 4:15-19 (1996).
Songsivilai & Lachmann, "Bispecific antibody : a tool for diagnosis and treatment of disease, " *Clin. Exp. Immunol.*, 79:315-321 (1990).
Stahli et al., "Distinction of Epitopes by Monoclonal Antibodies," *Methods in Enzymology*, 92: 242-253 (1983).
Swift et al., "Tissue-Specific Expression of the Rat Pancreatic Elastase I Gene in Transgenic Mice," *Cell*, 38: 639-646 (1984).
Tamura, et al., "Structural Correlates of an Anticarcinoma Antibody: Identification of Specificity-Determining Residues (SDRs) and Development of a Minimally Immunogenic Antibody Variant by Retention of SDRs Only," J. Immunology, 164(3): 1432-1441 (Feb. 2000).
Taylor et al., "A transgenic mouse that expresses a diversity of human sequence heavy and light chain immunoglobulins," *Nucleic Acids Research*, 20(23): 6287-6295 (1992).
Taylor et al., "Human immunoglobulin transgenes undergo rearrangements, somati mutation and class switching in mice that lack endogenous IgM," *International Immunology*, 6(4): 579-591 (1994).
Taylor DK, et al., "Thrombospondin-2 Influences the Proportion of Cartilage and Bone During Fracture Healing," Journal of Bone and Mineral Research, 24(6):1043-1054 (2009).
Thornton et at., "Prediction of progress at last," *Nature*, 354: 105-106 (1991).
Tuaillon et al., "Biased Utilization of DHQ52 and JH4 Gene Segments in a Human Ig Transgenic Minilocus is Independent of Antigenic Selection," *Journal of Immunology*, 152: 2912-2920 (1994).
Vajdos et al. "Comprehensive Functional Maps of the Antigen-binding Site of an Anti-ErbB2 Antibody Obtained with Shotgun Scanning Mutagenesis," J. Mol. Biol., 320: 415-428, (2002).
Veber and Freidinger, "The design of metabolically-stable peptide analogs," *TINS*, p. 392-396 (1985).
Verhoeyen et al., "Reshaping Human Antibodies: Grafting an Antilysozyme Activity," *Science*, 239:1534-1536 (1988).
Villa-Kamaroff et al., "A bacterial clone synthesizing proinsulin," *Proc. Natl. Acad. Sci. U.S.A.*, 75(8): 3727-3731 (1978).
Voss et al., "The role of enhancers in the regulation of cell-type-specific transcriptional control," *TIBS*, 11:287 (1986).
Ward et al., "Binding activities of a repertoire of single immunoglobulin variable domains secreted from *Escherichia coli,*" *Nature*, 334:544-546 (1989).
Wagner et al., "Nucleotide sequence of the thymidine kinase gene of herpes simplex virus type 1," *Proc. Natl. Acad. Sci. U.S.A.*, 78(3): 1444-1445 (1981).
World Health Organization Scientific Group on the Prevention and Management of Osteoporosis, "Prevention and Management of Osteoporosis: Report of a WHO Scientific Group," WHO Technical Report Series; 921, Geneva, Switzerland (2000).
Wu et al. "Humanization of a Murine Monoclonal Antibody by Simultaneous Optimization of Framework and CDR Residues," J. Mol. Biol., 294: 151-162 (1999).
Xiang et al., "Systemic Treatment with a Sclerostin Monoclonal Antibody Enhances Fracture Healing in the Rat Femoral Closed Fracture Model," ASBMR 31st Annual Meeting, Presentation No. SU0407 (2009).
Yamamoto, et al., "Identification of a Functional Promoter in the Long Terminal Repeat of Rous Sarcoma Virus," *Cell*, 22: 787-797 (1980).
Zorn, "Wnt signaling: Antagonistic Dickkopfs," *Current Biology*, 11:R592-R595 (2001).

* = significantly different from Vehicle

DKK1 ANTIBODIES AND METHODS OF USE

This application is a continuation of U.S. application Ser. No. 13/878,619, filed Apr. 10, 2013, now U.S. Pat. No. 9,879,072, which is a U.S. National Stage Application of PCT Application No. PCT/US11/58025, filed Oct. 27, 2011, which claims the benefit of U.S. Provisional Application No. 61/407,128, filed Oct. 27, 2010, each of which is hereby incorporated by reference.

The present application is being filed along with a sequence listing in electronic format. The sequence listing is provided as a file entitled A-1574-US-CNT-SeqListRev-121117_ST25.txt, created Dec. 13, 2017, which is 123.71 kb in size. The information in the electronic format of the sequence listing is incorporated herein by reference in its entirety.

FIELD OF THE INVENTION

The invention relates to selective binding agents for dickkopf-1 (DKK1) protein, and more particularly, to antibodies and antigen binding domains and CDR regions that mediate selective binding to DKK1 proteins.

BACKGROUND OF THE INVENTION

Two or three distinct phases of changes to bone mass occur over the life of an individual (see Riggs, West J. Med. 154:63 77 (1991)). The first phase occurs in both men and women and proceeds to attainment of a peak bone mass. This is achieved through linear growth of the endochondral growth plates and radial growth due to a rate of periosteal apposition. The second phase begins around age 30 for trabecular bone (flat bones more commonly found in the vertebrae and pelvis) and about age 40 for cortical bone (e.g., predominantly found in long bones such as in the limbs) and continues to old age. This phase is characterized by slow bone loss and occurs in both men and women. In women, a third phase of bone loss also occurs, most likely due to postmenopausal estrogen deficiencies. During this phase alone, women may lose an additional bone mass from the cortical bone and from the trabecular compartment (see Riggs, supra).

Loss of bone mineral content can be caused by a wide variety of conditions and may result in significant medical problems. For example, osteoporosis is a debilitating disease in humans and is characterized by marked decreases in skeletal bone mass and mineral density, structural deterioration of bone, including degradation of bone microarchitecture and corresponding increases in bone fragility (i.e., decreases in bone strength), and susceptibility to fracture in afflicted individuals. Osteoporosis in humans is generally preceded by clinical osteopenia (bone mineral density that is greater than one standard deviation but less than 2.5 standard deviations below the mean value for young adult bone), a condition found in approximately 25 million people in the United States. Another 7 8 million patients in the United States have been diagnosed with clinical osteoporosis (defined as bone mineral content greater than 2.5 standard deviations below that of mature young adult bone). The frequency of osteoporosis in the human population increases with age. Among Caucasians, osteoporosis is predominant in women who, in the United States, comprise 80% of the osteoporosis patient pool. The increased fragility and susceptibility to fracture of skeletal bone in the aged is aggravated by the greater risk of accidental falls in this population. Fractured hips, wrists, and vertebrae are among the most common injuries associated with osteoporosis. Hip fractures in particular are extremely uncomfortable and expensive for the patient, and for women, correlate with high rates of mortality and morbidity.

Although osteoporosis has been regarded as an increase in the risk of fracture due to decreased bone mass, few of the presently available treatments for skeletal disorders can increase the bone density of adults, and most of the presently available treatments work primarily by inhibiting further bone resorption rather than stimulating new bone formation. Estrogen is now being prescribed to retard bone loss. However, some controversy exists over whether patients gain any long term benefit and whether estrogen has any effect on patients over 75 years old. Calcitonin, osteocalcin with vitamin K, or high doses of dietary calcium, with or without vitamin D, have also been suggested for postmenopausal women. High doses of calcium, however, often have undesired gastrointestinal side effects, and serum and urinary calcium levels must be continuously monitored (e.g., Khosla and Riggs, Mayo Clin. Proc. 70:978982, 1995).

Other current therapeutic approaches to osteoporosis include bisphosphonates (e.g., Fosamax™, Actonel™, Bonviva™, Zometa™, olpadronate, neridronate, skelid, bonefos), parathyroid hormone, calcilytics, anabolic steroids, lanthanum and strontium salts, and sodium fluoride. Such therapeutics, however, are often associated with undesirable side effects (see Khosla and Riggs, supra).

Dickkopf-1 (DKK1) is a member of the dickkopf family of proteins that have been shown to be negative regulators of Wnt-signaling, which has a central role in bone development and formation (see, e.g., Glinka et al., Nature 391:357-62 (1998); Fedi et al., J Biol Chem 274(27):19465-72 (1999); Zorn, Curr Biol 11:R592-95 (2001); and Krupnik et al., Gene 238: 301-13 (1999)). DKK1 inhibits Wnt signaling through its interaction with the Wnt co-receptors LRP5 or LRP6 and the kremen proteins (see, for example, Bafico et al., Nature Cell Biol 3:683 (2001); Mao et al., Nature 411(17):321 (2001); Mao et al., Nature 417:664 (2002); and Semenov et al., Curr Biol 11:951-61 (2001). By binding LRP5 (LRP6) and kremen proteins, DKK1 prevents LRP5 or LRP6 from associating with members of the Wnt pathway and thus prevents Wnt-mediated signal transduction, which in turn results in the inhibition of bone formation.

The DKK1 receptor LRP5/6 is a key protein in regulating bone mass (see, for example, Gong et al., Cell 107:513-23 (2001); Patel, N Eng J Med 346(20):1572 (2002)). An autosomal recessive disorder characterized by low bone mass (osteoporosis-pseudoglioma syndrome, or "OPPG") has been identified as being caused by loss-of-function mutations in LRP5 (Gong et al., 2001). In addition, gain-of-function mutations in LRP5 have been shown to result in autosomal dominant high bone mass in humans (Little et al., Am J Human Genetics. 70(1):11-19, 2002). The same mutations in LRP5 that result in high bone mass can interfere with the ability of DKK1 to inhibit LRP5 signaling (see, for example, Boyden et al., N Eng J Med. 346(20):1513-1521, 2002). Thus, DKK1 is appropriately characterized as being a negative regulator of bone deposition.

Sclerostin, the product of the SOST gene, is absent in sclerosteosis, a skeletal disease illustrated by bone overgrowth and strong dense bones (Brunkow et al., Am. J. Hum. Genet., 68:577 589, 2001; Balemans et al., Hum. Mol. Genet., 10:537 543, 2001). Inhibitors of sclerostin have been shown to increase the rate of bone mineralization, and thus bone mineral density (Padhi et al., J Bone Miner Res. 2010 June; epublished ahead of print). Likewise, DKK1 has been shown to be involved in the regulation of bone formation, particularly in bone fracture repair, and its role in various other diseases that are associated with bone loss (e.g., cancer and diabetes).

Given the drawbacks of current therapies there is a need for improved therapeutics in the area of bone loss, such as osteoporosis, and improved fracture repair among other bone disorders.

SUMMARY OF THE INVENTION

Provided herein are novel DKK1 inhibitors that are effective in treating conditions requiring increased bone building, for example, fracture repair or bone loss associated with pathological conditions, such as multiple myeloma. In addition, provided herein are combinations of agents that increase bone anabolism including combinations of DKK1 and sclerostin inhibitors. These combinations can be used for treatment of, for example, osteoporosis, accelerating healing of fractures, and any number of conditions requiring an increase in the rate of bone building. The combination can be two separate inhibitors, for example, an anti-sclerostin antibody and an anti-DKK1 antibody, or can be a single molecular entity, for example, a bispecific molecule including a bispecific antibody.

Also provided herein are a variety of antibodies that bind DKK1. The anti-DKK1 agents may also block or reduce binding between DKK1 and LRP5 and/or LRP6, thereby stimulating at least one activity associated with Wnt signaling. The agents can be an antibody or an immunologically functional fragment thereof and thus include antibodies with a naturally occurring structure, as well as polypeptides that have an antigen binding domain (e.g., a domain antibody). The antibodies and fragments can be used to treat a variety of different diseases including preventing or treating conditions relating to loss of bone mass or to stimulate production of new bone, as well as various non-bone related disorders. Nucleic acids molecules, vectors, and host cells useful in the production of the antibodies and selective binding agents are also provided.

Some of the antibodies and immunologically functional fragments that are provided include one or more of the following light chain (LC) complementary determining regions (CDRs): (i) a LC CDR1 with at least 80% sequence identity to SEQ ID NO: 97, 103, 109, 115, 121, 127, 133, 139, 145, 151, 157, 163, 169, 175, 181, 187, 193, 199, 205, 211, 217, or 223; (ii) a LC CDR2 with at least 80% sequence identity to SEQ ID NO: 98, 104, 110, 116, 122, 128, 134, 139, 146, 152, 158, 164, 170, 176, 182, 188, 194, 200, 206, 212, 218, or 224; and (iii) a LC CDR3 with at least 80% sequence identity to SEQ ID NO: 99, 105, 111, 117, 123, 129, 135, 140, 147, 153, 159, 165, 171, 177, 183, 189, 195, 201, 207, 213, 219, or 225. Some of the antibodies and immunologically functional fragments that are provided include one or more of the preceding LC CDRs and/or one or more of the following heavy chain (HC) complementary determining regions (CDRs): (i) a HC CDR1 with at least 80% sequence identity to SEQ ID NO: 100, 106, 112, 118, 124, 130, 136, 142, 148, 154, 160, 166, 172, 178, 184, 190, 196, 202, 208, 214, 220, or 226; (ii) a HC CDR2 with at least 80% sequence identity to SEQ ID NO: 101, 107, 113, 119, 125, 131, 137, 143, 149, 155, 161, 167, 173, 179, 185, 191, 197, 203, 209, 215, 221, or 227; and (iii) a HC CDR3 with at least 80% sequence identity to SEQ ID NO: 102, 108, 114, 120, 126, 132, 138, 144, 150, 156, 162, 168, 174, 180, 186, 192, 198, 204, 210, 216, 222 or 228. Some of the antibodies and immunologically functional fragments thereof that are provided also include one or more LC CDRs and one or more HC CDRs above.

Such antibodies or fragments can specifically bind a DKK1 polypeptide. Certain antibodies or fragments include one, two, three, four, five or all six of the forgoing CDRs.

The light chain and heavy chains of other antibodies or fragments are as described above but have at least 90% sequence identity to the foregoing sequences. Still other antibodies or fragments thereof are ones having a light chain in which CDR1 has the amino acid sequence as set forth in SEQ ID NOs: 97, 103, 109, 115, 121, 127, 133, 139, 145, 151, 157, 163, 169, 175, 181, 187, 193, 199, 205, 211, 217, or 223, CDR2 has the amino acid sequence as set forth in SEQ ID NOs: 98, 104, 110, 116, 122, 128, 134, 139, 146, 152, 158, 164, 170, 176, 182, 188, 194, 200, 206, 212, 218, or 224 and/or CDR3 has the amino acid sequence as set forth in SEQ ID NOs: 99, 105, 111, 117, 123, 129, 135, 140, 147, 153, 159, 165, 171, 177, 183, 189, 195, 201, 207, 213, 219, or 225. Some antibodies and fragments may also have a heavy chain in which CDR1 has the amino acid sequence as set forth in SEQ ID NOs: 100, 106, 112, 118, 124, 130, 136, 142, 148, 154, 160, 166, 172, 178, 184, 190, 196, 202, 208, 214, 220, or 226, CDR2 has the amino acid sequence as set forth in SEQ ID NOs: 101, 107, 113, 119, 125, 131, 137, 143, 149, 155, 161, 167, 173, 179, 185, 191, 197, 203, 209, 215, 221, or 227 and/or HC CDR3 has the amino acid sequence as set forth in SEQ ID NOs: 102, 108, 114, 120, 126, 132, 138, 144, 150, 156, 162, 168, 174, 180, 186, 192, 198, 204, 210, 216, 222 or 228. Certain antibodies or fragments include a light chain CDR3 with the amino acid sequence of SEQ ID NOs: 99, 105, 111, 117, 123, 129, 135, 140, 147, 153, 159, 165, 171, 177, 183, 189, 195, 201, 207, 213, 219, or 225 and/or a heavy chain CDR3 with the amino acid sequence of SEQ ID NOs: 102, 108, 114, 120, 126, 132, 138, 144, 150, 156, 162, 168, 174, 180, 186, 192, 198, 204, 210, 216, 222 or 228.

Certain other antibodies and immunologically functional fragments that are provided include (a) a light chain variable region (VL) having 80%, 85%, 90%, 92%, 95% or greater sequence identity with SEQ ID NO: 10, 14, 18, 22, 26, 30, 34, 38, 42, 46, 50, 54, 58, 62, 66, 70, 74, 78, 82, 86, 90, or 94; (b) a heavy chain variable region (VH) having at least 80% sequence identity with SEQ ID NO: 12, 16, 20, 24, 28, 32, 36, 40, 44, 48, 52, 56, 60, 64, 68, 72, 76, 80, 84, 88, 92, or 96; or (c) a VL of (a) and a VH of (b).

Other antibodies or fragments are similar in structure but the VL has at least 90%, 92%, or more preferably 95% sequence identity with SEQ ID NOs: 10, 14, 18, 22, 26, 30, 34, 38, 42, 46, 50, 54, 58, 62, 66, 70, 74, 78, 82, 86, 90, or 94; and the VH has at least 90% sequence identity with SEQ ID NOs: 12, 16, 20, 24, 28, 32, 36, 40, 44, 48, 52, 56, 60, 64, 68, 72, 76, 80, 84, 88, 92, or 96. In certain antibodies or fragments, the VL has at least 98% sequence identity with SEQ ID NO:84, 28 or 32; and the VH has at least 98% sequence identity with SEQ ID NO: 10, 14, 18, 22, 26, 30, 34, 38, 42, 46, 50, 54, 58, 62, 66, 70, 74, 78, 82, 86, 90, or 94. Still other antibodies or fragments are ones that include a VL that has the amino acid sequence of SEQ ID NO: 10, 14, 18, 22, 26, 30, 34, 38, 42, 46, 50, 54, 58, 62, 66, 70, 74, 78, 82, 86, 90, or 94, and/or a VH that has the amino acid sequence of SEQ ID NOs: 12, 16, 20, 24, 28, 32, 36, 40, 44, 48, 52, 56, 60, 64, 68, 72, 76, 80, 84, 88, 92, or 96.

Some antibodies or fragments include a light chain that comprises or consists of the amino acid sequence of SEQ ID NOs: 10, 14, 18, 22, 26, 30, 34, 38, 42, 46, 50, 54, 58, 62, 66, 70, 74, 78, 82, 86, 90, or 94 and/or a heavy chain that comprises or consists of the amino acid sequence of SEQ ID NOs: 12, 16, 20, 24, 28, 32, 36, 40, 44, 48, 52, 56, 60, 64, 68, 72, 76, 80, 84, 88, 92, or 96.

Also included are isolated antibodies or an immunologically functional fragments thereof that specifically bind a mature human DKK1 protein expressed from the sequence depicted in SEQ ID NO: 1, wherein said antibody binds to an epitope comprising two loops, said loops being formed by disulfide bonds between amino acids 220 and 237 of SEQ ID NO: 2 and between cysteine residues 245 and 263 of SEQ ID NO:2.

Other antibodies or fragments that are disclosed compete with an antibody such as those described above for specific binding to a DKK1 polypeptide. For example, some antibodies and fragments compete with an antibody that consists of two identical heavy chains and two identical light chains, wherein the heavy chains comprise SEQ ID NO: 42 and said light chains comprise SEQ ID NO: 44.

The various antibodies and fragments that are provided may include a single light and/or heavy chain or a single variable light domain and/or a single variable heavy domain. Other antibodies and fragments include two light and/or two heavy chains. In those instances in which the antibody or fragment includes two light and/or heavy chains, the two light chains in some instances are identical to one another; likewise, the two heavy chains in some instances are identical. The antibodies that are provided may include, for example, monoclonal antibodies, a human antibody, a chimeric antibody, or a humanized antibody. The immunologically functional fragments may include, but are not limited to, a scFv, a Fab, a Fab', a F(ab')$_2$, or a domain antibody. In certain instances, the antibody or fragment dissociates from a DKK1 polypeptide with a $k_d$ ($k_{off}$) of $5\times10^{-4}$ or less.

Pharmaceutical compositions that include any of the foregoing antibodies and immunologically active fragments are also provided. Such compositions typically also include a buffer, a pharmaceutically acceptable diluent, a carrier, a solubilizer, an emulsifier or a preservative. The use of the foregoing antibodies and immunologically active fragments in the preparation of a pharmaceutical composition or medicament is also provided.

A variety of nucleic acids encoding the foregoing antibodies are also provided. Some nucleic acids, for instance, encode (a) a light chain CDR with the amino acid sequence as set forth in SEQ ID NOs: 9, 13, 17, 21, 25, 29, 33, 37, 41, 45, 49, 53, 57, 61, 65, 69, 73, 77, 81, 85, 89, and/or 93; and/or (b) a heavy chain CDR with the amino acid sequence as set forth in SEQ ID NOs: 11, 15, 19, 23, 27, 31, 35, 39, 43, 47, 51, 55, 59, 63, 67, 71, 75, 79, 83, 87, 91 and/or 95, such that the encoded CDR(s) encode an antibody or an immunologically functional fragment thereof that can specifically bind a DKK1 polypeptide. Certain other nucleic acids comprise or consist of a sequence that encodes a variable light region (VL) and/or a variable heavy region (VH) of an antibody or immunologically active fragment, wherein the VL has at least 80%, 90% or 95% sequence identity with SEQ ID NOs: 9, 13, 17, 21, 25, 29, 33, 37, 41, 45, 49, 53, 57, 61, 65, 69, 73, 77, 81, 85, 89, or 93 and the VH has at least 80% 90%, or 95% sequence identity with SEQ ID NOs: 11, 15, 19, 23, 27, 31, 35, 39, 43, 47, 51, 55, 59, 63, 67, 71, 75, 79, 83, 87, 91 or 95. Some of the nucleic acids include a sequence that encodes a VL that comprises or consists of SEQ ID NOs: 9, 13, 17, 21, 25, 29, 33, 37, 41, 45, 49, 53, 57, 61, 65, 69, 73, 77, 81, 85, 89, or 93 and/or a sequence that encodes a VH that comprises or consists of SEQ ID NOs: 11, 15, 19, 23, 27, 31, 35, 39, 43, 47, 51, 55, 59, 63, 67, 71, 75, 79, 83, 87, 91 or 95. Expression vectors comprising the foregoing nucleic acids are also disclosed herein, as are cells (e.g., CHO cells) that comprise such expression vectors. Methods of producing an antibody or an immunologically active fragment thereof by culturing cells that contain such expression vectors are also described.

In another aspect, the use of the foregoing binding agents, e.g., antibodies, or immunologically functional fragments or combination thereof in the treatment of a variety of diseases is disclosed. Certain methods, for instance, involve administering to a patient in need thereof an effective amount of an antibody or immunologically active fragment or combinations as described herein to bone trauma including but not limited to orthopedic procedures, dental procedures, implant surgery, joint replacement, bone grafting, bone cosmetic surgery and bone repair such as fracture healing, nonunion healing, delayed union healing and facial reconstruction. One or more compositions may be administered before, during and/or after the procedure, replacement, graft, surgery or repair or other disorders associated with bone damage.

Further provided herein are methods of treating or preventing loss of bone mass comprising administering to a patient in need thereof a therapeutically effective amount of an antibody or immunologically functional fragment thereof as described herein (e.g., an antibody or immunologically functional fragment that comprises at least one light chain CDR selected from the group consisting of amino acids depicted in SEQ ID NOs: 97, 103, 109, 115, 121, 127, 133, 139, 145, 151, 157, 163, 169, 175, 181, 187, 193, 199, 205, 211, 217, or 223, or amino acids depicted in SEQ ID NOs: 98, 104, 110, 116, 122, 128, 134, 139, 146, 152, 158, 164, 170, 176, 182, 188, 194, 200, 206, 212, 218, or 224 and the amino acids depicted in SEQ ID NOs: 99, 105, 111, 117, 123, 129, 135, 140, 147, 153, 159, 165, 171, 177, 183, 189, 195, 201, 207, 213, 219, or 225, and/or at least one heavy chain CDR selected from the group consisting of the amino acids depicted in SEQ ID NOs: 100, 106, 112, 118, 124, 130, 136, 142, 148, 154, 160, 166, 172, 178, 184, 190, 196, 202, 208, 214, 220, or 226, amino acids depicted in SEQ ID NOs: 101, 107, 113, 119, 125, 131, 137, 143, 149, 155, 161, 167, 173, 179, 185, 191, 197, 203, 209, 215, 221, or 227 and the amino acids depicted in SEQ ID NOs: 102, 108, 114, 120, 126, 132, 138, 144, 150, 156, 162, 168, 174, 180, 186, 192, 198, 204, 210, 216, 222 or 228). In one aspect of this embodiment, the patient is one who suffers from cancer that metastasizes to bone, and in another aspect, the patient is one who suffers from multiple myeloma. In yet another aspect, the patient is selected from patients who have osteoporosis, osteopenia, Paget's disease, periodontitis, rheumatoid arthritis, and bone loss due to immobilization. In yet other embodiments, the patient is selected from those who have bone damage that may or may not result from an underlying loss of bone mass such as that caused by osteoporosis or osteolytic lesions associated with cancer (e.g., multiple myeloma). Examples of such bone damage include but are not limited to orthopedic procedures, dental procedures, implant surgery, joint replacement (e.g., hip replacement, knee replacement, etc.), bone grafting, bone cosmetic surgery and bone repair such as fracture healing, nonunion healing, delayed union healing and facial reconstruction. One or more compositions may be administered before, during and/or after the procedure, replacement, graft, surgery or repair.

In yet other embodiments, the patient is selected from those who have bone loss that may or may not result from a condition such as that caused by osteoporosis, osteolytic lesions associated with cancer (e.g., multiple myeloma).

These and other aspects of the present invention will become apparent upon reference to the following detailed description and attached drawings.

DETAILED DESCRIPTION

Figure 1:
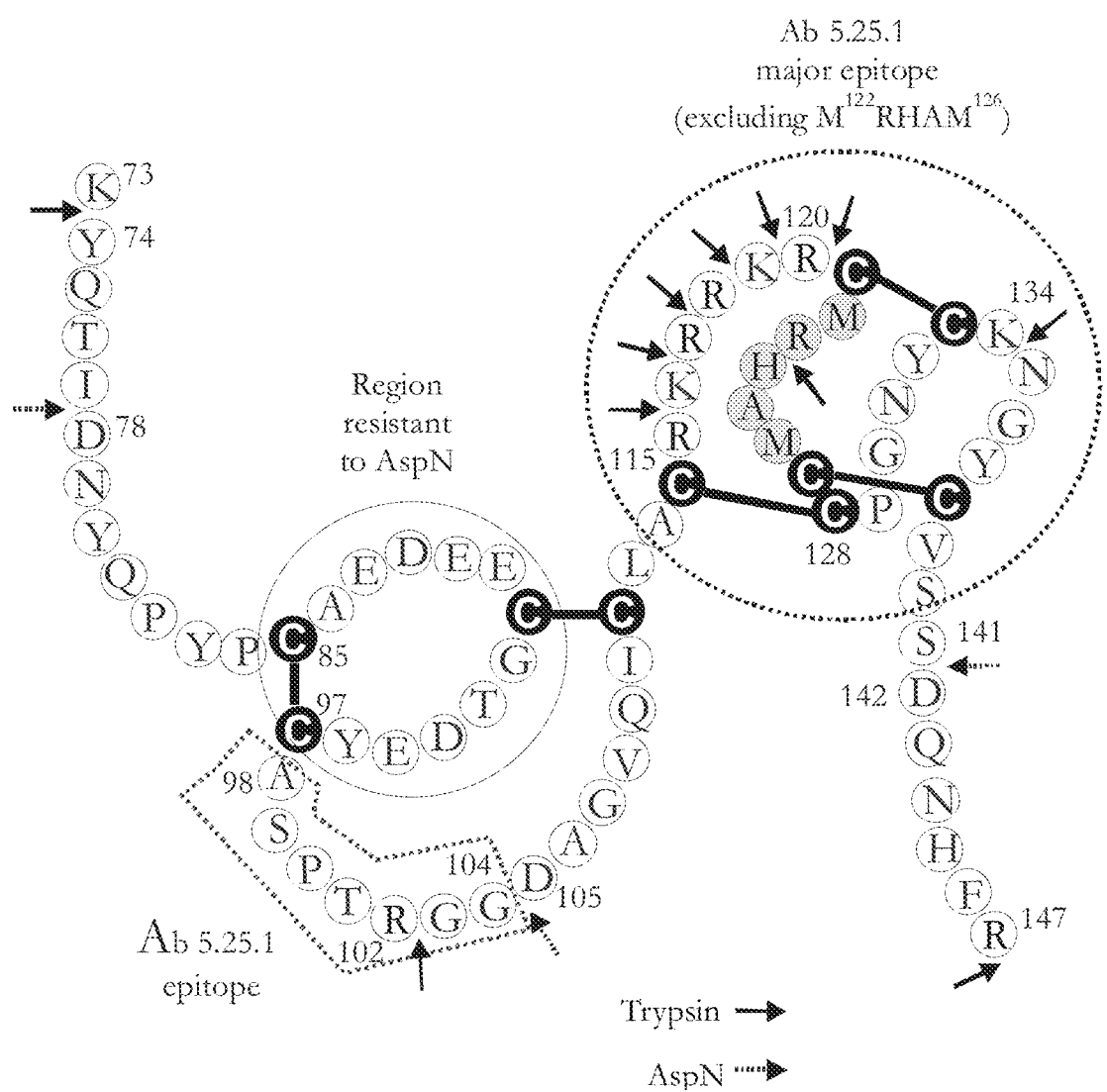
FIG. 1: Epitope sites of human DKK1 antibodies. Trypsin sites are indicated with solid arrows and AspN sites with dotted line arrows. Trypsin sites are in solid arrows and AspN sites in dotted arrows. The binding region for Ab 5.25.1 includes two discontinuous portions, the first from amino acids 98 to 104 and a region from amino acids 107-121 and 127-140. The last three disulfide bonds form a major epitope region where all tryptic sites can be protected by Ab 5.25.1. ARG102 is also protected from trypsin digestion. Removal of amino acids position 121-125 by CNBr treatment does not cause loss of binding. The region noted as resistant to AspN digestion may not be accessed for antibody binding.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990). Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The following terms utilized in this disclosure, unless otherwise indicated, will be understood to have the following meanings:

"DKK1" as used herein includes, for example, rat, murine, cynomolgous and human native forms of DKK1. Exemplary nucleotide sequences encoding human, murine, rat and cynomolgous DKK1 proteins are shown, respectively, in SEQ ID NOs: 1, 3, 5 and 7; the corresponding amino acid sequences are shown, respectively, in SEQ ID NOs: 2, 4, 6, and 8. The human DKK1 protein (SEQ ID NO: 2) has a leader sequence consisting of amino acids 1-31 of SEQ ID NO: 2. An exemplary rat DKK1 protein sequence is listed in GenBank Accession XP219804. The term also includes variants of such native sequences that are immunologically cross-reactive with these native proteins. These proteins can inhibit the interaction between LRP5 or LRP6 with Wnt. The term can also refer to a fragment of a native or variant form of DKK1 that contains an epitope to which an antibody can specifically bind.

The term "polynucleotide" or "nucleic acid" means single-stranded or double-stranded polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate. The term includes both single and double stranded forms.

The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty other proteins or portions thereof, or may include operably linked regulatory sequences that control expression of the coding region of the recited nucleic acid sequences, and/or may include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences".

The term "control sequence" refers to a polynucleotide sequence that can affect the expression and processing of coding sequences to which it is ligated. The nature of such control sequences may depend upon the host organism. In particular embodiments, control sequences for prokaryotes may include a promoter, a ribosomal binding site, and a transcription termination sequence. For example, control sequences for eukaryotes may include promoters comprising one or a plurality of recognition sites for transcription factors, transcription enhancer sequences, and transcription termination sequence. "Control sequences" according to the invention can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic makeup to the original parent cell, so long as the gene of interest is present.

The term "transduction" means the transfer of genes from one bacterium to another, usually by bacteriophage. "Transduction" also refers to the acquisition and transfer of eukaryotic cellular sequences by retroviruses.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, Molecular Cloning: A Laboratory Manual, Id.; Davis et al., 1986, Basic Methods in Molecular Biology, Elsevier; and Chu et al., 1981, Gene 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

The terms "polypeptide" or "protein" means a macromolecule having the amino acid sequence of a native protein, that is, a protein produced by a naturally-occurring and non-recombinant cell, or produced by a genetically-engineered or recombinant cell, and comprise molecules having the amino acid sequence of the native protein, or molecules having deletions from, additions to, and/or substitutions of one or more amino acids of the native sequence. The terms "polypeptide" and "protein" specifically encompass anti-DKK1 antibodies, or sequences that have deletions from, additions to, and/or substitutions of one or more amino acid of anti-DKK1 antibody. The term "polypeptide fragment" refers to a polypeptide that has an amino-terminal deletion, a carboxyl-terminal deletion, and/or an internal deletion as compared with the full-length native protein. Such fragments may also contain modified amino acids as compared with the native protein. In certain embodiments, fragments are about 5 to 500 amino acids long. For example, fragments may be at least 5, 6, 8, 10, 14, 20, 50, 70, 100, 110, 150, 200, 250, 300, 350, 400, or 450 amino acids long. Useful polypeptide fragments for this invention include immunologically functional fragments of antibodies, including binding domains. In the case of anti-DKK1 antibody, useful fragments include but are not limited to a CDR region, a variable domain of a heavy or light chain, a portion of an antibody chain or just its variable region including two CDRs, and the like.

The term "isolated protein" referred to herein means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Genomic DNA, cDNA, mRNA or other RNA, of synthetic origin, or any combination thereof may encode such an isolated protein. Preferably, the isolated protein is substantially free from proteins or polypeptides or other contaminants that are found in its natural environment that would interfere with its therapeutic, diagnostic, prophylactic, research or other use.

A "variant" of a polypeptide (e.g., an antibody) comprises an amino acid sequence wherein one or more amino acid residues are inserted into, deleted from and/or substituted into the amino acid sequence relative to another polypeptide sequence. Variants of the invention include fusion proteins.

A "derivative" of a polypeptide is a polypeptide (e.g., an antibody) that has been chemically modified in some manner distinct from insertion, deletion, or substitution variants, e.g., via conjugation to another chemical moiety.

The term "antibody" refers to an intact immunoglobulin of any isotype, or a fragment thereof that can compete with the intact antibody for specific binding to the target antigen, and includes chimeric, humanized, fully human, and bispecific antibodies. An intact antibody generally will comprise at least two full-length heavy chains and two full-length light chains, but in some instances may include fewer chains such as antibodies naturally occurring in camelids which may comprise only heavy chains. Antibodies according to the invention may be derived solely from a single source, or may be "chimeric," that is, different portions of the antibody may be derived from two different antibodies. For example, the CDR regions may be derived from a rat or murine source, while the framework region of the V region are derived from a different animal source, such as a human. The antibodies or binding fragments of the invention may be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below.

The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains according to the invention include kappa chains and lambda chains.

The term "heavy chain" includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the —COOH end. Heavy chains according to the invention may be of any isotype, including IgG (including IgG1, IgG2, IgG3 and IgG4 subtypes), IgA (including IgA1 and IgA2 subtypes), IgM and IgE.

The term "immunologically functional fragment" (or simply "fragment") of an immunoglobulin chain, as used herein, refers to a portion of an antibody light chain or heavy chain that lacks at least some of the amino acids present in a full-length chain but which is capable of binding specifically to an antigen. Such fragments are biologically active in that they bind specifically to the target antigen and can compete with intact antibodies for specific binding to a given epitope. In one aspect of the invention, such a fragment will retain at least one CDR present in the full-length light or heavy chain, and in some embodiments will comprise a single heavy chain and/or light chain or portion thereof. These biologically active fragments may be produced by recombinant DNA techniques, or may be produced by enzymatic or chemical cleavage of intact antibodies. Immunologically functional immunoglobulin fragments of the invention include, but are not limited to, Fab, Fab', F(ab')2, Fv, domain antibodies and single-chain antibodies, and may be derived from any mammalian source, including but not limited to human, mouse, rat, camelid or rabbit. It is contemplated further that a functional portion of the inventive antibodies, for example, one or more CDRs, could be covalently bound to a second protein or to a small molecule to create a therapeutic agent directed to a particular target in the body, possessing bifunctional therapeutic properties, or having a prolonged serum half-life.

A "Fab fragment" is comprised of one light chain and the CH1 and variable regions of one heavy chain. The heavy chain of a Fab molecule cannot form a disulfide bond with another heavy chain molecule.

An "Fc" region contains two heavy chain fragments comprising the CH2 and CH3 domains of an antibody and in some cases the lower hinge region. The two heavy chain fragments are held together by two or more disulfide bonds (typically in the hinge region) and by hydrophobic interactions of the CH3 domains.

A "Fab' fragment" contains one light chain and a portion of one heavy chain that contains the VH domain and the CH1 domain and also the region between the CH1 and CH2 domains, such that an interchain disulfide bond can be formed between the two heavy chains of two Fab' fragments to form a F(ab')$_2$ molecule.

A "F(ab')2 fragment" contains two light chains and two heavy chains containing a portion of the constant region between the CH1 and CH2 domains, such that an interchain disulfide bond is formed between the two heavy chains. A F(ab')2 fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203.

A "domain antibody" is an immunologically functional immunoglobulin fragment containing only the variable region of a heavy chain or the variable region of a light chain. In some instances, two or more VH regions are covalently joined with a peptide linker to create a bivalent domain antibody. The two VH regions of a bivalent domain antibody may target the same or different antigens.

A "bivalent antibody" comprises two antigen binding sites. In some instances, the two binding sites have the same antigen specificities. However, bivalent antibodies may be bispecific (see below).

A "multispecific antibody" is one that targets more than one antigen or epitope.

A "bispecific," "dual-specific" or "bifunctional" antibody is a hybrid antibody having two different antigen binding sites. Bispecific antibodies are a species of multispecific antibody and may be produced by a variety of methods including, but not limited to, fusion of hybridomas or linking of Fab' fragments. See, e.g., Songsivilai & Lachmann (1990), Clin. Exp. Immunol. 79:315-321; Kostelny et al. (1992), J. Immunol. 148:1547-1553. The two binding sites of a bispecific antibody will bind to two different epitopes, which may reside on the same or different protein targets.

The term "neutralizing antibody" refers to an antibody that binds to a ligand, prevents binding of the ligand to its binding partner and interrupts the biological response that otherwise would result from the ligand binding to its binding partner. In assessing the binding and specificity of an antibody or immunologically functional fragment thereof, an antibody or fragment will substantially inhibit binding of a ligand to its binding partner when an excess of antibody reduces the quantity of binding partner bound to the ligand by at least about 20%, 30%, 40%, 50%, 60%, 70%, 80%, 85%, 90%, 95%, 97%, 99% or more (as measured in an in vitro competitive binding assay). In the case of antibodies to DKK1, a neutralizing antibody will diminish the ability of DKK1 to bind LRP5 or LRP6, thereby inducing a measurable increase in Wnt activity.

The term "compete" when used in the context of antibodies that compete for the same epitope means competition between antibodies is determined by an assay in which the antibody or immunologically functional fragment under test prevents or inhibits specific binding of a reference antibody to a common antigen (e.g., DKK1 or a fragment thereof). Numerous types of competitive binding assays can be used, for example: solid phase direct or indirect radioimmunoassay (RIA), solid phase direct or indirect enzyme immunoassay (EIA), sandwich competition assay (see, e.g., Stahli et al. (1983) Methods in Enzymology 9:242-253); solid phase direct biotin-avidin EIA (see, e.g., Kirkland et al., (1986) J. Immunol. 137:3614-3619) solid phase direct labeled assay, solid phase direct labeled sandwich assay (see, e.g., Harlow and Lane (1988) Antibodies, A Laboratory Manual, Cold Spring Harbor Press); solid phase direct label RIA using 1-125 label (see, e.g., Morel et al. (1988) Molec. Immunol. 25:7-15); solid phase direct biotin-avidin EIA (see, e.g., Cheung, et al. (1990) Virology 176:546-552); and direct labeled RIA (Moldenhauer et al. (1990) Scand. J. Immunol. 32:77-82). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the examples herein. Usually, when a competing antibody is present in excess, it will inhibit specific binding of a reference antibody to a common antigen by at least 40%, 45%, 50%, 55%, 60%, 65%, 70% or 75%. In some instance, binding is inhibited by at least 80%, 85%, 90%, 95%, or 97% or more by a selective binding agent, such as an antibody, and additionally capable of being used in an animal to produce antibodies capable of binding to that antigen. An antigen may possess one or more epitopes that are capable of interacting with different antibodies.

The term "epitope" includes any determinant capable of specifically binding to an immunoglobulin or to a T-cell receptor. An epitope is a region of an antigen that is bound by an antibody that specifically targets that antigen, and when the antigen is a protein, includes specific amino acids that directly contact the antibody. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antibodies specific for a particular target antigen will preferentially recognize an epitope on the target antigen in a complex mixture of proteins and/or macromolecules.

An antibody of the invention is said to "specifically bind" its target antigen when the dissociation constant ($K_d$) is $1\times10^{-7}$ M. The antibody specifically binds antigen with "high affinity" when the Kd is $1\times10^{-8}$, higher affinity is M $5\times10^{-9}$ M, and with "very high affinity" when the Kd is $5\times10^{-10}$ M. In one embodiment of the invention, the antibody has a Kd of $1\times10^{-9}$ M and an off-rate of about $1\times10^{-4}$/sec. In one embodiment of the invention, the off-rate is $<1\times10^{-5}$. In other embodiments of the invention, the antibodies will bind to human DKK1 with a Kd of between about $1\times10^{-8}$ M and $1\times10^{-10}$ M, and in yet another embodiment it will bind with a Kd $2\times10^{-10}$. One of skill in the art will recognize that specifically binding does not mean exclusive binding, rather it allows for some degree of non-specific binding as is typical in biological reactions between groups with affinity to one another.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48: 1073.

In calculating percent identity, the sequences being compared are aligned in a way that gives the largest match between the sequences. The computer program used to determine percent identity is the GCG program package, which includes GAP (Devereux et al., 1984, Nucl Acid Res 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3.times. the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see Dayhoff et al., 1978, Atlas of Protein Sequence and Structure 5:345-352 for the PAM 250 comparison matrix; Henikoff et al., 1992, Proc. Natl. Acad. Sci. USA 89: 10915-10919 for the BLOSUM 62 comparison matrix) is also used by the algorithm.

Recommended parameters for determining percent identity for polypeptides or nucleotide sequences using the GAP program are the following:
Algorithm: Needleman et al., 1970, J. Mol. Biol. 48:443-453;
Comparison matrix: BLOSUM 62 from Henikoff et al., 1992, supra;
Gap Penalty: 12 (but with no penalty for end gaps)
Gap Length Penalty: 4
Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "osteopenia" refers to a patient with bone loss of at least one standard deviation compared with a standard patient considered to have normal bone mineral density (BMD). For present purposes, the measurement is determined by Dual Energy X-ray Absorptiometry (DEXA) and the patient's BMD is compared with an age and gender-matched standard (Z score). In determining osteopenia, BMD measurements may be taken of one or more bones.

The term "therapeutically effective amount" refers to the amount of an anti-DKK1 antibody determined to produce a therapeutic response in a mammal. Such therapeutically effective amounts are readily ascertained by one of ordinary skill in the art.

"Amino acid" includes its normal meaning in the art. The twenty naturally-occurring amino acids and their abbreviations follow conventional usage. See Immunology—A Synthesis, 2nd Edition, (E. S. Golub and D. R. Gren, eds.), Sinauer Associates: Sunderland, Mass. (1991). Stereoisomers (e.g., D-amino acids) of the twenty conventional amino acids, unnatural amino acids such as .alpha.-, .alpha.-disubstituted amino acids, N-alkyl amino acids, and other unconventional amino acids may also be suitable components for polypeptides of the invention. Examples of unconventional amino acids include: 4-hydroxyproline, gamma-carboxyglutamate, .epsilon.-N,N,N-trimethyllysine, .epsilon.-N-acetyllysine, O-phosphoserine, N-acetylserine, N-formylmethionine, 3-methylhistidine, 5-hydroxylysine, .sigma.-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

The present invention provides novel compositions comprising antibodies and antigen-binding sites of immunoglobulins specific for DKK1 (e.g., a polypeptide consisting of amino acids 32 to 266 of SEQ ID NO: 2). Some of these antibodies and antibody fragments can cross-react with DKK1 from several mammalian sources, including rat, mouse, cynomolgus monkey and human DKK1. Some of the antibodies and fragments have higher affinity for DKK1 from one species than another (e.g., some antibodies and fragments have higher affinity for human DKK1 as compared to rat or murine DKK1; other antibodies have higher affinity for rat or murine DKK1 as compared to human DKK1). The invention also provides novel neutralizing antibodies, including chimeric, humanized and human antibodies, as well as antibodies and immunologically functional fragments thereof that bind a conformational epitope in human DKK1. Nucleic acids encoding the antibodies and fragments are also disclosed, as well as methods for expressing the antibodies using these nucleic acids. In another aspect, the invention relates to molecules (e.g., immunologically functional fragments and polypeptides) that are capable of exhibiting immunological binding properties of antibody antigen-binding sites.

The antibodies and immunologically functional fragments that are disclosed herein have a variety of utilities. Some of the antibodies and fragments, for instance, are useful in specific binding assays, affinity purification of DKK1 or its ligands and in screening assays to identify other antagonists of DKK1 activity. Certain of the antibodies can be used to treat various diseases that are associated with the activity of DKK1. Some antibodies and fragments can thus be used in a variety of treatments related to bone such as increasing bone mineral density, synthesis of new bone, treatment of systemic bone loss (e.g., bone erosions), bone repair, and treatments for various forms of arthritis. Some antibodies can also be used to increase osteoclast activity and induce bone resorption. Certain of the antibodies and fragments that are disclosed, however, can be used to treat a variety of diverse diseases that are unrelated to bone diseases. As described in greater detail below, examples of such diseases include those in which it is desirable to promote stem cell renewal (e.g., diabetes and diseases of the muscle), inflammatory diseases (e.g., Crohn's and inflammatory bowel disease), neurological diseases, ocular diseases, renal diseases, and various skin disorders.

A variety of selective binding agents useful for regulating the activity of DKK1 are provided. These agents include, for instance, antibodies and immunologically functional fragments thereof that contain an antigen binding domain (e.g., single chain antibodies, domain antibodies, immunoadhesions, and polypeptides with an antigen binding region) and specifically bind to a DKK1 polypeptide (e.g., a human, rat and/or murine DKK1 polypeptide). Some of the agents, for example, are useful in inhibiting the binding of DKK1 to LRP5 and/or LRP6, and can thus be used to stimulate one or more activities associated with Wnt signaling.

Some of the binding agents that are provided have the structure typically associated with naturally occurring antibodies. The structural units of these antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kDa) and one full-length "heavy" chain (in certain embodiments, about 50-70 kDa). Each individual immunoglobulin chain is composed of several "immunoglobulin domains," each consisting of roughly 90 to 110 amino acids and expressing a characteristic folding pattern. These domains are the basic units of which antibody polypeptides are composed. The amino-terminal portion of each chain typically includes a variable domain that is responsible for antigen recognition. The carboxy-terminal portion is more conserved evolutionarily than the other end of the chain and is referred to as the "constant region" or "C region." Human light chains generally are classified as kappa and lambda light chains, and each of these contains one variable domain and one constant domain. Heavy chains are typically classified as mu, delta, gamma, alpha, or epsilon chains, and these define the antibody's isotype as IgM, IgD, IgG, IgA, and IgE, respectively. IgG has several subtypes, including, but not limited to, IgG1, IgG2, IgG3, and IgG4. IgM subtypes include IgM, and IgM2. IgA subtypes include IgA1 and IgA2. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that may be responsible for effector function. The number of heavy chain constant region domains will depend on the isotype. IgG heavy chains, for example, each contain three C region domains known as CH1, CH2 and CH3. The antibodies that are provided can have any of these isotypes and subtypes. In certain embodiments of the invention, the anti-DKK1 antibody is of the IgG1, IgG2 or IgG4 subtype.

In full-length light and heavy chains, the variable and constant regions are joined by a "J" region of about 12 or more amino acids, with the heavy chain also including a "D" region of about 10 more amino acids. See, e.g., Fundamental Immunology, 2nd ed., Ch. 7 (Paul, W., ed.) 1989, New York: Raven Press. The variable regions of each light/heavy chain pair typically form the antigen binding site.

Variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope on the target protein (e.g., DKK1). From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, National Institutes of Health, Bethesda, Md.), or Chothia & Lesk, 1987, J. Mol. Biol. 196: 901-917; Chothia et al., 1989, Nature 342: 878-883.

Provided in Table 1 are human (SEQ ID NOs: 1 and 2), mouse (SEQ ID NOs: 3 and 4), rat (SEQ ID NOs: 5 and 6) and cynomolgous monkey (SEQ ID NOs: 7 and 8) nucleic acid and protein DKK1 sequences, respectively. Also provided are specific examples of the light and heavy chains of antibodies that are provided herein and their corresponding nucleotide and amino acid sequences. The sequence identifiers are provided in the left most column, sequences (nucleic acid or protein) in the middle and internal designations for the sequences on the right most column. In addition, the respective CDR's are provided (SEQ ID NOs: 97-228). Vh=variable heavy chain; Vk=variable kappa light chain; Vl=variable lambda light chain.

TABLE 1

| SEQ ID NO | DNA or Protein | |
|---|---|---|
| 1 | ATGATGGCTCTGGGCGCAGCGGGAGCTACCCGGGTCTTTGTCGCGATGGTAGCGGCGGCTCTCGGC<br>GGCCACCCTCTGCTGGGAGTGAGCGCCACCTTGAACTCGGTTCTCAATTCCAACGCTATCAAGAAC<br>CTGCCCCCACCGCTGGGCGGCGCTGCGGGGCACCCAGGCTCTGCAGTCAGCGCCGCGCCGGGAATC<br>CTGTACCCGGGCGGGAATAAGTACCAGACCATTGACAACTACCAGCCGTACCCGTGCGCAGAGGAC<br>GAGGAGTGCGGCACTGATGAGTACTGCGCTAGTCCCACCCGCGGAGGGGACGCAGGCGTGCAAATC<br>TGTCTCGCCTGCAGGAAGCGCCGAAAACGCTGCATGCGTCACGCTATGTGCTGCCCCGGGAATTAC<br>TGCAAAAATGGAATATGTGTGTCTTCTGATCAAAATCATTTCCGAGGAGAAATTGAGGAAACCATC<br>ACTGAAAGCTTTGGTAATGATCATAGCACCTTGGATGGGTATTCCAGAAGAACCACCTTGTCTTCA<br>AAAATGTATCACACCAAAGGACAAGAAGGTTCTGTTTGTCTCAGGTCATCAGACTGTGCCTCAGGA<br>TTGTGTTGTGATAGACACTTCTGGTCCAAGATCTGTAAACCTGTCCTGAAAGAAGGTCAAGTGTGT<br>ACCAAGCATAGGAGAAAAGGCTCTCATGGACTAGAAATATTCCAGCGTTGTTACTGTGGAGAAGGT<br>CTGTCTTGCCGGATACAGAAAGATCACCATCAAGCCAGTAATTCTTCTAGGCTTCACACTTGTCAG<br>AGACAC | HUMAN<br>DKK1 |
| 2 | MMALGAAGAT RVFVAMVAAA LGGHPLLGVS ATLNSVLNSN AIKNLPPPLG GAAGHPGSAV<br>SAAPGILYPG GNKYQTIDNY QPYPCAEDEE CGTDEYCASP TRGGDAGVQI CLACRKRRKR<br>CMRHAMCCPG NYCKNGICVS SDQNHFRGEI EETITESFGN DHSTLDGYSR RTTLSSKMYH<br>TKGQEGSVCL RSSDCASGLC CDRHFWSKIC KPVLKEGQVC TKHRRKGSHG LEIFQRCYCG<br>EGLSCRIQKD HHQASNSSRL HTCQRH | |
| 3 | ATGATGGTTGTGTGTGCAGCGGCAGCTGTCCGGTTCTTGGCCGTGTTTACAATGATGGCTCTCTGC<br>AGCCTCCCTCTGCTAGGAGCCAGTGCCACCTTGAACTCAGTTCTCATCAATTCCAACGCGATCAAG<br>AACCTGCCCCCACCGCTGGGTGGTGCTGGGGGGCAGCCGGGCTCTGCTGTCAGTGTGGCGCCGGGA<br>GTTCTCTATGAGGGCGGGAACAAGTACCAGACTCTTGACAACTACCAGCCCTACCCTTGCGCTGAA<br>GATGAGGAGTGCGGCTCTGACGAGTACTGCTCCAGCCCCAGCCGCGGGGCAGCCGGCGTCGGAGGT<br>GTACAGATCTGTCTGGCTTGCCGAAAGCGCAGGAAGCGCTGCATGAGGCACGCTATGTGCTGCCCC<br>GGGAACTACTGCAAAAATGGAATATGCATGCCCTCTGACCACAGCCATTTTCCTCGAGGGGAGATT | Murine<br>DKK1 |

TABLE 1-continued

| SEQ ID NO | DNA or Protein | |
|---|---|---|
| | GAGGAAAGCATCATTGAAAACCTTGGTAATGACCACAACGCCGCCGCGGGGATGGATATCCCAGA<br>AGAACCACACTGACTTCAAAAATATATCACACCAAAGGACAAGAAGGCTCCGTCTGCCTCCGATCA<br>TCAGACTGTGCCGCAGGGCTGTGTTGTGCAAGACACTTCTGGTCCAAGATCTGTAAACCTGTCCTT<br>AAAGAAGGTCAGGTGTGCACCAAGCACAAACGGAAAGGCTCCCACGGGCTGGAGATATTCCAGCGC<br>TGTTACTGCGGGGAAGGCCTGGCTTGCAGGATACAGAAAGATCACCATCAAGCCAGCAATTCTTCT<br>AGGCTCCACACCTGCCAGAGACAC | |
| 4 | MMVVCAAAAVRFLAVFTMMALCSLPLLGASATLNSVLINSNAIKNLPPPLGGAGGQPGSAVSVAPG<br>VLYEGGNKYQTLDNYQPYPCAEDEECGSDEYCSSPSRGAAGVGGVQICLACRKRRKRCMRHAMCCP<br>GNYCKNGICMPSDHSHFPRGEIEESIIENLGNDHNAAAGDGYPRRTTLTSKIYHTKGQEGSVCLRS<br>SDCAAGLCCARHFWSKICKPVLKEGQVCTKHKRKGSHGLEIFQRCYCGEGLACRIQKDHHQASNSS<br>RLHTCQRH | |
| 5 | ATGACGGTTGTGCGTGCAGTGGCAGCTGTCCGGTTCTTGGTCGTGCTTACAACGATGGCTCTCTGC<br>AGCCTCCCTCCGCTCGGAGTCAGCGCCACTTTGAACTCAGTTCTCATCAATTCCAACGCGATCAAG<br>AACCTGCCCCCACCGCTGGGTGGTGCTGGGGGGCAGCCGGGCTCTGCTGTCAGCGTGGCGCCCGGA<br>GTCCTCTATGAGGGCGGGAACAAGTACCAGACTCTTGACAACTACCAGCCCTACCCTTGCGCGGAG<br>GATGAGGAGTGCGGCACTGACGAGTACTGCTCCAGTCCCAGCCGCGGGGCAGCCGGCGTGGGAGGT<br>GTACAAATCTGCCTGGCTTGCCGAAAGCGCAGGAAACGCTGCATGAGGCACGCTATGTGCTGCCCC<br>GGGAATTACTGCAAAAACGGAATATGCATGCCCTCTGACCACAGCCATTTACCTCGAGGGGAAATC<br>GAGGAAGGCATCATTGAAAACCTTGGCAATGACCACGGTGCCGGGGATGGATATCCCAGAAGAACC<br>ACACTGACTTCAAAAATATATCACACCAAAGGGCAAGAAGGCTCTGTCTGCCTCCGATCATCAGAC<br>TGCGCCACAGGGCTGTGTTGTGCAAGACATTTCTGGTCCAAGATCTGTAAACCTGTCCTTAAAGAA<br>GGTCAGGTATGCACCAAGCACAGAAGGAAAGGCTCCCACGGGCTGGAGATATTCCAGCGCTGTTAC<br>TGTGGGGAAGGTCTGGCTTGCAGGATACAGAAAGATCACCATCAAACCAGCAATTCTTCCAGGCTC<br>CACACCTGCCAGAGACAC | Rat<br>DKK1 |
| 6 | MTVVRAVAAVRFLVVLTTMALCSLPPLGVSATLNSVLINSNAIKNLPPPLGGAGGQPGSAVSVAPG<br>VLYEGGNKYQTLDNYQPYPCAEDEECGTDEYCSSPSRGAAGVGGVQICLACRKRRKRCMRHAMCCP<br>GNYCKNGICMPSDHSHLPRGEIEEGIIENLGNDHGAGDGYPRRTTLTSKIYHTKGQEGSVCLRSSD<br>CATGLCCARHFWSKICKPVLKEGQVCTKHRRKGSHGLEIFQRCYCGEGLACRIQKDHHQTSNSSRL<br>HTCQRH | |
| 7 | ATGATGGCTCTGGGCGCAGCAGGAGCTGCCCGGGTCTTGGTCGCGCTGGTAGCGGCGGCTCTTGGC<br>GGCCACCCTCTGCTGGGAGTGAGCGCCACCTTGAACTCGGTTCTCAATTCCAACGCGATCAAGAAC<br>CTGCCCCCACCGCTGGGCGGCGCTGCGGGGCACCCAGGCTCTGCAGTCAGCGCCGCGCCAGGAATT<br>CTGTACCCGGGCGGGAATAAGTACCAGACCATTGACAACTACCAGCCGTACCCTTGCGCAGAGGAT<br>GAGGAGTGCGGCACTGATGAGTACTGCGCTAGTCCCACCCGCGGAGGGGACGCGGGCGTGCAAATC<br>TGTCTCGCCTGCAGGAAGCGCCGAAAACGCTGCATGCGTCACGCTATGTGCTGCCCCGGGAATTAC<br>TGCAAAAATGGAATATGTGTGTCTTCTGATCAAAATAATTTCCAGGGAGAAATTGAGGAAACCATT<br>ACTGAAAGCTTTGGTAATGATCATAGCACTTTGGATGGGTATTCCAGAAGAACAACATTGTCTTCA<br>AAAATGTATCACAGCAAAGGACAAGAAGGTTCTGTGTGTCTCCGGTCATCAGACTGTGCCACAGGA<br>CTGTGTTGTGCTAGACACTTCTGGTCCAAGATCTGTAAACCTGTCCTCAAAGAAGGTCAAGTGTGT<br>ACCAAGCATAGAAGAAAAGGCTCTCATGGGCTAGAAATATTCCAGCGTTGTTACTGCGGAGAAGGT<br>CTGTCTTGCCGGATACAGAAAGATCACCATCAAGCCAGTAATTCTTCTAGGCTTCACACTTGTCAG<br>AGACAC | Cyno<br>DKK1 |
| 8 | MMALGAAGAARVLVALVAAALGGHPLLGVSATLNSVLNSNAIKNLPPPLGGAAGHPGSAVSAAPGI<br>LYPGGNKYQTIDNYQPYPCAEDEECGTDEYCASPTRGGDAGVQICLACRKRRKRCMRHAMCCPGNY<br>CKNGICVSSDQNNFRGEIEETITESFGNDHSTLDGYSRRTTLSSKMYHSKGQEGSVCLRSSDCATG<br>LCCARHFWSKICKPVLKEGQVCTKHRRKGSHGLEIFQRCYCGEGLSCRIQKDHHQASNSSRLHTCQ<br>RH | |
| 9 | GACATCCAGATGACCCAGTCTCCATCCTCCCTGTCTGCATCTGTAGGAGACAGAGTCACCATCACT<br>TGCCGGGCAAGTCAGGGCATTAGAGATGATTTAGGCTGGTTTCAGCAGAAACCAGGGAAAGCCCCT<br>AAGCGCCTGATCTATGCTGCATCCAGTTTGCAAAGTGGGGTCCCATCAAGGTTCAGCGGCAGTGGA<br>TCTGGGACAGAATTCACTCTCACAATCAGCAGCCTGCAGCCTGAAGATTTTGCAACTTATTACTGT<br>CTACAGCATAATAGTTACCCGTGCAGTTTTGGCCAGGGGACCAAGCTGGAGTTCAAA | 2.4.1<br>Vk |
| 10 | DIQMTQSPSSLSASVGDRVTITCRASQGIRDDLGWFQQKPGKAPKRLIYAASSLQSGVPSRFSGSG<br>SGTEFTLTISSLQPEDFATYYCLQHNSYPCSFGQGTKLEFK | |
| 11 | CAGGTTCAGCTAATGCAGTCTGGAGCTGAGGTGAAGAAGCCTGGGGCCTCAGTGAAGGTCTCCTGC<br>AAGGCTTCTGGTTACACCTTTACCAGCTATGGTATCAGCTGGGTGCGACAGGCCCCTGGACAAGGG<br>CTTGAGTGGATGGGATGGATCAGCGCTGACAATGGTCACACAAACTATGCACAGAAACTCCAGGGC<br>AGAGTCACCATGACCACAGACACATCCACGAGCACAGCCTACATGGAGCTGAGGAGCCTGAGATCT<br>GACGACACGGCCGTGTATTACTGTGCGAGAGATGGGGAGCTACTAAATTACTACTACTACTACGGT<br>ATGGACGTCTGGGGCCAAGGGACCACGGTCACCGTCTCCTCA | 2.4.1<br>Vh |
| 12 | QVQLMQSGAEVKKPGASVKVSCKASGYTFTSYGISWVRQAPGQGLEWMGWISADNGHTNYAQKLQG<br>RVTMTTDTSTSTAYMELRSLRSDDTAVYYCARDGELLNYYYYYGMDVWGQGTTVTVSS | |
| 13 | GATATTGTGATGACCCAGACTCCACTCTCTCTGTCCGTCATTCCTGGACAGCCGGCCTCCATCTCC<br>TGCAAGTCTAGTCAGAGCCTCCTGCATAGTGATGGAAAGACCTATTTGTACTGGTACCTGCAGAGG<br>CCAGGCCAGCCTCCACAGCTCCTGATCTATGAAGTTTCCAACCGGTTCTCTGGAGTGCCACATAGG<br>CTCAGTGGCAGCGGGTCAGGGACAGATTTCACACTGAAAATCAGCCGGGTGGAGGCTGAGGATGTT<br>GGGGTTTATTACTGCATGCAAAGTATACAGGTTCCGTGGACGTTCGGCCAAGGGACCAAGGTGGAA<br>ATCAAA | 2.20.1<br>Vk |

TABLE 1-continued

| SEQ ID NO | DNA or Protein | |
|---|---|---|
| 14 | DIVMTQTPLSLSVIPGQPASISCKSSQSLLHSDGKTYLYWYLQRPGQPPQLLIYEVSNRFSGVPHR LSGSGSGTDFTLKISRVEAEDVGVYYCMQSIQVPWTFGQGTKVEIK | |
| 15 | CAGTGTCAGGTGCAGCTGGTGGAGTCTGGGGGAGGCGTGGTCCAGCCTGGGAGGTCCCTGAGACTC TCCTGTGCAGCCTCTGGATTCACCTTCAGTAGCTATGGCATGCACTGGGTCCGCCAGGCTCCAGGC AAGGGGCTGGAGTGGGTGGCAGTTATATCATATGATGGAAGTGATAAATACTATGCAGACTCCGTG AAGGGCCGATTCACCATCTCCAGAGACAATTCCAAGAACACGCTGTATCTGCAAATGAACAGCCTG AGAGCTGAGGACACGGCTGTGTATTACTGTGCGAGAGATCAATGGGGTGGGAGCCCAGCCGGCCCC TGGGGCCAGGGAACCCTGGTCACCGTCTCCTCA | 2.20.1 Vh |
| 16 | QVQLVESGGGVVQPGRSLRLSCAASGFTFSSYGMHWVRQAPGKGLEWVAVISYDGSDKYYADSVKG RFTISRDNSKNTLYLQMNSLRAEDTAVYYCARDQWGGSPAGPWGQGTLVTVSS | |
| 17 | GAAATTGTGTTGACGCAGTCTCCAGGCACCCTGTCTTTGTCTCCAGGGGAAAGAGCCACCCTCTCC TGCAGGGCCAGTCAGAGTGTTAGCAGCAACTACTTAGCCTGGTACCAGCAGAAACCTGGCCAGGCT CCCAGGCTCCTCATCTATGGTGCATCCAGCAGGGCCACTGGCATCCCAGACAGGTTCAGTGGCAGT GGGTCTGGGACAGACTTCACTCTCACCATCAGCAGACTGGAGCCTGAAGATTTTGCAGTGTATTAC TGTCAGCAGTATGGTAGCTCACCGATCACCTTCGGCCAAGGGACACGACTGGAGATTAAA | 2.37.1 Vk |
| 18 | EIVLTQSPGTLSLSPGERATLSCRASQSVSSNYLAWYQQKPGQAPRLLIYGASSRATGIPDRFSGS GSGTDFTLTISRLEPEDFAVYYCQQYGSSPITFGQGTRLEIK | |
| 19 | CAGGTGCAGCTGGTGGAGTCTGGGGGAGGCGTGGTCCAGCCTGGGAGGTCCCTGAGACTCTCCTGT GCAGCCTCTGGATTCACCTTCAGTAGCTATGGCATGCACTGGGTCCGCCAGGCTCCAGGCAAGGGG CTGGAATGGGTGGCAGTTATATCATATGATGGAAGTGATAAATACTATGCAGACTCCGTGAAGGGC CGATTCACCTTCTCCAGAGACAATTCCAAGAACACGCTGTATCTGCAAATGAACAGCCTGAGAGCT GAGGACACGGCTGTGTATTACTGTGCGAGAGAATTGGGTATAGCAGCTTCCTTTGACTACTGGGGC CAGGGAACCCTGGTCACCGTCTCCTCA | 2.37.1 Vh |
| 20 | QVQLVESGGGVVQPGRSLRLSCAASGFTFSSYGMHWVRQAPGKGLEWVAVISYDGSDKYYADSVKG RFTFSRDNSKNTLYLQMNSLRAEDTAVYYCARELGIAASFDYWGQGTLVTVSS | |
| 21 | GATATTGTGATGACCCAGTCTCCACTCTCTCTGTCCGTCACCCCTGGACAGCCGGCCTCCATCTCC TGCAAGTCTAGTCAGAGCCTCCTGCACAGTGATGGAAAGACCTATTTGTATTGGTATCTGCAGAAG CCAGGCCAGCCTCCACAGCTCCTGATCTATGAAGTTTCCAACCGGTTCTCTGGAGTGCCAGATAGG TTCAGTGGCAGCGGGTCAGGGACAGATTTCACACTGAAATCAGCCGGTGGAGGTGAGGATGTT GGGGTCTATTACTGCATGCAAAGTATACAGGTTCCGTGGACGTTCGGCCAAGGGACCAAGGTGGAA ATCAAA | 2.40.1 Vk |
| 22 | DIVMTQSPLSLSVTPGQPASISCKSSQSLLHSDGKTYLYWYLQKPGQPPQLLIYEVSNRFSGVPDR FSGSGSGTDFTLKISRVEAEDVGVYYCMQSIQVPWTFGQGTKVEIK | |
| 23 | CAGGTGCAACTGGTGGAGTCTGGAGGAGGCGTGGTCCAGCCTGGGAGGTCCCTGAGACTCTCCTGT GCAGCCTCTGGATTCACCTTCAGTAGCTATGGCATGCACTGGGTCCGCCAGGCTCCAGGCAAGGGG CTGGGGTGGGTGGCAGTTATATCATATGATGGAAGTGATAAATACTATGCAGACTCCGTGAAGGGC CGATTCACCATCTCCAGAGACAATTCCAAGAACACGCTGTATCTGCAAATGAACAGCCTGAGAGCT GAGGACACGGCTGTGTATTACTGTGCGAGAGACCTCGTGGATACAGCTATGCCCTGGGGCCAAGGG ACCACGGTCACCGTCTCCTCA | 2.40.1 Vh |
| 24 | QVQLVESGGGVVQPGRSLRLSCAASGFTFSSYGMHWVRQAPGKGLGWVAVISYDGSDKYYADSVKG RFTISRDNSKNTLYLQMNSLRAEDTAVYYCARDLVDTAMPWGQGTTVTVSS | |
| 25 | GATATTGTGATGACCCAGACTCCACTCTCTCTGTCCGTCACCCCTGGACAGCCGGCCTCCATCTCC TGCAAGTCTAGTCAGAGCCTCCTGCATAGTGATGGAAAGACCTATTTGTATTGGTACCTGCAGAAG CCAGGCCAGCCTCCACAGCTCCTGATCTATGAAGTTTCCAACCGGTTCTCTGGAGTGCCAGATAGG TTCAGTGGCAGCGGGTCAGGGACAGATTTCACACTGAAAATCAGCCGGTGGAGGCTGAGGATGTT GGGGTTTATTACTGCATGCAAAGTAAACAGCTTCCATTCACTTTCGGCCCTGGGACCAAAGTGGAT ATCAAA | 2.41.1 Vk |
| 26 | DIVMTQTPLSLSVTPGQPASISCKSSQSLLHSDGKTYLYWYLQKPGQPPQLLIYEVSNRFSGVPDR FSGSGSGTDFTLKISRVEAEDVGVYYCMQSKQLPFTFGPGTKVDIK | |
| 27 | CAGGTGCAGCTGGTGGAGTCTGGGGGAGGCGTGGTCCAGCCTGGGAGGTCCCTGAGACTCTCCTGT GCAGCCTCTGGATTCACCTTCAGTAGCTATGGCATGCACTGGGTCCGCCAGGCTCCAGGCAAGGGG CTGGAGTGGGTGGCAGTTATATCATATGATGGAAGTGATAAATACTATGCAGACTCCGTGAAGGGC CGATTCACCATCTCCAGAGACAATTCCAAGAACACGCTGTATCTGCAAATGAACAGCCTGAGGGCT GAGGACACGGCTGTGTATTACTGTGCGAGAGCCGGGTACTCCCTCTACTACTACGGTATGGAC GTCTGGGGCCAAGGGACCACGGTCACCGTCTCCTCA | 2.41.1 Vh |
| 28 | QVQLVESGGGVVQPGRSLRLSCAASGFTFSSYGMHWVRQAPGKGLEWVAVISYDGSDKYYADSVKG RFTISRDNSKNTLYLQMNSLRAEDTAVYYCARAGYSLYYYYGMDVWGQGTTVTVSS | |
| 29 | GATATTGTGATGACCCAGACTCCACTCTCCCTGCCCGTCACCCCTGGAGAGCCGGCCTCCATCTCC TGCAGGTCTAGTCAGAGCCTCTTGGATAGTGATGATGGAGACACCTATTTGGACTGGTACCTGCAG AAGCCAGGGCAGTCTCCACAGCTCCTGATCTATACGCTTTCCTATCGGGCCTCTGGAGTCCCAGAC AGGTTCAGTGGCAGTGGGTCAGGCACTGATTTCACACTGAAAATCAGCAGGGTGGAGGCTGAGGAT | 2.47.1 Vk |

TABLE 1-continued

| SEQ ID NO | DNA or Protein | |
|---|---|---|
| | GTTGGAGTTTATTACTGCATGCAACGTATAGAGTTTCCATTCACTTTCGGCCCTGGGACCAAAGTG<br>GATATCAAA | |
| 30 | DIVMTQTPLSLPVTPGEPASISCRSSQSLLDSDDGDTYLDWYLQKPGQSPQLLIYTLSYRASGVPD<br>RFSGSGSGTDFTLKISRVEAEDVGVYYCMQRIEFPFTFGPGTKVDIK | |
| 31 | CAGGTGCAGCTGCAGGAGTCGGGCCCAGGACTGGTGAAGCCTTCACAGACCCTGTCCCTCACCTGC<br>ACTGTCTCTGGTGGCTCCATCAGCAGTGGTGGCTACTACTGGAGCTGGATCCGCCAGCACCCAGGG<br>AAGGGCCTGGAGTGGATTGGGGACATCTATTACAGTGGGAGCACCTACTACAACCCGTCCCTCAAG<br>AGTCGAGTTACCATATCAGTAGACACGTCTAAGAACCAGTTCTCCCTGAAGCTGAGCTCTGTGACT<br>GCCGCGGACACGGCCGTGTATTACTGTGCGAGAGATCGGGCTTACGGTGACTACGGGGGAGACTAC<br>TACTACGGTATGGACGTCTGGGGCCAAGGGACCACGGTCACCGTCTCCTCA | 2.47.1<br>Vh |
| 32 | QVQLQESGPGLVKPSQTLSLTCTVSGGSISSGGYYWSWIRQHPGKGLEWIGDIYYSGSTYYNPSLK<br>SRVTISVDTSKNQFSLKLSSVTAADTAVYYCARDRAYGDYGGDYYYGMDVWGQGTTVTVSS | |
| 33 | GACATCCAGATGACCCAGTCTCCATCCTCCCTGTCTGCATCTGTAGGAGACAGAGTCACCATCACT<br>TGCCAGGCGAGTCAGGACATTAACAACTATTTAAATTGGTATCAGCAGAAACCAGGGAAAGCCCCT<br>AATCTCCTGATCTACGATGCATCCAATTTGGAAACAGGGGTCCCATCAAGGTTCAGTGGAAGTGGA<br>TCTGGGACAGATTTTACTTTCACCATCAGCAGCCTGCAGCCTGCAGATATTGCAACATATTACTGT<br>CAACAATATGATGATTTCCCGCTCACTTTCGGCGGAGGGACCAAGGTGGAGATCAAA | 5.17.1<br>Vk |
| 34 | DIQMTQSPSSLSASVGDRVTITCQASQDINNYLNWYQQKPGKAPNLLIYDASNLETGVPSRFSGSG<br>SGTDFTFTISSLQPADIATYYCQQYDDFPLTFGGGTKVEIK | |
| 35 | CAGGTGCAACTGCAGGAGTCGGGCCCAGGACTGGTGAAGCCTTCGGAGACCCTGTCCCTCACCTGC<br>ACTGTCTCTGGTGGCTCCATCAGTAGTTACTACTGGAGCTGGATCCGGCAGCCCCCAGGGAAGGGA<br>CTGGAATGGATTGGGTATATCTATTACAGTGGGAACACCAATTACAACCCCTCCCTCAAGAGTCGA<br>GTCACCATATCAGTAGACACGTCCAAGAACCAGTTCTCCCTGAAGCTGAGGTCTGTGACCGCTGCG<br>GACACGGCCGTATATTACTGTGCGAGGTATAACTGGAACAACGACCTCTTTGACTACTGGGGCCAG<br>GGAACCCTGGTCACCGTCTCCTCA | 5.17.1<br>Vh |
| 36 | QVQLQESGPGLVKPSETLSLTCTVSGGSISSYYWSWIRQPPGKGLEWIGYIYYSGNTNYNPSLKSR<br>VTISVDTSKNQFSLKLRSVTAADTAVYYCARYNWNNDLFDYWGQGTLVTVSS | |
| 37 | GACATCCAGATGACCCAGTCTCCATCCTCCCTGTCTGCATCTGTAGGAGACAGAGTCACCATCACT<br>TGCCAGGCGAGTCAGGACATTAGCAACTATTTAAATTGGTATCAGCAGAAACCAGGGAAAGCCCCT<br>AAGCTCCTGATCTACGATGCATCCAATTTGGAAACTGGGGTCCCATCAAGGTTCAGTGGAAGTGGA<br>TCTGGGACAGATTTTACTTTCACCATCAGCAGCCTGCAGCCTGAAGATATTGCAACATATTACTGT<br>CAACAATATGATAATCTCCCTCTCACTTTCGGCGGAGGGACCAAGGTGGAGATCAAA | 5.23.1<br>Vk |
| 38 | DIQMTQSPSSLSASVGDRVTITCQASQDISNYLNWYQQKPGKAPKLLIYDASNLETGVPSRFSGSG<br>SGTDFTFTISSLQPEDIATYYCQQYDNLPLTFGGGTKVEIK | |
| 39 | CAGGTGCAGCTGGTGGAGTCTGGGGGAGGCGTGGTCCAGCCTGGGAGGTCCCTGAGACTCTCCTGT<br>GCAGCGTCTGGATTCACCTTCAGTAGCTATGGCATGCACTGGGTCCGCCAGGCTCCAGGCAAGGGG<br>CTGGAGTGGGTGGCAGTTATATGGTGTGATGGAAGTAATAAATACTATGCAGACTCCGTGAAGGGC<br>CGATTCACCATCTCCAGAGACAGTTCCAAGAACACGCTGTATCTGCAAATGAACAGCCTGAGAGCC<br>GAGGACACGGCTGTGTATTACTGTGCGAGAGGGGGCTATGGTTCGGGGAGTTATGAGGACTACTAC<br>TACGGTATGGACGTCTGGGGCCAAGGGACCACGGTCACCGTCTCCTCA | 5.23.1<br>Vh |
| 40 | QVQLVESGGGVVQPGRSLRLSCAASGFTFSSYGMHWVRQAPGKGLEWVAVIWCDGSNKYYADSVKG<br>RFTISRDSSKNTLYLQMNSLRAEDTAVYYCARGGYGSGSYEDYYYGMDVWGQGTTVTVSS | |
| 41 | GACATCCAGATGACCCAGTCTCCATCCTCCCTGTCTGCATCTGTAGGAGACAGAGTCACCATCACT<br>TGCCAGGCGAGTCAGGACATTAGTAAGGATTTAAATTGGTATCAGCAGAAACCAGGGAAAGCCCCT<br>AGGCTCCTGATCTACGATGCATCCAATTTGGAAACGGGGGTCCCATCAAGGTTCAGTGGAAGTGGA<br>TCTGGGACAGATTTTACTTTCACCATCAGCAGCCTGCAGCCTGAAGATATTGCAACATTTTACTGT<br>CAACAGTATGATCATCTCCCGATCGCCTTCGGCCAAGGGACACGACTGGAGATTAAA | 5.25.1<br>Vk |
| 42 | DIQMTQSPSSLSASVGDRVTITCQASQDISKDLNWYQQKPGKAPRLLIYDASNLETGVPSRFSGSG<br>SGTDFTFTISSLQPEDIATFYCQQYDHLPIAFGQGTRLEIK | |
| 43 | CAGGTGCAGCTGGTGCAGTCTGGGGCTGAGGTGAAGAAGCCTGGGGCCTCAGTGAAGGTCTCCTGC<br>AAGGCTTCTGGATACACCTTCACCAGTTATGATATCAACTGGGTGCGACAGGCCACTGGCCAAGGG<br>CTTGAGTGGATGGGATGGATGGACCCTAACAGTGGTAACACAGGCTATGCACAGAAGTTCCAGGGC<br>AGAGTCACCATGACCAGGAACACCTCCATAAGCACAGCCTTCATGGAGCTGAGCAGCCTGAGATCT<br>GAGGACACGGCCGTGTATTACTGTGCGAGAACGGACTACTTCTACTTCGGTATGGACGTCTGGGGC<br>CAAGGGACCACGGTCACCGTCTCCTCA | 5.25.1<br>Vh |
| 44 | QVQLVQSGAEVKKPGASVKVSCKASGYTFTSYDINWVRQATGQGLEWMGWMDPNSGNTGYAQKFQG<br>RVTMTRNTSISTAFMELSSLRSEDTAVYYCARTDYFYFGMDVWGQGTTVTVSS | |
| 45 | GACATCCAGGTGACCCAGTCTCCATCCTCCCTGTCTGCATCTGTAGGAGACAGAGTCACCATCACT<br>TGCCAGGCGAGTCAGGACATTAGCAACTATTTAAATTGGTATCAGCAGAAACCAGGGAAAGCCCCT<br>AAGTTCCTGATCTACGATGCATCCAATTTGGAAGCAGGGGTCCCATCAAGGTTCAGTGGAAGTGGA<br>TCTGGGACAGATTTTACTTTCACCATCAGCAGCCTGCAGCCTGAAGATATTGCAACATATTACTGT<br>CAACAGTATGATAATCTCCCGCTCACTTTCGGCGGAGGGACCAAGGTGGAGATCAAA | 5.31.1<br>Vk |

TABLE 1-continued

| SEQ ID NO | DNA or Protein | |
|---|---|---|
| 46 | DIQVTQSPSSLSASVGDRVTITCQASQDISNYLNWYQQKPGKAPKFLIYDASNLEAGVPSRFSGSG<br>SGTDFTFTISSLQPEDIATYYCQQYDNLPLTFGGGTKVEIK | |
| 47 | CAGGTGCAGTTGGTGGAGTCTGGGGGAGGCGTGGTCCAGCCTGGGAGGTCCCTGAGACTCTCCTGT<br>GCAGCGTCTGGATTCACCTTCAGTAGCTATGGCATGCACTGGGTCCGCCAGGCTCCAGGCAAGGGG<br>CTGGAGTGGGTGGCAGTTATATGGTATGATGGAAGAAATAAATACTATGCAGACTCCGTGAAGGGC<br>CGATTCACCATCTCCAGAGACAATTCCAAGAACACGCTGTATCTGCAAATGAACAGCCTGAGAGCC<br>GAGGACACGGCTGTGTATTACTGTGCGAGAGGGGGGGAGCAGTGGCTGATTACAACTACTACTAC<br>GGTATGGACGTCTGGGGCCAAGGGACCACGGTCACCGTCTCCTCA | 5.31.1<br>Vh |
| 48 | QVQLVESGGGVVQPGRSLRLSCAASGFTFSSYGMHWVRQAPGKGLEWVAVIWYDGRNKYYADSVKG<br>RFTISRDNSKNTLYLQMNSLRAEDTAVYYCARGGGAVADYNYYYGMDVWGQGTTVTVSS | |
| 49 | GACATCCAGATGACCCAGTCTCCATCCTCCCTGTCTGCATCTGTAGGAGACAGAGTCACCATCACT<br>TGCCAGGCGAGTCAGGACATTAGCAAGGATTTAAATTGGTATCAGCAGAAACCAGGGAAAGCCCCT<br>AAGCTCCTGATCTACGATGCATCCAATTTGGAAACAGGGGTCCCATCAAGGTTCAGTGGAAGTGGA<br>TCTGGGACAGATTTTACTTTCACCATCAGCAGCCTGCAGCCTGAAGATATTGCAACATATTACTGT<br>CAACAGTATGATGATCTCCCGATCACCTTCGGCCAAGGGACACGACTGGAGATTAAA | 5.32.1<br>Vk |
| 50 | DIQMTQSPSSLSASVGDRVTITCQASQDISKDLNWYQQKPGKAPKLLIYDASNLETGVPSRFSGSG<br>SGTDFTFTISSLQPEDIATYYCQQYDDLPITFGQGTRLEIK | |
| 51 | CAGGTGCAGCTGGTACAGTCTGGGGCTGAGGTGAAGAAGCCTGGGGCCTCAGTGAAGGTCTCCTGC<br>AAGGCCTCTGGATTCACCTTCACCAGTTATGATATCAGCTGGGTGCGACAGGCCACTGGACTAGGG<br>CTTGAGTGGATGGGATGGATGAACCCTAGCAGTGGTTACACAGGCTATGCACAGAACTTCCAGGGC<br>AGAGTCACCATGACCTGGAACACCTCCATAAGCACAGTCTACATGGAGCTGAGCAGCCTGAGATCT<br>GAGGACACGGCCGTGTATTACTGTGCGAGAACGGACTACTACTACTACGGTATGGACGTCTGGGGC<br>CGAGGGACCACGGTCACCGTCTCCTCA | 5.32.1<br>Vh |
| 52 | QVQLVQSGAEVKKPGASVKVSCKASGFTFTSYDISWVRQATGLGLEWMGWMNPSSGYTGYAQNFQG<br>RVTMTWNTSISTVYMELSSLRSEDTAVYYCARTDYYYYGMDVWGRGTTVTVSS | |
| 53 | GACATCCGGTTGACCCAGTCTCCATCCTCCCTGTCTGCATCTGTAGGAGACAGAGTCACCATCACT<br>TGCCAGGCGAGTCAGGACATTAGCAACTATTTAAATTGGTATCAGCAGGAACCAGGGAAAGCCCCT<br>AAGCTCCTGATCTACGATGCATCCAATTTGGAAACAGGGGTCCCATCAAGGTTCAGTGGAAGTGGA<br>TCTGGGACAGATTTTACTTTCACCATCAGCAGCCTGCAGCCTGAAGATATTGCAACATATTACTGT<br>CAACAGTATGATAATTTCCCGCTCACTTTCGGCGGAGGGACCAAGGTGGAGATCAAA | 5.40.1<br>Vk |
| 54 | DIRLTQSPSSLSASVGDRVTITCQASQDISNYLNWYQQEPGKAPKLLIYDASNLETGVPSRFSGSG<br>SGTDFTFTISSLQPEDIATYYCQQYDNFPLTFGGGTKVEIK | |
| 55 | CAGGTGCTACTGCAGGAGTCGGGCCCAGGACTGGTGAAGCCTTCGGAGACCCTGTCCCTCACCTGC<br>ACTGTCTCTGGTGGCTCCATCAGTAGTTACTACTGGAGCTGGATCCGGCAGCCCCAGGGAAGGGA<br>CTGGAGTGGATTGGGTATGTCTATTACAGTGGGAGCACCAGCTACAACCCCTCCCTCAAGAGTCGA<br>GTCACCATATCAATGTACACGTCCAAGACCGAGTTCTCCCTGAAGCTGAGCTCTGTGACCGCTGCG<br>GACACGGCCGTGTATTACTGTGCGAGGTATAACTGGAACAACGACCTCTTTGACTACTGGGGCCAG<br>GGAACCCTGGTCACCGTCTCCTCA | 5.40.1<br>Vh |
| 56 | QVLLQESGPGLVKPSETLSLTCTVSGGSISSYYWSWIRQTPGKGLEWIGYVYYSGSTSYNPSLKSR<br>VTISMYTSKTEFSLKLSSVTAADTAVYYCARYNWNNDLFDYWGQGTLVTVSS | |
| 57 | TCCTATGTGTTGACTCAGCCACCCTCGGTGTCAGTGGCCCCAGGACAGACGGCCAGGATTACCTGT<br>GGGGGAAACAACATTGGAAGTAAAAGTGTGCACTGGTACCAGCAGAAGCCAGGCCAGGCCCCTGTG<br>CTGGTCGTCTATGATGATAGCGACCGGCCCTCAGGGATCCCTGAGCGATTCTCTGGCTCCAACTCT<br>GGGAACACGGCCACCCTGACCATCAGCAGGGTCGAAGCCGGGGATGAGGCCGACTATTACTGTCAG<br>GTGTTGGATAGTAGTAGTGATCATGTGATATTCGGCGGAGGGACCAAGCTGACCGTCCTA | 5.65.1<br>Vl |
| 58 | SYVLTQPPSVSVAPGQTARITCGGNNIGSKSVHWYQQKPGQAPVLVVYDDSDRPSGIPERFSGSNS<br>GNTATLTISRVEAGDEADYYCQVLDSSSDHVIFGGGTKLTVL | |
| 59 | TCCTATGTGTTGACTCAGCCACCCTCGGTGTCAGTGGCCCCAGGACAGACGGCCAGGATTACCTGT<br>GGGGGAAACAACATTGGAAGTAAAAGTGTGCACTGGTACCAGCAGAAGCCAGGCCAGGCCCCTGTG<br>CTGGTCGTCTATGATGATAGCGACCGGCCCTCAGGGATCCCTGAGCGATTCTCTGGCTCCAACTCT<br>GGGAACACGGCCACCCTGACCATCAGCAGGGTCGAAGCCGGGGATGAGGCCGACTATTACTGTCAG<br>GTGTTGGATAGTAGTAGTGATCATGTGATATTCGGCGGAGGGACCAAGCTGACCGTCCTA | 5.65.1<br>Vh |
| 60 | EVQLLESGGGLVQPGGSLRLSCAASGFTSGNYAMSWVRQAPGKGLEWVSAISGGGGTTYYADSVEG<br>RFTISRDNSKNTLYLQLNSLRAEDTAVYYCAKEFGELEPRFDYWGQGTLVTVSS | |
| 61 | TCCTATGTGCTGACTCAGCCACCCTCGGTGTCAGTGGCCCCAGGACAGACGGCCAGGATTACCTGT<br>GGGGGAAACAACATTGGAAGTGAAAGTGTGCACTGGTACCAGCAGAAGCCAGGCCAGGCCCCTGTG<br>CTGGTCGTCTATGATGATAGCGACCGGCCCTCAGGGATCCCTGAGCGATTCTCTGGCTCCAACTCT<br>GGGAACACGGCCACCCTGACCATCAGCAGGGTCGAAGCCGGGGATGAGGCCGACTATTACTGTCAG<br>GTGTGGGATAGTAGTAATGATCATGTGGTTTTCGGCGGAGGGACCAAGCTGACCGTCCTA | 5.76.1<br>Vl |
| 62 | SYVLTQPPSVSVAPGQTARITCGGNNIGSESVHWYQQKPGQAPVLVVYDDSDRPSGIPERFSGSNS<br>GNTATLTISRVEAGDEADYYCQVWDSSNDHVVFGGGTKLTVL | |

TABLE 1-continued

| SEQ ID NO | DNA or Protein | | |
|---|---|---|---|
| 63 | CAGCTGCAGCTGCAGGAGTCGGGCCCAGGACTGGTGAAGCCTTCGGAGACCCTGTCCCTCACCTGC ACTGTCTCTGGTGGCTCCATCAGCAGTAGTAATTACTACTGGGGCTGGATCCGCCAGCCCCCGGGG AAGGGGCTGGAGTGGATTGGGACTATCTATTATAGTGGGAGCACCTACTACACCCCGTCCCTCAAG AGTCGAGTCACCATATCCGTAGACACGTCCAAGAACCAGTTCTCCCTGAAGCTGAGCTCTGTGACC GCCGCAGACACGGCTGTCTATTACTGTGCGAGAGAGAGGGCGATAGCAGTGGCTGCTATAGTCTTC TTTGACTACTGGGGCCAGGGAACCCTGGTCACCGTCTCCTCA | 5.76.1 Vh | |
| 64 | QLQLQESGPGLVKPSETLSLTCTVSGGSISSSNYYWGWIRQPPGKGLEWIGTIYYSGSTYYTPSLK SRVTISVDTSKNQFSLKLSSVTAADTAVYYCARERAIAVAAIVFFDYWGQGTLVTVSS | | |
| 65 | TCCTATGTGCTGACTCAGTCACCCTCGGTGTCAGTGGCCCCAGGACAGACGGCCAGGATTACCTGT GGGGGAAACAACATTGGAAGTAAAAGTGTGCACTGGTACCAGCAGAAGCCAGGCCAGGCCCCTGTG CTGGTCGTCTATGATGATAGCGACCGGCCCTCAGGGATCCCTGAGCGATTCTCTGGCTCCAACTCT GGGAACACGGCCACCCTGACCATCAGCAGGGTCGAAGCCGGGGATGAGGCCGACTACTACTGTCAG GTGTGGGATAGTAGTAGTGATCATTGGGTGTTCGGCGGAGGGACCAAGCTGACCGTCCTA | 5.77.1 Vl | |
| 66 | QSPSVSVAPGQTARITCGGNNIGSKSVHWYQQKPGQAPVLVVYDDSDRPSGIPERFSGSNSGNTAT LTISRVEAGDEADYYCQVWDSSSDHWVFGGGTKLTVL | | |
| 67 | CAGGTGCAGCTGGTGCAGTCTGGGGCTGAGGTGAAGAAGCCTGGGGCCTCAGTGAAGGTCTCCTGC AAGGCTTCTGGATACACCTTCACCAGTTATGATATCAACTGGGTGCGACAGGCCACTGGACAAGGG CTTGAGTGGATGGGATGGATGAATCTTAACAGTGATAACACAGGCTATGCACAGAAGTTCCAGGGC AGAGTCACCATGACCAGGAACACCTCCATAAGCACTGCCTACATGGAGCTGAGCAGCCTGAGATCT GAGGACACGGCCGTGTATTACTGTGCGAGTATAGCAGCTCGTCGCGACTACAACTACTACGGTATG GACGTCTGGGGCCAAGGGACCAAGGTCACCGTCTCCTCA | 5.77.1 Vh | |
| 68 | QVQLVQSGAEVKKPGASVKVSCKASGYTFTSYDINWVRQATGQGLEWMGWMNLNSDNTGYAQKFQG RVTMTRNTSISTAYMELSSLRSEDTAVYYCASIAARRDYNYYGMDVWGQGTKVTVSS | | |
| 69 | GAAATTGTGTTGACGCAGTCTCCAGGCACCCTGTCTGTGTCTCCAGGGGAAAGAGCCACCCTCTCC TGCAGGGCCAGTCAGAGTGTTAGCAGCAGCTACTTAGCCTGGTATCAGCAGAAACCTGGCCAGGCT CCCAGGCTCCTCATCTATGGTGCATCCGGCAGGGCCACTGGCATCCCAGACAGGTTCAGTGGCAGT GGGTCTGGGACAGACTTCATTCTCACCATCAGCAGACTGGAGCCTGAAGATTTTGCAGTGTATTAC TGTCAGCAGTATGGTAGCTCATTCACTTTCGGCGGAGGGACCAAGGTGGAGATCAAA | 5.78.1 Vk | |
| 70 | EIVLTQSPGTLSVSPGERATLSCRASQSVSSSYLAWYQQKPGQAPRLLIYGASGRATGIPDRFSGS GSGTDFILTISRLEPEDFAVYYCQQYGSSFTFGGGTKVEIK | | |
| 71 | CAGGTGCAGCTGGTGGAGTCTGGGGGAGGCGTGGTCCAGCCTGGGAGGTCCCTGAGACTCTCCTGT GCAGCCTCTGGATTCACCTTCAGTAGCTATGGCATGCACTGGGTCCGCCAGGCTCCAGGCAAGGGG CTGGAGTGGGTGGCAGTTATATTATATGATGGAAGTGATAATTACTATGCAGACTCCGTGAAGGGC CGATTCACCATCTCCAGAGACAATTCCAAGAACACGCTGTATCTGCAAATGAACAGCCTGAGAGCT GAGGACACGGCTGTGTATTACTGTGCGAGAGAAGGGATAGCAGTGGCTGGGGACTACTACTACTAC GGTATGGACGTCTGGGGCCAAGGGACCACGGTCACCGTCTCCTCA | 5.78.1 Vh | |
| 72 | QVQLVESGGGVVQPGRSLRLSCAASGFTFSSYGMHWVRQAPGKGLEWVAVILYDGSDNYYADSVKG RFTISRDNSKNTLYLQMNSLRAEDTAVYYCAREGIAVAGDYYYGMDVWGQGTTVTVSS | | |
| 73 | CAGTCAGTGCTGACGCAGCCGCCCTCAGTGTCTGGGGCCCCAGGGCAGAGGGTCACCATCTCCTGC ACTGGGAGCAGCTCCAACATCGGGGCAGATTATGATGTACACTGGTACCAGCAGCTTCCAGGAACA GCCCCCAAACTCCTCATCTATGATTACAGCAATCGGCCCTCAGGGGTCCCTGACCGATTCTCTGGC TCCAAGTCTGGCACCTCAGCCTCCCTGGCCATCACTGGGCTCCAGGCTGAGGATGAGGCTGATTAT TACTGCCAGTCCTATGACAACAGCCTGAGTGGTTATGTGGTATTCGGCGGAGGGACCAAGCTGACC GTCCTA | 5.80.1 Vl | |
| 74 | QSVLTQPPSVSGAPGQRVTISCTGSSSNIGADYDVHWYQQLPGTAPKLLIYDYSNRPSGVPDRFSG SKSGTSASLAITGLQAEDEADYYCQSYDNSLSGYVVFGGGTKLTVL | | |
| 75 | GAGGTGCAGCTGGTGCAGTCTGGAGCAGAGGTGAAAAAGCCCGGGGAGTCTCTGAAGATCTCCTGT AAGGGTTCTGGATACAGCTTTACCAGCTACTGGATCGGCTGGGTGCGCCAGATGCCCGGGAAAGGC CTGGAGTGGATGGGGATCATCTATCCTGGTGACTCTGATACCAGATACAGCCCGTCCTTCCAAGGC CAGGTCACCATCTCAGCCGACAAGTCCATCAGCACCGCCTACCTGCAGTGGAGCAGCCTGACGGCC TCGGACACCGCCATGTATTACTGTGCGAGACAGGGAGAGAGCTTTGACTACTGGGGCCAGGGAACC CTGGTCACCGTCTCCTCA | 5.80.1 Vh | |
| 76 | EVQLVQSGAEVKKPGESLKISCKGSGYSFTSYWIGWRQMPGKGLEWMGIIYPGDSDTRYSPSFQG QVTISADKSISTAYLQWSSLTASDTAMYYCARQGESFDYWGQGTLVTVSS | | |
| 77 | CAGTCTGTGCTGACGCAGCCGCCCTCAGTGTCTGGGGCCCCAGGGCAGAGGGTCACCATCTCCTGC ACTGGGAGCAGCTCCAACATCGGGGCAGGTTATGATGTACACTGGTACCAGCAGCTTCCAAGAACA GCCCCCAAACTCCTCATCTATGGTAACAGCAATCGGCCCTCAGGGGTCCCTGACCGATTCTCTGAC TCCAAGTCTGGCACCTCAGCCTCCCTGGCCATCACTGGCTCCAGGCTGAGGATGAGGCTGATTAT TACTGCCAGTCCTATGACAGCAGCCTGAGTGTGATATTCGGCGGAGGGACCAAGCTGACCGTCCTA | 5.85.1 Vl | |
| 78 | QSVLTQPPSVSGAPGQRVTISCTGSSSNIGAGYDVHWYQQLPRTAPKLLIYGNSNRPSGVPDRFSD SKSGTSASLAITGLQAEDEADYYCQSYDSSLSVIFGGGTKLTVL | | |

TABLE 1-continued

| SEQ ID NO | DNA or Protein | |
|---|---|---|
| 79 | GAGGTGCAGCTGGTGCAGTCTGGAGCAGAGGTGAAAAAGCCCGGGGAGTCTCTGAAGATCTCCTGT AAGGTTTCTGGATACAGCTTTACCACCTACTGGATCGGCTGGGTGCCAGATGCCCGGGAAGGGC CTGGACTGGATGGGGATCATCTATCCTGGTGACTCTGATACCAGATACAGCCCGTCCTTCCAAGGC CAGGTCACCATCTCAGCCGACAAGTCCATCAGCACCGCCTACCTGCAGTGGAGCAGCCTGAAGGCC TCGGACACCGCCATGTATTACTGTGCGAGACAAGGTATAGCGTTTGACTACTGGGGCCAGGGAACC CTGGTCACCGTCTCCTCA | 5.85.1 Vh |
| 80 | EVQLVQSGAEVKKPGESLKISCKVSGYSFTTYWIGWVRQMPGKGLDWMGIIYPGDSDTRYSPSFQG QVTISADKSISTAYLQWSSLKASDTAMYYCARQGIAFDYWGQGTLVTVSS | |
| 81 | GATATTGTGATGACCCAGACTCCACTCTCTCTGTCCGTCACCCCTGGACAGCCGGCCTCCATCTCC TGCAAGTCTGGTCAGAGCCTCCTGCATAGTGATGGAAAGACCTATTTGTATTGGTACCTGCAGAAG CCAGGGCAGCCTCCACAGTTCCTGATCTATGAAGTTTCCAACCGGTTCTCTAGAGTGCCAGATAGG TTCAGTGGCAGCGGGTCAGGGACAGATTTCACACTGAGAATCAGCCGGGTGGAGGCTGAGGATGTT GGAATTTATTACTGCATGCAAAGTATACAGCTTCCGTGGACGTTCGGCCAAGGGACCCAGGTGGAA ATCAAA | 6.37.5 Vk |
| 82 | DIVMTQTPLSLSVTPGQPASISCKSGQSLLHSDGKTYLYWYLQKPGQPPQFLIYEVSNRFSRVPDR FSGSGSGTDFTLRISRVEAEDVGIYYCMQSIQLPWTFGQGTQVEIK | |
| 83 | CAGGTGCAGCTGGTGGAGTCTGGGGGAGGCGTGGTCCAGCCTGGGAGGTCCCTGAGACTCTCCTGT GCAGCCTCTGGATTCACCTTCAGTGGCTATGGCATGCACTGGGTCCGCCAGGCTCCAGGCAAGGGG CTGGAGTGGGTGGCAGTTATATCATATGATGGAAATGATAAATACTATGCAGACTCCGTGAAGGGC CGATTCACCATCTCCAGAGACAATGCCAAGAACACGCTGTATCTGCAAATGAACAGCCTGAGAGCT GAGGACACGGCTGTGTATTACTGTGCGAGAGAGCTACGGGTCCTCTGGGGCCAGGGAACCCTGGTC ACCGTCTCTAGT | 6.37.5 Vh |
| 84 | QVQLVESGGGVVQPGRSLRLSCAASGFTFSGYGMHWVRQAPGKGLEWVAVISYDGNDKYYADSVKG RFTISRDNAKNTLYLQMNSLRAEDTAVYYCARELRVLWGQGTLVTVSS | |
| 85 | GATATTGTGATGACCCAGACTCCACTCTCTCTGTCCGTCACCCCTGGACAGCCGGCCTCCATCTCC TGCAAGTCTGGTCAGAGCCTCCTGCATAATGATGGAAAGACCTATTTGTATTGGTACCTGCAGAAG CCAGGGCAGCCTCCACAGTTCCTGATCTATGAAGTTTCCAACCGGTTCTCTAGAGTGCCAGATAGG TTCAGTGGCAGCGGGTCAGGGACAGATTTCACACTGAAAATCAGCCGGGTGGAGGCTGAGGATGTT GGAATTTATTACTGCATGCAAAGTATACAGCTTCCGTGGACGTTCGGCCAAGGGACCCAGGTGGAA ATCAAA | 6.116.6 |
| 86 | DIVMTQTPLSLSVTPGQPASISCKSGQSLLHNDGKTYLYWYLQKPGQPPQFLIYEVSNRFSRVPDR FSGSGSGTDFTLKISRVEAEDVGIYYCMQSIQLPWTFGQGTQVEIK | |
| 87 | CAGGTGCAGCTGGTGGAGTCTGGGGGAGGCGTGGTCCAGCCTGGGAGGTCCCTGAGACTCTCCTGT GCAGCCTCTGGATTCACCTTCAGTGGCTATGGCATGCACTGGGTCCGCCAGGCTCCAGGCAAGGGG CTGGAGTGGGTGGCAGTTATATCATATGATGGAAATGATAAATACTATGCAGACTCCGTGAAGGGC CGATTCACCATCTCCAGAGACAATGCCAAGAACACGCTGTATCTGCAAATGAACAGCCTGAGAGCT GAGGACACGGCTGTTTATTACTGTGCGAGAGAGCTACGGGTCCTCTGGGGCCAGGGAACCCTGGTC ACCGTCTCCTCA | 6.116.6 Vh |
| 88 | QVQLVESGGGVVQPGRSLRLSCAASGFTFSGYGMHWVRQAPGKGLEWVAVISYDGNDKYYADSVKG RFTISRDNAKNTLYLQMNSLRAEDTAVYYCARELRVLWGQGTLVTVSS | |
| 89 | GATATTGTGATGACCCAGACTCCACTCTCTCTGTCCGTCACCCCTAGACAGCCGGCCTCCATCTCC TGCAAGTCTAGTCAGAGCCTCCTGCATAGTGATGGAAAGACCTATTTGTATTGGTACCTGCAGAAG CCAGGGCAGCCTCCACAGTTCCTGATCTATGAAGTTTCCAACCGGTTCTCTGGAGTGCCAGATAGG TTCAGTGGCAGCGGGTCAGGGACAGATTTCACACTGAAAATCAGCCGGGTGGAGGCTGAGGATGTT GGGGTTTATTACTGCATGCAAAGTATACAGCTTCCGTGGACGTTCGGCCAAGGGACCAAGGTGGAA ATCAAA | 6.139.5 Vk |
| 90 | DIVMTQTPLSLSVTPRQPASISCKSSQSLLHSDGKTYLYWYLQKPGQPPQFLIYEVSNRFSGVPDR FSGSGSGTDFTLKISRVEAEDVGVYYCMQSIQLPWTFGQGTKVEIK | |
| 91 | CAGGTGCAGCTGGTGGAGTCTGGGGGAGGCGTGGTCCAGCCTGGGAGGTCCCTGAGACTCTCCTGT GCAGCCTCTGGATTCACCTTCAGTAGCTATGGCATGCACTGGGTCCGCCAGGCTCCAGGCAAGGGG CTGGAGTGGGTGGCAGTTATATCATATGATGGAGGTGATCAATACTATGCAGACTCCGTGAAGGGC CGATTCACCATCTCCAGAGACAATTCCAAGAACACGCTGTATCTGCAAATGAACAGCCTGAGAACT GAGGACACGGCTGAGTATTACTGTGCGAGAGAGCTCCGGGTCCTCTGGGGCCAGGGAACCCTGGTC ACCGTCTCCTCA | 6.139.5 Vh |
| 92 | QVQLVESGGGVVQPGRSLRLSCAASGFTFSSYGMHWVRQAPGKGLEWVAVISYDGGDQYYADSVKG RFTISRDNSKNTLYLQMNSLRTEDTAEYYCARELRVLWGQGTLVTVSS | |
| 93 | TCCTATGTGCTGACTCAGCCACCCTCGGTGTCAGTGGCCCCAGGACAGACGGCCAGGATTACCTGT GGGGGAAACAACATTGGAAGTAAAAGTGTACACTGGTACCAGCAGAAGCCAGGCCAGGCCCCTGTG CTGGTCGTCTATGATGATAGTGACCGGCCCTCTGAGATCCCTGAGCGATTCTCTGGCTCCAACTCT GGGAACACGGCCACCCTGACCATCAGCAGGGTCGAAGCCGGGGATGAGGCCGACTATTACTGTCAG GTGTGGGATAGTAGTAGTGATCATGTGGTATTCGGCGGAGGGACCAGGCTGACCGTCCTA | 6.147.4 Vl |
| 94 | YVLTQPPSVSVAPGQTARITCGGNNIGSKSVHWYQQKPGQAPVLVVYDDSDRPSEIPERFSGSNSG NTATLTISRVEAGDEADYYCQVWDSSSDHVVFGGGTRLTVL | |

TABLE 1-continued

| SEQ ID NO | DNA or Protein | |
|---|---|---|
| 95 | CAGGTGCAGCTGGTGGAGTCTGGGGGAGGCGTGGTCCAGCCTGGGAGGTCCCTGAGACTCTCCTGT GCAGCGTCTGGATTCACCTTCAGTCGCTATGACATGCACTGGGTCCGCCAGGCTCCAGGCAAGGGG CTGGAGTGGGTGGCAATTATATTCTATGATGGCAGCAATAAATACTATGCAGACCCCGTGAAGGGC CGATTCACCATCTCCAGAGACAATTCAAAGAACACACTGTATCTGCAAATGAACAGCCTGAGAGCC GAGGACACGGCTGTGTATTACTGTGCGACTCTAGCAGCAGCTTTTGACTACTGGGGCCAGGGAACC CTGGTCACCGTCTCCTCA | 6.147.4 Vh |
| 96 | QVQLVESGGGVVQPGRSLRLSCAASGFTFSRYDMHWVRQAPGKGLEWVAIIFYDGSNKYYADPVKG RFTISRDNSKNTLYLQMNSLRAEDTAVYYCATLAAAFDYWGQGTLVTVSS | |
| 97 | RASQGIRDDLG | 2.4.1 |
| 98 | AASSLQS | |
| 99 | LQHNSYPCS | |
| 100 | SYGIS | |
| 101 | WISADNGHTNYAQKLQG | |
| 102 | DGELLNYYYYYGMDV | |
| 103 | KSSQSLLHSDGKTYLY | 2.20.1 |
| 104 | EVSNRFS | |
| 105 | MQSIQVPWT | |
| 106 | SYGMH | |
| 107 | VISYDGSDKYYADSVKG | |
| 108 | DQWGGSPAGP | |
| 109 | RASQSVSSNYLA | 2.37.1 |
| 110 | GASSRAT | |
| 111 | QQYGSSPIT | |
| 112 | SYGMH | |
| 113 | VISYDGSDKYYADSVKG | |
| 114 | ELGIAASFDY | |
| 115 | KSSQSLLHSDGKTYLY | 2.40.1 |
| 116 | EVSNRFS | |
| 117 | MQSIQVPWT | |
| 118 | SYGMH | |
| 119 | VISYDGSDKYYADSVKG | |
| 120 | DLVDTAMP | |
| 121 | KSSQSLLHSDGKTYLY | 2.41.1 |
| 122 | EVSNRFS | |
| 123 | MQSKQLPFT | |
| 124 | SYGMH | |
| 125 | VISYDGSDKYYADSVKG | |
| 126 | AGYSLYYYYGMDV | |
| 127 | RSSQSLLDSDDGDTYLD | 2.47.1 |
| 128 | TLSYRAS | |
| 129 | MQRIEFPMQRIEFP | |
| 130 | SGGYYWS | |

TABLE 1-continued

| SEQ ID NO | DNA or Protein | |
|---|---|---|
| 131 | DIYYSGSTYYNPSLKS | |
| 132 | DRAYGDYGGDYYYGMDV | |
| 133 | QASQDINNYLN | 5.17.1 |
| 134 | DASNLET | |
| 135 | QQYDDFPLT | |
| 136 | SYYWS | |
| 137 | YIYYSGNTNYNPSLKS | |
| 138 | YNWNNDLFDY | |
| 139 | QASQDISNYLN | 5.23.1 |
| 140 | DASNLET | |
| 141 | QQYDNLPLT | |
| 142 | SYGMH | |
| 143 | VIWCDGSNKYYADSVKG | |
| 144 | GGYGSGSYEDYYYGMDV | |
| 145 | QASQDISKDLN | 5.25.1 |
| 146 | DASNLET | |
| 147 | QQYDNLPLT | |
| 148 | SYGMH | |
| 149 | WMDPNSGNTGYAQKFQG | |
| 150 | TDYFYFGMDV | |
| 151 | QASQDISNYLN | 5.31.1 |
| 152 | DASNLEA | |
| 153 | QQYDNLPLT | |
| 154 | SYGMH | |
| 155 | VIWYDGRNKYYADSVKG | |
| 156 | GGGAVADYNYYYGMDV | |
| 157 | QASQDISKDLN | 5.32.1 |
| 158 | DASNLET | |
| 159 | QQYDDLPIT | |
| 160 | SYDIS | |
| 161 | WMNPSSGYTGYAQNFQG | |
| 162 | TDYYYYGMDV | |
| 163 | QASQDISNYLN | 5.40.1 |
| 164 | DASNLET | |
| 165 | QQYDNFPLT | |
| 166 | SYYWS | |
| 167 | YVYYSGSTSYNPSLKS | |
| 168 | YNWNNDLFDY | 5.65.1 |
| 169 | GGNNIGSKSVH | |

TABLE 1-continued

| SEQ ID NO | DNA or Protein | |
|---|---|---|
| 170 | DDSDRPS | |
| 171 | QVLDSSSDHVI | |
| 172 | NYAMS | |
| 173 | AISGGGGTTYYADSVEG | |
| 174 | EFGELEPRFDY | |
| 175 | GGNNIGSESVH | 5.76.1 |
| 176 | DDSDRPS | |
| 177 | QVWDSSNDHVV | |
| 178 | SSNYYWG | |
| 179 | TIYYSGSTYYTPSLKS | |
| 180 | ERAIAVAAIVFFDY | |
| 181 | GGNNIGSKSVH | 5.77.1 |
| 182 | DDSDRPS | |
| 183 | QVWDSSSDHWV | |
| 184 | SYDIN | |
| 185 | WMNLNSDNTGYAQKFQG | |
| 186 | IAARRDYNYYGMDV | |
| 187 | RASQSVSSSYLA | 5.78.1 |
| 188 | GASGRAT | |
| 189 | QQYGSSFT | |
| 190 | SYGMH | |
| 191 | VILYDGSDNYYADSVKG | |
| 192 | EGIAVAGDYYYYGMDV | |
| 193 | TGSSSNIGADYDVH | 5.80.1 |
| 194 | DYSNRPS | |
| 195 | QSYDNSLSGYVV | |
| 196 | SYWIG | |
| 197 | IIYPGDSDTRYSPSFQG | |
| 198 | QGESFDY | |
| 199 | TGSSSNIGAGYDVH | 5.85.1 |
| 200 | GNSNRPS | |
| 201 | QSYDSSLSVI | |
| 202 | TYWIG | |
| 203 | IIYPGDSDTRYSPSFQG | |
| 204 | QGIAFDY | |
| 205 | KSGQSLLHSDGKTYLY | 6.37.5 |
| 206 | EVSNRFS | |
| 207 | MQSIQLPWT | |
| 208 | GYGMH | |

TABLE 1-continued

| SEQ ID NO | DNA or Protein | |
|---|---|---|
| 209 | VISYDGNDKYYADSVKG | |
| 210 | ELRVL | |
| 211 | KSGQSLLHNDGKTYLY | 6.116.6 |
| 212 | EVSNRFS | |
| 213 | MQSIQLPWT | |
| 214 | GYGMH | |
| 215 | VISYDGNDKYYADSVKG | |
| 216 | ELRVL | |
| 217 | AASGFTFSRYDMH | 6.139.5 |
| 218 | IFYDGSNKYYAD | |
| 219 | ATLAAAFDY | |
| 220 | SYGMH | |
| 221 | VISYDGGDQYYADSVKG | |
| 222 | ELRVL | |
| 223 | GGNNIGSKSVH | 6.147.4 |
| 224 | DDSDRPS | |
| 225 | QVWDSSSDHVV | |
| 226 | RYDMH | |
| 227 | IIFYDGSNKYYADPVKG | |
| 228 | LAAAFDY | |
| 229 | CGAACTGTGGCTGCACCATCTGTCTTCATCTTCCCGCCATCTGATGAGCAGTTGAAATCTGGAACT GCCTCTGTTGTGTGCCTGCTGAATAACTTCTATCCCAGAGAGGCCAAAGTACAGTGGAAGGTGGAT AACGCCCTCCAATCGGGTAACTCCCAGGAGAGTGTCACAGAGCAGGACAGCAAGGACAGCACCTAC AGCCTCAGCAGCACCCTGACGCTGAGCAAAGCAGACTACGAGAAACACAAAGTCTACGCCTGCGAA GTCACCCATCAGGGCCTGAGCTCGCCCGTCACAAAGAGCTTCAACAGGGGAGAG | kappa light chain |
| 230 | RTVAAPSVFIFPPSDEQLKSGTASVVCLLNNFYPREAKVQWKVDNALQSGNSQESVTEQDSKDSTY SLSSTLTLSKADYEKHKVYACEVTHQGLSSPVTKSFNRGEC | |
| 231 | GGTCAGCCCAAGGCCAACCCCACTGTCACTCTGTTCCCGCCCTCCTCTGAGGAGCTCCAAGCCAAC AAGGCCACACTAGTGTGTCTGATCAGTGACTTCTACCCGGGAGCTGTGACAGTGGCCTGGAAGGCA GATGGCAGCCCCGTCAAGGCGGGAGTGGAGACCACCAAACCCTCCAAACAGAGCAACAACAAGTAC GCGGCCAGCAGCTACCTGAGCCTGACGCCCGAGCAGTGGAAGTCCCACAGAAGCTACAGCTGCCAG GTCACGCATGAAGGGAGCACCGTGGAGAAGACAGTGGCCCCCTACAGAATGTTCA | lambda light chain C1 |
| 232 | GQPKANPTVTLFPPSSEELQANKATLVCLISDFYPGAVTVAWKADGSPVKAGVETTKPSKQSNNKY AASSYLSLTPEQWKSHRSYSCQVTHEGSTVEKTVAPTECS | |
| 233 | GGTCAGCCCAAGGCTGCCCCCTCGGTCACTCTGTTCCCGCCCTCCTCTGAGGAGCTTCAAGCCAAC AAGGCCACACTGGTGTGTCTCATAAGTGACTTCTACCCGGGAGCCGTGACAGTGGCCTGGAAGGCA GATAGCAGCCCCGTCAAGGCGGGAGTGGAGACCACCACACCCTCCAAACAAAGCAACAACAAGTAC GCGGCCAGCAGCTATCTGAGCCTGACGCCTGAGCAGTGGAAGTCCCACAGAAGCTACAGCTGCCAG GTCACGCATGAAGGGAGCACCGTGGAGAAGACAGTGGCCCCCTACAGAATGTTCA | lambda light chain C2 |
| 234 | GQPKAAPSVTLFPPSSEELQANKATLVCLISDFYPGAVTVAWKADSSPVKAGVETTTPSKQSNNKY AASSYLSLTPEQWKSHRSYSCQVTHEGSTVEKTVAPTECS | |
| 235 | GGTCAGCCCAAGGCTGCCCCCTCGGTCACTCTGTTCCCACCCTCCTCTGAGGAGCTTCAAGCCAAC AAGGCCACACTGGTGTGTCTCATAAGTGACTTCTACCCGGGAGCCGTGACAGTGGCCTGGAAGGCA GATAGCAGCCCCGTCAAGGCGGGAGTGGAGACCACCACACCCTCCAAACAACAACAACAAGTAC GCGGCCAGCAGCTACCTGAGCCTGACGCCTGAGCAGTGGAAGTCCCACAAAAGCTACAGCTGCCAG GTCACGCATGAAGGGAGCACCGTGGAGAAGACAGTGGCCCCCTACAGAATGTTCA | lambda light chain C3 |
| 236 | GQPKAAPSVTLFPPSSEELQANKATLVCLISDFYPGAVTVAWKADSSPVKAGVETTTPSKQSNNKY AASSYLSLTPEQWKSHKSYSCQVTHEGSTVEKTVAPTECS | |

TABLE 1-continued

| SEQ ID NO | DNA or Protein |
|---|---|
| 237 | GGTCAGCCCAAGGCTGCCCCATCGGTCACTCTGTTCCCGCCCTCCTCTGAGGAGCTTCAAGCCAAC lambda<br>AAGGCCACACTGGTGTGCCTGATCAGTGACTTCTACCCGGGAGCTGTGAAAGTGGCCTGGAAGGCA C6<br>GATGGCAGCCCCGTCAACACGGGAGTGGAGACCACCACACCCTCCAAACAGAGCAACAACAAGTAC light<br>GCGGCCAGCAGCTACCTGAGCCTGACGCCTGAGCAGTGGAAGTCCCACAGAAGCTACAGCTGCCAG chain<br>GTCACGCATGAAGGGAGCACCGTGGAGAAGACAGTGGCCCCTGCAGAATGTGCA |
| 238 | GQPKAAPSVTLFPPSSEELQANKATLVCLISDFYPGAVKVAWKADGSPVNTGVETTTPSKQSNNKY<br>AASSYLSLTPEQWKSHRSYSCQVTHEGSTVEKTVAPAECA |
| 239 | GGTCAGCCCAAGGCTGCCCCCTCGGTCACTCTGTTCCCACCCTCCTCTGAGGAGCTTCAAGCCAAC lambda<br>AAGGCCACACTGGTGTGTCTCGTAAGTGACTTCTACCCGGGAGCCGTGACAGTGGCCTGGAAGGCA C7<br>GATGGCAGCCCCGTCAAGGTGGGAGTGGAGACCACCAAACCCTCCAAACAAAGCAACAACAAGTAT light<br>GCGGCCAGCAGCTACCTGAGCCTGACGCCCGAGCAGTGGAAGTCCCACAGAAGCTACAGCTGCCGG chain<br>GTCACGCATGAAGGGAGCACCGTGGAGAAGACAGTGGCCCCTGCAGAATGCTCT |
| 240 | GQPKAAPSVTLFPPSSEELQANKATLVCLVSDFYPGAVTVAWKADGSPVKVGVETTKPSKQSNNKY<br>AASSYLSLTPEQWKSHRSYSCRVTHEGSTVEKTVAPAECS |
| 241 | GCCTCCACCAAGGGCCCATCGGTCTTCCCCCTGGCGCCCTGCTCCAGGAGCACCTCCGAGAGCACA IgG2<br>GCGGCCCTGGGCTGCCTGGTCAAGGACTACTTCCCCGAACCGGTGACGGTGTCGTGGAACTCAGGC heavy<br>GCTCTGACCAGCGGCGTGCACACCTTCCCAGCTGTCCTACAGTCCTCAGGACTCTACTCCCTCAGC chain<br>AGCGTGGTGACCGTGCCCTCCAGCAACTTCGGCACCCAGACCTACACCTGCAACGTAGATCACAAG<br>CCCAGCAACACCAAGGTGGACAAGACAGTTGAGCGCAAATGTTGTGTCGAGTGCCCACCGTGCCCA<br>GCACCACCTGTGGCAGGACCGTCAGTCTTCCTCTTCCCCCCAAAACCCAAGGACACCCTCATGATC<br>TCCCGGACCCCTGAGGTCACGTGCGTGGTGGTGGACGTGAGCCACGAAGACCCCGAGGTCCAGTTC<br>AACTGGTACGTGGACGGCGTGGAGGTGCATAATGCCAAGACAAAGCCACGGGAGGAGCAGTTCAAC<br>AGCACGTTCCGTGTGGTCAGCGTCCTCACCGTTGTGCACCAGGACTGGCTGAACGGCAAGGAGTAC<br>AAGTGCAAGGTCTCCAACAAAGGCCTCCCAGCCCCCATCGAGAAAACCATCTCCAAAACCAAAGGG<br>CAGCCCCGAGAACCACAGGTGTACACCCTGCCCCCATCCCGGGAGGAGATGACCAAGAACCAGGTC<br>AGCCTGACCTGCCTGGTCAAAGGCTTCTACCCCAGCGACATCGCCGTGGAGTGGGAGAGCAATGGG<br>CAGCCGGAGAACAACTACAAGACCACACCTCCCATGCTGGACTCCGACGGCTCCTTCTTCCTCTAC<br>AGCAAGCTCACCGTGGACAAGAGCAGGTGGCAGCAGGGGAACGTCTTCTCATGCTCCGTGATGCAT<br>GAGGCTCTGCACAACCACTACACGCAGAAGAGCCTCTCCCTGTCTCCGGGTAAA |
| 242 | ASTKGPSVFPLAPCSRSTSESTAALGCLVKDYFPEPVTVSWNSGALTSGVHTFPAVLQSSGLYSLS<br>SVVTVPSSNFGTQTYTCNVDHKPSNTKVDKTVERKCCVECPPCPAPPVAGPSVFLFPPKPKDTLMI<br>SRTPEVTCVVVDVSHEDPEVQFNWYVDGVEVHNAKTKPREEQFNSTFRVVSVLTVVHQDWLNGKEY<br>KCKVSNKGLPAPIEKTISKTKGQPREPQVYTLPPSREEMTKNQVSLTCLVKGFYPSDIAVEWESNG<br>QPENNYKTTPPMLDSDGSFFLYSKLTVDKSRWQQGNVFSCSVMHEALHNHYTQKSLSLSPGK |
| 243 | GCCAGCACCAAGGGGCCATCCGTCTTCCCCCTGGCGCCCTGCTCCAGGAGCACCTCCGAGAGCACA IgG4<br>GCCGCCCTGGGCTGCCTGGTCAAGGACTACTTCCCCGAACCGGTGACGGTGTCGTGGAACTCAGGC heavy<br>GCCCTGACCAGCGGCGTGCACACCTTCCCGGCTGTCCTACAGTCCTCAGGACTCTACTCCCTCAGC chain<br>AGCGTGGTGACCGTGCCCTCCAGCAGCTTGGGCACGAAGACCTACACCTGCAACGTAGATCACAAG<br>CCCAGCAACACCAAGGTGGACAAGAGAGTTGAGTCCAAATATGGTCCCCCATGCCCATCATGCCCA<br>GCACCTGAGTTCGAGGGGGGACCATCAGTCTTCCTGTTCCCCCCAAAACCCAAGGACACTCTCATG<br>ATCTCCCGGACCCCTGAGGTCACGTGCGTGGTGGTGGACGTGAGCCAGGAAGACCCCGAGGTCCAG<br>TTCAACTGGTACGTGGATGGCGTGGAGGTGCATAATGCCAAGACAAAGCCGCGGGAGGAGCAGTTC<br>AACAGCACGTACCGTGTGGTCAGCGTCCTCACCGTCCTGCACCAGGACTGGCTGAACGGCAAGGAG<br>TACAAGTGCAAGGTCTCCAACAAAGGCCTCCCGTCCTCCATCGAGAAAACCATCTCCAAAGCCAAA<br>GGGCAGCCCCGAGAGCCACAGGTGTACACCCTGCCCCCATCCCAGGAGGAGATGACCAAGAACCAG<br>GTCAGCCTGACCTGCCTGGTCAAAGGCTTCTACCCCAGCGACATCGCCGTGGAGTGGGAGAGCAAT<br>GGGCAGCCGGAGAACAACTACAAGACCACGCCTCCCGTGCTGGACTCCGACGGCTCCTTCTTCCTC<br>TACAGCAGGCTAACCGTGGACAAGAGCAGGTGGCAGGAGGGGAATGTCTTCTCATGCTCCGTGATG<br>CATGAGGCTCTGCACAACCACTACACACAGAAGAGCCTCTCCCTGTCTCTGGGTAAA |
| 244 | ASTKGPSVFPLAPCSRSTSESTAALGCLVKDYFPEPVTVSWNSGALTSGVHTFPAVLQSSGLYSLS<br>SVVTVPSSSLGTKTYTCNVDHKPSNTKVDKRVESKYGPPCPSCPAPEFLGGPSVFLFPPKPKDTLM<br>ISRTPEVTCVVVDVSQEDPEVQFNWYVDGVEVHNAKTKPREEQFNSTYRVVSVLTVLHQDWLNGKE<br>YKCKVSNKGLPSSIEKTISKAKGQPREPQVYTLPPSQEEMTKNQVSLTCLVKGFYPSDIAVEWESN<br>GQPENNYKTTPPVLDSDGSFFLYSRLTVDKSRWQEGNVFSCSVMHEALHNHYTQKSLSLSLGK |

One of skill in the art will appreciate the distinction between sequences shown in Table 1 that encompass variable regions of both the heavy and light chains compared to sequences of the full length antibody, which additional comprise constant regions. Variable domains can be combined with appropriate constant domains using standard technology well known in the art. Each of the light chains listed in Table 1 can be combined with any of the heavy chains shown in Table 1 (e.g., polypeptides depicted in SEQ ID NOs: 242 or 244) to form an antibody. In some instances, the antibodies include at least one heavy chain and one light chain from those listed in Table 1. In other instances, the antibodies contain two identical light chains and two identical heavy chains. As an example, an antibody or immunologically functional fragment may include two L1 light chains and two H1 heavy chains, or two L2 light chains and two H3 heavy chains, or two L2 light chains and two H4 heavy chains or two L2 and two H5 heavy chains and other similar combinations of pairs of light chains and pairs of heavy chains as listed in Table 1.

Other antibodies that are provided are variants of antibodies formed by combination of the heavy and light chains shown in Table 1 and comprise light and/or heavy chains that each have at least 70%, 75%, 80%, 85%, 90%, 95%, 97% or 99% identity to the amino acid sequences of these chains. In some instances, such antibodies include at least one heavy chain and one light chain, whereas in other instances such variant forms contain two identical light chains and two identical heavy chains.

Certain antibodies comprise a light chain variable domain comprising a sequence of amino acids that differs from the sequence of a light chain variable domain described herein at only 1, 2, 3, 4, 5, 6, 7, 8, 9, 10, 11, 12, 13, 14 or 15 amino acid residues, wherein each such sequence difference is independently either a deletion, insertion or substitution of one amino acid. The light chain variable region in some antibodies comprises a sequence of amino acids that has at least 70%, 75%, 80%, 85%, 90%, 95%, 97% or 99% sequence identity to the amino acid sequences of the light chain variable regions in Table 1

Some antibodies that are provided comprise a heavy chain variable domain comprising a sequence of amino acids that differs from the sequence of a heavy chain variable domain in Table 1 at only 1, 2, 3, 4, 5, 6, 7, 8, 9, 10, 11, 12, 13, 14 or 15 amino acid residues, wherein each such sequence difference is independently either a deletion, insertion or substitution of one amino acid. The heavy chain variable region in some antibodies comprises a sequence of amino acids that has at least 70%, 75%, 80%, 85%, 90%, 95%, 97% or 99% sequence identity to the amino acid sequences of the heavy chain variable region shown in Table 1. Still other antibodies or immunologically functional fragments include variant forms of a variant light chain and a variant heavy chain as just described.

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991.

The antibodies and immunological functional fragments that are provided can include one, two, three, four, five or all six of the CDRs listed above. Some antibodies or fragments include both the light chain CDR3 and the heavy chain CDR3. Certain antibodies have variant forms of the CDRs, with one or more (i.e., 2, 3, 4, 5 or 6) of the CDRs each having at least 80%, 85%, 90% or 95% sequence identity to a CDR sequence. For example, the antibody or fragment can include both a light chain CDR3 and a heavy chain CDR3 that each have at least 80%, 85%, 90% or 95% sequence identity to the light chain CDR3 sequence and the heavy chain CDR3, respectively. The CDR sequences of some of the antibodies that are provided may also differ from the CDR sequences in Table 1 such that the amino acid sequence for any given CDR differs from the sequence listed in Table 1 by no more than 1, 2, 3, 4 or 5 amino acid residues. Differences from the listed sequences usually are conservative substitutions (see below).

Polypeptides comprising one or more of the light or heavy chain CDRs may be produced by using a suitable vector to express the polypeptides in a suitable host cell as described in greater detail below. The heavy and light chain variable regions and the CDRs that are disclosed in Table 1 can be used to prepare any of the various types of immunologically functional fragments that are known in the art including, but not limited to, domain antibodies, Fab fragments, Fab' fragments, F(ab')$_2$ fragments, Fv fragments, single-chain antibodies and scFvs.

When an antibody is said to bind an epitope within specified residues, such as DKK1, for example, what is meant is that the antibody specifically binds to a polypeptide consisting of the specified residues (e.g., a specified segment of DKK1). Such an antibody does not necessarily contact every residue within DKK1. Nor does every single amino acid substitution or deletion within DKK1 necessarily significantly affect binding affinity. Exact epitope specificity of an antibody can be determined in variety of ways. One approach, for example, involves testing a collection of overlapping peptides of about 15 amino acids spanning the sequence of DKK1 and differing in increments of a small number of amino acids (e.g., 3 amino acids). The peptides are immobilized within the wells of a microtiter dish. Immobilization can be effected by biotinylating one terminus of the peptides. Optionally, different samples of the same peptide can be biotinylated at the N and C terminus and immobilized in separate wells for purposes of comparison. This is useful for identifying end-specific antibodies. Optionally, additional peptides can be included terminating at a particular amino acid of interest. This approach is useful for identifying end-specific antibodies to internal fragments of DKK1. An antibody or immunologically functional fragment is screened for specific binding to each of the various peptides. The epitope is defined as occurring with a segment of amino acids that is common to all peptides to which the antibody shows specific binding.

Antibodies and functional fragments thereof that bind to a conformational epitope that is located in the carboxy-terminal portion of DKK1 (see Table 1) are also provided. The carboxy-terminus of DKK1 contains several cysteine residues that form a cluster of disulfide bonds which create several loops. The invention provides antibodies that bind to two of these loops, thereby neutralizing the ability of DKK1 to suppress Wnt activity. Exemplary antibodies capable of binding to the aforementioned conformational epitope are the monoclonal antibodies 11H10 and 1F11, each of which comprises a light chain and a heavy chain. These antibodies are described in detail in U.S. Pat. No. 7,709,611.

The epitope comprising these two loops is formed by disulfide bonds between cysteine residues 220 and 237 of SEQ ID NO: 2 and between cysteine residues 245 and 263 of SEQ ID NO:2. The body of the two loops that form the epitope thus includes amino acids 221-236 and 246-262 of SEQ ID NO: 2. Segments within this loop that are involved in binding include amino acids 221-229 of SEQ ID NO:2 and amino acids 246-253 of SEQ ID NO: 2. Thus, certain antibodies and fragments that are provided herein specifically bind to the foregoing region(s). Some of the antibodies and fragments, for instance, bind to a peptide comprising or consisting of amino acids 221 to 262 of SEQ ID NO: 2.

In one aspect of the invention, peptides comprising or consisting of amino acids 221-229 and/or 246-253 of SEQ ID NO: 2 are provided. Other peptides comprise or consist of amino acids 221-236 and/or 246-262 of SEQ ID NO: 2. Still other peptides that are provided comprise or consist of the region from 221 to 262 of SEQ ID NO: 2 or amino acids 221-253 of SEQ ID NO:2. Such peptides are shorter than the full-length protein sequence of a native DKK1 (e.g., the peptides may include one or more of the forgoing regions and be 8, 9, 10, 11, 12, 13, 14, 15, 20, 21, 22, 23, 24, 25, 30, 40, 50, 75, 100, 150, or 200 amino acids in length). These peptides may be fused to another peptide to increase immunogenicity and thus be in the form of a fusion protein.

Antibodies and immunologically functional fragments thereof that compete with one the exemplified antibodies or functional fragments for specific binding to DKK1 are also provided. Such antibodies and fragments may also bind to the same epitope as one of the exemplified antibodies. Antibodies and fragments that compete with or bind to the same epitope as the exemplified antibody or fragment are expected to show similar functional properties. The exemplified antibodies and fragment include those described above, including those with the heavy and light chains, variable region domains and CDRs listed in Table 1. Competing antibodies or immunologically functional fragments can include those that bind to the epitope described in the section on antibodies and epitopes above.

As a specific example, some competing antibodies or fragments include those that specifically bind a DKK1 protein consisting of amino acids 32 to 266 of SEQ ID NO: 2 and can prevent or reduce the binding to human DKK1 of an antibody that consists of two identical heavy chains and two identical light chains. Other competing antibodies prevent or reduce the binding to human DKK1 of an antibody that consists of two identical heavy chains and two identical light chains such as those listed in Table 1.

The antibodies that are provided include monoclonal antibodies that bind to DKK1. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a transgenic animal having human immunoglobulin sequences) with a DKK1 immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds a DKK1 polypeptide. Such hybridoma cell lines, and anti-DKK1 monoclonal antibodies produced by them, are encompassed by the present invention.

Monoclonal antibodies secreted by a hybridoma cell line can be purified using any useful technique known in the antibody arts. Hybridomas or mAbs may be further screened to identify mAbs with particular properties, such as the ability to block a Wnt induced activity. Examples of such screens are provided in the examples below.

Chimeric and humanized antibodies based upon the foregoing sequences are also provided. Monoclonal antibodies for use as therapeutic agents may be modified in various ways prior to use. One example is a "chimeric" antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., Proc. Natl. Acad. Sci. USA 81:6851-6855 (1985). CDR grafting is described, for example, in U.S. Pat. Nos. 6,180,370, 5,693,762, 5,693, 761, 5,585,089, and 5,530,101.

Generally, the goal of making a chimeric antibody is to create a chimera in which the number of amino acids from the intended patient species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the V region or selected CDRs from a rodent antibody often are grafted into a human antibody, replacing the naturally-occurring V regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. Nos. 5,585,089, and 5,693,762; Jones et al., 1986, Nature 321:522-25; Riechmann et al., 1988, Nature 332:323-27; Verhoeyen et al., 1988, Science 239: 1534-36). In certain embodiments, constant regions from species other than human can be used along with the human variable region(s) to produce hybrid antibodies.

Fully human antibodies are also provided. Methods are available for making fully human antibodies specific for a given antigen without exposing human beings to the antigen ("fully human antibodies"). One means for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (MAbs) in mouse, an animal that can be immunized with any desirable antigen. Using fully human antibodies can minimize the immunogenic and allergic responses that can sometimes be caused by administering mouse or mouse-derivatized Mabs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, for example, Jakobovits et al., 1993, Proc. Natl. Acad. Sci. USA 90:2551-2555; Jakobovits et al., 1993, Nature 362:255-258; and Bruggermann et al., 1993, Year in Immunol. 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602. Additional methods relating to transgenic mice for making human antibodies are described in U.S. Pat. Nos. 5,545,807; 6,713,610; 6,673,986; 6,162,963; 5,545,807; 6,300,129; 6,255,458; 5,877,397; 5,874,299 and 5,545,806; in PCT publications WO91/10741, WO90/04036, and in EP 546073B1 and EP 546073A1.

The transgenic mice described above, referred to herein as "HuMab" mice, contain a human immunoglobulin gene minilocus that encodes unrearranged human heavy (μ and gamma) and kappa light chain immunoglobulin sequences, together with targeted mutations that inactivate the endogenous μ and .kappa. chain loci (Lonberg et al., 1994, Nature 368: 856-859).

Accordingly, the aforementioned mice exhibit reduced expression of mouse IgM or kappa and in response to immunization, and the introduced human heavy and light chain transgenes undergo class switching and somatic mutation to generate high affinity human IgG kappa monoclonal antibodies (Lonberg et al., supra.; Lonberg and Huszar, 1995, Intern. Rev. Immunol., 13: 65-93; Harding and Lonberg, 1995, Ann. N.Y Acad. Sci 764: 536-546). The preparation of HuMab mice is described in detail in Taylor et al., 1992, Nucleic Acids Research, 20: 6287-6295; Chen et al., 1993, International Immunology 5: 647-656; Tuaillon et al., 1994, J. Immunol. 152: 2912-2920; Lonberg et al., 1994, Nature 368: 856-859; Lonberg, 1994, Handbook of Exp. Pharmacology 113: 49-101; Taylor et al., 1994, International Immunology 6: 579-591; Lonberg and Huszar, 1995, Intern. Rev. Immunol. 13: 65-93; Harding and Lonberg, 1995, Ann. N.Y Acad. Sci. 764: 536-546; Fishwild et al., 1996, Nature Biotechnology 14: 845-851. See further U.S. Pat. Nos. 5,545,806; 5,569,825; 5,625,126; 5,633,425; 5,789,650; 5,877,397; 5,661,016; 5,814,318; 5,874,299; and 5,770,429; as well as U.S. Pat. No. 5,545,807; International Publication Nos. WO 93/1227; WO 92/22646; and WO 92/03918. Technologies utilized for producing human antibodies in these transgenic mice are disclosed also in WO 98/24893, and Mendez et al., 1997, Nature Genetics 15: 146-156. For example, the HCO7 and HCO12 transgenic mice strains can be used to generate human anti-DKK1 antibodies.

Using hybridoma technology, antigen-specific human MAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries (as disclosed in Hoogenboom et al., 1991, J. Mol. Biol. 227:381; and Marks et al., 1991, J. Mol. Biol. 222:581). Phage display techniques mimic immune selection through the display of antibody repertoires on the surface of filamentous bacteriophage, and subsequent selection of phage by their binding to an antigen of choice. One such technique is described in PCT Publication No. WO99/10494, which describes the isolation of high affinity and functional agonistic antibodies for MPL- and msk-receptors using such an approach.

The anti-DKK1 agents provided herein may also block or reduce binding between DKK1 and LRP5 and/or LRP6, thereby stimulating at least one activity associated with Wnt signaling. The agents can be an antibody or an immunologically functional fragment thereof and thus include antibodies with a naturally occurring structure, as well as polypeptides that have an antigen binding domain (e.g., a domain antibody). The antibodies and fragments can be used to treat a variety of different diseases including preventing or treating conditions relating to loss of bone mass or to stimulate production of new bone, as well as various non-bone related disorders. Nucleic acids molecules, vectors, and host cells useful in the production of the antibodies and selective binding agents are also provided.

Some of the antibodies and immunologically functional fragments that are provided include one or more of the following light chain (LC) complementary determining regions (CDRs): (i) a LC CDR1 with at least 80% sequence identity to SEQ ID NO: 97, 103, 109, 115, 121, 127, 133, 139, 145, 151, 157, 163, 169, 175, 181, 187, 193, 199, 205, 211, 217, or 223; (ii) a LC CDR2 with at least 80% sequence identity to SEQ ID NO: 98, 104, 110, 116, 122, 128, 134, 139, 146, 152, 158, 164, 170, 176, 182, 188, 194, 200, 206, 212, 218, or 224; and (iii) a LC CDR3 with at least 80% sequence identity to SEQ ID NO: 99, 105, 111, 117, 123, 129, 135, 140, 147, 153, 159, 165, 171, 177, 183, 189, 195, 201, 207, 213, 219, or 225. Some of the antibodies and immunologically functional fragments that are provided include one or more of the preceding LC CDRs and/or one or more of the following heavy chain (HC) complementary determining regions (CDRs): (i) a HC CDR1 with at least 80% sequence identity to SEQ ID NO: 100, 106, 112, 118, 124, 130, 136, 142, 148, 154, 160, 166, 172, 178, 184, 190, 196, 202, 208, 214, 220, or 226; (ii) a HC CDR2 with at least 80% sequence identity to SEQ ID NO: 101, 107, 113, 119, 125, 131, 137, 143, 149, 155, 161, 167, 173, 179, 185, 191, 197, 203, 209, 215, 221, or 227; and (iii) a HC CDR3 with at least 80% sequence identity to SEQ ID NO: 102, 108, 114, 120, 126, 132, 138, 144, 150, 156, 162, 168, 174, 180, 186, 192, 198, 204, 210, 216, 222 or 228. Some of the antibodies and immunologically functional fragments thereof that are provided also include one or more LC CDRs and one or more HC CDRs above.

Such antibodies or fragments can specifically bind a DKK1 polypeptide. Certain antibodies or fragments include one, two, three, four, five or all six of the forgoing CDRs.

The light chain and heavy chains of other antibodies or fragments are as described above but have at least 90% sequence identity to the foregoing sequences. Still other antibodies or fragments thereof are ones having a light chain in which CDR1 has the amino acid sequence as set forth in SEQ ID NOs: 97, 103, 109, 115, 121, 127, 133, 139, 145, 151, 157, 163, 169, 175, 181, 187, 193, 199, 205, 211, 217, or 223, CDR2 has the amino acid sequence as set forth in SEQ ID NOs: 98, 104, 110, 116, 122, 128, 134, 139, 146, 152, 158, 164, 170, 176, 182, 188, 194, 200, 206, 212, 218, or 224 and/or CDR3 has the amino acid sequence as set forth in SEQ ID NOs: 99, 105, 111, 117, 123, 129, 135, 140, 147, 153, 159, 165, 171, 177, 183, 189, 195, 201, 207, 213, 219, or 225. Some antibodies and fragments may also have a heavy chain in which CDR1 has the amino acid sequence as set forth in SEQ ID NOs: 100, 106, 112, 118, 124, 130, 136, 142, 148, 154, 160, 166, 172, 178, 184, 190, 196, 202, 208, 214, 220, or 226, CDR2 has the amino acid sequence as set forth in SEQ ID NOs: 101, 107, 113, 119, 125, 131, 137, 143, 149, 155, 161, 167, 173, 179, 185, 191, 197, 203, 209, 215, 221, or 227 and/or HC CDR3 has the amino acid sequence as set forth in SEQ ID NOs: 102, 108, 114, 120, 126, 132, 138, 144, 150, 156, 162, 168, 174, 180, 186, 192, 198, 204, 210, 216, 222 or 228. Certain antibodies or fragments include a light chain CDR3 with the amino acid sequence of SEQ ID NOs: 99, 105, 111, 117, 123, 129, 135, 140, 147, 153, 159, 165, 171, 177, 183, 189, 195, 201, 207, 213, 219, or 225 and/or a heavy chain CDR3 with the amino acid sequence of SEQ ID NOs: 102, 108, 114, 120, 126, 132, 138, 144, 150, 156, 162, 168, 174, 180, 186, 192, 198, 204, 210, 216, 222 or 228.

Certain other antibodies and immunologically functional fragments that are provided include (a) a light chain variable region (VL) having 80%, 85%, 90%, 92%, 95% or greater sequence identity with SEQ ID NOs: 10, 14, 18, 22, 26, 30, 34, 38, 42, 46, 50, 54, 58, 62, 66, 70, 74, 78, 82, 86, 90, or 94; (b) a heavy chain variable region (VH) having at least 80% sequence identity with SEQ ID NOs: 12, 16, 20, 24, 28, 32, 36, 40, 44, 48, 52, 56, 60, 64, 68, 72, 76, 80, 84, 88, 92, or 96; or (c) a VL of (a) and a VH of (b).

Other antibodies or fragments are similar in structure but the VL has at least 90%, 92%, or more preferably 95% sequence identity with SEQ ID NOs: 10, 14, 18, 22, 26, 30, 34, 38, 42, 46, 50, 54, 58, 62, 66, 70, 74, 78, 82, 86, 90, or 94; and the VH has at least 90% sequence identity with SEQ ID NOs: 12, 16, 20, 24, 28, 32, 36, 40, 44, 48, 52, 56, 60, 64, 68, 72, 76, 80, 84, 88, 92, or 96. In certain antibodies or fragments, the VL has at least 98% sequence identity with SEQ ID NOs: 10, 14, 18, 22, 26, 30, 34, 38, 42, 46, 50, 54, 58, 62, 66, 70, 74, 78, 82, 86, 90, or 94; and the VH has at least 98% sequence identity with SEQ ID NOs: 12, 16, 20, 24, 28, 32, 36, 40, 44, 48, 52, 56, 60, 64, 68, 72, 76, 80, 84, 88, 92, or 96. Still other antibodies or fragments are ones that include a VL that has the amino acid sequence of SEQ ID NOs: 10, 14, 18, 22, 26, 30, 34, 38, 42, 46, 50, 54, 58, 62, 66, 70, 74, 78, 82, 86, 90, or 94, and/or a VH that has the amino acid sequence of SEQ ID NOs: 12, 16, 20, 24, 28, 32, 36, 40, 44, 48, 52, 56, 60, 64, 68, 72, 76, 80, 84, 88, 92, or 96.

Some antibodies or fragments include a light chain that comprises or consists of the amino acid sequence of SEQ ID NOs: 10, 14, 18, 22, 26, 30, 34, 38, 42, 46, 50, 54, 58, 62, 66, 70, 74, 78, 82, 86, 90, or 94 and/or a heavy chain that comprises or consists of the amino acid sequence of SEQ ID NOs: 12, 16, 20, 24, 28, 32, 36, 40, 44, 48, 52, 56, 60, 64, 68, 72, 76, 80, 84, 88, 92, or 96.

Also included are isolated antibodies or an immunologically functional fragments thereof that specifically bind a mature human DKK1 protein expressed from the sequence depicted in SEQ ID NO: 1, wherein said antibody binds to an epitope comprising two loops, said loops being formed by disulfide bonds between amino acids 220 and 237 of SEQ ID NO: 2 and between cysteine residues 245 and 263 of SEQ ID NO:2.

Other antibodies or fragments that are disclosed compete with an antibody such as those described above for specific binding to a DKK1 polypeptide. For example, some antibodies and fragments compete with an antibody that consists of two identical heavy chains and two identical light chains, wherein the heavy chains comprise SEQ ID NO: 42 and said light chains comprise SEQ ID NO: 44.

The various antibodies and fragments that are provided may include a single light and/or heavy chain or a single variable light domain and/or a single variable heavy domain. Other antibodies and fragments include two light and/or two heavy chains. In those instances in which the antibody or fragment includes two light and/or heavy chains, the two light chains in some instances are identical to one another; likewise, the two heavy chains in some instances are identical. The antibodies that are provided may include, for example, monoclonal antibodies, a human antibody, a chimeric antibody, or a humanized antibody. The immunologically functional fragments may include, but are not limited to, a scFv, a Fab, a Fab', a F(ab')$^2$, or a domain antibody. In certain instances, the antibody or fragment dissociates from a DKK1 polypeptide with a $k_d$ ($k_{off}$) of $5 \times 10^{-4}$ or less.

Pharmaceutical compositions that include any of the foregoing antibodies and immunologically active fragments are also provided. Such compositions typically also include a buffer, a pharmaceutically acceptable diluent, a carrier, a solubilizer, an emulsifier or a preservative. The use of the foregoing antibodies and immunologically active fragments in the preparation of a pharmaceutical composition or medicament is also provided.

A variety of nucleic acids encoding the foregoing antibodies are also provided. Some nucleic acids, for instance, encode (a) a light chain CDR with the amino acid sequence as set forth in SEQ ID NOs: 9, 13, 17, 21, 25, 29, 33, 37, 41, 45, 49, 53, 57, 61, 65, 69, 73, 77, 81, 85, 89, and/or 93; and/or (b) a heavy chain CDR with the amino acid sequence as set forth in SEQ ID NOs: 11, 15, 19, 23, 27, 31, 35, 39, 43, 47, 51, 55, 59, 63, 67, 71, 75, 79, 83, 87, 91 and/or 95, such that the encoded CDR(s) encode an antibody or an immunologically functional fragment thereof that can specifically bind a DKK1 polypeptide. Certain other nucleic acids comprise or consist of a sequence that encodes a variable light region (VL) and/or a variable heavy region (VH) of an antibody or immunologically active fragment, wherein the VL has at least 80%, 90% or 95% sequence identity with SEQ ID NOs: 9, 13, 17, 21, 25, 29, 33, 37, 41, 45, 49, 53, 57, 61, 65, 69, 73, 77, 81, 85, 89, or 93 and the VH has at least 80% 90%, or 95% sequence identity with SEQ ID NOs: 11, 15, 19, 23, 27, 31, 35, 39, 43, 47, 51, 55, 59, 63, 67, 71, 75, 79, 83, 87, 91 or 95. Some of the nucleic acids include a sequence that encodes a VL that comprises or consists of SEQ ID NOs: 9, 13, 17, 21, 25, 29, 33, 37, 41, 45, 49, 53, 57, 61, 65, 69, 73, 77, 81, 85, 89, or 93 and/or a sequence that encodes a VH that comprises or consists of SEQ ID NOs: 11, 15, 19, 23, 27, 31, 35, 39, 43, 47, 51, 55, 59, 63, 67, 71, 75, 79, 83, 87, 91 or 95. Expression vectors comprising the foregoing nucleic acids are also disclosed herein, as are cells (e.g., CHO cells) that comprise such expression vectors. Methods of producing an antibody or an immunologically active fragment thereof by culturing cells that contain such expression vectors are also described.

Provided herein are novel DKK1 antibodies that are effective in treating conditions requiring increased bone building, for example, fracture repair or bone loss associated with pathological conditions, such as multiple myeloma. In addition, provided herein are combinations of agents that increase bone anabolism including combinations of DKK1 and sclerostin inhibitors. These combinations can be used for treatment of, for example, osteoporosis, increase the rate of fracture healing, and any number of conditions requiring an increase in the rate of bone building. The combination therapeutic can take the form of two separate inhibitors, for example, an anti-sclerostin antibody and an anti-DKK1 antibody, or can be a single molecular entity, for example, a bispecific antibody.

As used herein, a bispecific antibody binds one antigen on one of its two binding arms, and binds a different antigen on its second arm. Thus a bispecific antibody has two distinct antigen binding arms and is monovalent for each antigen it binds. Bispecific and bifunctional DKK1 antibodies provided herein can include one or more CDRs or one or more variable regions as described above. A bispecific or bifunctional antibody in some instances is an artificial hybrid antibody having two different heavy/light chain pairs and two different binding sites. These bispecific antibodies may be produced by a variety of methods including, but not limited to, fusion of hybridomas or linking of Fab' fragments. See, e.g., Songsivilai & Lachmann, 1990, Clin. Exp. Immunol. 79: 315-321; Kostelny et al., 1992, J. Immunol. 148: 1547-1553.

Bispecific molecules can also be created according to the invention by fusion. In one example, an antibody of the invention can be linked (e.g., by expressing fused proteins, chemical linking, high affinity non-covalent association or the like) to one or more other binding molecules. Examples of such binding molecules include but are not limited to another antibody, antibody fragment, peptide or binding mimetic, such that a bispecific molecule results.

Bispecific molecules can also comprise a first binding specificity for sclerostin and a second binding specificity for a second target. For example, the second target can be another epitope of sclerostin different from the first epitope. Another example is a bispecific molecule comprising at least one first binding specificity for sclerostin and a second binding specificity for an epitope within DKK1. Another example is a bispecific molecule comprising at least one first binding specificity for sclerostin and a second binding specificity for an epitope within LRP4. Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., an Fab, Fab', F(ab')$_2$, Fv, or a single chain Fv from a novel anti-DKK1 antibody sequence provided herein. It may also be a light chain or heavy chain dimer, or any minimal fragment such as a Fv or a single chain construct as described in Ladner eta/. U.S. Pat. No. 4,946,778.

Bispecific molecules can be prepared by chemically conjugating the binding portions using methods known in the art. When the binding portions are proteins or peptides, a variety of coupling or cross-linking agents can be used for covalent conjugation. Examples include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl4-(N-maleimidomethyl) cyclohaxane-1carboxylate (sulfo-SMCC) (see e.g., Karpovsky et a/, 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83, and Glennie et al., 1987 J. Immunol. 139: 2367-2375. Conjugating agents include SATA and sulfo-SMCC, both available from Pierce Chemical Co. (Rockford, Ill.). When the binding portions are antibodies, they can be conjugated by sulfhydryl bonding of the hinge regions of the two heavy chains. In one embodiment, the hinge region is modified to contain an odd number of sulfhydryl residues such that there is a free sulfhydryl group that has not formed a disulfide linkage with a corresponding heavy or light chain counterpart.

Bispecific molecules may comprise at least two single chain molecules. Non-limiting examples of methods for preparing bispecific molecules are described various patent publications including in U.S. Pat. Nos. 5,260,203; 5,455, 030; 4,881,175; 5,132,405; 5,091,513; 5,476,786; 5,013, 653; 5,258,498; 5,482,858; and U.S. Patent Application No. 2010/0076178.

Examples of partners for either combination therapy with DKK1 inhibitors or bi- or multi-specific molecules including DKK1 binding portions include sclerostin antibodies or binding fragments that specifically recognize sclerostin proteins. Sclerostin has been previously described as being involved in regulating bone density through wnt signaling pathways (PCT WO 06/119107).

There is a report of a combination of a DKK1 antibody and a sclerostin antibody where it is suggested that this combination can increase the bone mineral density of cancellous or spongy bone more than either alone in model animals (PCT WO 09/047356) and improved the increase in total bone mineral content, density and cortical thickness. However, in those examples intact bone was used, not fractured bone.

Reports indicate that DKK1 expression is elevated in fracture models of non-unions (Bajada, et al., 2009 Bone; 45(4):726-35.). Likewise, healthy bone expresses lower levels of DKK1 helping to explain the limited effect of DKK1 antibodies alone on BMD in intact bone (see Example 15). Thus, combinations of sclerostin and DKK1 inhibitors to treat fractures are particularly useful given the surprisingly strong healing response including the significant increase in the peak load in a relatively short period.

Variants

Some of the antibodies or immunologically functional fragments that are provided are variant forms of the antibodies and fragments disclosed above (e.g., those having the sequences listed in Table 1). For instance, some of the antibodies or fragments are ones having one or more conservative amino acid substitutions in one or more of the heavy or light chains, variable regions or CDRs listed in Table 1.

Naturally-occurring amino acids may be divided into classes based on common side chain properties: [0149] 1) hydrophobic: norleucine, Met, Ala, Val, Leu, Ile; [0150] 2) neutral hydrophilic: Cys, Ser, Thr, Asn, Gln; [0151] 3) acidic: Asp, Glu; [0152] 4) basic: His, Lys, Arg; [0153] 5) residues that influence chain orientation: Gly, Pro; and [0154] 6) aromatic: Trp, Tyr, Phe. Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of the above classes for a member from another class. Such substituted residues may be introduced into regions of the antibody that are homologous with human antibodies, or into the non-homologous regions of the molecule.

In making such changes, according to certain embodiments, the hydropathic index of amino acids may be considered. The hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic profile in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within .+−0.2 is included. In some aspects of the invention, those which are within .+−0.1 are included, and in other aspects of the invention, those within .+−0.0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding or immunogenicity, that is, with a biological property of the protein.

The following hydrophilicity values have been assigned to these amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within .+/−.2 is included, in other embodiments, those which are within .+/−.1 are included, and in still other embodiments, those within .+/−.0.5 are included. In some instances, one may also identify epitopes from primary amino acid sequences on the basis of hydrophilicity. These regions are also referred to as "epitopic core regions."

A skilled artisan will be able to determine suitable variants of polypeptides as set forth herein using well-known techniques. One skilled in the art may identify suitable areas of the molecule that may be changed without destroying activity by targeting regions not believed to be important for activity. The skilled artisan also will be able to identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using assays for DKK1 neutralizing activity, (see examples below) thus yielding information regarding which amino acids can be changed and which must not be changed. In other words, based on information gathered from such routine experiments, one skilled in the art can readily determine the amino acid positions where further substitutions should be avoided either alone or in combination with other mutations.

A number of scientific publications have been devoted to the prediction of secondary structure. See Moult, 1996, Curr. Op. in Biotech. 7:422-427; Chou et al., 1974, Biochemistry 13:222-245; Chou et al., 1974, Biochemistry 113:211-222; Chou et al., 1978, Adv. Enzymol. Relat. Areas Mol. Biol. 47:45-148; Chou et al., 1979, Ann. Rev. Biochem. 47:251-276; and Chou et al., 1979, Biophys. J. 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., 1999, Nucl. Acid. Res. 27:244-247. It has been suggested (Brenner et al., 1997, Curr. Op. Struct. Biol. 7:369-376) that there are a limited number of folds in a given polypeptide or protein and that once a critical number of structures have been resolved, structural prediction will become dramatically more accurate.

Additional methods of predicting secondary structure include "threading" (Jones, 1997, Curr. Opin. Struct. Biol. 7:377-87; Sippl et al., 1996, Structure 4:15-19), "profile analysis" (Bowie et al., 1991, Science 253:164-170; Gribskov et al., 1990, Meth. Enzym. 183:146-159; Gribskov et al., 1987, Proc. Nat. Acad. Sci. 84:4355-4358), and "evolutionary linkage" (See Holm, 1999, supra; and Brenner, 1997, supra).

In some embodiments of the invention, amino acid substitutions are made that: (1) reduce susceptibility to proteolysis, (2) reduce susceptibility to oxidation, (3) alter binding affinity for forming protein complexes, (4) alter ligand or antigen binding affinities, and/or (4) confer or modify other physicochemical or functional properties on such polypeptides. For example, single or multiple amino acid substitutions (in certain embodiments, conservative amino acid substitutions) may be made in the naturally-occurring sequence. Substitutions can be made in that portion of the antibody that lies outside the domain(s) forming intermolecular contacts). In such embodiments, conservative amino acid substitutions can be used that do not substantially change the structural characteristics of the parent sequence (e.g., one or more replacement amino acids that do not disrupt the secondary structure that characterizes the parent or native antibody). Examples of art-recognized polypeptide secondary and tertiary structures are described in Proteins, Structures and Molecular Principles (Creighton, Ed.), 1984, W. H. New York: Freeman and Company; Introduction to Protein Structure (Branden and Tooze, eds.), 1991, New York: Garland Publishing; and Thornton et at., 1991, Nature 354: 105, which are each incorporated herein by reference.

The invention also encompasses glycosylation variants of the inventive antibodies wherein the number and/or type of glycosylation site(s) has been altered compared to the amino acid sequences of the parent polypeptide. In certain embodiments, antibody protein variants comprise a greater or a lesser number of N-linked glycosylation sites than the native antibody. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate or alter this sequence will prevent addition of an N-linked carbohydrate chain present in the native polypeptide. For example, the glycosylation can be reduced by the deletion of an Asn or by substituting the Asn with a different amino acid. In other embodiments, one or more new N-linked sites are created. Antibodies typically have a N-linked glycosylation site in the Fc region.

Additional preferred antibody variants include cysteine variants wherein one or more cysteine residues in the parent or native amino acid sequence are deleted from or substituted with another amino acid (e.g., serine). Cysteine variants are useful, inter alia when antibodies must be refolded into a biologically active conformation. Cysteine variants may have fewer cysteine residues than the native antibody, and typically have an even number to minimize interactions resulting from unpaired cysteines.

The heavy and light chains, variable regions domains and CDRs that are disclosed can be used to prepare polypeptides that contain an antigen binding region that can specifically bind to a DKK1 polypeptide. For example, one or more of the CDRs listed in Table 1 can be incorporated into a molecule (e.g., a polypeptide) covalently or noncovalently to make an immunoadhesion. An immunoadhesion may incorporate the CDR(s) as part of a larger polypeptide chain, may covalently link the CDR(s) to another polypeptide chain, or may incorporate the CDR(s) noncovalently. The CDR(s) enable the immunoadhesion to bind specifically to a particular antigen of interest (e.g., a DKK1 polypeptide or epitope thereof).

Mimetics (e.g., peptide mimetics" or "peptidomimetics") based upon the variable region domains and CDRs that are described herein are also provided. These analogs can be peptides, non-peptides or combinations of peptide and non-peptide regions. Fauchere, 1986, Adv. Drug Res. 15: 29; Veber and Freidinger, 1985, TINS p. 392; and Evans et al., 1987, J. Med. Chem. 30: 1229, which are incorporated herein by reference for any purpose. Peptide mimetics that are structurally similar to therapeutically useful peptides may be used to produce a similar therapeutic or prophylactic effect. Such compounds are often developed with the aid of computerized molecular modeling. Generally, peptidomimetics of the invention are proteins that are structurally similar to an antibody displaying a desired biological activity, such as here the ability to specifically bind DKK1, but have one or more peptide linkages optionally replaced by a linkage selected from: —CH2NH—, —CH2S—, —CH2-CH.2-, —CH—CH— (cis and trans), —COCH2-, —CH(OH)CH2-, and —CH2SO—, by methods well known in the art. Systematic substitution of one or more amino acids of a consensus sequence with a D-amino acid of the same type (e.g., D-lysine in place of L-lysine) may be used in certain embodiments of the invention to generate more stable proteins. In addition, constrained peptides comprising a consensus sequence or a substantially identical consensus sequence variation may be generated by methods known in the art (Rizo and Gierasch, 1992, Ann. Rev. Biochem. 61: 387), incorporated herein by reference), for example, by adding internal cysteine residues capable of forming intramolecular disulfide bridges which cyclize the peptide.

Derivatives of the antibodies and immunologically functional fragments that are described herein are also provided. The derivatized antibody or fragment may comprise any molecule or substance that imparts a desired property to the antibody or fragment, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Other derivatives include covalent or aggregative conjugates of anti-DKK1 antibodies, or fragments thereof, with other proteins or polypeptides, such as by expression of recombinant fusion proteins comprising heterologous polypeptides fused to the N-terminus or C-terminus of an anti-DKK1 antibody polypeptide. For example, the conjugated peptide may be a heterologous signal (or leader) polypeptide, e.g., the yeast alpha-factor leader, or a peptide such as an epitope tag. Anti-DKK1 antibody-containing fusion proteins can comprise peptides added to facilitate purification or identification of the anti-DKK1 antibody (e.g., poly-His). An anti-DKK1 antibody polypeptide also can be linked to the FLAG peptide as described in Hopp et al., Bio/Technology 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers that contain one or more anti-DKK1 antibody polypeptides may be employed as DKK1 antagonists. Oligomers may be in the form of covalently-linked or non-covalently-linked dimers, trimers, or higher. Oligomers comprising two or more anti-DKK1 antibody polypeptides are contemplated for use, with one example being a homodimer. Other oligomers include heterodimers, homotrimers, heterotrimers, homotetramers, heterotetramers, etc.

One embodiment is directed to oligomers comprising multiple anti-DKK1 antibody polypeptides joined via covalent or non-covalent interactions between peptide moieties fused to the anti-DKK1 antibody polypeptides. Such peptides may be peptide linkers (spacers), or peptides that have the property of promoting oligomerization. Leucine zippers and certain polypeptides derived from antibodies are among the peptides that can promote oligomerization of anti-DKK1 antibody polypeptides attached thereto, as described in more detail below.

In particular embodiments, the oligomers comprise from two to four anti-DKK1 antibody polypeptides. The anti-DKK1 antibody moieties of the oligomer may be in any of the forms described above, e.g., variants or fragments. Preferably, the oligomers comprise anti-DKK1 antibody polypeptides that have DKK1 binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in Current Protocols in Immunology, Suppl. 4, pages 10.19.1-10.19.11.

One embodiment of the present invention is directed to a dimer comprising two fusion proteins created by fusing a DKK1 binding fragment of an anti-DKK1 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 and U.S. Pat. Nos. 5,426,048 and 5,262,522 (each of which is hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of an anti-DKK1 antibody such as disclosed herein may be substituted for the variable portion of an antibody heavy and/or light chain.

Alternatively, the oligomer is a fusion protein comprising multiple anti-DKK1 antibody polypeptides, with or without peptide linkers (spacer peptides). Among the suitable peptide linkers are those described in U.S. Pat. Nos. 4,751,180 and 4,935,233.

Another method for preparing oligomeric anti-DKK1 antibody derivatives involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an anti-DKK1 antibody fragment or derivative fused to a leucine zipper peptide are expressed in suitable host cells, and the soluble oligomeric anti-DKK1 antibody fragments or derivatives that form are recovered from the culture supernatant.

Some antibodies that are provided have a binding affinity ($K_a$) for DKK1 of at least $10^4$ or $10^5$/M x seconds measured, for instance, as described in the examples below. Other antibodies have a $k_a$ of at least $10^6$, $10^7$, $10^8$ or $10^9$/M x seconds. Certain antibodies that are provided have a low disassociation rate. Some antibodies, for instance, have a $K_{off}$ of $1\times10^{-4}s^{-1}$, $1\times10^{-5}s^{-1}$ or lower.

In another aspect, the present invention provides an anti-DKK1 antibody having a half-life of at least one day in vitro or in vivo (e.g., when administered to a human subject). In one embodiment, the antibody has a half-life of at least three days. In another embodiment, the antibody or portion thereof has a half-life of four days or longer. In another embodiment, the antibody or portion thereof has a half-life of eight days or longer. In another embodiment, the antibody or antigen-binding portion thereof is derivatized or modified such that it has a longer half-life as compared to the underivatized or unmodified antibody. In another embodiment, the antibody contains point mutations to increase serum half life, such as described in WO 00/09560.

Nucleic acids that encode one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing are also provided. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids that encode the epitope to which certain of the antibodies provided herein bind are also provided. Thus, some nucleic acids encode amino acids 221-229 and/or 246-253 of SEQ ID NO:2 are included, as are nucleic acids that encode amino acids 221-236 and/or 246-262 of SEQ ID NO:2 and those that encode amino acids 221 to 262 of SEQ ID NO:2 or amino acids 221-253 of SEQ ID NO:2. Nucleic acids encoding fusion proteins that include these peptides are also provided.

DNA encoding antibody polypeptides (e.g., heavy or light chain, variable domain only, or full length) may be isolated from B-cells of mice that have been immunized with DKK1 or an immunogenic fragment thereof. The DNA may be isolated by conventional procedures such as polymerase chain reaction (PCR). Phage display is another example of a known technique whereby derivatives of antibodies may be prepared. In one approach, polypeptides that are components of an antibody of interest are expressed in any suitable recombinant expression system, and the expressed polypeptides are allowed to assemble to form antibody molecules.

Exemplary nucleic acids that encode the light and heavy chains, variable regions and CDRs of the antibodies and immunologically functional fragments that are provided are listed in Table 1 above. Due to the degeneracy of the genetic code, each of the polypeptide sequences listed in Table 1 is also encoded by a large number of other nucleic acid sequences besides those listed in Table 1. The present invention provides each degenerate nucleotide sequence encoding each antibody of the invention.

The invention further provides nucleic acids that hybridize to other nucleic acids (e.g., nucleic acids comprising a nucleotide sequence listed in Tables 1-3) under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, a moderately stringent hybridization condition uses a prewashing solution containing 5.times. sodium chloride/sodium citrate (SSC), 0.5% SDS, 1.0 mM EDTA (pH 8.0), hybridization buffer of about 50% formamide, 6.times.SSC, and a hybridization temperature of 55° C. (or other similar hybridization solutions, such as one containing about 50% formamide, with a hybridization temperature of 42.degree. C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other.

The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA.

Changes can be introduced by mutation into a nucleic acid, thereby leading to changes in the amino acid sequence of a polypeptide (e.g., an antibody or antibody derivative of the invention) that it encodes. Mutations can be introduced using any technique known in the art. In one embodiment, one or more particular amino acid residues are changed using, for example, a site-directed mutagenesis protocol. In another embodiment, one or more randomly selected residue is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. Alternatively, one or more mutations can be introduced into a nucleic acid that selectively change the biological activity of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., a DKK1 binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses In another aspect, the present invention provides vectors comprising a nucleic acid encoding a polypeptide of the invention or a portion thereof (e.g., a fragment containing one or more CDRs or one or more variable region domains). Examples of vectors include, but are not limited to, plasmids, viral vectors, non-episomal mammalian vectors and expression vectors, for example, recombinant expression vectors. The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell (for example, *E. coli*) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

The non-human antibodies that are provided can be, for example, derived from any antibody-producing animal, such as mouse, rat, rabbit, goat, donkey, or non-human primate (such as monkey (e.g., cynomologous or rhesus monkey) or ape (e.g., chimpanzee)). Non-human antibodies can be used, for instance, in in vitro cell culture and cell-culture based applications, or any other application where an immune response to the antibody does not occur or is insignificant, can be prevented, is not a concern, or is desired. In certain embodiments of the invention, the antibodies may be produced by immunizing with full-length DKK1 or with the carboxy-terminal half of DKK1. Alternatively, the certain non-human antibodies may be raised by immunizing with amino acids 221-236 and/or amino acids 246-262 of SEQ ID NO:2, which are segments of human DKK1 that form part of the epitope to which certain antibodies provided herein bind (e.g., the 11H10, see FIG. 1). The antibodies may be polyclonal, monoclonal, or may be synthesized in host cells by expressing recombinant DNA.

Fully human antibodies may be prepared as described above by immunizing transgenic animals containing human immunoglobulin loci or by selecting a phage display library that is expressing a repertoire of human antibodies.

The monoclonal antibodies (mAbs) of the invention can be produced by a variety of techniques, including conventional monoclonal antibody methodology, e.g., the standard somatic cell hybridization technique of Kohler and Milstein, 1975, Nature 256: 495. Alternatively, other techniques for producing monoclonal antibodies can be employed, for example, the viral or oncogenic transformation of B-lymphocytes. One suitable animal system for preparing hybridomas is the murine system, which is a very well established procedure. Immunization protocols and techniques for isolation of immunized splenocytes for fusion are known in the art. For such procedures, B cells from immunized mice are fused with a suitable immortalized fusion partner, such as a murine myeloma cell line. If desired, rats or other mammals besides can be immunized instead of mice and B cells from such animals can be fused with the murine myeloma cell line to form hybridomas. Alternatively, a myeloma cell line from a source other than mouse may be used. Fusion procedures for making hybridomas also are well known.

The single chain antibodies that are provided may be formed by linking heavy and light chain variable domain (Fv region) fragments (see, e.g., Table 1) via an amino acid bridge (short peptide linker), resulting in a single polypeptide chain. Such single-chain Fvs (scFvs) may be prepared by fusing DNA encoding a peptide linker between DNAs encoding the two variable domain polypeptides (VL and VH). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different VL and VH-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol Biol. 178:379-87.

Antibodies provided herein that are of one subclass can be changed to antibodies from a different subclass using subclass switching methods. For example, the variable domains depicted in Table 1 can be attached to constant domains of any desired Ig subtype. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See, e.g., Lantto et al., 2002, Methods Mol. Biol. 178:303-16.

Accordingly, the antibodies that are provided include a desired isotype (for example, IgA, IgG1, IgG2, IgG3, IgG4, IgE, and IgD) as well as Fab or F(ab') 2 fragments thereof. Moreover, if an IgG4 is desired, it may also be desired to introduce a point mutation in the hinge region as described in Bloom et al., 1997, Protein Science 6:407) to alleviate a tendency to form intra-H chain disulfide bonds that can lead to heterogeneity in the IgG4 antibodies.

Moreover, techniques for deriving antibodies having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, BioTechnology, 10:779.

Conservative modifications may be made to the heavy and light chains described in Table 1 (and corresponding modifications to the encoding nucleic acids) to produce an anti-DKK1 antibody having functional and biochemical characteristics. Methods for achieving such modifications are described above.

Antibodies and functional fragments thereof according to the invention may be further modified in various ways. For example, if they are to be used for therapeutic purposes, they may be conjugated with polyethylene glycol (pegylated) to prolong the serum half-life or to enhance protein delivery. Alternatively, the V region of the subject antibodies or fragments thereof may be fused with the Fc region of a different antibody molecule. The Fc region used for this purpose may be modified so that it does not bind complement, thus reducing the likelihood of inducing cell lysis in the patient when the fusion protein is used as a therapeutic agent. In addition, the subject antibodies or functional fragments thereof may be conjugated with human serum albumin to enhance the serum half-life of the antibody or fragment thereof. Another useful fusion partner for the inventive antibodies or fragments thereof is transthyretin (TTR). TTR has the capacity to form a tetramer, thus an antibody-TTR fusion protein can form a multivalent antibody which may increase its binding avidity.

Alternatively, substantial modifications in the functional and/or biochemical characteristics of the antibodies and fragments described herein may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain. A "conservative amino acid substitution" may involve a substitution of a native amino acid residue with a nonnative residue that has little or no effect on the polarity or charge of the amino acid residue at that position. Furthermore, any native residue in the polypeptide may also be substituted with alanine, as has been previously described for alanine scanning mutagenesis.

Amino acid substitutions (whether conservative or nonconservative) of the subject antibodies can be implemented by those skilled in the art by applying routine techniques. Amino acid substitutions can be used to identify important residues of the antibodies provided herein, or to increase or decrease the affinity of these antibodies for human DKK1 or for modifying the binding affinity of other anti-DKK1 antibodies described herein.

The anti-DKK1 antibodies and immunological functional fragments can be prepared by any of a number of conventional techniques. For example, anti-DKK1 antibodies may be produced by recombinant expression systems, using any technique known in the art. See, for example, Monoclonal Antibodies, Hybridomas: A New Dimension in Biological Analyses, Kennet et al. (eds.) Plenum Press, New York (1980): and Antibodies: A Laboratory Manual, Harlow and Lane (eds.), Cold Spring Harbor Laboratory Press, Cold Spring Harbor, N.Y. (1988).

Antibodies of the present invention can be expressed in hybridoma cell lines or in cell lines other than hybridomas. Expression constructs encoding the antibodies can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. Nos. 4,399,216, 4,912,040, 4,740,461, and 4,959,455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs of the invention typically comprise a nucleic acid molecule encoding a polypeptide comprising one or more of the following: a heavy chain constant region (e.g., CH1, CH2 and/or CH3); a heavy chain variable region; a light chain constant region; a light chain variable region; one or more CDRs of the light or heavy chain of the anti-DKK1 antibody. These nucleic acid sequences are inserted into an appropriate expression vector using standard ligation techniques. In one embodiment, the 11H10 heavy or light chain constant region is appended to the C-terminus of the DKK1-specific heavy or light chain variable region and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964). Suitable expression vectors can be purchased, for example, from Invitrogen Life Technologies or BD Biosciences (formerly "Clontech"). Other useful vectors for cloning and expressing the antibodies and fragments of the invention include those described in Bianchi and McGrew, Biotech Biotechnol Bioeng 84(4):439-44 (2003). Additional suitable expression vectors are discussed, for example, in Methods Enzymol, vol. 185 (D. V. Goeddel, ed.), 1990, New York: Academic Press, which is hereby incorporated by reference.

Typically, expression vectors used in any of the host cells contain sequences for plasmid or virus maintenance and for cloning and expression of exogenous nucleotide sequences. Such sequences, collectively referred to as "flanking sequences" typically include one or more of the following operatively linked nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

Optionally, the vector may contain a "tag"-encoding sequence, that is, an oligonucleotide molecule located at the 5' or 3' end of the coding sequence, the oligonucleotide sequence encoding polyHis (such as hexaHis), or another "tag" for which commercially available antibodies exist, such as FLAG©, HA (hemaglutinin from influenza virus), or myc. The tag is typically fused to the antibody protein upon expression, and can serve as a means for affinity purification of the antibody from the host cell. Affinity purification can be accomplished, for example, by column chromatography using antibodies against the tag as an affinity matrix. Optionally, the tag can subsequently be removed from the purified antibody polypeptide by various means such as using certain peptidases for cleavage.

Flanking sequences in the expression vector may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen™ column chromatography (Chatsworth, Calif.), or other methods known to the skilled artisan. The selection of suitable enzymes to accomplish this purpose will be readily apparent to those skilled in the art.

An origin of replication is typically a part of prokaryotic expression vectors, particularly those purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitis virus (VSV), or papillomaviruses such as HPV or BPV) are useful for cloning vectors in mammalian cells. Generally, a mammalian origin of replication is not needed for mammalian expression vectors (for example, the SV40 origin is often used only because it contains the early promoter).

The expression and cloning vectors of the present invention will typically contain a promoter that is recognized by the host organism and operably linked to nucleic acid encoding the anti-DKK1 antibody or immunologically functional fragment thereof Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continuous gene product production; that is, there is little or no experimental control over gene expression. A large number of promoters, recognized by a variety of potential host cells, are well known. A suitable promoter is operably linked to the DNA encoding anti-DKK1 antibody by removing the promoter from the source DNA by restriction enzyme digestion or amplifying the promoter by polymerase chain reaction and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and—most preferably Simian Virus 40 (SV40). Other suitable mammalian promoters include heterologous mammalian promoters, for example, heat-shock promoters and the actin promoter.

Particular promoters useful in the practice of the recombinant expression vectors of the invention include, but are not limited to: the SV40 early promoter region (Bemoist and Chambon, 1981, Nature 290: 304-10); the CMV promoter; the promoter contained in the 3' long terminal repeat of Rous sarcoma virus (Yamamoto, et al., 1980, Cell 22: 787-97); the herpes thymidine kinase promoter (Wagner et al., 1981, Proc. Natl. Acad. Sci. U.S.A. 78: 1444-45); the regulatory sequences of the metallothionine gene (Brinster et al., 1982, Nature 296: 39-42); prokaryotic expression vectors such as the beta-lactamase promoter (Villa-Kamaroff et al., 1978, Proc. Natl. Acad. Sci. U.S.A., 75: 3727-31); or the tac promoter (DeBoer et al., 1983, Proc. Natl. Acad. Sci. U.S.A. 80: 21-25). Also available for use are the following animal transcriptional control regions, which exhibit tissue specificity and have been utilized in transgenic animals: the elastase I gene control region that is active in pancreatic acinar cells (Swift et al., 1984, Cell 38: 63946; Ornitz et al., 1986, Cold Spring Harbor Symp. Quant. Biol. 50: 399409; MacDonald, 1987, Hepatology 7: 425-515); the insulin gene control region that is active in pancreatic beta cells (Hanahan, 1985, Nature 315: 115-22); the mouse mammary tumor virus control region that is active in testicular, breast, lymphoid and mast cells (Leder et al., 1986, Cell 45: 485-95); the albumin gene control region that is active in liver (Pinkert et al., 1987, Genes and Devel. 1: 268-76); the alpha-feto-protein gene control region that is active in liver (Krumlauf et al., 1985, Mol. Cell. Biol. 5: 1639-48; Hammer et al., 1987, Science 235: 53-58); the alpha 1-antitrypsin gene control region that is active in the liver (Kelsey et al., 1987, Genes and Devel. 1: 161-71); the beta-globin gene control region that is active in myeloid cells (Mogram et al., 1985, Nature 315: 338-40; Kollias et al., 1986, Cell 46: 89-94); the myelin basic protein gene control region that is active in oligodendrocyte cells in the brain (Readhead et al., 1987, Cell 48: 703-12); the myosin light chain-2 gene control region that is active in skeletal muscle (Sani, 1985, Nature 314: 283-86); the gonadotropic releasing hormone gene control region that is active in the hypothalamus (Mason et al., 1986, Science 234: 1372-78); and most particularly the immunoglobulin gene control region that is active in lymphoid cells (Grosschedl et al., 1984, Cell 38: 647-58; Adames et al., 1985, Nature 318: 533-38; Alexander et al., 1987, Mol. Cell Biol. 7: 1436-44).

An enhancer sequence may be inserted into the vector to increase the transcription in higher eukaryotes of a nucleic acid encoding an anti-DKK1 antibody or immunologically functional fragment thereof of the present invention. Enhancers are cis-acting elements of DNA, usually about 10-300 bp in length, that act on promoters to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). An enhancer sequence from a virus also can be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a nucleic acid molecule, it is typically placed at a site 5' to the promoter.

In expression vectors, a transcription termination sequence is typically located 3' of the end of a polypeptide-coding region and serves to terminate transcription. A transcription termination sequence used for expression in prokaryotic cells typically is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes used in expression vectors encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Examples of selectable markers include the kanamycin resistance gene, the ampicillin resistance gene and the tetracycline resistance gene. A bacterial neomycin resistance gene can also be used for selection in both prokaryotic and eukaryotic host cells.

Other selection genes can be used to amplify the gene that will be expressed. Amplification is a process whereby genes that cannot in single copy be expressed at high enough levels to permit survival and growth of cells under certain selection conditions are reiterated in tandem within the chromosomes of successive generations of recombinant cells. Examples of suitable amplifiable selectable markers for mammalian cells include dihydrofolate reductase (DHFR) and promoterless thymidine kinase. In the use of these markers mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively increased, thereby permitting survival of only those cells in which the selection gene has been amplified. Under these circumstances, DNA adjacent to the selection gene, such as DNA encoding an antibody of the invention, is co-amplified with the selection gene. As a result, increased quantities of anti-DKK1 polypeptide are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, for example where glycosylation is desired in a eukaryotic host cell expression system, various presequences can be manipulated to improve glycosylation or yield. For example, the peptidase cleavage site of a particular signal peptide can be altered, or pro-sequences added, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated yet active form of the desired polypeptide, if the enzyme cuts at such area within the mature polypeptide.

Where a commercially available expression vector lacks some of the desired flanking sequences as described above, the vector can be modified by individually ligating these sequences into the vector. After the vector has been chosen and modified as desired, a nucleic acid molecule encoding an anti-DKK1 antibody or immunologically functional fragment thereof is inserted into the proper site of the vector.

The completed vector containing sequences encoding the inventive antibody or immunologically functional fragment thereof is inserted into a suitable host cell for amplification and/or polypeptide expression. The transformation of an expression vector for an anti-DKK1 antibody immunologically functional fragment thereof into a selected host cell may be accomplished by well-known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan.

The transformed host cell, when cultured under appropriate conditions, synthesizes an anti-DKK1 antibody or functional fragment thereof that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (ATCC), such as Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, the best cell line for expressing a particular DNA construct may be selected by testing various cell lines to determine which ones have the highest levels of expression levels and produce antibodies with constitutive DKK1 binding properties.

In certain embodiments, the invention also provides compositions comprising the subject anti-DKK1 antibodies or immunologically functional fragments thereof together with one or more of the following: a pharmaceutically acceptable diluent; a carrier; a solubilizer; an emulsifier; a preservative; and/or an adjuvant. Such compositions may contain an effective amount of the anti-DKK1 antibody or immunologically functional fragment thereof. Thus, the use of the antibodies and immunologically active fragments that are provided herein in the preparation of a pharmaceutical composition or medicament is also included. Such compositions can be used in the treatment of a variety of diseases such as listed below in the section on exemplary utilities.

Acceptable formulation components for pharmaceutical preparations are nontoxic to recipients at the dosages and concentrations employed. In addition to the antibodies and immunologically functional fragments that are provided, compositions according to the invention may contain components for modifying, maintaining or preserving, for example, the pH, osmolarity, viscosity, clarity, color, isotonicity, odor, sterility, stability, rate of dissolution or release, adsorption or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see Remington's Pharmaceutical Sciences, 18th Edition, (A. R. Gennaro, ed.), 1990, Mack Publishing Company), hereby incorporated by reference.

The primary vehicle or carrier in a pharmaceutical composition may be either aqueous or non-aqueous in nature. Suitable vehicles or carriers for such compositions include water for injection, physiological saline solution or artificial cerebrospinal fluid, possibly supplemented with other materials common in compositions for parenteral administration. Neutral buffered saline or saline mixed with serum albumin are further exemplary vehicles. Compositions comprising anti-DKK1 antibodies or immunologically functional fragments thereof may be prepared for storage by mixing the selected composition having the desired degree of purity with optional formulation agents in the form of a lyophilized cake or an aqueous solution. Further, the anti-DKK1 antibodies or immunologically functional fragments thereof may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

A pharmaceutical composition may involve an effective quantity of anti-DKK1 antibodies or immunologically functional fragments thereof in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert materials, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions are in the form of sustained- or controlled-delivery formulations. Techniques for formulating a variety of other sustained- or controlled-delivery means, such as liposome carriers, bioerodible microparticles or porous beads and depot injections can be used (see, for e.g., PCT/US93/00829, which describes the controlled release of porous polymeric microparticles for the delivery of pharmaceutical compositions). Sustained-release preparations may include semipermeable polymer matrices in the form of shaped articles, e.g. films, or microcapsules, polyesters, hydrogels, polylactides (U.S. Pat. No. 3,773,919 and EP 058,481), copolymers of L-glutamic acid and gamma ethyl-L-glutamate (Sidman et al., 1983, Biopolymers 22: 547-556), poly (2-hydroxyethyl-methacrylate) (Langer et al., 1981, J Biomed Mater Res 15: 167-277) and Langer, 1982, Chem Tech 12: 98-105), ethylene vinyl acetate (Langer et al., ibid.) or poly-D(-)-3-hydroxybutyric acid (EP 133,988). Sustained release compositions may also include liposomes, which can be prepared by any of several methods known in the art. See e.g., Eppstein et al., 1985, Proc. Natl. Acad. Sci. USA 82: 3688-3692; EP 036,676; EP 088,046 and EP 143,949.

The pharmaceutical composition to be used for in vivo administration typically is sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The present invention provides kits for producing a multi-dose or single-dose administration units. For example, kits according to the invention may each contain both a first container having a dried protein and a second container having an aqueous diluent, including for example single and multi-chambered pre-filled syringes (e.g., liquid syringes, lyosyringes or needle-free syringes).

The pharmaceutical compositions of the invention can be delivered parenterally, typically by injection. Injections can be intraocular, intraperitoneal, intraportal, intramuscular, intravenous, intrathecal, intracerebral (intra-parenchymal), intracerebroventricular, intraarterial, intralesional, perilesional or subcutaneous. Eye drops can be used for intraocular administration. In some instances, injections may be localized to the vicinity of a particular bone or bones to which the treatment is targeted. For parenteral administration, the antibodies may be administered in a pyrogen-free, parenterally acceptable aqueous solution comprising the desired anti-DKK1 antibodies or immunologically functional fragments thereof in a pharmaceutically acceptable vehicle. A particularly suitable vehicle for parenteral injection is sterile distilled water in which the anti-DKK1 antibodies or immunologically functional fragments thereof are formulated as a sterile, isotonic solution, properly preserved.

Pharmaceutical compositions comprising the subject anti-DKK1 antibodies and functional fragments thereof may be administered by bolus injection or continuously by infusion, by implantation device, sustained release systems or other means for accomplishing prolonged release. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous release. The preparation may be formulated with agent, such as injectable microspheres, bio-erodible particles, polymeric compounds (such as polylactic acid; polyglycolic acid; or copoly (lactic/glycolic) acid (PLGA), beads or liposomes, that can provide controlled or sustained release of the product which may then be delivered via a depot injection. Formulation with hyaluronic acid has the effect of promoting sustained duration in the circulation.

The subject compositions comprising an anti-DKK1 antibody or functional fragment thereof may be formulated for inhalation. In these embodiments, an anti-DKK1 antibody is formulated as a dry powder for inhalation, or anti-DKK1 antibody inhalation solutions may also be formulated with a propellant for aerosol delivery, such as by nebulization. Pulmonary administration is further described in PCT/US94/001875, which describes pulmonary delivery of chemically modified proteins, and which is hereby incorporated by reference.

Certain pharmaceutical compositions of the invention can be delivered through the digestive tract, such as orally. The subject anti-DKK1 antibodies or immunologically functional fragments thereof that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized. Additional agents can be included to facilitate absorption of the anti-DKK1 antibody or functional fragment thereof. For oral administration, modified amino acids may be used to confer resistance to digestive enzymes. Diluents, flavorings, low melting point waxes, vegetable oils, lubricants, suspending agents, tablet disintegrating agents, and binders may also be employed.

The subject compositions comprising anti-DKK1 antibodies or immunologically functional fragments thereof also may be used ex vivo. In such instances, cells, tissues or organs that have been removed from the patient are exposed to or cultured with the anti-DKK1 antibody. The cultured cells may then be implanted back into the patient or a different patient or used for other purposes.

In certain embodiments, anti-DKK1 antibodies or immunologically functional fragments thereof can be delivered by implanting certain cells that have been genetically engineered, using methods such as those described herein, to express and secrete the polypeptide. Such cells may be animal or human cells, and may be autologous, heterologous, or xenogenic, or may be immortalized. In order to decrease the chance of an immunological response, the cells may be encapsulated to avoid infiltration of surrounding tissues. Encapsulation materials are typically biocompatible, semi-permeable polymeric enclosures or membranes that allow the release of the protein product(s) but prevent the destruction of the cells by the patient's immune system or by other detrimental factors from the surrounding tissues.

Dosage

The pharmaceutical compositions that are provided can be administered for prophylactic and/or therapeutic treatments. An "effective amount" refers generally to an amount that is a sufficient, but non-toxic, amount of the active ingredient (i.e., an anti-DKK1 antibody or immunologically functional fragment thereof) to achieve the desired effect, which is a reduction or elimination in the severity and/or frequency of symptoms and/or improvement or remediation of damage. A "therapeutically effective amount" refers to an amount that is sufficient to remedy a disease state or symptoms, or otherwise prevent, hinder, retard or reverse the progression of a disease or any other undesirable symptom. A "prophylactically effective amount" refers to an amount that is effective to prevent, hinder or retard the onset of a disease state or symptom.

In general, toxicity and therapeutic efficacy of the antibody or fragment can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred.

The data obtained from cell culture and/or animal studies can be used in formulating a range of dosages for humans. The dosage of the active ingredient typically lines within a range of circulating concentrations that include the ED50 with little or no toxicity. The dosage can vary within this range depending upon the dosage form employed and the route of administration utilized.

The effective amount of a pharmaceutical composition comprising anti-DKK1 antibodies or immunologically functional fragments thereof to be employed therapeutically or prophylactically will depend, for example, upon the therapeutic context and objectives. One skilled in the art will appreciate that the appropriate dosage levels for treatment, according to certain embodiments, will thus vary depending, in part, upon the molecule delivered, the indication for which the anti-DKK1 antibody is being used, the route of administration, and the size (body weight, body surface or organ size) and/or condition (the age and general health) of the patient. A clinician may titer the dosage and modify the route of administration to obtain the optimal therapeutic effect. Typical dosages range from about 0.1 µg/kg to up to about 100 mg/kg or more, depending on the factors mentioned above. In certain embodiments, the dosage may range from 0.1 µg/kg up to about 150 mg/kg; or 1 µg/kg up to about 100 mg/kg; or 5 µg/kg up to about 50 mg/kg.

The dosing frequency will depend upon the pharmacokinetic parameters of the anti-DKK1 antibody or immunologically functional fragment thereof in the formulation. For example, a clinician will administer the composition until a dosage is reached that achieves the desired effect. The composition may therefore be administered as a single dose, or as two or more doses (which may or may not contain the same amount of the desired molecule) over time, or as a continuous infusion via an implantation device or catheter. Treatment may be continuous over time or intermittent. Further refinement of the appropriate dosage is routinely made by those of ordinary skill in the art and is within the ambit of tasks routinely performed by them. Appropriate dosages may be ascertained through use of appropriate dose-response data.

To treat a medical disorder by targeting DKK1, a composition comprising the subject anti-DKK1 antibodies or immunologically functional fragments thereof may be administered to the patient in an amount and for a time sufficient to induce a sustained improvement in at least one indicator that reflects the severity of the disorder. An improvement is considered "sustained" if the patient exhibits the improvement on at least two occasions separated by at least one to seven days, or in some instances one to six weeks. The appropriate interval will depend to some extent on what disease condition is being treated; it is within the purview of the skilled physician to determine the appropriate interval for determining whether the improvement is sustained. The degree of improvement is determined based on signs or symptoms, and may also employ questionnaires that are administered to the patient, such as quality-of-life questionnaires.

Various indicators that reflect the extent of the patient's illness may be assessed for determining whether the amount and time of the treatment is sufficient. The baseline value for the chosen indicator or indicators is established by examination of the patient prior to administration of the first dose of antibody. Preferably, the baseline examination is done within about 60 days of administering the first dose. If the antibody is being administered to treat acute symptoms, such as for example to treat a broken bone, the first dose is administered as soon as practically possible after the injury has occurred.

Improvement is induced by administering the subject anti-DKK1 antibodies or immunologically functional fragments thereof until the patient manifests an improvement over baseline for the chosen indicator or indicators. In treating chronic conditions, this degree of improvement is obtained by repeatedly administering this medicament over a period of at least a month or more, e.g., for one, two, or three months or longer, or indefinitely. A period of one to six weeks, or even a single dose, often is sufficient for treating acute conditions. For injuries or acute conditions, a single dose may be sufficient.

Although the extent of the patient's illness after treatment may appear improved according to one or more indicators, treatment may be continued indefinitely at the same level or at a reduced dose or frequency. Once treatment has been reduced or discontinued, it later may be resumed at the original level if symptoms should reappear.

The subject anti-DKK1 antibodies and immunologically functional fragments thereof can be used to detect DKK1 in biological samples. Such uses allow the identification of cells or tissues that produce the protein or serve as a diagnostic for detecting pathological conditions in which DKK1 is overproduced or underproduced. The antibodies and fragments that are provided can also be used in methods to screen for a molecule that binds to DKK1. A variety of competitive screening methods, for example, can be used. In some methods, a DKK1 molecule or fragment thereof to which an anti-DKK1 antibody binds, is contacted with an antibody or fragment disclosed herein together with another molecule (i.e., a candidate molecule). A reduction in binding between the antibody or fragment and DKK1 is an indication that the molecule binds DKK1. Binding of the antibody or fragment can be detected using a variety of methods, e.g., an ELISA. Detection of binding between the anti-DKK1 antibody or fragment to DKK1 can be simplified by detectably labeling the antibody. In some methods, a molecule that exhibits binding in the initial screen is further analyzed to determine whether it inhibits a DKK1 activity (e.g., whether the molecule activates Wnt signaling).

Activity of a DKK1 inhibitor or a sclerostin inhibitor or combinations (e.g., respective binding agents) may be measured in a variety of ways. Binding agent-mediated increases in bone mineral content or bone density may be measured using single- and dual-energy X-ray absorptometry, ultrasound, computed tomography, radiography, and magnetic resonance imaging. The amount of bone mass may also be calculated from body weights or by using other methods (see Guinness-Hey, Metab. Bone Dis. Relat. Res., 5:177-181 (1984)). Animals and particular animal models are used in the art for testing the effect of the pharmaceutical compositions and methods on, for example, parameters of bone loss, bone resorption, bone formation, bone strength, or bone mineralization that mimic conditions of human disease such as osteoporosis and osteopenia. Examples of such models include the ovariectomized rat model (Kalu, Bone and Mineral, 15:175-192 (1991); Frost and Jee, Bone and Mineral, 18:227-236 (1992); and Jee and Yao, J. Musculoskel. Neuron. Interact., 1:193-207 (2001)). The methods for measuring binding agent activity described herein also may be used to determine the efficacy of other inhibitors.

In humans, bone mineral density can be determined clinically using dual x-ray absorptiometry (DXA) of, for example, the hip and spine. Other techniques include quantitative computed tomography (QCT), ultrasonography, single-energy x-ray absorptiometry (SXA), and radiographic absorptiometry. Common central skeletal sites for measurement include the spine and hip; peripheral sites include the forearm, finger, wrist and heel. Except for ultrasonography, the American Medical Association notes that BMD techniques typically involve the use of x-rays and are based on the principle that attenuation of the radiation depends on thickness and composition of the tissues in the radiation path. All techniques involve the comparison of results to a normative database.

Alternatively, a physiological response to one or more binding agents can be gauged by monitoring bone marker levels. Bone markers are products created during the bone remodeling process and are released by bone, osteoblasts, and/or osteoclasts. Fluctuations in bone resorption and/or bone formation "marker" levels imply changes in bone remodeling/modeling. The International Osteoporosis Foundation (IOF) recommends using bone markers to monitor bone density therapies (see, e.g., Delmas et al., Osteoporos Int., Suppl. 6:S2-17 (2000), incorporated herein by reference). Markers indicative of bone resorption (or osteoclast activity) include, for example, C-telopeptide (e.g., C-terminal telopeptide of type 1 collagen (CTX) or serum cross-linked C-telopeptide), N-telopeptide (N-terminal telopeptide of type 1 collagen (NTX)), deoxypyridinoline (DPD), pyridinoline, urinary hydroxyproline, galactosyl hydroxylysine, and tartrate-resistant acid phosphatase (e.g., serum tartrate-resistant acid phosphatase isoform 5b). Bone formation/mineralization markers include, but are not limited to, bone-specific alkaline phosphatase (BSAP), peptides released from N- and C-terminal extension of type I procollagen (P1NP, PICP), and osteocalcin (OstCa). Several kits are commercially-available to detect and quantify markers in clinical samples, such as urine and blood.

Upon administration, a therapeutic agent preferably reduces the level of one or more markers of bone resorption, such as the serum level of C-telopeptide of type I collagen (CTX). Accordingly, the invention further provides a method of monitoring therapy, i.e., the physiological response to a sclerostin binding agent or other sclerostin inhibitor. The method comprises administering a therapeutic, then measuring the level of one or more markers of bone resorption. In addition, the method can comprise measuring the level of one or more markers of bone formation before administration. The level of bone resorption marker during and/or after treatment may be compared to a pre-treatment level, or alternatively may be compared to a standard range typical of that patient population. One of ordinary skill in the art can readily determine a suitable standard range by testing a representative number of patients of like age, gender, disease level, and/or other characteristics of the patient population. The level of bone resorption marker can be reduced by at least about 5% (e.g., about 10%, about 20%, or about 30%) by a single dose of therapeutic. In some embodiments, the dose of therapeutic reduces the level of bone resorption marker at least about 40% (e.g., about 50%, about 60%, or about 70%) compared to the level of the bone resorption marker prior to administering. In addition, the bone resorption marker level may be reduced for at least about 3 days (e.g., about 7 days, about 2 weeks, about 3 weeks, about 1 month, about 5 weeks, about 6 weeks, about 7 weeks, about 2 months, about 9 weeks, about 10 weeks, about 11 weeks, or about 3 months) after administration of a single dose.

In addition to decreasing the level of bone resorption markers, the amount of therapeutic administered to a patient also can increase the level of one or more markers of bone formation, such as the serum level of BSAP, the serum level of P1NP, and/or the serum level of OstCa. A single dose of therapeutic can increase the level of a bone formation marker by, for example, at least about 5% (e.g., about 10%, about 20%, or about 30%). In some embodiments, the dose of therapeutic elevates the level of a bone formation marker at least about 40% (e.g., about 50%, about 60%, or about 70%). In other embodiments, the dose of therapeutic increases the level of one or more bone formation markers by at least about 75% (e.g., about 80%, about 90%, about 100%, or about 110%). In yet other embodiments, the dose of therapeutic increases the level of a bone formation marker by at least about 120% (e.g., about 130%, about 140%, about 150%, about 160% or about 170%). In alternative embodiments, the therapeutic increases the level of bone formation marker by least about 180% (e.g., about 190% or about 200%). Bone formation marker levels ideally remain elevated (compared to bone formation marker levels pre-treatment or to a standard range typical of that patient population) for at least about 3 days (e.g., about 7 days, about 2 weeks, about 3 weeks, about 1 month, about 5 weeks, about 6 weeks, about 7 weeks, about 2 months, about 9 weeks, about 10 weeks, about 11 weeks, or about 3 months) after administration of a single dose of the therapeutic.

Typically, BMD is can be measured "total body" (e.g., head, trunk, arms, and legs) or at the hip (e.g., total hip and/or femoral neck), spine (e.g., lumbar spine), wrist, finger, shin bone and/or heel. In osteoporosis diagnosis, a patient's BMD is compared to the peak density of a 30-year old healthy adult (i.e., a "young adult"), creating the so-called "T-score." A patient's BMD also may be compared to an "age-matched" bone density (see, e.g., World Health Organization Scientific Group on the Prevention and Management of Osteoporosis, "Prevention and management of osteoporosis: report of a WHO scientific group." WHO Technical Report Series; 921, Geneva, Switzerland (2000)). The difference between a patient's BMD and that of a healthy, young adult is conventionally referred to in terms of the multiple of a "standard deviation," which typically equals about 10% to about 12% decrease in bone density. The World Health Organization proposed four diagnostic categories based on BMD T-scores. A BMD value within 1 standard deviation of the young adult reference mean (T-score≤-1) is "normal." Low bone mass (osteopenia) is indicated by a BMD value more than 1 standard deviation below the young adult mean, but less than 2 standard deviations (T-score<-1 and >-2.5). A T-score of more than 2.5 standard deviations below the norm supports a diagnosis of osteoporosis. If a patient additionally suffers from one or more fragility fractures, the patient qualifies as having severe osteoporosis.

The therapeutic may be administered to a patient to improve bone mineral density regardless of the patient's T-score. The therapeutic may be administered at a dose and for a time period effective to increase BMD in the patient by at least about 1% (about 2%, about 3%, about 4%, about 5%, or about 6%). In some embodiments, BMD is increased by at least about 8% (e.g., at least about 10%, about 12%, about 15%, or about 18%). In other embodiments, BMD is increased by the therapeutic at least about 20% (e.g., at least about 22%, about 25%, or about 28%) at the hip, spine, wrist, finger, shin bone, and/or heel. In yet other embodiments, BMD is increased at least about 30% (e.g., at least about 32%, about 35%, about 38%, or about 40%). In other words, the BMD can be increased to the range of about 1 to about 2.5 standard deviations (preferably a range of about 0 to about 1 standard deviations) below the normal BMD of a healthy young adult.

Alterations in bone remodeling or modeling can lead to fluctuations in mineral concentrations throughout the body. Bone is one of the principal regulators of calcium levels in the bloodstream. Osteoclast-mediated bone resorption releases stored calcium into the systemic circulation, while osteoblast-mediated bone formation removes calcium from circulation to incorporate into bone tissue. In normal bone modeling/remodeling, these processes cycle to maintain healthy, strong bone and maintain free calcium levels at about 8.5 mg/dL to about 10.5 mg/dL (e.g., about 2.2 mmol/L to about 2.6 mmol/L). Bone disorders, other illnesses, and even certain therapies can disrupt systemic calcium levels with dire consequences. Hypercalcemia is associated with high levels of calcium in the blood (e.g., greater than 12 mg/dL or 3 mmol/L). Extraordinarily high calcium levels leads to, for example, fatigue, confusion, constipation, decreased appetite, frequent urination, heart problems, and bone pain. Hypocalcemia is an electrolyte imbalance indicated by an abnormally low level of calcium in the blood (e.g., less than about 9 mg/dL or 2.2 mmol/L). Calcium levels of <7.5 mg/dL (<1.87 mmol/L) or less are considered severe hypocalcemia and may be accompanied by clinical symptoms.

Methods of Treatment and Uses

The inventive methods are useful for treating or preventing bone-related disorders, such as bone-related disorders associated with abnormal osteoblast or osteoclast activity. Indeed, the therapeutics of the present invention can be administered to a human suffering from a bone related disorder selected from the group consisting of achondroplasia, cleidocranial dysostosis, enchondromatosis, fibrous dysplasia, Gaucher's Disease, hypophosphatemia, X-linked hypophosphatemic rickets, Marfan's syndrome, multiple hereditary exotoses, neurofibromatosis, osteogenesis imperfecta, osteopetrosis, osteopoikilosis, sclerotic lesions, pseudoarthrosis, pyogenic osteomyelitis, periodontal disease, anti-epileptic drug induced bone loss, primary and secondary hyperparathyroidism, familial hyperparathyroidism syndromes, weightlessness induced bone loss, osteoporosis in men, postmenopausal bone loss, spinal fusion, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, Fabry Disease, Turner Syndrome, Down Syndrome, Klinefelter Syndrome, leprosy, Perthe's Disease, adolescent idiopathic scoliosis, infantile onset multi-system inflammatory disease, Winchester Syndrome, Menkes Disease, Wilson's Disease, ischemic bone disease (such as Legg-Calve-Perthes disease and regional migratory osteoporosis), anemic states, conditions caused by steroids, glucocorticoid-induced bone loss, heparin-induced bone loss, bone marrow disorders, scurvy, malnutrition, calcium deficiency, osteoporosis, osteopenia, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, chemotherapy-associated bone loss, tumor-induced bone loss, cancer-related bone loss, hormone ablative bone loss, multiple myeloma, drug-induced bone loss, anorexia nervosa, disease-associated facial bone loss, disease-associated cranial bone loss, disease-associated bone loss of the jaw, disease-associated bone loss of the skull, bone loss associated with aging, facial bone loss associated with aging, cranial bone loss associated with aging, jaw bone loss associated with aging, skull bone loss associated with aging, and bone loss associated with space travel.

The inventive methods need not cure the patient of the disorder or completely protect against the onset of a bone-related disorder to achieve a beneficial biological response. The methods may be used prophylactically, meaning to protect, in whole or in part, against a bone-related disorder or symptom thereof. The methods also may be used therapeutically to ameliorate, in whole or in part, a bone-related disorder or symptom thereof, or to protect, in whole or in part, against further progression of a bone-related disorder or symptom thereof. Indeed, the materials and methods of the invention are particularly useful for increasing bone mineral density and maintaining the increased BMD over a period of time. In this regard, the invention provides a method of treating a bone-related disorder, which method comprises (a) administering one or more amounts of a sclerostin binding agent effective to increase BMD measured for the total body (e.g., head, trunk, arms, and legs) or at the hip (e.g., total hip and/or femoral neck), spine (e.g., lumbar spine), wrist, finger, shin bone and/or heel by about 1%, about 2%, about 3%, about 6%, about 8%, about 10%, about 12%, about 15%, about 18%, about 20%, about 25%, or 30% or more. One or more administrations of a pharmaceutical composition comprising the sclerostin binding agent may be carried out over a therapeutic period of, for example, about 1 month to about 18 months (e.g., about 2 months, about 3 months, about 4 months, about 5 months, about 6 months, about 7 months, about 8 months, about 9 months, about 10 months, or about 11 months). The method further includes (b) subsequently administering one or more amounts of a sclerostin binding agent effective to maintain bone mineral density. By "maintain bone mineral density" is meant that the increased BMD resulting from step (a) does not fall more than about 1% to about 5% over the course of step (b) (e.g., about 6 months, about 9 months about 1 year, about 18 months, about 2 years, or over the course of the patient's life). It will be appreciated that a patient can require alternate treatment phases for increasing bone density and maintaining bone density.

It is contemplated that the therapeutic use of DKK1 inhibitors, as described herein, alone or in combination with another anabolic agent, e.g., a sclerostin inhibitor such as a neutralizing antibody, is beneficial to any condition requiring bone repair whether it is aggravated by an underlying bone loss condition or not. Particular examples of bone repair that are not always associated with bone loss include fracture repair such as delayed healing or nonunion healing. Thus, one of skill in the art will understand that certain indications described herein may or may not be exacerbated by bone loss associated with, for example, osteoporosis, or any other bone loss condition described herein. Thus in further embodiments it is contemplated that compositions of the present invention are useful for improving outcomes in orthopedic procedures, periodontal diseases, oral bone loss, dental procedures, dental implants, implant surgery, joint replacement, bone grafting, bone cosmetic surgery and bone repair such as fracture healing, spinal fusion, implant fixation (e.g., joint replacement such as hip or knew), nonunion healing, delayed union healing and facial reconstruction. One or more compositions may be administered before, during and/or after the procedure, replacement, graft, surgery or repair.

In another aspect, the use of the foregoing therapeutic modalities including antibodies or immunologically functional fragments in the treatment of a variety of diseases is disclosed. Certain methods, for instance, involve administering to a patient in need thereof an effective amount of an antibody or immunologically active fragment as described herein to treat arthritis, diseases responsive to stem cell renewal, inflammatory diseases, neurological diseases, ocular diseases, renal diseases, pulmonary diseases, and skin diseases. Some treatment methods involve treating rheumatoid arthritis, psoriatic arthritis or osteoarthritis. Certain antibodies and fragments are used to treat a disease that: (a) is responsive to stem cell renewal and is selected from the group consisting of diabetes, chronic heart failure and diseases of the muscle; (b) is an inflammatory disease selected from the group consisting of Crohn's disease, colitis, and inflammatory bowel disease; (c) is a neurological disease selected from the group consisting of Alzheimer's disease, Parkinson's disease, and Huntington's disease; (d) is an ocular disease selected from the group consisting of macular degeneration and retinopathies; (e) is a renal disease selected from the group consisting of end stage renal disease, chronic renal disease, glomerulonephritis, tubulointerstitial nephritis, and IgA nephropathy; (f) is a pulmonary disease selected from the group consisting of chronic obstructive pulmonary disease, idiopathic pulmonary fibrosis, and cystic fibrosis; or (g) is a skin disease resulting from chemotherapy-induced damage to the intestinal epithelium.

Sclerostin inhibitors, e.g., sclerostin binding agents, have been shown to promote bone formation and inhibit (or slow) bone resorption with minimal fluctuations in systemic calcium levels (e.g., calcium levels fluctuate 10% or less from baseline serum calcium levels). Thus it presents itself as a possible partner therapeutic with the DKK1 inhibitors presented herein to increase therapeutic responsiveness.

Several ailments and pharmaceutical therapies alter system calcium levels, and thereby impact bone density in a negative way and as such therapeutics of the current invention are useful, including combinations thereof, to treat bone loss in these conditions. Hypercalcemia and hypocalcemia can result from, for example, chronic kidney disease, renal diseases, renal failure, primary or secondary hyperparathyroidism, pseudohyperparathyroidism, hypoparathyroidism, pseudohypoparathyroidism, magnesium depletion, alcoholism, bisphosphonate therapy, severe hypermagnesemia, vitamin D deficiency, hyperphosphatemia, acute pancreatitis, hungry bone syndrome, chelation, osteoblastic metastases, sepsis, surgery, chemotherapy, neoplasia syndrome, familial hypocalciuric hypercalcemia, sarcoidosis, tuberculosis, berylliosis, histoplasmosis, Candidiasis, Coccidioidomycosis, histiocytosis X, Hodgkin's or Non-Hodgkin's lymphoma, Crohn's disease, Wegener's granulomatosis, leukemia, pneumonia, silicone-induced granulomas, immobilization, or drug therapy, such as administration of thiazide diuretics, lithium, estrogens, fluorides, glucose, and insulin. In addition, serum calcium fluctuations are a side effect of many existing bone-related therapies, such as bisphosphonate and parathyroid hormone therapy. Because of the potentially life-threatening consequences of calcium imbalance, patients susceptible to hypocalcemia or hypercalcemia may need to forego certain therapy options.

Accordingly, the materials and method of the invention, particularly combinations, are advantageous in treating patients that are susceptible or sensitive to unstable calcium levels. The amount of sclerostin binding agent administered to a human in the context of this aspect of the invention is an amount that does not result in hypocalcemia or hypercalcemia (e.g., clinically-significant hypocalcemia or hypercalcemia). In addition, the invention provides a method of treating a bone-related disorder in a human suffering from or at risk of hypocalcemia or hypercalcemia or a human in which treatment with bisphosphonate, a parathyroid hormone, or parathyroid hormone analog is contraindicated. The method comprises administering to the human an amount of a sclerostin binding agent effective to increase the level of a marker of bone formation, such as serum levels of BSAP, P1NP, and/or OstCa and/or reduce the level of a marker of bone resorption, such as CTX.

Further provided herein are methods of treating or preventing loss of bone mass comprising administering to a patient in need thereof a therapeutically effective amount of an antibody comprising a variable region selected from SEQ ID NOs: 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94 and 96, or immunologically functional fragment thereof as described herein (e.g., an antibody or immunologically functional fragment that comprises at least one light chain CDR selected from the group consisting of SEQ ID NOs: 97 to 227 and 228. In one aspect of this embodiment, the patient is one who suffers from cancer that metastasizes to bone, and in another aspect, the patient is one who suffers from multiple myeloma. One of skill in the art will appreciate that these compositions, alone or in combination with one or more other therapeutics, can be useful for the formulation of a medicament. Antibodies of the present invention are suitable for treatment of bone related disorders. The antibody depicted in SEQ ID NOs: 42 and 44 for use in treatment of bone fracture. The antibody depicted in SEQ ID NOs: 42 and 44 for use in treatment of gap union defects. The antibody depicted in SEQ ID NOs: 42 and 44 in combination with an inhibitory sclerostin antibody for use in treatment of bone fracture. The antibody depicted in SEQ ID NOs: 42 and 44 in combination with an inhibitory sclerostin antibody for use in treatment of gap union defects. It is understood that the term 'bone fracture' is meant to include one or more fractures in a patient in need of treatment.

Particular conditions which may be treated by the compositions of the present invention include dysplasias, wherein growth or development of bone is abnormal. Representative examples of such conditions include achondroplasia, cleidocranial dysostosis, enchondromatosis, fibrous dysplasia, Gaucher's Disease, Marfan's syndrome, multiple hereditary exotoses, neurofibromatosis, osteogenesis imperfecta, osteopetrosis, osteopoikilosis, sclerotic lesions, pseudoarthrosis, and pyogenic osteomyelitis.

Other conditions that may be treated or prevented include a wide variety of causes of osteopenia, osteoporosis and bone loss. Representative examples of such conditions include periodontal disease, anti-epileptic drug induced bone loss, primary and secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell disease, ischemic bone disease (such as Legg-Calve-Perthes disease, regional migratory osteoporosis), anemic states, conditions caused by steroids, glucocorticoid-induced bone loss, heparin-induced bone loss, bone marrow disorders, scurvy, malnutrition, calcium deficiency, idiopathic osteopenia or osteoporosis, congenital osteopenia or osteoporosis, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, fibrous dysplasia, chemotherapy associated bone loss, tumor induced bone loss, cancer-related bone loss, hormone ablative bone loss, multiple myeloma, drug-induced bone loss, anorexia nervosa, disease associated facial bone loss, disease associated cranial bone loss, disease associated bone loss of the jaw, disease associated bone loss of the skull, and bone loss associated with space travel. Further conditions relate to bone loss associated with aging, including facial bone loss associated with aging, cranial bone loss associated with aging, jaw bone loss associated with aging, and skull bone loss associated with aging.

As permitted in certain national jurisdictions, references disclosed herein are hereby incorporated by reference in their entireties as if each was incorporated individually, for any purpose including enabling and describing the invention. The following examples are provided solely to illustrate certain aspects of the antibodies, fragments and compositions that are provided herein and thus should not be construed to limit the scope of the claimed invention.

EXAMPLES

Example 1

Preparation of the Human DKK1 (huDKK1) Immunogen

The cloning of human DKK1 was as described in U.S. Pat. No. 6,344,541 with the following modifications. Two different epitope tagged versions of human DKK1 were used as an immunogen, one contained the FLAG epitope and the other was an fc-fusion molecule. Both epitope tags were appended to the carboxy-terminus of human DKK1 using standard molecular biology techniques obvious to those skilled in the art.

The epitope tagged versions of human DKK1 were cloned into an expression vector for expression in CHO cells. Human DKK1 variants containing either the FLAG or Fc epitopes were purified from conditioned medium for use as an antigen to generate anti-huDKK1 antibodies. Epitope-tagged huDKK1 was purified from concentrated conditioned media (CM). Other protein production and purification procedures known to those skilled in the art may also be used.

Example 2

Immunization and Titering

Recombinant FLAG-tagged human DKK1 (FLAG-DKK1) and recombinant Fc-tagged human DKK1 (DKK1-fc) were used as antigens. Monoclonal antibodies against DKK1 were developed by sequentially immunizing Xeno-Mouse® mice (Abgenix, Inc. Fremont, Calif.) (see, e.g., U.S. Pat. No. 7,435,871 and the description therein). Xeno-Mouse animals were immunized via footpad route for all injections. Anti-DKK antibody titers in the serum from immunized XenoMouse mice were determined by ELISA.

Example 3

Recovery of Lymphocytes, B-Cell Isolations, Fusions and Generation of Hybridomas Lymph nodes were harvested and pooled from each cohort. The total effluent was collected as the CD90-negative fraction (most of these cells were expected to be B cells). The fusion was performed by mixing washed enriched B cells from above and nonsecretory myeloma P3X63Ag8.653 cells purchased from ATCC, catalogue CRL 1580 (Kearney et al, J. Immunol. 123, 1979, 1548-1550) at a ratio of 1:1. Electro-cell fusion (ECF) was performed using a fusion generator, model ECM2001, Genetronic, Inc., San Diego, Calif. The fusion chamber size used was 2.0 mL After ECF, the cell suspensions were carefully removed from the fusion chamber under sterile conditions and transferred into a sterile tube containing the same volume of Hybridoma Culture Medium (DMEM (JRH Biosciences)). The cells were incubated and then centrifuged. The cells were resuspended in a small volume of Hybridoma Selection Medium (Hybridoma Culture Medium supplemented with 0.5× HA (Sigma, catalogue A9666)), and the volume was adjusted appropriately with more Hybridoma Selection Medium. The cells were mixed gently and pipetted into 96-well plates and allowed to grow.

Example 4

After sufficient culture, hybridoma supernatants were screened for DKK1-specific monoclonal antibodies. In the Primary screen, the ELISA plates were coated with 50 µL/well of Flag tagged rhDKK1 (2 µg/mL) then incubated at 4° C. overnight. After incubation, the plates were washed with Washing Buffer three times and then 200 µL/well Blocking Buffer were added and the plates were incubated at room temperature. After incubation, the plates were washed with Washing Buffer three times. Aliquots (50 µL/well) of hybridoma supernatants and positive and negative controls were added, and the plates incubated at room temperature for 2 h.

After incubation, the plates were washed with washing buffer. Fifty µL/well of detection antibody was added and the plates incubated at room temperature for 1 hour. After incubation, the plates were washed three times with Washing Buffer and then 50 µL/well of TMB was added, and the plates were allowed to develop for approximately 10 minutes (until negative control wells barely started to show color). 50 µL/well stop solution was then added and the plates were read on an ELISA plate reader at a wavelength of 650 nm. The cutoff point OD was set at two-fold above the OD of the negative control.

The old culture supernatants from the positive hybridoma cells growth wells based on primary screen were removed completely and the DKK1 positive hybridoma cells were suspended with fresh hybridoma culture medium and transferred to 24-well plates. After 2 days a secondary confirmation screen was conducted where the positive hybridomas in the first screening were confirmed in Flag tagged rhDKK1 coated ELISA (described as above) and Flag tagged irrelevant antigen coated ELISA. Three sets of detection system for antigen coated ELISA, one set for hIgG detection, one set for human Ig kappa light chain detection and the other set for human lambda light chain detection in order to demonstrate fully human composition for both IgG and Ig kappa or IgG and Ig lambda or IgG and Ig kappa plus lambda. Only hIgG detection was used for irrelevant antigen coated ELISA. The three sets of antigen coated ELISA procedures were identical to the descriptions above except the three different detection antibodies were used separately. Final selection was based on a positive signal on antigen and a negative signal on irrelevant antigen.

The human IgG/kappa or IgG/lambda DKK1 specific monoclonal antibodies generated are detailed in Table 2.

TABLE 2

| Cohort | XenoMouse Strain (Human Isotype) | Immunogen | Human anti-DKK1 IgG Abs | IgGκ | IgGλ |
|---|---|---|---|---|---|
| 1 | XMG4 (IgG4) | FLAG-DKK1 | 5 | 5 | N.A. |
| 2 | XMG2 (IgG2) | FLAG-DKK1 | 42 | 42 | N.A. |
| 3 | XMG2-KL (IgG2) | FLAG-DKK1 | 7 | 0 | 7 |
| 4 | XMG2-KL (IgG2) | DKK1-fc | 6 | 1 | 5 |
| 5 | XMG4-KL (IgG4) | FLAG-DKK1 | 85 | 43 | 42 |
| 6 | XMG2-KL (IgG2) | FLAG-DKK1 | 158 | 91 | 68 |
| 7 | XmG4-KL (IgG4) | FLAG-DKK1 | 41 | 19 | 23 |

Hybridomas secreting antibodies deemed to be of functional interest were single-cell cloned by limiting dilution. Screening of single-cell cloned hybridomas for DKK1 antibody was performed by ELISA as described above. Hybridoma clones were cultured in Hybridoma Culture Medium and expanded using standard tissue culture techniques to produce exhausted culture supernatant containing secreted monoclonal antibody. Freezer stocks of hybridoma clones were also generated.

Example 5

Selection of Hybridomas Producing Neutralizing Antibodies to Human DKK1 by Bioactivity The hybridomas obtained as described in Example 2 were tested utilizing a TCF/lef-luciferase reporter construct in which luciferase expression is under the control of the canonical Wnt pathway. When cells transfected with this construct are exposed to biologically active Wnt, luciferase activity is induced. The Wnt induced luciferase activity can be suppressed by adding recombinant DKK1 protein to the cells that contain this construct. For the present experiments, both Wnt3a and DKK1 first were added to the cells in amounts optimized to suppress about 80% of the Wnt-dependent luciferase expression. The further addition of an anti-DKK1 antibody with neutralizing activity to these same cells is expected to restore Wnt activity, thus resulting in increased luciferase expression. Supernatants from the hybridomas were thus tested to determine whether they were capable of restoring luciferase expression in cells transfected with the Wnt/luciferase construct. Luciferase activity was quantified as described below.

On day zero, freshly trypsinized 293T cells were plated on fibronectin-coated 96 well plates. The cells were then co-transfected with DNA encoding firefly luciferase and DNA encoding renilla luciferase. On day 1, for each well, TCF/lef-luciferase DNA and 1 ng renilla luciferase DNA in 30 µl of DMEM were mixed with Polyfect Transfection Reagent™ (Qiagen 301107) and incubated for 10 minutes at room temperature to allow formation of a PolyFect-DNA complex. Following this incubation, 100 µl of growth medium were added to the complex. Then the culture medium was removed from each well and the complex in growth medium was added to the well. The growth medium in the wells was removed three hours later and replaced with conditioned medium containing Wnt3a, recombinant human DKK1 and anti-DKK1 hybridoma conditioned medium.

After three days, the cells were washed once with PBS, and to each well were added passive lysis buffer. Plates were shaken for 20 minutes at room temperature to induce lysis. Ten µl of lysate per assay were used to perform the assay in 96 well white plates according to the manufacturer's protocol. Luminescent signals from firefly and renilla luciferases were both recorded and the ratio of those signals was used to determine the EC50 and to plot dose-response curves. First, the substrate of firefly luciferase was injected into a well with cell lysate and the luminescent signal recorded; then the substrate of renilla luciferase was injected into the same well and the resulting second luminescent signal was recorded.

The stromal cell line ST2, derived from mouse bone marrow, was used as an additional screen for isolating anti-DKK1 antibodies with neutralizing activity. In response to Wnt3a signaling, ST2 cells differentiate into osteoblasts which express the osteoblast marker protein alkaline phosphatase (ALP). The induction of ALP by Wnt3a in these cells can be blocked by adding the Wnt inhibitor DKK1 to the culture medium. ALP expression can be restored under these conditions by exposing the cells to an agent capable of neutralizing DKK1 activity, such as a neutralizing anti-DKK1 antibody.

In summary, of the hybridomas were screened in the ELISA assay, 344 bound DKK1 in the ELISA assays and 25 were positive in one or both of the neutralization assays (TCR/lef reporter assay or ST2 cell assay). The hybridomas exhibiting the best activity from each of the three campaigns are shown in table 3. As can be seen from the cellular activities of these antibodies those derived from the second (5.X.x) and third (6.X.x) campaigns, that is those generated in the KL mice, in general exhibited better cell-based activities as is evident from the lower EC50s than those generated in the first (2.X.x) campaign with the Xenomouse.

TABLE 3

| Antibody | TCF EC50 (nM) | ST2 EC50 (nM) |
|---|---|---|
| 2.20.1 | 10.67 | 34.67 |
| 2.37.1 | 40.18 | 145.33 |
| 2.4.1 | 38.59 | 17.2 |
| 2.40.1 | 1.28 | 2.47 |
| 2.41.1 | 32.07 | 89.07 |
| 2.47.1 | 60.7 | NA |
| 5.17.1 | 3.48 | 8.24 |
| 5.23.1 | 1.01 | 4.29 |
| 5.25.1 | 1.88 | 5.96 |
| 5.31.1 | 5.29 | 10.38 |
| 5.32.1 | 1.01 | 3.48 |
| 5.40.1 | 3.75 | 7.24 |
| 5.65.1 | 4.21 | 5.87 |
| 5.76.1 | 2.55 | 4.09 |
| 5.77.1 | 2.14 | 6.23 |
| 5.78.1 | 3.75 | 5.70 |
| 5.80.1 | 3.22 | 5.03 |
| 5.85.1 | 4.53 | 10.55 |
| 6.116.6 | 4.69 | 2.77 |
| 6.139.5 | 9.78 | 3.93 |
| 6.147.4 | 3.95 | 2.57 |
| 6.37.5 | 6.57 | 3.98 |

Example 6

Cloning and Sequence Analysis of Antibodies

Total RNA was prepared from anti-DKK1 hybridoma cell lines. DNA sequences were provided by Abgenix or obtained by sequencing of cloned RACE (rapid amplification of cDNA ends) PCR (polymerase chain reaction) products.

Example 7

Expression and Purification of Human Anti-huDKK1 Antibodies in CHO Cells

The anti DKK1 cell lines were created by transfecting CHO host cells with the expression plasmids pDC323-anti DKK1 kappa and pDC324 [anti-DKK1-IgG2] for 2.40.3, 6.35.5, 6.116.6 HC-IgG2 and LC-kappa using a standard electroporation procedure. After transfection of the host cell line with the expression plasmids the cells were grown in—GHT selection medium containing 4% dialysed fetal bovine serum (ds or dfFBS) for 2-3 weeks to allow for selection of the plasmid and recovery of the cells. Serum was then removed from the medium and the cells were grown in GHT selective medium until they achieved >85% viability. This pool of transfected cells was then cultured in medium containing [150-300] nM MTX followed by medium containing 500-1000 nM MTX to select for high expressing cells.

Anti-huDKK1-1 antibody expressing cell lines were expanded using aseptic cell culture techniques. Cells were inoculated into a bioreactor upon expansion and the culture fed as needed. At harvest, cells were centrifuged and conditioned media filtered. Human anti-huDKK1 antibodies were purified from conditioned medium on Protein A sepharose. Purified DKK1 antibody was buffer exchanged to the buffer of choice.

Example 8

ELISA-Based Cross Blocking Assay

Liquid volumes used in this example were those typically used in 96-well plate ELISAs (e.g. 50-200 ul/well). Ab-X and Ab-Y, in this example were assumed to have molecular weights of about 145 Kd and to have 2 DKK1 binding sites per antibody molecule. An anti-DKK1 antibody (Ab-X) was coated (e.g. 50 ul of 1 ug/ml) onto a 96-well ELISA plate for at least one hour. After this coating step the antibody solution was removed, the plate washed with wash solution and was then blocked using an appropriate blocking solution and procedures known in the art. Blocking solution was removed from the ELISA plate and a second anti-DKK1 antibody (Ab-Y), which was being tested for its ability to cross-block the coated antibody, was added in excess (e.g. 50 ul of 10 ug/ml) in blocking solution to the appropriate wells of the ELISA plate.

Following this, a limited amount (e.g. 50 ul of 10 ng/ml) of huDKK1 in blocking solution was then added to the appropriate wells and the plate was incubated for at least one hour at room temperature while shaking and the plate was then washed. An appropriate amount of a DKK1 detection reagent in blocking solution was added to the ELISA plate and incubated for at least one hour at room temperature.

The plate was then washed with wash solution and developed with an appropriate reagent. The background signal for the assay was defined as the signal obtained in wells with the coated antibody (in this case Ab-X), second solution phase antibody (in this case Ab-Y), DKK1 buffer only (i.e. no DKK1) and DKK1 detection reagents. The positive control signal for the assay was defined as the signal obtained in wells with the coated antibody (in this case Ab-X), second solution phase antibody buffer only (i.e. no second solution phase antibody), DKK1 and DKK1 detection reagents. The ELISA assay needs to be run in such a manner so as to have the positive control signal be at least 6 times the background signal.

Ab-X and Ab-Y are defined as cross-blocking if, either in format 1 or in format 2, the solution phase anti-DKK1 antibody was able to cause a reduction of between 60% and 100%, specifically between 70% and 100%, and more specifically between 80% and 100%, of the DKK1 detection signal (i.e. the amount of DKK1 bound by the coated antibody) as compared to the DKK1 detection signal obtained in the absence of the solution phase anti-DKK1 antibody (i.e. the positive control wells). It will be understood by one of skill in the art that the term 'cross block' is not intended to encompass only complete blockage of binding of the test molecule, rather it can include a range of decreased binding less than 100% as described here. In one example, an isolated antibody or fragment thereof that cross blocks the binding of antibody depicted in SEQ ID NOs: 42 and 44 to human DKK1 and/or is cross-blocked from binding to human DKK1 by the antibody depicted in SEQ ID NOs: 42 and 44. Antibodies that are cross blocked from binding human DKK1 by the binding of antibody depicted in SEQ ID NOs: 42 and 44 include those that have 60% reduction in binding to human DKK1, 70% reduction in binding to human DKK1, 80% reduction in binding to human DKK1, 90% reduction in binding to human DKK1 or 95% reduction in binding to human DKK1. Antibodies that cross block binding of human DKK1 by the binding of antibody depicted in SEQ ID NOs: 42 and 44 include those that reduce its binding by 60% in binding to human DKK1, 70% reduction in binding to human DKK1, 80% reduction in binding to human DKK1, 90% reduction in binding to human DKK1 or 95% reduction in binding to human DKK1. Antibodies that were capable of cross blocking one another are referred to herein as being in the same bin.

In the event that a tagged version of DKK1 is used in the ELISA, such as a N-terminal His-tagged DKK1 (R & D Systems, Minneapolis, Minn., USA; 2005 catalog number 1406-ST-025) then an appropriate type of DKK1 detection reagent would include an HRP labeled anti-His antibody. In addition to using N-terminal His-tagged DKK1, one could also use C-terminal His-tagged DKK1. Furthermore, various other tags and tag binding protein combinations that are known in the art could be used in this ELISA-based cross-blocking assay (e.g. HA tag with anti-HA antibodies; FLAG tag with anti-FLAG antibodies; biotin tag with streptavidin).

The human anti-huDKK1 neutralizing antibodies described herein recognize two distinct epitopes as evident by the inability of the antibodies to cross block one another. The first epitope is referred to as 11H10 that has been described previously (U.S. Pat. No. 7,709,611). The second epitope is described below and is referred to as 5.25.1 (SEQ ID NOs: 42 and 44).

Example 9

Characterization of Human DKK1 Epitopes that Bind 5.25.1 Antibody

Human DKK1 contains two disulfide-rich domains located near the N-terminus and at the end of the C-terminus, referred to here as the N- and C-terminal disulfide domains. The N-terminal disulfide domain (hereinafter, "disulfide domain 1" or "D1") contains 55 amino acids residues (amino acids 85-139 of SEQ ID NO:2) and has 10 cysteines forming 5 intramolecular disulfide bonds. The C-terminal disulfide domain (hereinafter, "disulfide domain 2", or "D2") contains 75 amino acids (amino acids 189-263 of SEQ ID NO:2) and contains 10 cysteines that also form 5 intramolecular disulfide bridges. These two disulfide domains are separated by a stretch of about 50 amino acids. Disulfide domain 2 (D2) of DKK1 has been proposed to have a molecular structure similar to the canonical colipase fold, the crystal structure of which has been determined using porcine colipase (Aravind, A. and Koonin, E. V., Current Biology 8:R477-479 (1998)). Intramolecular disulfide linkages among the 10 cysteine residues in the N-terminal D1 domain of DKK molecule have recently been determined.

Treatment with a reducing agent abolished the ability of DKK1 to bind 5.25.1, thus indicating that the epitope targeted by this antibody is conformational (or discontinous) and requires the maintenance of intact disulfide bonds in the D1 and D2 domains. To characterize this conformational epitope, a strategy was applied that involved fragmenting human DKK1 with cyanogen bromide (CNBr) and several different proteases, then analyzing the fragments and testing them for their ability to bind to the antibody. Digestion was also performed in the presence of 5.25.1 to detect those amino acid residues or sequence regions that is protected from proteolysis due to antibody binding. The resulting data permitted the location of the epitope(s) to be elucidated. In essence, the DKK1 proteolytic digestion was carried out in the absence or presence of antibody 5.25.1 and then subjected to HPLC peptide mapping. A partial or complete reduction in the height of an HPLC peak and/or the detection of a newly generated peak in a sample exposed to antibody may be observed.

After each peptide digest, the reaction products were separated by HPLC, the individual peaks were collected and the peptides identified and mapped by N-terminal sequencing. To determine if the peptides could bind 5.25.1, they were subjected to real time biospecific interaction assays with a BiaCore workstation, using a sensorgram surface covalently bound with HuDKK1 as a biosensor for binding. HPLC peptide mapping was performed under standard conditions.

CNBr Digestion

CNBr cleavage of hDKK1 generated two large fragments. These were CNBr1 and CNBr2, which represented, respectively, D2 and D1 disulfide domains. CNBr1 consisted of two peptides (amino acids 179-206 of SEQ ID NO:2 and amino acids 207-266 [or 274 if including the added C-terminal flag peptide] of SEQ ID NO:2) held together by 5 disulfide bonds. CNBr2 similarly consisted of two peptides (amino acids 32-122 of SEQ ID NO:2 and amino acids 127-178 of SEQ ID NO:2), also held together by 5 disulfide bonds (Table 4). The results of BiaCore analysis indicated that 5.25.1 was capable of binding significantly to CNBr2 but did not bind at all to CNBr1. Thus, it was concluded that 5.25.1 binds to an epitope region located in D1 disulfide domain of HuDKK1.

Trypsin Digestion

Human DKK1 was next digested with trypsin, which cleaves after ARG and LYS residues. About 200 μg of DKK1 at 0.5-1.0 mg/ml were incubated in PBS (pH 7.2) for 20 h at 37° C. with 8 μg of one or the other of these proteases to achieve complete digestion of the DKK1.

HPLC chromatography of tryptic digests yielded multiple peaks, which were collected, dried, and reconstituted into 0.1M sodium phosphate buffer, pH 7.2. Table 4 depicts DKK1 Peptide fragments containing the N-terminal disulfide domain D1 derived from CNBr cleavage and proteolytic digestions.

TABLE 4

| Fragment | Number of peptides | Sequence positions with reference to SEQ ID NO: 2 |
|---|---|---|
| CNBr2 | 2 | 32-122 and 127-178 |
| T2 (or T3)[1] | 5 | 74-102, 103-115, 121-123, 124-134, & 135-147 |
| T4[2] | 1 | 74-147 |
| AspN1 (AspN2) | 2 | 78-104 & 105-141 |

[1]Peptides were derived from trypsin digestion of HuDKK1 alone.
[2]Peptide is derived from trypsin digestion of HuDKK1 in the presence of 5.25.1 antibody.

Sequence analysis was conducted on the peptide peaks recovered from HPLC after trypsin digestion. Peptide peaks containing peptide sequences without disulfide linkages were also confirmed by LC-MS/MS analysis. Molecular mass of fragments containing multiple disulfide-linked peptides was confirmed by matrix-assisted laser desorption mass spectrometric analysis (MALDI-MS). Two peaks, T2 (retention time 40.7 min using 1 mm i.d. column or 43.5 minutes using 2.1 mm column) and T3 (retention time 41.9 min using 1 mm i.d. column or 44.7 minutes using 2.1 mm column), were confirmed to contain sequences that mapped to disulfide domain 1, while T1 peptide (retention time 35 min in 1 mm C18 column or 36.5 min in 2.1 C4 column) mapped to disulfide domain D2. None of T1, T2, and T3 bound to 5.25.1 when tested by BiaCore binding experiments. T2 and T3 are large peptide fragments consisted of five small peptides (3 to 13 amino acids in length) held together by the five disulfide bonds in D1 domain with amino acids 74-102, 103-115, 121-123, 124-134, 135-147 of SEQ ID:2 (Table 4). One small segment of the sequence at disulfide domain 1 was missing from T2 and T3. This missing sequence containing all Lys and Arg, was amino acids 116-120 (sequence of ARG-ARG-LYS-ARG) of SEQ ID NO:2.

Human DKK1 was also incubated with 5.25.1 at a molar ratio of 1:1 to 1:3 in PBS buffer for 1 h at room temperature. Aliquot of the DKK1/antibody complex was then digested by trypsin under conditions as described above. HPLC peptide mapping profile of the tryptic digest is completely identical to that obtained from the DKK1 digest in the absence of antibody 5.25.1, except that T2 and T3 peaks disappeared and a new peak T4 (retention time 41.3 minutes using 1 mm column or 44.3 minutes using 2.1 mm i.d. column) became detectable. T4 is also a the N-terminal domain D1 peptide, but only contains a single amino acid sequence with amino acids 74-147 of sequence ID NO:2 (Table 4). In Biacore binding assay, T4 binds to 5.25.1 and can compete for 5.25.1 binding with Sensorchip surface-bound DKK1.

AspN Digestion

To further delineate the 5.25.1-binding epitope, HuDKK1 was digested with protease AspN and the resulting fragments analyzed as described above. Of the major HPLC peaks generated by AspN digestion, peaks that bound antibody 5.25.1 were AspN1, AspN2 and AspN3. Sequence analysis indicated that AspN1 and AspN2 were derived from disulfide domain D1. AspN1 and AspN2 were identical in amino acid sequence and each of them consisted of two peptides held together by five disulfide bonds in disulfide domain D1. These two peptides consisted of amino acids 78-104 and 105-141 of SEQ ID NO:2 (see Table 4). AspN3 is a partial digestion product whose sequence contains both Domains D1 and D2 sequences. Two other peaks, AspN4 and AspN5, were also isolated and confirmed to be disulfide-linked peptides in domain D2, AspN4 or AspN5 does not compete with DKK1 for 5.25.1 binding.

Analysis of Digestion Results

The above results indicate that 5.25.1 binds to non-linear epitopes of human DKK1 located in disulfide domain D1. As exemplified in FIG. 1, epitope regions are deduced with the observations described in the following:

Trypsin cleavage (R at position 102, and RKRRKR between positions 115 and 120 and K at position 134 in FIG. 1) generates five peptides linked by disulfides. This D1 domain tryptic peptide fraction loses 5.25.1 binding activity.

Antibody 5.25.1 can bind to DKK1 to protect all cleavage sites on D1 domain from trypsin proteolysis (R at position 99, and RKRRKR between positions 115 and 120 and K at position 134). The obtained D1 tryptic fragment, recovered at a distinct retention time, is a single polypeptide chain, indicating that all Arg and Lys's in D1 are protected from proteolysis and therefore are closely located at the epitope region or involved in epitope binding. Binding activity is maintained in D1 fragments generated Asp N or CNBr cleavage. To maintain binding activity, the observed minimal fragment size for D1 domain is amino acids 78-141, except that Asp-N had clipped the peptide bond between Gly 105 and Asp at position 105, leaving this large disulfide loop (formed between Cys 97 and Cys 111) not being connected together.

CNBr cleavage for removal of amino acids 123-126 (sequence of ARG-HIS-ALA-MET) and AspN cleavage of Gly114-Asp115 peptide bond do not influence CNBr2 and AspN1 (or AspN2) fragments from 5.25.1 binding, therefore, sequences in these region are not in the epitope. A highly negatively charged region (amino acids 83-91) in D1 is resistant to GluC and AspN digestion in the absence of Ab, indicating that this region is not accessible for proteolysis (may be due to steric hindrance) and is also inaccessible to 5.25.1.

In summary, epitopes residing in HuDKK1 for 5.25.1 binding include discontinuous sequences at the N-terminal disulfide domain D1: amino acids 98-104, 107-121, and 129-140 of SEQ ID NO:2. And the D1 domain disulfide bonds have to remain intact to retain a correct conformation or three-dimensional structure for 5.25.1 to bind.

Example 10

Binding Affinity of Monoclonal Antibodies Against DKK1

Analyses were performed to study the binding of human anti-huDKK1 antibodies to DKK1 using BiaCore 2000 (BIACORE, Uppsala, Sweden). BiaCore allowed us to determine the kd of the selected antibodies. Those antibodies with a lower kd are more desirable as they bind hDKK1 longer than those with a larger kd, and thus are more likely to engender a greater response. The binding sensorgrams were analyzed and the data are summarized below.

TABLE 5

| Antibody | kd (1/s) |
| --- | --- |
| 2.20.1 | 2.40E−04 |
| 2.37.1 | 2.40E−03 |
| 2.4.1 | 6.00E−04 |
| 2.40.1 | 6.27E−05 |
| 2.41.1 | 1.30E−03 |
| 2.47.1 | 9.20E−04 |
| 5.17.1 | 3.03E−04 |
| 5.23.1 | 1.81E−04 |
| 5.25.1 | <2e−5 |
| 5.31.1 | 1.05E−04 |
| 5.32.1 | 1.91E−04 |
| 5.40.1 | 2.81E−04 |
| 5.65.1 | 5.25E−04 |
| 5.76.1 | 2.41E−04 |
| 5.77.1 | <2e−5 |
| 5.78.1 | 1.91E−04 |
| 5.80.1 | <2e−5 |
| 6.116.6 | 2.00E−05 |
| 6.139.5 | 2.09E−04 |
| 6.147.4 | 2.51E−04 |
| 6.37.5 | 4.00E−05 |

In addition to the off rate, other parameters such as ka (on-rate), KD (affinity), cell-based and in vivo activity are also factors influencing overall selection of therapeutics. The data in table 5 also indicated that those antibodies derived from the latter immunizations of the KL mice yielded antibodies with more desirable Kd's. The binding to huDkk4 was also tested for several of the antibodies to determine specificity and it was determined that human anti-huDKK1 antibodies had at least a 50-fold increased specificity towards DKK1 than to Dkk4, with 5.25.1 and 5.32.1 exhibiting no detectable binding to Dkk4.

Interestingly when the sensorgrams generated from the BiaCore analysis of the second campaign antibodies, which contained antibodies in both the 11H10 and 5.25.1 bins, were analyzed it became apparent that differences exist between the bins. The antibodies from the 11H10 bin, at a given antibody concentration, gave a higher binding signal than did antibodies from the 5.25.1 bin. An increased maximal signal is observed from the 11H10 bin antibodies (2.40.2 and 5.80.2 and 5.80.3).

It was apparent from the BiaCore results that the human anti-huDKK1 antibodies varied in affinity for DKK1, and that the affinity for several of these to human DKK1 exceeded the sensitivity limits of the BiaCore assay. Accordingly, the affinity of several of these antibodies to DKK1 was further assessed by an equilibrium binding analysis using the more sensitive KinExAtm 3000. For these measurements, Reacti-Gel 6× beads (Pierce, Rockford, Ill.) were pre-coated with human, cynomologous or mouse DKK1 and blocked with BSA. One hundred pM, 300 pM, or 1000 pM of the antibody was mixed with various concentrations of human, mouse or cyno DKK1, ranging in concentration from 1 pM to 50 nM, and equilibrated at room temperature for 8 hours. The mixtures were then passed over the DKK1-coated beads. The amount of bead-bound anti-DKK1 antibody was quantified using goat anti-human-IgG antibody labeled with a fluorescent tag (Cy5; Jackson Immuno Research, West Grove, Pa.). The amount of fluorescent signal measured was proportional to the concentration of free anti-DKK1 antibody in each reaction mixture at equilibrium. The dissociation equilibrium constant (Kd) was obtained from nonlinear regression of the competition curves using a dual-curve one-site homogeneous binding model using the KinExA software. Results of the KinExA assays for the selected antibodies are shown in table 6.

TABLE 6

| Antibody | $K_{D\ human}$ (pM) | $K_{D\ mouse}$ (pM) | $K_{D\ cyno}$ (pM) |
| --- | --- | --- | --- |
| 2.40.1 | 220 | 480 | 220 |
| 5.25.1 | 3 | 150 | |
| 5.32.1 | 3 | 40 | |
| 5.77.1 | 8 | 140 | |
| 5.80.1 | 60 | 25 | |
| 6.116.6 | 25 | 40 | 40 |
| 6.139.5 | 110 | | |
| 6.147.4 | 125 | | |
| 6.37.5 | 30 | 50 | 35 |

Example 11

Only 11H10 Bin Antibodies Block Binding of huDKK1 to LRP6 and Kremin2

The ability of 11H10 bin and 5.25.1 bin antibodies to block binding of DKK1 to the Wnt co-receptor LRP6 or to Kremin2 was examined using co-immunoprecipitation procedures. Recombinant mouse LRP6-His and rhDKK1-Flag or recombinant human kremen2-his and hDKK1-flag were pre-incubated with or without the anti-DKK1 antibody in HANKs balanced salt solution with shaking overnight to allow complex formation.

Figure 2:
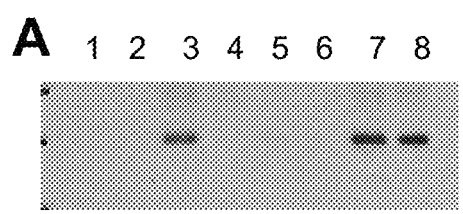
FIG. 2: Panel A lane 1 only LRP6-His is included; lane 2 rhDKK1-Flag; lane 3 hLRP6-His+hDKK1-Flag; lane 4 hLRP6-His+hDKK1-Flag+5.80.1; lane 5 hLRP6-His+hDKK1-Flag+6.37.5; lane 6 hLRP6-His+hDKK1-Flag+r11H10; lane 7 hLRP6-His+hDKK1-Flag+5.25.1; lane 8 hLRP6-His+hDKK1-Flag+5.77.1. Panel B lane 1 only LRP6-His is included; lane 2 rhDKK1-Flag; lane 3 hLRP6-His+hDKK1-Flag; lane 4 hLRP6-His+hDKK1-Flag+0.5 µg 5.80.1; lane 5 hLRP6-His+hDKK1-Flag+5 µg 5.80.1; lane 6 hLRP6-His+hDKK1-Flag+0.5 µg 6.37.5; lane 7 hLRP6-His+hDKK1-Flag+5 µg 6.37.5; lane 8 hLRP6-His+hDKK1-Flag+0.5 µg r11H10; lane 9 hLRP6-His+hDKK1-Flag+5 µg r11H10; lane 10 hLRP6-His+hDKK1-Flag+5 µg 5.25.1; lane 11 hLRP6-His+hDKK1-Flag+5 µg 5.77.1.
Figure 2:
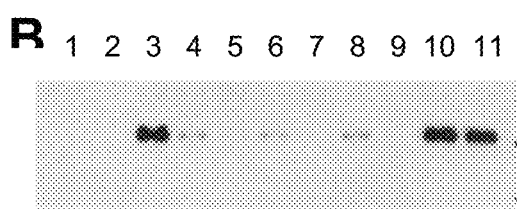

In FIG. 2A rhDKK1-flag was incubated with LRP6-His and 5 μg of one of the neutralizing DKK1 antibodies from either the 11H10 bin (5.80.1, 6.37.5 or r11H10) or the 5.25.1 bin (5.25.1, 5.77.1). The mixture was immunoprecipitated with an anti-his antibody that would bind his-tagged LRP6 and pull down associated DKK1. The immunoprecipitated was then subjected to Western blotting analysis using an anti-flag antibody that recognized rhDKK1. In this way DKK1 associated with LRP6 in solution and the ability of neutralizing-DKK1 antibodies to compete for the binding of DKK1 to LRP6, and by inference to LRP5, could be measured. In lane 1 only LRP6-His is included; lane 2 rhDKK1-Flag; lane 3 hLRP6-His+hDKK1-Flag; lane 4 hLRP6-His+hDKK1-Flag+5.80.1; lane 5 hLRP6-His+hDKK1-Flag+6.37.5; lane 6 hLRP6-His+hDKK1-Flag+r11H10; lane 7 hLRP6-His+hDKK1-Flag+5.25.1; lane 8 hLRP6-His+hDKK1-Flag+5.77.1. The data indicated that all three 11H10 bin antibodies, but not the 5.25.1 bin antibodies, can block the interaction of DKK1 to LRP6.

In a similar manner the ability of the same aforementioned antibodies to block the binding of DKK1 to Kremin2, and by inference to Kremin1, was determined (FIG. 2B). In lane 1 only LRP6-His is included; lane 2 rhDKK1-Flag; lane 3 hLRP6-His+hDKK1-Flag; lane 4 hLRP6-His+hDKK1-Flag+0.5 µg 5.80.1; lane 5 hLRP6-His+hDKK1-Flag+5 µg 5.80.1; lane 6 hLRP6-His+hDKK1-Flag+0.5 µg 6.37.5; lane 7 hLRP6-His+hDKK1-Flag+5 µg 6.37.5; lane 8 hLRP6-His+hDKK1-Flag+0.5 µg r11H10; lane 9 hLRP6-His+hDKK1-Flag+5 µg r11H10; lane 10 hLRP6-His+hDKK1-Flag+5 µg 5.25.1; lane 11 hLRP6-His+hDKK1-Flag+5 µg 5.77.1.

The data indicated that all three 11H10 bin antibodies, but not the 5.25.1 bin antibodies, can block the interaction of DKK1 to Kremin2. The data presented in this experiment suggest that the two different antibody bins exhibit different mechanism of actions in the ability to neutralize DKK1 activity on Wnt signaling.

Example 12

In Vivo Activity of Selected Antibodies

Experiments were conducted to determine whether neutralization of DKK1 in a mouse animal model would cause an increase in bone mineral density (BMD) and in serum osteocalcin, a marker for bone formation. The antibodies tested were 2.40.2, 5.32.5, 5.80, 6.37.5, 6.116.6 and were purified as described above.

Figure 3:
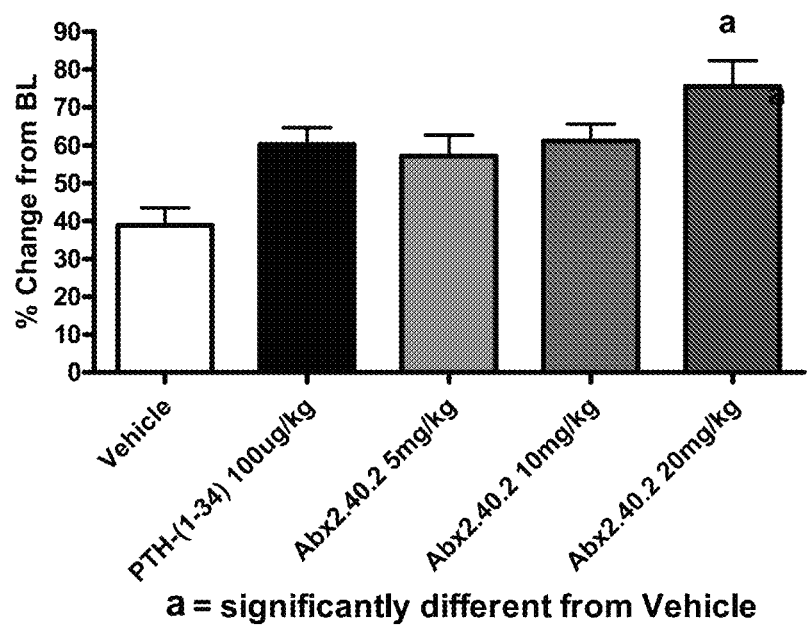
FIG. 3: Shows the percent change in tibia bone mineral density at three weeks for vehicle, PTH and different amounts of antibody 2.40.2. The 20 mg/kg dose was significantly different from the vehicle.

In the first experiment four-week-old male BDF-1 mice (APR 233757, Charles River) were injected subcutaneously over a three-week period with one of three doses of the purified 2.40.2 monoclonal antibody (5, 10, or 20 mg/kg). Five mice were used per group. Negative control mice were injected with vehicle (PBS), and positive control mice were injected with parathyroid hormone (amino acids 1-34), which is known to stimulate increased bone density in these mice (Dempster et al., Endocrine Reviews 14(6):690-709 (1993)). One hundred µg/kg of PTH (1-34) was used per injection. The results for percent change in tibia bone mineral density at three weeks are shown below in FIG. 3.

Figure 4:
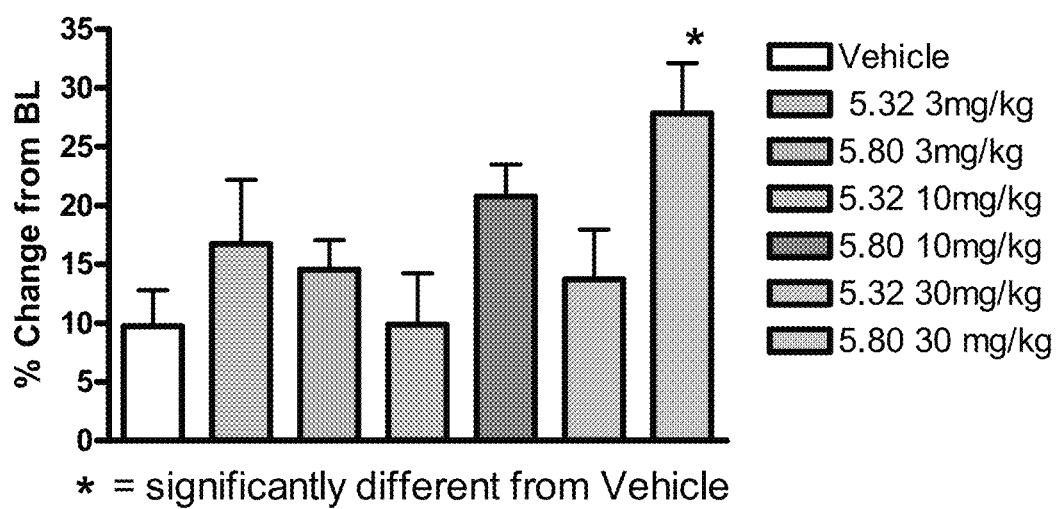
FIG. 4: Antibody 5.32.1 from the 5.25.1 bin and 5.80.1 from the 11H10 bin were tested in vivo for their ability to increase osteocalcin. Eight-week-old male BDF-1 mice were injected subcutaneously over a two-week period with one of three doses of the purified monoclonal antibody (3, 10, or 30 mg/kg). Six mice were used per group. Negative control mice were injected with vehicle (PBS).

To compare the in vivo efficacy of the two different antibody bins, representative antibodies were selected from each bin. The antibodies selected were 5.32.1 from the 5.25.1 bin and 5.80.1 from the 11H10 bin. Both these antibodies bound mouse DKK1 with similar affinities. Eight-week-old male BDF-1 mice (APR 233757, Charles River) were injected subcutaneously over a two-week period with one of three doses of the purified monoclonal antibody (3, 10, or 30 mg/kg). Six mice were used per group. Negative control mice were injected with vehicle (PBS). The data are presented in FIG. 4 as percent change from baseline in bone mineral density of the lumbar vertebrae and indicate that the 11H10 bin antibody (5.80.1) exhibits superior bone building activity than the 5.25.1 bin antibody (5.32.1).

Figure 5:
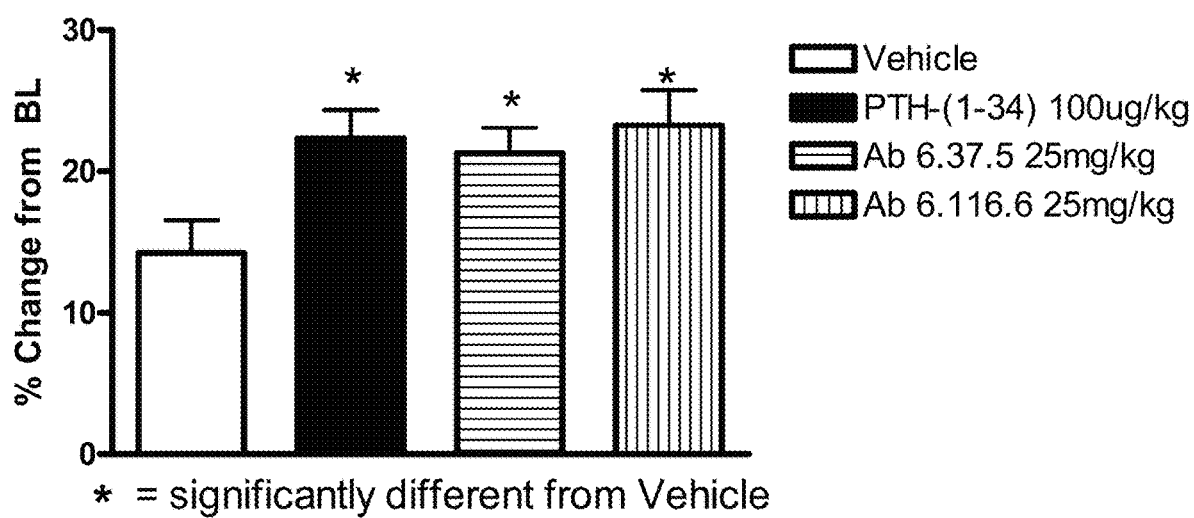
FIG. 5: Mice were injected subcutaneously twice per week for three weeks with 25 mg/kg of the respective antibodies (6.37.5 and 6.116.6). Ten mice were used per group. Control groups were injected with vehicle (twice per week) or PTH (100 µg/kg five times per week). The data are presented as percent change from baseline in bone mineral density of the lumbar vertebrae.

In another experiment two additional antibodies from the 11H10 bin were injected into 8-week old, male BDF-1 mice. These mice were injected subcutaneously twice per week for three weeks with 25 mg/kg of the respective antibodies (6.37.5 and 6.116.6). Ten mice were used per group. Control groups were injected with vehicle (twice per week) or PTH (100 µg/kg five times per week). The data are presented below in FIG. 5 as percent change from baseline in bone mineral density of the lumbar vertebrae and indicated that these antibodies increased bone density to a similar degree as PTH.

Figure 6:
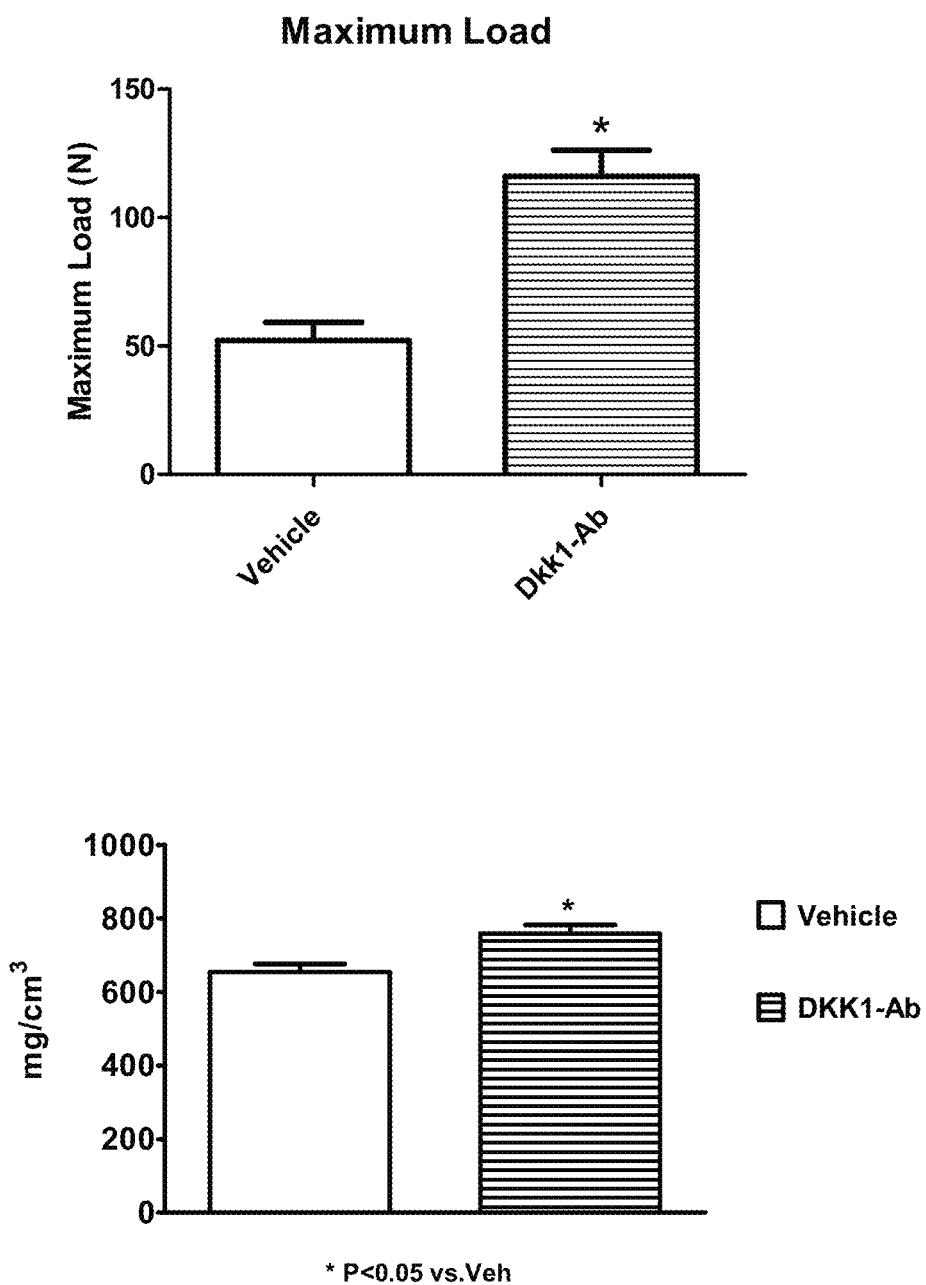
FIG. 6: An additional study was conducted with the rat 11H10 bin antibody in a rat closed fracture healing model. The fully rat 11H10 bin antibody r11H10 was utilized in this study as a surrogate molecule to the fully human antibodies described herein. Improvement in maximum load and BMD achieved with Anti-DKK1 treatment at the fracture callus indicating the acceleration of fracture healing.

An additional study was conducted with the rat 11H10 bin antibody in a rat closed fracture healing model. The fully rat 11H10 bin antibody r11H10 was utilized in this study as a surrogate molecule to the fully human antibodies described herein. The length of this study precluded the use of the fully human DKK1 antibodies due to the rodent immune response directed against human antibodies. Briefly a closed fracture was generated in femur of 7-7.5 month old male rats (see methodology in Example 14). The femur was stabilized by insertion of a fine needle (18 G) into the femur marrow space prior to fracture. The animals were then treated with vehicle or r11H10 (25 mg/kg two times per week). Fractures were allowed to heal for seven weeks. At the completion of the study the fractured femur was analyzed for bone mineral density, biomechanical strength and bridging. Anti-DKK1 treated animals showed significant improvement in all these parameters, indicating that Anti-DKK1 therapy will be useful for the treatment of fracture healing, and other indications where bone regeneration is needed. FIG. 6 shows the improvement in maximum load and BMD achieved with Anti-DKK1 treatment at the fracture callus indicating the acceleration of fracture healing.

Example 13

Detection of DKK1 in Human and Animal Model Serum and Tissue Samples

The antibodies described herein have been used to detect DKK1 levels in human samples, including but not limited to serum. To develop this type of assay it was important that two antibodies be selected that did not recognize the same epitope, such as the two distinct epitopes described herein. To assay for DKK1 in human serum or other tissues a standard curve was first established using recombinant huDKK1. It was preferable that this standard curve was established in human serum lacking, or containing low levels, of huDKK1. Typically the range of the standard curve we use for serum is between 25 pg/ml and 10 ng/ml huDKK1, although this range may need to be adjusted depending upon the minimal and maximal values of huDKK1 obtained in the samples being analyzed. An example of the protocol used is as follows, but modifications obvious to those skilled in the art may be taken depending upon the specific antibodies and samples utilized.

First the human serum to be analyzed was loaded into a non-binding half-area plate. A predetermined amount of biotinylated-antibody from epitope X (such as 11H10) and a predetermined amount of horseradish peroxidase (HRP) labeled antibody from epitope Y (such as 5.25.1) was added to the well with 50 mg/ml Rabbit IgG in I-block buffer to reach a total volume in the well including serum of 60 µl. This mixture was placed on a shaker for 30 minutes and then incubated at 4° C. overnight.

Following the overnight incubation 50 µl of solution was transferred into a 396 well plate. This plate was then incubated for 1 hour at room temperature with mixing. The well was washed with PBS and a detection solution was added. The plate was then analyzed on an appropriate reader. The assay was run in duplicate and concentration of DKK1 in serum was determined by comparison with the standard curve. The data are useful in determining whether patients have altered DKK1 levels in the tissue or serum sample being analyzed.

Figure 7:
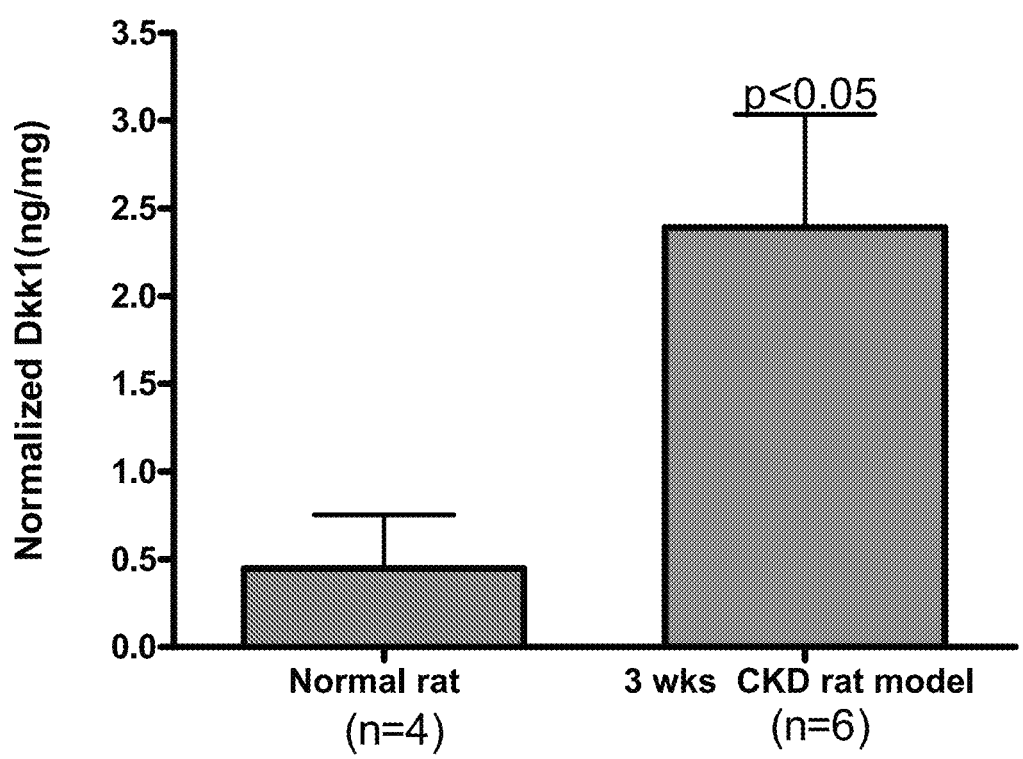
FIG. 7: DKK1 in serum isolated from animal models of disease was detected and DKK1 protein levels are approximately five-fold elevated at 3-weeks after induction of kidney damage with the pharmacological agent.

In addition to using the antibodies described herein for the detection of human DKK1 in human serum, the antibodies can also be used to detect DKK1 in serum isolated from animal models of disease. As a non-inclusive example, the protocol as described above was used to detect DKK1 levels in a rat chronic kidney disease (CKD) model. An extract of diseased and controls kidneys were prepared and the level of rat DKK1 protein was determined. The data are shown in FIG. 7 and demonstrate that DKK1 protein levels are approximately five-fold elevated at 3-weeks after induction of kidney damage with the pharmacological agent. These results indicate that DKK1 is involved in the progression of kidney disease and suggest that that pharmacological modulation of DKK1 is of therapeutic utility in kidney disease. Likewise, the methods describes in this example can be used to identify other disease states where DKK1 modulation may have therapeutic utility.

Example 14

Sclerostin and DKK1 are negative regulators of bone formation. Inhibition of sclerostin by systemic treatment with a sclerostin monoclonal antibody (Scl-Ab) significantly increased bone formation, bone mass and bone strength in animal models of osteoporosis (Li X D, et al. J Bone Miner Res 2009; 24:578). Furthermore, treatment with Scl-Ab enhanced fracture healing in animal models of bone repair (Ke H Z, et al. Trans ORS 2009; 34:22; Ominsky M, et al. ASBMR abstract September 2009; Denver, Colo.). Similarly, neutralization of DKK1 by systemic administration of the monoclonal antibody r11H10 (DKK1-Ab) increased bone mineral density (BMD) and strength at the fracture sites of mouse (Komatsu D E, et al. J Orthop Res 2010; DOI 10.1002/JOR.21078) and rat fracture models. We hypothesized that combination of Scl-Ab and DKK1-Ab may have a synergetic effect on stimulating bone formation and increasing bone strength in fractured and non-fractured bone in an adult rat model.

Study Design: Seven to 7.5 months old male Sprague-Dawley (SD) rats (mean body weight 580 g) underwent unilateral closed femoral mid-diaphyseal fracture as reported previously (Bonnarens F, et al. J Orthop Res 1984; 2: 97-101). Briefly, an 18 gauge syringe needle was inserted into the medullary canal through the femoral condyles, and served as an internal fixation. The femur then underwent transverse fracture via blunt impact loading at the anterior (lateral) aspect of the thigh. One day after fracture, animals (n=14-18/group) were subcutaneously injected with either saline vehicle or Scl-Ab, or DKK1-Ab (r11H10) or combination of Scl-Ab and DKK1-Ab (Combination). Both Scl-Ab and DKK1-Ab were given by subcutaneous injection at 25 mg/kg twice per week. At 7 weeks post-fracture, animals were euthanized; the fractured and intact, contralateral (CL) femurs were collected for densitometry and biomechanics. This study was approved by Amgen's Institution Animal Care and Use Committee.

Densitometry: Femurs were scanned ex vivo by DXA (GE Lunar PIXImus II) at the fracture region (mid 30% of the fractured femur) or the corresponding region in the CL femur to determine areal bone mineral density (BMD). Both femurs were also scanned using a desktop micro-CT system (eXplore Locus SP, GE Healthcare, London, Ontario, Canada) and reconstructed to a resolution of 30 µm. Bone mineral content (BMC, threshold of 800 mg/cc) of the central 1 mm of the fracture callus were assessed after subtraction of the original cortex as previously described (Taylor D K, et al. J Bone Miner Res 2009; 24:1043-1054). Callus bone volume as a percent of total volume (BV/TV) was quantified using a variable threshold (570 mg/cc for vehicle, Scl-Ab and DKK1-Ab; 615 mg/cc for Combination). For the intact CL femur, regions spanning 10% of the femur height at the midshaft (threshold 800 mg/cc) for cortical bone and distal femur trabecular bone (threshold 450 mg/cc for vehicle and DKK1-Ab, 550 mg/cc for Scl-Ab, and 600 mg/cc for combination) were examined. Average cortical bone area and cancellous bone volume fraction (BV/TV) were assessed at these sites, respectively.

Biomechanics: Femurs were tested in 3-point bending to failure at the center of the fracture callus or at the midshaft of contralateral femur, and bone strength parameters were assessed (MTS 858 Mini Bionix II; span length=20 mm; displacement rate=0.1 mm/sec).

Statistical analyses: GraphPad Prism (v. 5.01) was used to perform the statistic analysis. Group variances were compared by F test. If the group variances were significantly heterogeneous ($p \leq 0.05$), the data were log-transformed and resubmitted assess the variance. When differences between group variances were not significant, an unpaired t-test was used to perform the group mean comparisons between the vehicle and Scl-Ab or DKK1-Ab. When group variances remained heterogeneous ($p \leq 0.05$), then the comparison was conducted using the Mann Whitney test. Data reported as Mean+SE, and $p<0.05$ considered as significance.

RESULTS: Fractured femurs: both Scl-Ab and DKK1-Ab showed similar improvement of bone mass and bone strength at fractured callus, as demonstrated by an 11% increase at diaphyseal BMD by DXA, and a 24-26% increase at BMC by µCT and a 40-60% increase in BV/TV by µCT at central 1 mm of fracture callus; and a 76-122% increase in peak load of fractured bone, respectively, compared with vehicle. Combination treatment of Scl-Ab and DKK1-Ab greatly enhanced bone mass and bone strength at fractured callus, to levels significantly greater than either one alone. Compared with vehicle, there was a 39%, 60% and 93% increase in diaphyseal BMD, BMC and BV/TV at central 1 mm of fracture callus, respectively, in the Combination group. These changes led to a 230% increase in peak load in the Combination group as compared with vehicle. In addition, BMD, BMC and BV/TV, and peak load were significantly higher in the Combination group compared with Scl-Ab alone or DKK1-Ab alone groups.

Intact Contralateral Femurs:

DKK1-Ab did not significantly affect diaphyseal BMD, cortical bone area and cancellous bone BV/TV and bone strength in intact contralateral femurs. However, Scl-Ab significantly increased mid-diaphyseal cortical bone BMD by 6% and cortical bone area by 10%, and distal femur cancellous bone BV/TV by 43%, respectively, compared with vehicle. These increases in bone mass at both cortical and cancellous bone sites under Scl-Ab treatments associated with a 17% increase in peak load compared with vehicle.

Similar to the fractured bone, combination of Scl-Ab and DKK1-Ab significantly increased contralateral femoral mid-diaphyseal BMD by 12%, cortical bone area by 17% and distal femur cancellous bone BV/TV by 107%, and peak load by 27% compared with vehicle. The mean values for diaphyseal BMD and distal femur cancellous BV/TV in Combination group were significantly greater than those observed for the Scl-Ab and DKK1-Ab alone groups, while cortical area and peak load in the Combination group were significantly greater by 15% and 21% than the DKK1-Ab alone group, respectively.

What is claimed:

1. An isolated antibody or fragment thereof that specifically binds to an epitope comprising amino acids 98-104 of SEQ ID NO:2, and comprises six CDRs, wherein the six CDRs comprise the amino acid sequences of SEQ ID NOs: 133-138, 157-162, 163-168, 175-180, or 181-186.

2. The antibody or fragment of claim 1 that increases bone mineral density in a patient.

3. The antibody or fragment of claim 1, wherein the antibody or fragment thereof comprises a heavy chain variable region comprising the amino acid sequence of SEQ ID NO: 36, 52, 56, 64, or 68.

4. The antibody or fragment of claim 1, wherein the antibody or fragment thereof comprises a light chain variable region comprising the amino acid sequence of SEQ ID NO: 34, 50, 54, 62, or 66.

5. An antibody or fragment thereof that specifically binds to an epitope comprising ammino acids 98-104 of SEQ ID NO:2, wherein the antibody or fragment thereof comprises a light chain variable region and a heavy chain variable region comprising the amino acid sequences of SEQ ID NOs: 34, and 36, respectively; 42 and 44, respectively; 50 and 52, respectively; 54, and 56, respectively; 62 and 64, respectively; or 66 and 68, respectively.

6. The antibody or fragment of claim 5, wherein the antibody is antibody 5.17.1, 5.25.1, 5.32.1, 5.40.1, 5.76.1, or 5.77.1.

7. A pharmaceutical composition comprising the antibody or fragment of claim 1.

8. The antibody or fragment thereof of claim 1 in combination with one or more of a pharmaceutically acceptable excipient, diluent or carrier.

* * * * *

SEQUENCE LISTING

<160> NUMBER OF SEQ ID NOS: 244

<210> SEQ ID NO 1
<211> LENGTH: 798
<212> TYPE: DNA
<213> ORGANISM: Homo sapiens

<400> SEQUENCE: 1

```
atgatggctc tgggcgcagc gggagctacc cgggtctttg tcgcgatggt agcggcggct      60
ctcggcggcc accctctgct ggagtgagc gccaccttga actcggttct caattccaac     120
gctatcaaga acctgccccc accgctgggc ggcgctgcgg ggcacccagg ctctgcagtc     180
agcgccgcgc cgggaatcct gtacccgggc gggaataagt accagaccat tgacaactac     240
cagccgtacc cgtgcgcaga ggacgaggag tgcggcactg atgagtactg cgctagtccc     300
acccgcggag gggacgcagg cgtgcaaatc tgtctcgcct gcaggaagcg ccgaaaacgc     360
tgcatgcgtc acgctatgtg ctgccccggg aattactgca aaatggaat atgtgtgtct     420
tctgatcaaa atcatttccg aggagaaatt gaggaaacca tcactgaaag ctttggtaat     480
gatcatagca ccttggatgg gtattccaga gaaccacct tgtcttcaaa aatgtatcac     540
accaaaggac aagaaggttc tgtttgtctc aggtcatcag actgtgcctc aggattgtgt     600
tgtgatagac acttctggtc caagatctgt aaacctgtcc tgaaagaagg tcaagtgtgt     660
accaagcata ggagaaaagg ctctcatgga ctagaaatat tccagcgttg ttactgtgga     720
gaaggtctgt cttgccggat acagaaagat caccatcaag ccagtaattc ttctaggctt     780
cacacttgtc agagacac                                                   798
```

<210> SEQ ID NO 2
<211> LENGTH: 266
<212> TYPE: PRT
<213> ORGANISM: Homo sapiens

<400> SEQUENCE: 2

```
Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala Thr
            20                  25                  30

Leu Asn Ser Val Leu Asn Ser Asn Ala Ile Lys Asn Leu Pro Pro Pro
        35                  40                  45

Leu Gly Gly Ala Ala Gly His Pro Gly Ser Ala Val Ser Ala Ala Pro
    50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Lys Arg Cys Met Arg His Ala Met Cys Cys
        115                 120                 125

Pro Gly Asn Tyr Cys Lys Asn Gly Ile Cys Val Ser Ser Asp Gln Asn
    130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175
```

```
Lys Met Tyr His Thr Lys Gly Gln Glu Gly Ser Val Cys Leu Arg Ser
            180                 185                 190

Ser Asp Cys Ala Ser Gly Leu Cys Cys Asp Arg His Phe Trp Ser Lys
        195                 200                 205

Ile Cys Lys Pro Val Leu Lys Glu Gly Gln Val Cys Thr Lys His Arg
    210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His
            260                 265

<210> SEQ ID NO 3
<211> LENGTH: 816
<212> TYPE: DNA
<213> ORGANISM: Mus musculus

<400> SEQUENCE: 3
atgatggttg tgtgtgcagc ggcagctgtc cggttcttgg ccgtgtttac aatgatggct      60
ctctgcagcc tccctctgct aggagccagt gccaccttga actcagttct catcaattcc    120
aacgcgatca gaacctgccc cccaccgctg gtggtgctg gggggcagcc gggctctgct    180
gtcagtgtgg cgccgggagt tctctatgag gcgggaaca agtaccagac tcttgacaac    240
taccagccct acccttgcgc tgaagatgag gagtgcggct ctgacgagta ctgctccagc    300
cccagccgcg gggcagccgg cgtcggaggt gtacagatct gtctggcttg ccgaaagcgc    360
aggaagcgct gcatgaggca cgctatgtgc tgccccggga actactgcaa aaatggaata    420
tgcatgccct ctgaccacag ccattttcct gaggggaga ttgaggaaag catcattgaa    480
aaccttggta atgaccacaa cgccgccgcg ggggatggat atcccagaag aaccacactg    540
acttcaaaaa tatatcacac caaaggacaa gaaggctccg tctgcctccg atcatcagac    600
tgtgccgcag gctgtgttg tgcaagacac ttctggtcca agatctgtaa acctgtcctt    660
aaagaaggtc aggtgtgcac caagcacaaa cggaaaggct cccacgggct ggagatattc    720
cagcgctgtt actgcgggga aggcctggct tgcaggatac agaaagatca ccatcaagcc    780
agcaattctt ctaggctcca cacctgccag agacac                              816

<210> SEQ ID NO 4
<211> LENGTH: 272
<212> TYPE: PRT
<213> ORGANISM: Mus musculus

<400> SEQUENCE: 4

Met Met Val Val Cys Ala Ala Ala Ala Val Arg Phe Leu Ala Val Phe
1               5                   10                  15

Thr Met Met Ala Leu Cys Ser Leu Pro Leu Leu Gly Ala Ser Ala Thr
            20                  25                  30

Leu Asn Ser Val Leu Ile Asn Ser Asn Ala Ile Lys Asn Leu Pro Pro
        35                  40                  45

Pro Leu Gly Gly Ala Gly Gly Gln Pro Gly Ser Ala Val Ser Val Ala
    50                  55                  60

Pro Gly Val Leu Tyr Glu Gly Gly Asn Lys Tyr Gln Thr Leu Asp Asn
65                  70                  75                  80

Tyr Gln Pro Tyr Pro Cys Ala Glu Asp Glu Glu Cys Gly Ser Asp Glu
                85                  90                  95
```

```
Tyr Cys Ser Ser Pro Ser Arg Gly Ala Ala Gly Val Gly Gly Val Gln
            100                 105                 110

Ile Cys Leu Ala Cys Arg Lys Arg Lys Arg Cys Met Arg His Ala
        115                 120                 125

Met Cys Cys Pro Gly Asn Tyr Cys Lys Asn Gly Ile Cys Met Pro Ser
    130                 135                 140

Asp His Ser His Phe Pro Arg Gly Glu Ile Glu Ser Ile Ile Glu
145                 150                 155                 160

Asn Leu Gly Asn Asp His Asn Ala Ala Ala Gly Asp Gly Tyr Pro Arg
                165                 170                 175

Arg Thr Thr Leu Thr Ser Lys Ile Tyr His Thr Lys Gly Gln Glu Gly
                180                 185                 190

Ser Val Cys Leu Arg Ser Ser Asp Cys Ala Ala Gly Leu Cys Cys Ala
                195                 200                 205

Arg His Phe Trp Ser Lys Ile Cys Lys Pro Val Leu Lys Glu Gly Gln
        210                 215                 220

Val Cys Thr Lys His Lys Arg Lys Gly Ser His Gly Leu Glu Ile Phe
225                 230                 235                 240

Gln Arg Cys Tyr Cys Gly Glu Gly Leu Ala Cys Arg Ile Gln Lys Asp
                245                 250                 255

His His Gln Ala Ser Asn Ser Ser Arg Leu His Thr Cys Gln Arg His
            260                 265                 270

<210> SEQ ID NO 5
<211> LENGTH: 810
<212> TYPE: DNA
<213> ORGANISM: Rattus norvegicus

<400> SEQUENCE: 5
atgacggttg tgcgtgcagt ggcagctgtc cggttcttgg tcgtgcttac aacgatggct      60
ctctgcagcc tccctccgct cggagtcagc gccactttga actcagttct catcaattcc    120
aacgcgatca agaacctgcc cccaccgctg gtggtgctg gggggcagcc gggctctgct     180
gtcagcgtgg cgcccggagt cctctatgag gcgggaaca agtaccagac tcttgacaac    240
taccagccct acccttgcgc ggaggatgag gagtgcggca ctgacgagta ctgctccagt    300
cccagccgcg gggcagccgg cgtgggaggt gtacaaatct gcctggcttg ccgaaagcgc    360
aggaaacgct gcatgaggca cgctatgtgc tgccccggga attactgcaa aaacggaata    420
tgcatgccct ctgaccacag ccatttacct cgaggggaaa tcgaggaagg catcattgaa    480
aaccttggca atgaccacgg tgccggggat ggatatccca agaaccac actgacttca     540 aaatatatc acaccaaagg gcaagaaggc tctgtctgcc tccgatcatc agactgcgcc    600
acagggctgt gttgtgcaag acatttctgg tccaagatct gtaaacctgt ccttaaagaa    660
ggtcaggtat gcaccaagca cagaaggaaa ggctcccacg gctggagat attccagcgc     720 tgttactgtg gggaaggtct ggcttgcagg atacagaaag atcaccatca aaccagcaat    780
tcttccaggc tccacacctg ccagagacac                                      810

<210> SEQ ID NO 6
<211> LENGTH: 270
<212> TYPE: PRT
<213> ORGANISM: Rattus norvegicus

<400> SEQUENCE: 6

Met Thr Val Val Arg Ala Val Ala Ala Val Arg Phe Leu Val Val Leu
```

```
  1               5                  10                 15
Thr Thr Met Ala Leu Cys Ser Leu Pro Pro Leu Gly Val Ser Ala Thr
                 20                 25                 30
Leu Asn Ser Val Leu Ile Asn Ser Asn Ala Ile Lys Asn Leu Pro Pro
                 35                 40                 45
Pro Leu Gly Gly Ala Gly Gly Gln Pro Gly Ser Ala Val Ser Val Ala
                 50                 55                 60
Pro Gly Val Leu Tyr Glu Gly Gly Asn Lys Tyr Gln Thr Leu Asp Asn
 65                                 70                 75                 80
Tyr Gln Pro Tyr Pro Cys Ala Glu Asp Glu Glu Cys Gly Thr Asp Glu
                         85                 90                 95
Tyr Cys Ser Ser Pro Ser Arg Gly Ala Ala Gly Val Gly Gly Val Gln
                 100                105                110
Ile Cys Leu Ala Cys Arg Lys Arg Arg Lys Arg Cys Met Arg His Ala
                 115                120                125
Met Cys Cys Pro Gly Asn Tyr Cys Lys Asn Gly Ile Cys Met Pro Ser
                 130                135                140
Asp His Ser His Leu Pro Arg Gly Glu Ile Glu Gly Ile Ile Glu
145                     150                155                160
Asn Leu Gly Asn Asp His Gly Ala Gly Asp Gly Tyr Pro Arg Arg Thr
                 165                170                175
Thr Leu Thr Ser Lys Ile Tyr His Thr Lys Gly Gln Glu Gly Ser Val
                 180                185                190
Cys Leu Arg Ser Ser Asp Cys Ala Thr Gly Leu Cys Cys Ala Arg His
                 195                200                205
Phe Trp Ser Lys Ile Cys Lys Pro Val Leu Lys Glu Gly Gln Val Cys
                 210                215                220
Thr Lys His Arg Arg Lys Gly Ser His Gly Leu Glu Ile Phe Gln Arg
225                     230                235                240
Cys Tyr Cys Gly Glu Gly Leu Ala Cys Arg Ile Gln Lys Asp His His
                 245                250                255
Gln Thr Ser Asn Ser Ser Arg Leu His Thr Cys Gln Arg His
                 260                265                270
```

<210> SEQ ID NO 7
<211> LENGTH: 798
<212> TYPE: DNA
<213> ORGANISM: Macaca fascicularis

<400> SEQUENCE: 7

| | | |
|---|---|---|
| atgatggctc tgggcgcagc aggagctgcc cgggtcttgg tcgcgctggt agcggcggct | 60 |
| cttggcggcc accctctgct gggagtgagc gccaccttga actcggttct caattccaac | 120 |
| gcgatcaaga acctgccccc accgctgggc ggcgctgcgg gcacccagg ctctgcagtc | 180 |
| agcgccgcgc caggaattct gtaccccggc gggaataagt accagaccat tgacaactac | 240 |
| cagccgtacc cttgcgcaga ggatgaggag tgcggcactg atgagtactg cgctagtccc | 300 |
| acccgcggag ggacgcgggt cgtgcaaatc tgtctcgcct gcaggaagcg ccgaaaacgc | 360 |
| tgcatgcgtc acgctatgtg ctgccccggg aattactgca aaatggaat atgtgtgtct | 420 |
| tctgatcaaa ataatttccg aggggaaatt gaggaaacca ttactgaaag ctttggtaat | 480 |
| gatcatagca ctttggatgg gtattccaga agaacaacat tgtcttcaaa aatgtatcac | 540 |
| agcaaaggac aagaaggttc tgtgtgtctc cggtcatcag actgtgccac aggactgtgt | 600 |
| tgtgctagac acttctggtc caagatctgt aaacctgtcc tcaagaagg tcaagtgtgt | 660 |

```
accaagcata gaagaaaagg ctctcatggg ctagaaatat tccagcgttg ttactgcgga    720
gaaggtctgt cttgccggat acagaaagat caccatcaag ccagtaattc ttctaggctt    780
cacacttgtc agagacac                                                  798
```

<210> SEQ ID NO 8
<211> LENGTH: 266
<212> TYPE: PRT
<213> ORGANISM: Macaca fascicularis

<400> SEQUENCE: 8

```
Met Met Ala Leu Gly Ala Ala Gly Ala Ala Arg Val Leu Val Ala Leu
1               5                   10                  15

Val Ala Ala Leu Gly Gly His Pro Leu Leu Gly Val Ser Ala Thr
            20                  25                  30

Leu Asn Ser Val Leu Asn Ser Asn Ala Ile Lys Asn Leu Pro Pro
        35                  40                  45

Leu Gly Gly Ala Ala Gly His Pro Gly Ser Ala Val Ser Ala Ala Pro
    50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Lys Arg Cys Met Arg His Ala Met Cys Cys
        115                 120                 125

Pro Gly Asn Tyr Cys Lys Asn Gly Ile Cys Val Ser Ser Asp Gln Asn
    130                 135                 140

Asn Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Ser Lys Gly Gln Glu Gly Ser Val Cys Leu Arg Ser
            180                 185                 190

Ser Asp Cys Ala Thr Gly Leu Cys Cys Ala Arg His Phe Trp Ser Lys
        195                 200                 205

Ile Cys Lys Pro Val Leu Lys Glu Gly Gln Val Cys Thr Lys His Arg
    210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His
            260                 265
```

<210> SEQ ID NO 9
<211> LENGTH: 321
<212> TYPE: DNA
<213> ORGANISM: Homo sapiens

<400> SEQUENCE: 9

```
gacatccaga tgacccagtc tccatcctcc ctgtctgcat ctgtaggaga cagagtcacc     60
atcacttgcc gggcaagtca gggcattaga gatgatttag ctggtttca gcagaaacca    120 gggaaagccc ctaagcgcct gatctatgct gcatccagtt tgcaaagtgg ggtcccatca    180
```

```
aggttcagcg gcagtggatc tgggacagaa ttcactctca caatcagcag cctgcagcct      240
gaagattttg caacttatta ctgtctacag cataatagtt acccgtgcag ttttggccag      300
gggaccaagc tggagttcaa a                                                321
```

<210> SEQ ID NO 10
<211> LENGTH: 107
<212> TYPE: PRT
<213> ORGANISM: Homo sapiens

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asp Asp
            20                  25                  30

Leu Gly Trp Phe Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Cys
                85                  90                  95

Ser Phe Gly Gln Gly Thr Lys Leu Glu Phe Lys
            100                 105
```

<210> SEQ ID NO 11
<211> LENGTH: 372
<212> TYPE: DNA
<213> ORGANISM: Homo sapiens

<400> SEQUENCE: 11

```
caggttcagc taatgcagtc tggagctgag gtgaagaagc ctggggcctc agtgaaggtc      60
tcctgcaagg cttctggtta cacctttacc agctatggta tcagctgggt gcgacaggcc      120
cctggacaag gcttgagtg gatgggatgg atcagcgctg acaatggtca cacaaactat      180
gcacagaaac tccagggcag agtcaccatg accacagaca catccacgag cacagcctac      240
atggagctga ggagcctgag atctgacgac acggccgtgt attactgtgc gagagatggg      300
gagctactaa attactacta ctactacggt atggacgtct ggggccaagg gaccacggtc      360
accgtctcct ca                                                          372
```

<210> SEQ ID NO 12
<211> LENGTH: 124
<212> TYPE: PRT
<213> ORGANISM: Homo sapiens

<400> SEQUENCE: 12

```
Gln Val Gln Leu Met Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Asp Asn Gly His Thr Asn Tyr Ala Gln Lys Leu
    50                  55                  60

Gln Gly Arg Val Thr Met Thr Thr Asp Thr Ser Thr Ser Thr Ala Tyr
```

```
                65                  70                  75                  80
Met Glu Leu Arg Ser Leu Arg Ser Asp Asp Thr Ala Val Tyr Tyr Cys
                        85                  90                  95

Ala Arg Asp Gly Glu Leu Leu Asn Tyr Tyr Tyr Tyr Gly Met Asp
                100                 105                 110

Val Trp Gly Gln Gly Thr Thr Val Thr Val Ser Ser
        115                 120

<210> SEQ ID NO 13
<211> LENGTH: 336
<212> TYPE: DNA
<213> ORGANISM: Homo sapiens

<400> SEQUENCE: 13
gatattgtga tgacccagac tccactctct ctgtccgtca ttcctggaca gccggcctcc      60
atctcctgca agtctagtca gagcctcctg catagtgatg gaaagaccta tttgtactgg     120
tacctgcaga ggccaggcca gcctccacag ctcctgatct atgaagtttc caaccggttc     180
tctggagtgc cacataggct cagtggcagc gggtcaggga cagatttcac actgaaaatc     240
agccgggtgg aggctgagga tgttggggtt tattactgca tgcaaagtat acaggttccg     300
tggacgttcg gccaagggac caaggtggaa atcaaa                                336

<210> SEQ ID NO 14
<211> LENGTH: 112
<212> TYPE: PRT
<213> ORGANISM: Homo sapiens

<400> SEQUENCE: 14

Asp Ile Val Met Thr Gln Thr Pro Leu Ser Leu Ser Val Ile Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Arg Pro Gly Gln Pro
        35                  40                  45

Pro Gln Leu Leu Ile Tyr Glu Val Ser Asn Arg Phe Ser Gly Val Pro
    50                  55                  60

His Arg Leu Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Val Pro Trp Thr Phe Gly Gln Gly Thr Lys Val Glu Ile Lys
            100                 105                 110

<210> SEQ ID NO 15
<211> LENGTH: 363
<212> TYPE: DNA
<213> ORGANISM: Homo sapiens

<400> SEQUENCE: 15
cagtgtcagg tgcagctggt ggagtctggg ggaggcgtgg tccagcctgg gaggtccctg      60
agactctcct gtgcagcctc tggattcacc ttcagtagct atggcatgca ctgggtccgc     120
caggctccag gcaaggggct ggagtgggtg gcagttatat catatgatgg aagtgataaa     180
tactatgcag actccgtgaa gggccgattc accatctcca gagacaattc caagaacacg     240
ctgtatctgc aaatgaacag cctgagagct gaggacacgg ctgtgtatta ctgtgcgaga     300
gatcaatggg gtgggagccc agccggcccc tggggccagg gaaccctggt caccgtctcc     360
``` tca                                                                    363

<210> SEQ ID NO 16
<211> LENGTH: 119
<212> TYPE: PRT
<213> ORGANISM: Homo sapiens

<400> SEQUENCE: 16

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Val Arg Gln Ala Pro Gly Lys Gly Leu Glu Trp Val
        35                  40                  45

Ala Val Ile Ser Tyr Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Gln Trp Gly Gly Ser Pro Ala Gly Pro Trp Gly Gln Gly
                100                 105                 110

Thr Leu Val Thr Val Ser Ser
        115

<210> SEQ ID NO 17
<211> LENGTH: 324
<212> TYPE: DNA
<213> ORGANISM: Homo sapiens

<400> SEQUENCE: 17
gaaattgtgt tgacgcagtc tccaggcacc ctgtctttgt ctccagggga aagagccacc        60
ctctcctgca gggccagtca gagtgttagc agcaactact tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt ttgcagtgta ttactgtcag cagtatggta gctcaccgat caccttcggc       300
caagggacac gactggagat taaa                                              324

<210> SEQ ID NO 18
<211> LENGTH: 108
<212> TYPE: PRT
<213> ORGANISM: Homo sapiens

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro

Ile Thr Phe Gly Gln Gly Thr Arg Leu Glu Ile Lys
            100                 105

<210> SEQ ID NO 19
<211> LENGTH: 357
<212> TYPE: DNA
<213> ORGANISM: Homo sapiens

<400> SEQUENCE: 19
caggtgcagc tggtggagtc tgggggaggc gtggtccagc ctggagggtc cctgagactc    60
tcctgtgcag cctctggatt caccttcagt agctatggca tgcactgggt ccgccaggct   120
ccaggcaagg ggctggaatg ggtggcagtt atatcatatg atggaagtga taaatactat   180
gcagactccg tgaagggccg attcaccttc tccagagaca attccaagaa cacgctgtat   240
ctgcaaatga acagcctgag agctgaggac acggctgtgt attactgtgc gagagaattg   300
ggtatagcag cttcctttga ctactggggc cagggaaccc tggtcaccgt ctcctca      357

<210> SEQ ID NO 20
<211> LENGTH: 119
<212> TYPE: PRT
<213> ORGANISM: Homo sapiens

<400> SEQUENCE: 20

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Tyr Ala Asp Ser Val
    50                  55                  60

Lys Gly Arg Phe Thr Phe Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Gly Ile Ala Ala Ser Phe Asp Tyr Trp Gly Gln Gly
            100                 105                 110

Thr Leu Val Thr Val Ser Ser
        115

<210> SEQ ID NO 21
<211> LENGTH: 336
<212> TYPE: DNA
<213> ORGANISM: Homo sapiens

<400> SEQUENCE: 21
gatattgtga tgacccagtc tccactctct ctgtccgtca cccctggaca gccggcctcc    60
atctcctgca agtctagtca gagcctcctg cacagtgatg gaaagaccta tttgtattgg   120
tatctgcaga agccaggcca gcctccacag ctcctgatct atgaagtttc caaccggttc   180
tctggagtgc cagataggtt cagtggcagc gggtcaggga cagatttcac actgaaaatc   240
agccgggtgg aggctgagga tgttggggtc tattactgca tgcaaagtat acaggttccg   300
tggacgttcg gccaagggac caaggtggaa atcaaa                             336

<210> SEQ ID NO 22

```
<211> LENGTH: 112
<212> TYPE: PRT
<213> ORGANISM: Homo sapiens

<400> SEQUENCE: 22
```

| | | | | | | | | | | | | | | |
|---|---|---|---|---|---|---|---|---|---|---|---|---|---|---|
| Asp | Ile | Val | Met | Thr | Gln | Ser | Pro | Leu | Ser | Leu | Ser | Val | Thr | Pro | Gly |
| 1 | | | | 5 | | | | | 10 | | | | | 15 | |

| Gln | Pro | Ala | Ser | Ile | Ser | Cys | Lys | Ser | Ser | Gln | Ser | Leu | Leu | His | Ser |
|---|---|---|---|---|---|---|---|---|---|---|---|---|---|---|---|
| | | | 20 | | | | | 25 | | | | | 30 | | |

| Asp | Gly | Lys | Thr | Tyr | Leu | Tyr | Trp | Tyr | Leu | Gln | Lys | Pro | Gly | Gln | Pro |
|---|---|---|---|---|---|---|---|---|---|---|---|---|---|---|---|
| | | | 35 | | | | | 40 | | | | | 45 | | |

| Pro | Gln | Leu | Leu | Ile | Tyr | Glu | Val | Ser | Asn | Arg | Phe | Ser | Gly | Val | Pro |
|---|---|---|---|---|---|---|---|---|---|---|---|---|---|---|---|
| | 50 | | | | | 55 | | | | | 60 | | | | |

| Asp | Arg | Phe | Ser | Gly | Ser | Gly | Ser | Gly | Thr | Asp | Phe | Thr | Leu | Lys | Ile |
|---|---|---|---|---|---|---|---|---|---|---|---|---|---|---|---|
| 65 | | | | | 70 | | | | | 75 | | | | | 80 |

| Ser | Arg | Val | Glu | Ala | Glu | Asp | Val | Gly | Val | Tyr | Tyr | Cys | Met | Gln | Ser |
|---|---|---|---|---|---|---|---|---|---|---|---|---|---|---|---|
| | | | | 85 | | | | | 90 | | | | | 95 | |

| Ile | Gln | Val | Pro | Trp | Thr | Phe | Gly | Gln | Gly | Thr | Lys | Val | Glu | Ile | Lys |
|---|---|---|---|---|---|---|---|---|---|---|---|---|---|---|---|
| | | | 100 | | | | | 105 | | | | | 110 | | |

```
<210> SEQ ID NO 23
<211> LENGTH: 351
<212> TYPE: DNA
<213> ORGANISM: Homo sapiens
<400> SEQUENCE: 23
caggtgcaac tggtggagtc tggaggaggc gtggtccagc ctgggaggtc cctgagactc      60
tcctgtgcag cctctggatt caccttcagt agctatggca tgcactgggt ccgccaggct     120
ccaggcaagg ggctggggtg gtggcagtt atatcatatg atggaagtga taaatactat     180
gcagactccg tgaagggccg attcaccatc tccagagaca attccaagaa cacgctgtat     240
ctgcaaatga acagcctgag agctgaggac acggctgtgt attactgtgc gagagacctc     300
gtggatacag ctatgccctg gggccaaggg accacggtca ccgtctcctc a              351

<210> SEQ ID NO 24
<211> LENGTH: 117
<212> TYPE: PRT
<213> ORGANISM: Homo sapiens

<400> SEQUENCE: 24
```

| Gln | Val | Gln | Leu | Val | Glu | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Gly | Met | His | Trp | Val | Arg | Gln | Ala | Pro | Gly | Lys | Gly | Leu | Gly | Trp | Val |
|---|---|---|---|---|---|---|---|---|---|---|---|---|---|---|---|
| | | | 35 | | | | | 40 | | | | | 45 | | |

| Ala | Val | Ile | Ser | Tyr | Asp | Gly | Ser | Asp | Lys | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Asp | Leu | Val | Asp | Thr | Ala | Met | Pro | Trp | Gly | Gln | Gly | Thr | Thr |
|---|---|---|---|---|---|---|---|---|---|---|---|---|---|---|---|
| | | | 100 | | | | | 105 | | | | | 110 | | |

| Val | Thr | Val | Ser | Ser |
|---|---|---|---|---|
| | | | 115 | | |

<210> SEQ ID NO 25
<211> LENGTH: 336
<212> TYPE: DNA
<213> ORGANISM: Homo sapiens

<400> SEQUENCE: 25
gatattgtga tgacccagac tccactctct ctgtccgtca cccctggaca gccggcctcc      60
atctcctgca agtctagtca gagcctcctg catagtgatg gaaagaccta tttgtattgg     120
tacctgcaga agccaggcca gcctccacag ctcctgatct atgaagtttc caaccggttc     180
tctggagtgc cagataggtt cagtggcagc gggtcaggga cagatttcac actgaaaatc     240
agccgggtgg aggctgagga tgttggggtt tattactgca tgcaaagtaa acagcttcca     300
ttcactttcg gccctgggac caaagtggat atcaaa                               336

<210> SEQ ID NO 26
<211> LENGTH: 112
<212> TYPE: PRT
<213> ORGANISM: Homo sapiens

<400> SEQUENCE: 26

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Lys Gln Leu Pro Phe Thr Phe Gly Pro Gly Thr Lys Val Asp Ile Lys
            100                 105                 110

<210> SEQ ID NO 27
<211> LENGTH: 366
<212> TYPE: DNA
<213> ORGANISM: Homo sapiens

<400> SEQUENCE: 27
caggtgcagc tggtggagtc tgggggaggc gtggtccagc ctggggaggtc cctgagactc     60 tcctgtgcag cctctggatt caccttcagt agctatggca tgcactgggt ccgccaggct    120
ccaggcaagg ggctggagtg ggtggcagtt atatcatatg atggaagtga taaatactat    180
gcagactccg tgaagggccg attcaccatc tccagagaca attccaagaa cacgctgtat    240
ctgcaaatga acagcctgag ggctgaggac acggctgtgt attactgtgc gagagccggg    300 tactcccttct actactacta cggtatggac gtctggggcc aagggaccac ggtcaccgtc    360
tcctca                                                                366

<210> SEQ ID NO 28
<211> LENGTH: 122
<212> TYPE: PRT
<213> ORGANISM: Homo sapiens

<400> SEQUENCE: 28

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Tyr Ser Leu Tyr Tyr Tyr Tyr Gly Met Asp Val Trp
            100                 105                 110

Gly Gln Gly Thr Thr Val Thr Val Ser Ser
            115                 120
```

<210> SEQ ID NO 29
<211> LENGTH: 339
<212> TYPE: DNA
<213> ORGANISM: Homo sapiens

<400> SEQUENCE: 29

```
gatattgtga tgacccagac tccactctcc ctgcccgtca cccctggaga gccggcctcc      60
atctcctgca ggtctagtca gagcctcttg gatagtgatg atggagacac ctatttggac     120
tggtacctgc agaagccagg gcagtctcca cagctcctga tctatacgct ttcctatcgg     180
gcctctggag tcccagacag gttcagtggc agtgggtcag gcactgattt cacactgaaa     240
atcagcaggg tggaggctga ggatgttgga gtttattact gcatgcaacg tatagagttt     300
ccattcactt tcggccctgg gaccaaagtg gatatcaaa                            339
```

<210> SEQ ID NO 30
<211> LENGTH: 113
<212> TYPE: PRT
<213> ORGANISM: Homo sapiens

<400> SEQUENCE: 30

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asp Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Phe Thr Phe Gly Pro Gly Thr Lys Val Asp Ile
            100                 105                 110

Lys
```

<210> SEQ ID NO 31
<211> LENGTH: 381
<212> TYPE: DNA

<213> ORGANISM: Homo sapiens

<400> SEQUENCE: 31

```
caggtgcagc tgcaggagtc gggcccagga ctggtgaagc cttcacagac cctgtccctc      60
acctgcactg tctctggtgg ctccatcagc agtggtggct actactggag ctggatccgc     120
cagcacccag ggaagggcct ggagtggatt ggggacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg cgcgagagat     300
cgggcttacg gtgactacgg gggagactac tactacggta tggacgtctg gggccaaggg     360
accacggtca ccgtctcctc a                                                381
```

<210> SEQ ID NO 32
<211> LENGTH: 127
<212> TYPE: PRT
<213> ORGANISM: Homo sapiens

<400> SEQUENCE: 32

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Asp Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Ala Tyr Gly Asp Tyr Gly Gly Asp Tyr Tyr Tyr
            100                 105                 110

Gly Met Asp Val Trp Gly Gln Gly Thr Thr Val Thr Val Ser Ser
        115                 120                 125

<210> SEQ ID NO 33
<211> LENGTH: 321
<212> TYPE: DNA
<213> ORGANISM: Homo sapiens

<400> SEQUENCE: 33

```
gacatccaga tgacccagtc tccatcctcc ctgtctgcat ctgtaggaga cagagtcacc      60
atcacttgcc aggcgagtca ggacattaac aactatttaa attggtatca gcagaaacca     120
gggaaagccc ctaatctcct gatctacgat gcatccaatt ggaaacaggg gtcccatca     180
aggttcagtg aagtggatc tgggacagat tttactttca ccatcagcag cctgcagcct     240
gcagatattg caacatatta ctgtcaacaa tatgatgatt cccgctcac tttcggcgga     300
gggaccaagg tggagatcaa a                                                321
```

<210> SEQ ID NO 34
<211> LENGTH: 107
<212> TYPE: PRT
<213> ORGANISM: Homo sapiens

<400> SEQUENCE: 34

Asp Ile Gln Met Thr Gln Ser Pro Ser Ser Leu Ser Ala Ser Val Gly

```
                1               5                  10                 15
            Asp Arg Val Thr Ile Thr Cys Gln Ala Ser Gln Asp Ile Asn Asn Tyr
                            20                  25                  30

Leu Asn Trp Tyr Gln Gln Lys Pro Gly Lys Ala Pro Asn Leu Leu Ile
                            35                  40                  45

Tyr Asp Ala Ser Asn Leu Glu Thr Gly Val Pro Ser Arg Phe Ser Gly
                            50                  55                  60

Ser Gly Ser Gly Thr Asp Phe Thr Phe Thr Ile Ser Ser Leu Gln Pro
             65                  70                  75                  80

Ala Asp Ile Ala Thr Tyr Tyr Cys Gln Gln Tyr Asp Asp Phe Pro Leu
                            85                  90                  95

Thr Phe Gly Gly Gly Thr Lys Val Glu Ile Lys
                            100                 105

<210> SEQ ID NO 35
<211> LENGTH: 354
<212> TYPE: PRT
<213> ORGANISM: Homo sapiens

<400> SEQUENCE: 35

Cys Ala Gly Gly Thr Gly Cys Ala Ala Cys Thr Gly Cys Ala Gly Gly
 1               5                  10                  15

Ala Gly Thr Cys Gly Gly Cys Cys Cys Ala Gly Gly Ala Cys Thr Gly
                20                  25                  30

Gly Gly Thr Gly Ala Ala Gly Cys Cys Thr Thr Cys Gly Gly Ala Gly
                35                  40                  45

Ala Cys Cys Cys Thr Gly Thr Cys Cys Cys Thr Cys Ala Cys Cys Thr
             50                  55                  60

Gly Cys Ala Cys Thr Gly Thr Cys Thr Cys Thr Gly Gly Thr Gly Gly
 65                  70                  75                  80

Cys Thr Cys Cys Ala Thr Cys Ala Gly Thr Ala Gly Thr Thr Ala Cys
                85                  90                  95

Thr Ala Cys Thr Gly Gly Ala Gly Cys Thr Gly Gly Ala Thr Cys Cys
                100                 105                 110

Gly Gly Cys Ala Gly Cys Cys Cys Cys Ala Gly Gly Gly Ala Ala Gly
                115                 120                 125

Gly Gly Gly Ala Cys Thr Gly Gly Ala Ala Thr Gly Gly Ala Thr Thr
                130                 135                 140

Gly Gly Gly Thr Ala Thr Ala Thr Cys Thr Ala Thr Thr Ala Cys Ala
145                 150                 155                 160

Gly Thr Gly Gly Gly Ala Ala Cys Ala Cys Ala Ala Thr Thr Ala Thr
                165                 170                 175

Cys Ala Ala Cys Cys Cys Thr Cys Cys Cys Thr Cys Ala Ala Gly Ala
                180                 185                 190

Ala Gly Thr Cys Gly Ala Gly Thr Cys Ala Cys Cys Ala Thr Ala Thr
                195                 200                 205

Cys Ala Gly Thr Ala Gly Ala Cys Ala Cys Gly Thr Cys Cys Ala Ala
                210                 215                 220

Gly Ala Ala Cys Cys Ala Gly Thr Thr Cys Thr Cys Cys Cys Thr Gly
225                 230                 235                 240

Ala Ala Gly Cys Thr Gly Ala Gly Gly Thr Cys Thr Gly Thr Gly Ala
                245                 250                 255

Cys Cys Gly Cys Thr Gly Cys Gly Gly Ala Cys Ala Cys Gly Gly Cys
                260                 265                 270
```

Cys Gly Thr Ala Thr Ala Thr Ala Cys Thr Gly Cys Gly
            275                 280                 285

Ala Gly Gly Thr Ala Thr Ala Ala Cys Thr Gly Ala Ala Cys Ala
            290                 295                 300

Ala Cys Gly Ala Cys Cys Thr Cys Thr Thr Thr Gly Ala Cys Thr Ala
305                 310                 315                 320

Cys Thr Gly Gly Gly Gly Cys Cys Ala Gly Gly Gly Ala Ala Cys Cys
            325                 330                 335

Cys Thr Gly Gly Thr Cys Ala Cys Cys Gly Thr Cys Thr Cys Cys Thr
            340                 345                 350

Cys Ala

<210> SEQ ID NO 36
<211> LENGTH: 118
<212> TYPE: PRT
<213> ORGANISM: Homo sapiens

<400> SEQUENCE: 36

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Tyr Asn Trp Asn Asn Asp Leu Phe Asp Tyr Trp Gly Gln Gly Thr
            100                 105                 110

Leu Val Thr Val Ser Ser
        115

<210> SEQ ID NO 37
<211> LENGTH: 321
<212> TYPE: DNA
<213> ORGANISM: Homo sapiens

<400> SEQUENCE: 37
gacatccaga tgacccagtc tccatcctcc ctgtctgcat ctgtaggaga cagagtcacc        60
atcacttgcc aggcgagtca ggacattagc aactatttaa attggtatca gcagaaacca       120
gggaaagccc ctaagctcct gatctacgat gcatccaatt tggaaactgg ggtcccatca       180
aggttcagtg gaagtggatc tgggacagat tttactttca ccatcagcag cctgcagcct       240
gaagatattg caacatatta ctgtcaacaa tatgataatc tccctctcac tttcggcgga       300
gggaccaagg tggagatcaa a                                                  321

<210> SEQ ID NO 38
<211> LENGTH: 107
<212> TYPE: PRT
<213> ORGANISM: Homo sapiens

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105

<210> SEQ ID NO 39
<211> LENGTH: 378
<212> TYPE: DNA
<213> ORGANISM: Homo sapiens

<400> SEQUENCE: 39
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg gcctggagtg gtggcagtt atatggtgtg atggaagtaa taaatactat     180
gcagactccg tgaagggccg attcaccatc tccagagaca gttccaagaa cacgctgtat     240
ctgcaaatga acagcctgag agccgaggac acggctgtgt attactgtgc gagagggggc     300
tatggttcgg ggagttatga ggactactac tacggtatgg acgtctgggg ccaagggacc     360
acggtcaccg tctcctca                                                   378

<210> SEQ ID NO 40
<211> LENGTH: 126
<212> TYPE: PRT
<213> ORGANISM: Homo sapiens

<400> SEQUENCE: 40

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Cys Asp Gly Ser Asn Lys Tyr Tyr Ala Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Gly Ser Gly Ser Tyr Glu Asp Tyr Tyr Tyr Gly
            100                 105                 110

Met Asp Val Trp Gly Gln Gly Thr Thr Val Thr Val Ser Ser
        115                 120                 125

<210> SEQ ID NO 41
<211> LENGTH: 321
<212> TYPE: DNA
<213> ORGANISM: Homo sapiens

<400> SEQUENCE: 41

```
gacatccaga tgacccagtc tccatcctcc ctgtctgcat ctgtaggaga cagagtcacc    60
atcacttgcc aggcgagtca ggacattagt aaggatttaa attggtatca gcagaaacca   120
gggaaagccc ctaggctcct gatctacgat gcatccaatt tggaaacggg ggtcccatca   180
aggttcagtg gaagtggatc tgggacagat tttactttca ccatcagcag cctgcagcct   240
gaagatattg caacatttta ctgtcaacag tatgatcatc tcccgatcgc cttcggccaa   300
gggacacgac tggagattaa a                                             321
```

<210> SEQ ID NO 42
<211> LENGTH: 107
<212> TYPE: PRT
<213> ORGANISM: Homo sapiens

<400> SEQUENCE: 42

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Lys Asp
            20                  25                  30

Leu Asn Trp Tyr Gln Gln Lys Pro Gly Lys Ala Pro Arg Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Phe Tyr Cys Gln Gln Tyr Asp His Leu Pro Ile
                85                  90                  95

Ala Phe Gly Gln Gly Thr Arg Leu Glu Ile Lys
            100                 105
```

<210> SEQ ID NO 43
<211> LENGTH: 357
<212> TYPE: DNA
<213> ORGANISM: Homo sapiens

<400> SEQUENCE: 43

```
caggtgcagc tggtgcagtc tggggctgag gtgaagaagc ctggggcctc agtgaaggtc    60
tcctgcaagg cttctggata caccttcacc agttatgata tcaactgggt gcgacaggcc   120
actggccaag gcttgagtg gatgggatgg atggacccta acagtggtaa cacaggctat   180
gcacagaagt tccagggcag agtcaccatg accaggaaca cctccataag cacagccttc   240
atggagctga gcagcctgag atctgaggac acggccgtgt attactgtgc gagaacggac   300
tacttctact cggtatgga cgtctggggc caagggacca cggtcaccgt ctcctca      357
```

<210> SEQ ID NO 44
<211> LENGTH: 119
<212> TYPE: PRT
<213> ORGANISM: Homo sapiens

<400> SEQUENCE: 44

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45
```

Gly Trp Met Asp Pro Asn Ser Gly Asn Thr Gly Tyr Ala Gln Lys Phe
        50                  55                  60

Gln Gly Arg Val Thr Met Thr Arg Asn Thr Ser Ile Ser Thr Ala Phe
65                  70                  75                  80

Met Glu Leu Ser Ser Leu Arg Ser Glu Asp Thr Ala Val Tyr Tyr Cys
                85                  90                  95

Ala Arg Thr Asp Tyr Phe Tyr Phe Gly Met Asp Val Trp Gly Gln Gly
                100                 105                 110

Thr Thr Val Thr Val Ser Ser
        115

<210> SEQ ID NO 45
<211> LENGTH: 321
<212> TYPE: DNA
<213> ORGANISM: Homo sapiens

<400> SEQUENCE: 45
gacatccagg tgacccagtc tccatcctcc ctgtctgcat ctgtaggaga cagagtcacc        60
atcacttgcc aggcgagtca ggacattagc aactatttaa attggtatca gcagaaacca      120
gggaaagccc ctaagttcct gatctacgat gcatccaatt tggaagcagg ggtcccatca      180
aggttcagtg gaagtggatc tgggacagat tttactttca ccatcagcag cctgcagcct      240
gaagatattg caacatatta ctgtcaacag tatgataatc tcccgctcac tttcggcgga      300
gggaccaagg tggagatcaa a                                                 321

<210> SEQ ID NO 46
<211> LENGTH: 107
<212> TYPE: PRT
<213> ORGANISM: Homo sapiens

<400> SEQUENCE: 46

Asp Ile Gln Val Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Phe Leu Ile
            35                  40                  45

Tyr Asp Ala Ser Asn Leu Glu Ala Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
                100                 105

<210> SEQ ID NO 47
<211> LENGTH: 375
<212> TYPE: DNA
<213> ORGANISM: Homo sapiens

<400> SEQUENCE: 47
caggtgcagt tggtggagtc tgggggaggc gtggtccagc ctggagggtc cctgagactc        60
tcctgtgcag cgtctggatt caccttcagt agctatggca tgcactgggt ccgccaggct      120
ccaggcaagg ggctggagtg ggtggcagtt atatggtatg atggaagaaa taaatactat      180

```
gcagactccg tgaagggccg attcaccatc tccagagaca attccaagaa cacgctgtat    240
ctgcaaatga acagcctgag agccgaggac acggctgtgt attactgtgc gagaggggg    300 ggagcagtgg ctgattacaa ctactactac ggtatggacg tctggggcca agggaccacg    360
gtcaccgtct cctca                                                    375
```

<210> SEQ ID NO 48
<211> LENGTH: 125
<212> TYPE: PRT
<213> ORGANISM: Homo sapiens

<400> SEQUENCE: 48

```
Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Ala Val Ala Asp Tyr Asn Tyr Tyr Gly Met
            100                 105                 110

Asp Val Trp Gly Gln Gly Thr Thr Val Thr Val Ser Ser
        115                 120                 125
```

<210> SEQ ID NO 49
<211> LENGTH: 321
<212> TYPE: DNA
<213> ORGANISM: Homo sapiens

<400> SEQUENCE: 49

```
gacatccaga tgacccagtc tccatcctcc ctgtctgcat ctgtaggaga cagagtcacc     60
atcacttgcc aggcgagtca ggacattagc aaggatttaa attggtatca gcagaaacca    120
gggaaagccc ctaagctcct gatctacgat gcatccaatt tggaaacagg ggtcccatca    180
aggttcagtg gaagtggatc tgggacagat tttactttca ccatcagcag cctgcagcct    240
gaagatattg caacatatta ctgtcaacag tatgatgatc tcccgatcac cttcggccaa    300
gggacacgac tggagattaa a                                              321
```

<210> SEQ ID NO 50
<211> LENGTH: 107
<212> TYPE: PRT
<213> ORGANISM: Homo sapiens

<400> SEQUENCE: 50

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Lys Asp
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60
```

```
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asp Leu Pro Ile
                 85                  90                  95

Thr Phe Gly Gln Gly Thr Arg Leu Glu Ile Lys
            100                 105
```

<210> SEQ ID NO 51
<211> LENGTH: 357
<212> TYPE: DNA
<213> ORGANISM: Homo sapiens

<400> SEQUENCE: 51

```
caggtgcagc tggtacagtc tggggctgag gtgaagaagc ctggggcctc agtgaaggtc    60
tcctgcaagg cctctggatt caccttcacc agttatgata tcagctgggt gcgacaggcc   120
actggactag gcttgagtg gatgggatgg atgaacccta gcagtggtta cacaggctat   180
gcacagaact tccagggcag agtcaccatg acctggaaca cctccataag cacagtctac   240
atggagctga gcagcctgag atctgaggac acggccgtgt attactgtgc gagaacggac   300
tactactact acggtatgga cgtctggggc cgagggacca cggtcaccgt ctcctca     357
```

<210> SEQ ID NO 52
<211> LENGTH: 119
<212> TYPE: PRT
<213> ORGANISM: Homo sapiens

<400> SEQUENCE: 52

```
Gln Val Gln Leu Val Gln Ser Gly Ala Glu Val Lys Lys Pro Gly Ala
  1               5                  10                  15

Ser Val Lys Val Ser Cys Lys Ala Ser Gly Phe Thr Phe Thr Ser Tyr
                 20                  25                  30

Asp Ile Ser Trp Val Arg Gln Ala Thr Gly Leu Gly Leu Glu Trp Met
             35                  40                  45

Gly Trp Met Asn Pro Ser Ser Gly Tyr Thr Gly Tyr Ala Gln Asn Phe
     50                  55                  60

Gln Gly Arg Val Thr Met Thr Trp Asn Thr Ser Ile Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Thr Asp Tyr Tyr Tyr Tyr Gly Met Asp Val Trp Gly Arg Gly
                100                 105                 110

Thr Thr Val Thr Val Ser Ser
            115
```

<210> SEQ ID NO 53
<211> LENGTH: 321
<212> TYPE: DNA
<213> ORGANISM: Homo sapiens

<400> SEQUENCE: 53

```
gacatccggt tgacccagtc tccatcctcc ctgtctgcat ctgtaggaga cagagtcacc    60
atcacttgcc aggcgagtca ggacattagc aactatttaa attggtatca gcaggaacca   120
gggaaagccc ctaagctcct gatctacgat gcatccaatt tggaaacagg ggtcccatca   180
aggttcagtg aagtggatc tgggacagat tttactttca ccatcagcag cctgcagcct   240
gaagatattg caacatatta ctgtcaacag tatgataatt tcccgctcac tttcggcgga   300
```
gggaccaagg tggagatcaa a                                              321

<210> SEQ ID NO 54
<211> LENGTH: 107
<212> TYPE: PRT
<213> ORGANISM: Homo sapiens

<400> SEQUENCE: 54

Asp Ile Arg Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Glu Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Phe Pro Leu
                85                  90                  95

Thr Phe Gly Gly Gly Thr Lys Val Glu Ile Lys
            100                 105

<210> SEQ ID NO 55
<211> LENGTH: 354
<212> TYPE: DNA
<213> ORGANISM: Homo sapiens

<400> SEQUENCE: 55
caggtgctac tgcaggagtc gggcccagga ctggtgaagc cttcggagac cctgtccctc     60
acctgcactg tctctggtgg ctccatcagt agttactact ggagctggat ccggcagacc    120
ccagggaagg gactgagtg gattgggtat gtctattaca gtgggagcac cagctacaac     180
ccctccctca agagtcgagt caccatatca atgtacacgt ccaagaccga gttctccctg    240
aagctgagct ctgtgaccgc tgcggacacg gccgtgtatt actgtgcgag gtataactgg    300
aacaacgacc tctttgacta ctggggccag ggaaccctgg tcaccgtctc ctca           354

<210> SEQ ID NO 56
<211> LENGTH: 118
<212> TYPE: PRT
<213> ORGANISM: Homo sapiens

<400> SEQUENCE: 56

Gln Val Leu Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Thr Pro Gly Lys Gly Leu Glu Trp Ile
        35                  40                  45

Gly Tyr Val Tyr Tyr Ser Gly Ser Thr Ser Tyr Asn Pro Ser Leu Lys
    50                  55                  60

Ser Arg Val Thr Ile Ser Met Tyr Thr Ser Lys Thr Glu Phe Ser Leu
65                  70                  75                  80

Lys Leu Ser Ser Val Thr Ala Ala Asp Thr Ala Val Tyr Tyr Cys Ala
                85                  90                  95

Arg Tyr Asn Trp Asn Asn Asp Leu Phe Asp Tyr Trp Gly Gln Gly Thr

Leu Val Thr Val Ser Ser
      115

<210> SEQ ID NO 57
<211> LENGTH: 324
<212> TYPE: DNA
<213> ORGANISM: Homo sapiens

<400> SEQUENCE: 57
tcctatgtgt tgactcagcc accctcggtg tcagtggccc caggacagac ggccaggatt     60
acctgtgggg gaaacaacat tggaagtaaa agtgtgcact ggtaccagca gaagccaggc    120
caggcccctg tgctggtcgt ctatgatgat agcgaccggc cctcagggat ccctgagcga    180
ttctctggct ccaactctgg gaacacggcc accctgacca tcagcagggt cgaagccggg    240
gatgaggccg actattactg tcaggtgttg atagtagta gtgatcatgt gatattcggc    300
ggagggacca agctgaccgt ccta                                          324

<210> SEQ ID NO 58
<211> LENGTH: 108
<212> TYPE: PRT
<213> ORGANISM: Homo sapiens

<400> SEQUENCE: 58

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Leu Asp Ser Ser Ser Asp His
                85                  90                  95

Val Ile Phe Gly Gly Gly Thr Lys Leu Thr Val Leu
            100                 105

<210> SEQ ID NO 59
<211> LENGTH: 324
<212> TYPE: DNA
<213> ORGANISM: Homo sapiens

<400> SEQUENCE: 59
tcctatgtgt tgactcagcc accctcggtg tcagtggccc caggacagac ggccaggatt     60
acctgtgggg gaaacaacat tggaagtaaa agtgtgcact ggtaccagca gaagccaggc    120
caggcccctg tgctggtcgt ctatgatgat agcgaccggc cctcagggat ccctgagcga    180
ttctctggct ccaactctgg gaacacggcc accctgacca tcagcagggt cgaagccggg    240
gatgaggccg actattactg tcaggtgttg atagtagta gtgatcatgt gatattcggc    300
ggagggacca agctgaccgt ccta                                          324

<210> SEQ ID NO 60
<211> LENGTH: 120
<212> TYPE: PRT
<213> ORGANISM: Homo sapiens

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ser Gly Asn Tyr
            20                  25                  30

Ala Met Ser Trp Val Arg Gln Ala Pro Gly Lys Gly Leu Glu Trp Val
        35                  40                  45

Ser Ala Ile Ser Gly Gly Gly Thr Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Lys Glu Phe Gly Glu Leu Glu Pro Arg Phe Asp Tyr Trp Gly Gln
            100                 105                 110

Gly Thr Leu Val Thr Val Ser Ser
            115                 120

<210> SEQ ID NO 61
<211> LENGTH: 324
<212> TYPE: DNA
<213> ORGANISM: Homo sapiens

<400> SEQUENCE: 61
tcctatgtgc tgactcagcc accctcggtg tcagtggccc caggacagac ggccaggatt       60
acctgtgggg gaaacaacat tggaagtgaa agtgtgcact ggtaccagca gaagccaggc      120
caggcccctg tgctggtcgt ctatgatgat agcgaccggc cctcagggat ccctgagcga      180
ttctctggct ccaactctgg gaacacggcc accctgacca tcagcagggt cgaagccggg      240
gatgaggccg actattactg tcaggtgtgg gatagtagta atgatcatgt ggttttcggc      300
ggagggacca agctgaccgt ccta                                            324

<210> SEQ ID NO 62
<211> LENGTH: 108
<212> TYPE: PRT
<213> ORGANISM: Homo sapiens

<400> SEQUENCE: 62

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Glu Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asn Asp His
                85                  90                  95

Val Val Phe Gly Gly Gly Thr Lys Leu Thr Val Leu
            100                 105

<210> SEQ ID NO 63
<211> LENGTH: 372

<212> TYPE: DNA
<213> ORGANISM: Homo sapiens

<400> SEQUENCE: 63

```
cagctgcagc tgcaggagtc gggcccagga ctggtgaagc cttcggagac cctgtccctc      60
acctgcactg tctctggtgg ctccatcagc agtagtaatt actactgggg ctggatccgc     120
cagcccccgg ggaaggggct ggagtggatt gggactatct attatagtgg gagcacctac     180
tacacccccgt ccctcaagag tcgagtcacc atatccgtag acacgtccaa gaaccagttc    240
tccctgaagc tgagctctgt gaccgccgca gacacggctg tctattactg tgcgagagag     300
agggcgatag cagtggctgc tatagtcttc tttgactact ggggccaggg aaccctggtc     360
accgtctcct ca                                                        372
```

<210> SEQ ID NO 64
<211> LENGTH: 124
<212> TYPE: PRT
<213> ORGANISM: Homo sapiens

<400> SEQUENCE: 64

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Tyr Trp Gly Trp Ile Arg Gln Pro Pro Gly Lys Gly Leu Glu
        35                  40                  45

Trp Ile Gly Thr Ile Tyr Tyr Ser Gly Ser Thr Tyr Tyr Thr Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Arg Ala Ile Ala Val Ala Ala Ile Val Phe Phe Asp
            100                 105                 110

Tyr Trp Gly Gln Gly Thr Leu Val Thr Val Ser Ser
        115                 120
```

<210> SEQ ID NO 65
<211> LENGTH: 324
<212> TYPE: DNA
<213> ORGANISM: Homo sapiens

<400> SEQUENCE: 65

```
tcctatgtgc tgactcagtc accctcggtg tcagtggccc caggacagac ggccaggatt      60
acctgtgggg gaaacaacat tggaagtaaa agtgtgcact ggtaccagca gaagccaggc     120
caggcccctg tgctggtcgt ctatgatgat agcgaccggc cctcagggat ccctgagcga     180
ttctctggct ccaactctgg gaacacggcc accctgacca tcagcagggt cgaagccggg     240
gatgaggccg actactactg tcaggtgtgg gatagtagta gtgatcattg ggtgttcggc     300
ggagggacca agctgaccgt ccta                                            324
```

<210> SEQ ID NO 66
<211> LENGTH: 103
<212> TYPE: PRT
<213> ORGANISM: Homo sapiens

<400> SEQUENCE: 66

Gln Ser Pro Ser Val Ser Val Ala Pro Gly Gln Thr Ala Arg Ile Thr
1               5                   10                  15

Cys Gly Gly Asn Asn Ile Gly Ser Lys Ser Val His Trp Tyr Gln Gln
            20                  25                  30

Lys Pro Gly Gln Ala Pro Val Leu Val Val Tyr Asp Asp Ser Asp Arg
            35                  40                  45

Pro Ser Gly Ile Pro Glu Arg Phe Ser Gly Ser Asn Ser Gly Asn Thr
            50                  55                  60

Ala Thr Leu Thr Ile Ser Arg Val Glu Ala Gly Asp Glu Ala Asp Tyr
65                  70                  75                  80

Tyr Cys Gln Val Trp Asp Ser Ser Ser Asp His Trp Val Phe Gly Gly
                85                  90                  95

Gly Thr Lys Leu Thr Val Leu
                100

<210> SEQ ID NO 67
<211> LENGTH: 369
<212> TYPE: DNA
<213> ORGANISM: Homo sapiens

<400> SEQUENCE: 67
caggtgcagc tggtgcagtc tggggctgag gtgaagaagc ctggggcctc agtgaaggtc      60
tcctgcaagg cttctggata caccttcacc agttatgata tcaactgggt gcgacaggcc     120
actggacaag ggcttgagtg gatgggatgg atgaatctta acagtgataa cacaggctat     180
gcacagaagt tccagggcag agtcaccatg accaggaaca cctccataag cactgcctac     240
atggagctga gcagcctgag atctgaggac acggccgtgt attactgtgc gagtatagca     300
gctcgtcgcg actacaacta ctacggtatg gacgtctggg gccaagggac caaggtcacc     360
gtctcctca                                                            369

<210> SEQ ID NO 68
<211> LENGTH: 123
<212> TYPE: PRT
<213> ORGANISM: Homo sapiens

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
            35                  40                  45

Gly Trp Met Asn Leu Asn Ser Asp Asn Thr Gly Tyr Ala Gln Lys Phe
            50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ile Ala Ala Arg Arg Asp Tyr Asn Tyr Tyr Gly Met Asp Val
                100                 105                 110

Trp Gly Gln Gly Thr Lys Val Thr Val Ser Ser
            115                 120

<210> SEQ ID NO 69
<211> LENGTH: 321
<212> TYPE: DNA

<213> ORGANISM: Homo sapiens

<400> SEQUENCE: 69

```
gaaattgtgt tgacgcagtc tccaggcacc ctgtctgtgt ctccagggga aagagccacc    60
ctctcctgca gggccagtca gagtgttagc agcagctact tagcctggta tcagcagaaa   120
cctggccagg ctcccaggct cctcatctat ggtgcatccg gcagggccac tggcatccca   180
gacaggttca gtggcagtgg gtctgggaca gacttcattc tcaccatcag cagactggag   240
cctgaagatt ttgcagtgta ttactgtcag cagtatggta gctcattcac tttcggcgga   300
gggaccaagg tggagatcaa a                                             321
```

<210> SEQ ID NO 70
<211> LENGTH: 107
<212> TYPE: PRT
<213> ORGANISM: Homo sapiens

<400> SEQUENCE: 70

Glu Ile Val Leu Thr Gln Ser Pro Gly Thr Leu Ser Val Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Gly Arg Ala Thr Gly Ile Pro Asp Arg Phe Ser
    50                  55                  60

Gly Ser Gly Ser Gly Thr Asp Phe Ile Leu Thr Ile Ser Arg Leu Glu
65                  70                  75                  80

Pro Glu Asp Phe Ala Val Tyr Tyr Cys Gln Gln Tyr Gly Ser Ser Phe
                85                  90                  95

Thr Phe Gly Gly Gly Thr Lys Val Glu Ile Lys
            100                 105

<210> SEQ ID NO 71
<211> LENGTH: 375
<212> TYPE: DNA
<213> ORGANISM: Homo sapiens

<400> SEQUENCE: 71

```
caggtgcagc tggtggagtc tgggggaggc gtggtccagc ctgggaggtc cctgagactc    60
tcctgtgcag cctctggatt caccttcagt agctatggca tgcactgggt ccgccaggct   120
ccaggcaagg ggctggagtg gtggcagtt atattatatg atggaagtga taattactat   180
gcagactccg tgaagggccg attcaccatc tccagagaca attccaagaa cacgctgtat   240
ctgcaaatga acagcctgag agctgaggac acggctgtgt attactgtgc gagagaaggg   300
atagcagtgg ctggggacta ctactactac ggtatggacg tctggggcca agggaccacg   360
gtcaccgtct cctca                                                    375
```

<210> SEQ ID NO 72
<211> LENGTH: 125
<212> TYPE: PRT
<213> ORGANISM: Homo sapiens

<400> SEQUENCE: 72

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr

```
                    20                  25                  30
Gly Met His Trp Val Arg Gln Ala Pro Gly Lys Gly Leu Glu Trp Val
            35                  40                  45
Ala Val Ile Leu Tyr Asp Gly Ser Asp Asn Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Gly Ile Ala Val Ala Gly Asp Tyr Tyr Tyr Gly Met
            100                 105                 110
Asp Val Trp Gly Gln Gly Thr Thr Val Thr Val Ser Ser
            115                 120                 125

<210> SEQ ID NO 73
<211> LENGTH: 336
<212> TYPE: DNA
<213> ORGANISM: Homo sapiens

<400> SEQUENCE: 73
cagtcagtgc tgacgcagcc gccctcagtg tctggggccc cagggcagag ggtcaccatc      60
tcctgcactg ggagcagctc caacatcggg gcagattatg atgtacactg gtaccagcag     120
cttccaggaa cagcccccaa actcctcatc tatgattaca gcaatcggcc ctcaggggtc     180
cctgaccgat tctctggctc caagtctggc acctcagcct ccctggccat cactgggctc     240
caggctgagg atgaggctga ttattactgc cagtcctatg acaacagcct gagtggttat     300
gtggtattcg gcggagggac caagctgacc gtccta                                336

<210> SEQ ID NO 74
<211> LENGTH: 112
<212> TYPE: PRT
<213> ORGANISM: Homo sapiens

<400> SEQUENCE: 74

Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Asp
            20                  25                  30
Tyr Asp Val His Trp Tyr Gln Gln Leu Pro Gly Thr Ala Pro Lys Leu
        35                  40                  45
Leu Ile Tyr Asp Tyr Ser Asn Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Asp Asn Ser
                85                  90                  95
Leu Ser Gly Tyr Val Val Phe Gly Gly Gly Thr Lys Leu Thr Val Leu
            100                 105                 110

<210> SEQ ID NO 75
<211> LENGTH: 348
<212> TYPE: DNA
<213> ORGANISM: Homo sapiens

<400> SEQUENCE: 75
gaggtgcagc tggtgcagtc tggagcagag gtgaaaaagc ccggggagtc tctgaagatc      60
```

```
tcctgtaagg gttctggata cagctttacc agctactgga tcggctgggt gcgccagatg    120
cccgggaaag gctggagtg gatggggatc atctatcctg gtgactctga taccagatac     180
agcccgtcct tccaaggcca ggtcaccatc tcagccgaca gtccatcag caccgcctac     240 ctgcagtgga gcagcctgac ggcctcggac accgccatgt attactgtgc gagacaggga   300
gagagctttg actactgggg ccagggaacc ctggtcaccg tctcctca               348
```

```
<210> SEQ ID NO 76
<211> LENGTH: 116
<212> TYPE: PRT
<213> ORGANISM: Homo sapiens

<400> SEQUENCE: 76
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Thr Ala Ser Asp Thr Ala Met Tyr Tyr Cys
                85                  90                  95

Ala Arg Gln Gly Glu Ser Phe Asp Tyr Trp Gly Gln Gly Thr Leu Val
            100                 105                 110

Thr Val Ser Ser
        115

```
<210> SEQ ID NO 77
<211> LENGTH: 330
<212> TYPE: DNA
<213> ORGANISM: Homo sapiens

<400> SEQUENCE: 77
```

```
cagtctgtgc tgacgcagcc gccctcagtg tctggggccc cagggcagag ggtcaccatc    60
tcctgcactg ggagcagctc caacatcggg gcaggttatg atgtacactg gtaccagcag   120
cttccaagaa cagccccaa actcctcatc tatggtaaca gcaatcggcc ctcagggtc     180 cctgaccgat tctctgactc caagtctggc acctcagcct ccctggccat cactggcctc   240
caggctgagg atgaggctga ttattactgc cagtcctatg acagcagcct gagtgtgata   300
ttcggcggag ggaccaagct gaccgtccta                                    330
```

```
<210> SEQ ID NO 78
<211> LENGTH: 110
<212> TYPE: PRT
<213> ORGANISM: Homo sapiens

<400> SEQUENCE: 78
```

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Arg Thr Ala Pro Lys Leu
            35                  40                  45

Leu Ile Tyr Gly Asn Ser Asn Arg Pro Ser Gly Val Pro Asp Arg Phe
            50                  55                  60

Ser Asp Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                85                  90                  95

Leu Ser Val Ile Phe Gly Gly Gly Thr Lys Leu Thr Val Leu
            100                 105                 110

<210> SEQ ID NO 79
<211> LENGTH: 348
<212> TYPE: DNA
<213> ORGANISM: Homo sapiens

<400> SEQUENCE: 79
gaggtgcagc tggtgcagtc tggagcagag gtgaaaaagc ccggggagtc tctgaagatc       60
tcctgtaagg tttctggata cagctttacc acctactgga tcggctgggt gcgccagatg      120
cccgggaaag gcctggactg gatggggatc atctatcctg gtgactctga taccagatac      180
agcccgtcct tccaaggcca ggtcaccatc tcagccgaca gtccatcag caccgcctac       240 ctgcagtgga gcagcctgaa ggcctcggac accgccatgt attactgtgc gagacaaggt     300
atagcgtttg actactgggg ccagggaacc ctggtcaccg tctcctca                  348

<210> SEQ ID NO 80
<211> LENGTH: 116
<212> TYPE: PRT
<213> ORGANISM: Homo sapiens

<400> SEQUENCE: 80

Glu Val Gln Leu Val Gln Ser Gly Ala Glu Val Lys Lys Pro Gly Glu
 1               5                  10                  15

Ser Leu Lys Ile Ser Cys Lys Val Ser Gly Tyr Ser Phe Thr Thr Tyr
            20                  25                  30

Trp Ile Gly Trp Val Arg Gln Met Pro Gly Lys Gly Leu Asp Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
 65                 70                  75                  80

Leu Gln Trp Ser Ser Leu Lys Ala Ser Asp Thr Ala Met Tyr Tyr Cys
                85                  90                  95

Ala Arg Gln Gly Ile Ala Phe Asp Tyr Trp Gly Gln Gly Thr Leu Val
            100                 105                 110

Thr Val Ser Ser
        115

<210> SEQ ID NO 81
<211> LENGTH: 336
<212> TYPE: DNA
<213> ORGANISM: Homo sapiens

<400> SEQUENCE: 81
gatattgtga tgacccagac tccactctct ctgtccgtca cccctggaca gccggcctcc       60
atctcctgca gtctggtca gagcctcctg catagtgatg gaaagaccta tttgtattgg      120
tacctgcaga agccaggcca gcctccacag ttcctgatct atgaagtttc caaccggttc    180
tctagagtgc cagataggtt cagtggcagc gggtcaggga cagatttcac actgagaatc    240

```
agccgggtgg aggctgagga tgttggaatt tattactgca tgcaaagtat acagcttccg    300
tggacgttcg gccaagggac ccaggtggaa atcaaa                              336
```

<210> SEQ ID NO 82
<211> LENGTH: 112
<212> TYPE: PRT
<213> ORGANISM: Homo sapiens

<400> SEQUENCE: 82

Asp Ile Val Met Thr Gln Thr Pro Leu Ser Leu Ser Val Thr Pro Gly
1               5                   10                  15

Gln Pro Ala Ser Ile Ser Cys Lys Ser Gly Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Phe Leu Ile Tyr Glu Val Ser Asn Arg Phe Ser Arg Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Met Gln Ser
                85                  90                  95

Ile Gln Leu Pro Trp Thr Phe Gly Gln Gly Thr Gln Val Glu Ile Lys
            100                 105                 110

<210> SEQ ID NO 83
<211> LENGTH: 342
<212> TYPE: DNA
<213> ORGANISM: Homo sapiens

<400> SEQUENCE: 83

```
caggtgcagc tggtggagtc tgggggaggc gtggtccagc ctgggaggtc cctgagactc    60
tcctgtgcag cctctggatt caccttcagt ggctatggca tgcactgggt ccgccaggct    120
ccaggcaagg ggctggagtg ggtggcagtt atatcatatg atggaaatga taaatactat    180
gcagactccg tgaagggccg attcaccatc tccagagaca atgccaagaa cacgctgtat    240
ctgcaaatga acagcctgag agctgaggac acggctgtgt attactgtgc gagagagcta    300
cgggtcctct ggggccaggg aaccctggtc accgtctcta gt                       342
```

<210> SEQ ID NO 84
<211> LENGTH: 114
<212> TYPE: PRT
<213> ORGANISM: Homo sapiens

<400> SEQUENCE: 84

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asp Lys Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Arg Val Leu Trp Gly Gln Gly Thr Leu Val Thr Val
            100                 105                 110

Ser Ser

<210> SEQ ID NO 85
<211> LENGTH: 336
<212> TYPE: DNA
<213> ORGANISM: Homo sapiens

<400> SEQUENCE: 85
gatattgtga tgacccagac tccactctct ctgtccgtca cccctggaca gccggcctcc      60
atctcctgca agtctggtca gagcctcctg cataatgatg gaaagaccta tttgtattgg     120
tacctgcaga agccaggcca gcctccacag ttcctgatct atgaagtttc aaccggttc      180 tctagagtgc cagataggtt cagtggcagc gggtcaggga cagatttcac actgaaaatc     240
agccgggtgg aggctgagga tgttggaatt tattactgca tgcaaagtat acagcttccg     300
tggacgttcg gccaagggac ccaggtggaa atcaaa                                336

<210> SEQ ID NO 86
<211> LENGTH: 112
<212> TYPE: PRT
<213> ORGANISM: Homo sapiens

<400> SEQUENCE: 86

Asp Ile Val Met Thr Gln Thr Pro Leu Ser Leu Ser Val Thr Pro Gly
1               5                  10                  15

Gln Pro Ala Ser Ile Ser Cys Lys Ser Gly Gln Ser Leu Leu His Asn
            20                  25                  30

Asp Gly Lys Thr Tyr Leu Tyr Trp Tyr Leu Gln Lys Pro Gly Gln Pro
        35                  40                  45

Pro Gln Phe Leu Ile Tyr Glu Val Ser Asn Arg Phe Ser Arg Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ser
                85                  90                  95

Ile Gln Leu Pro Trp Thr Phe Gly Gln Gly Thr Gln Val Glu Ile Lys
            100                 105                 110

<210> SEQ ID NO 87
<211> LENGTH: 342
<212> TYPE: DNA
<213> ORGANISM: Homo sapiens

<400> SEQUENCE: 87
caggtgcagc tggtggagtc tgggggaggc gtggtccagc ctggaggtc cctgagactc       60 tcctgtgcag cctctggatt caccttcagt ggctatggca tgcactgggt ccgccaggct     120
ccaggcaagg ggctggagtg ggtggcagtt atatcatatg atggaaatga taatactat     180 gcagactccg tgaagggccg attcaccatc tccagacaca tgccaagaa cacgctgtat     240 ctgcaaatga acagcctgag agctgaggac acggctgttt attactgtgc gagagagcta     300
cgggtcctct ggggccaggg aaccctggtc accgtctcct ca                         342

<210> SEQ ID NO 88
<211> LENGTH: 114
<212> TYPE: PRT

<213> ORGANISM: Homo sapiens

<400> SEQUENCE: 88

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asp Lys Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Arg Val Leu Trp Gly Gln Gly Thr Leu Val Thr Val
            100                 105                 110

Ser Ser

<210> SEQ ID NO 89
<211> LENGTH: 336
<212> TYPE: DNA
<213> ORGANISM: Homo sapiens

<400> SEQUENCE: 89
gatattgtga tgacccagac tccactctct ctgtccgtca cccctagaca gccggcctcc      60
atctcctgca agtctagtca gagcctcctg catagtgatg gaaagaccta tttgtattgg     120
tacctgcaga agccaggcca gcctccacag ttcctgatct atgaagtttc caaccgcttc     180
tctggagtgc cagataggtt cagtggcagc gggtcaggga cagatttcac actgaaaatc     240
agccgggtgg aggctgagga tgttggggtt tattactgca tgcaaagtat acagcttccg     300
tggacgttcg gccaagggac caaggtggaa atcaaa                               336

<210> SEQ ID NO 90
<211> LENGTH: 112
<212> TYPE: PRT
<213> ORGANISM: Homo sapiens

<400> SEQUENCE: 90

Asp Ile Val Met Thr Gln Thr Pro Leu Ser Leu Ser Val Thr Pro Arg
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Phe Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Trp Thr Phe Gly Gln Gly Thr Lys Val Glu Ile Lys
            100                 105                 110

<210> SEQ ID NO 91
<211> LENGTH: 342

<212> TYPE: DNA
<213> ORGANISM: Homo sapiens

<400> SEQUENCE: 91

```
caggtgcagc tggtggagtc tgggggaggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt atatcatatg atggaggtga tcaatactat   180
gcagactccg tgaagggccg attcaccatc tccagagaca attccaagaa cacgctgtat   240
ctgcaaatga acagcctgag aactgaggac acggctgagt attactgtgc gagagagctc   300
cgggtcctct ggggccaggg aaccctggtc accgtctcct ca                      342
```

<210> SEQ ID NO 92
<211> LENGTH: 114
<212> TYPE: PRT
<213> ORGANISM: Homo sapiens

<400> SEQUENCE: 92

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Ser Tyr Asp Gly Gly Asp Gln Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Thr Glu Asp Thr Ala Glu Tyr Tyr Cys
                85                  90                  95
Ala Arg Glu Leu Arg Val Leu Trp Gly Gln Gly Thr Leu Val Thr Val
            100                 105                 110
Ser Ser
```

<210> SEQ ID NO 93
<211> LENGTH: 324
<212> TYPE: DNA
<213> ORGANISM: Homo sapiens

<400> SEQUENCE: 93

```
tcctatgtgc tgactcagcc accctcggtg tcagtggccc caggacagac ggccaggatt    60
acctgtgggg gaaacaacat tggaagtaaa agtgtacact ggtaccagca gaagccaggc   120
caggcccctg tgctggtcgt ctatgatgat agtgaccggc cctcagagat ccctgagcga   180
ttctctggct ccaactctgg gaacacggcc accctgacca tcagcagggt cgaagccggg   240
gatgaggccg actattactg tcaggtgtgg gatagtagta gtgatcatgt ggtattcggc   300
ggagggacca ggctgaccgt ccta                                          324
```

<210> SEQ ID NO 94
<211> LENGTH: 107
<212> TYPE: PRT
<213> ORGANISM: Homo sapiens

<400> SEQUENCE: 94

```
Tyr Val Leu Thr Gln Pro Pro Ser Val Ser Val Ala Pro Gly Gln Thr
1               5                   10                  15
```

Ala Arg Ile Thr Cys Gly Gly Asn Asn Ile Gly Ser Lys Ser Val His
            20                  25                  30

Trp Tyr Gln Gln Lys Pro Gly Gln Ala Pro Val Leu Val Val Tyr Asp
        35                  40                  45

Asp Ser Asp Arg Pro Ser Glu Ile Pro Glu Arg Phe Ser Gly Ser Asn
50                  55                  60

Ser Gly Asn Thr Ala Thr Leu Thr Ile Ser Arg Val Glu Ala Gly Asp
65                  70                  75                  80

Glu Ala Asp Tyr Tyr Cys Gln Val Trp Asp Ser Ser Asp His Val
                85                  90                  95

Val Phe Gly Gly Gly Thr Arg Leu Thr Val Leu
            100                 105

<210> SEQ ID NO 95
<211> LENGTH: 348
<212> TYPE: DNA
<213> ORGANISM: Homo sapiens

<400> SEQUENCE: 95
caggtgcagc tggtggagtc tgggggaggc gtggtccagc ctggagggtc cctgagactc      60
tcctgtgcag cgtctggatt caccttcagt cgctatgaca tgcactgggt ccgccaggct     120
ccaggcaagg ggctggagtg ggtggcaatt atattctatg atggcagcaa taaatactat     180
gcagaccccg tgaagggccg attcaccatc tccagagaca attcaaagaa cacactgtat     240
ctgcaaatga acagcctgag agccgaggac acggctgtgt attactgtgc gactctagca     300
gcagcttttg actactgggg ccagggaacc ctggtcaccg tctcctca                  348

<210> SEQ ID NO 96
<211> LENGTH: 116
<212> TYPE: PRT
<213> ORGANISM: Homo sapiens

<400> SEQUENCE: 96

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Asp Met His Trp Val Arg Gln Ala Pro Gly Lys Gly Leu Glu Trp Val
        35                  40                  45

Ala Ile Ile Phe Tyr Asp Gly Ser Asn Lys Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Ala Ala Ala Phe Asp Tyr Trp Gly Gln Gly Thr Leu Val
            100                 105                 110

Thr Val Ser Ser
        115

<210> SEQ ID NO 97
<211> LENGTH: 11
<212> TYPE: PRT
<213> ORGANISM: Homo sapiens

<400> SEQUENCE: 97

Arg Ala Ser Gln Gly Ile Arg Asp Asp Leu Gly

```
1               5                   10
```

<210> SEQ ID NO 98
<211> LENGTH: 7
<212> TYPE: PRT
<213> ORGANISM: Homo sapiens

<400> SEQUENCE: 98

```
Ala Ala Ser Ser Leu Gln Ser
1               5
```

<210> SEQ ID NO 99
<211> LENGTH: 9
<212> TYPE: PRT
<213> ORGANISM: Homo sapiens

<400> SEQUENCE: 99

```
Leu Gln His Asn Ser Tyr Pro Cys Ser
1               5
```

<210> SEQ ID NO 100
<211> LENGTH: 5
<212> TYPE: PRT
<213> ORGANISM: Homo sapiens

<400> SEQUENCE: 100

```
Ser Tyr Gly Ile Ser
1               5
```

<210> SEQ ID NO 101
<211> LENGTH: 17
<212> TYPE: PRT
<213> ORGANISM: Homo sapiens

<400> SEQUENCE: 101

```
Trp Ile Ser Ala Asp Asn Gly His Thr Asn Tyr Ala Gln Lys Leu Gln
1               5                   10                  15

Gly
```

<210> SEQ ID NO 102
<211> LENGTH: 15
<212> TYPE: PRT
<213> ORGANISM: Homo sapiens

<400> SEQUENCE: 102

```
Asp Gly Glu Leu Leu Asn Tyr Tyr Tyr Tyr Gly Met Asp Val
1               5                   10                  15
```

<210> SEQ ID NO 103
<211> LENGTH: 16
<212> TYPE: PRT
<213> ORGANISM: Homo sapiens

<400> SEQUENCE: 103

```
Lys Ser Ser Gln Ser Leu Leu His Ser Asp Gly Lys Thr Tyr Leu Tyr
1               5                   10                  15
```

<210> SEQ ID NO 104
<211> LENGTH: 7
<212> TYPE: PRT
<213> ORGANISM: Homo sapiens

<400> SEQUENCE: 104

Glu Val Ser Asn Arg Phe Ser

<210> SEQ ID NO 105
<211> LENGTH: 9
<212> TYPE: PRT
<213> ORGANISM: Homo sapiens

<400> SEQUENCE: 105

Met Gln Ser Ile Gln Val Pro Trp Thr
1               5

<210> SEQ ID NO 106
<211> LENGTH: 5
<212> TYPE: PRT
<213> ORGANISM: Homo sapiens

<400> SEQUENCE: 106

Ser Tyr Gly Met His
1               5

<210> SEQ ID NO 107
<211> LENGTH: 17
<212> TYPE: PRT
<213> ORGANISM: Homo sapiens

<400> SEQUENCE: 107

Val Ile Ser Tyr Asp Gly Ser Asp Lys Tyr Tyr Ala Asp Ser Val Lys
1               5                   10                  15

Gly

<210> SEQ ID NO 108
<211> LENGTH: 10
<212> TYPE: PRT
<213> ORGANISM: Homo sapiens

<400> SEQUENCE: 108

Asp Gln Trp Gly Gly Ser Pro Ala Gly Pro
1               5                   10

<210> SEQ ID NO 109
<211> LENGTH: 12
<212> TYPE: PRT
<213> ORGANISM: Homo sapiens

<400> SEQUENCE: 109

Arg Ala Ser Gln Ser Val Ser Ser Asn Tyr Leu Ala
1               5                   10

<210> SEQ ID NO 110
<211> LENGTH: 7
<212> TYPE: PRT
<213> ORGANISM: Homo sapiens

<400> SEQUENCE: 110

Gly Ala Ser Ser Arg Ala Thr
1               5

<210> SEQ ID NO 111
<211> LENGTH: 9
<212> TYPE: PRT
<213> ORGANISM: Homo sapiens

<400> SEQUENCE: 111

Gln Gln Tyr Gly Ser Ser Pro Ile Thr

-continued

```
1               5

<210> SEQ ID NO 112
<211> LENGTH: 5
<212> TYPE: PRT
<213> ORGANISM: Homo sapiens

<400> SEQUENCE: 112

Ser Tyr Gly Met His
1               5

<210> SEQ ID NO 113
<211> LENGTH: 17
<212> TYPE: PRT
<213> ORGANISM: Homo sapiens

<400> SEQUENCE: 113

Val Ile Ser Tyr Asp Gly Ser Asp Lys Tyr Tyr Ala Asp Ser Val Lys
1               5                   10                  15

Gly

<210> SEQ ID NO 114
<211> LENGTH: 10
<212> TYPE: PRT
<213> ORGANISM: Homo sapiens

<400> SEQUENCE: 114

Glu Leu Gly Ile Ala Ala Ser Phe Asp Tyr
1               5                   10

<210> SEQ ID NO 115
<211> LENGTH: 16
<212> TYPE: PRT
<213> ORGANISM: Homo sapiens

<400> SEQUENCE: 115

Lys Ser Ser Gln Ser Leu Leu His Ser Asp Gly Lys Thr Tyr Leu Tyr
1               5                   10                  15

<210> SEQ ID NO 116
<211> LENGTH: 7
<212> TYPE: PRT
<213> ORGANISM: Homo sapiens

<400> SEQUENCE: 116

Glu Val Ser Asn Arg Phe Ser
1               5

<210> SEQ ID NO 117
<211> LENGTH: 9
<212> TYPE: PRT
<213> ORGANISM: Homo sapiens

<400> SEQUENCE: 117

Met Gln Ser Ile Gln Val Pro Trp Thr
1               5

<210> SEQ ID NO 118
<211> LENGTH: 5
<212> TYPE: PRT
<213> ORGANISM: Homo sapiens

<400> SEQUENCE: 118

Ser Tyr Gly Met His
```

```
<210> SEQ ID NO 119
<211> LENGTH: 17
<212> TYPE: PRT
<213> ORGANISM: Homo sapiens

<400> SEQUENCE: 119

Val Ile Ser Tyr Asp Gly Ser Asp Lys Tyr Tyr Ala Asp Ser Val Lys
1               5                   10                  15

Gly

<210> SEQ ID NO 120
<211> LENGTH: 8
<212> TYPE: PRT
<213> ORGANISM: Homo sapiens

<400> SEQUENCE: 120

Asp Leu Val Asp Thr Ala Met Pro
1               5

<210> SEQ ID NO 121
<211> LENGTH: 16
<212> TYPE: PRT
<213> ORGANISM: Homo sapiens

<400> SEQUENCE: 121

Lys Ser Ser Gln Ser Leu Leu His Ser Asp Gly Lys Thr Tyr Leu Tyr
1               5                   10                  15

<210> SEQ ID NO 122
<211> LENGTH: 7
<212> TYPE: PRT
<213> ORGANISM: Homo sapiens

<400> SEQUENCE: 122

Glu Val Ser Asn Arg Phe Ser
1               5

<210> SEQ ID NO 123
<211> LENGTH: 9
<212> TYPE: PRT
<213> ORGANISM: Homo sapiens

<400> SEQUENCE: 123

Met Gln Ser Lys Gln Leu Pro Phe Thr
1               5

<210> SEQ ID NO 124
<211> LENGTH: 5
<212> TYPE: PRT
<213> ORGANISM: Homo sapiens

<400> SEQUENCE: 124

Ser Tyr Gly Met His
1               5

<210> SEQ ID NO 125
<211> LENGTH: 17
<212> TYPE: PRT
<213> ORGANISM: Homo sapiens

<400> SEQUENCE: 125

Val Ile Ser Tyr Asp Gly Ser Asp Lys Tyr Tyr Ala Asp Ser Val Lys
```

Gly

<210> SEQ ID NO 126
<211> LENGTH: 13
<212> TYPE: PRT
<213> ORGANISM: Homo sapiens

<400> SEQUENCE: 126

Ala Gly Tyr Ser Leu Tyr Tyr Tyr Gly Met Asp Val
1               5                   10

<210> SEQ ID NO 127
<211> LENGTH: 17
<212> TYPE: PRT
<213> ORGANISM: Homo sapiens

<400> SEQUENCE: 127

Arg Ser Ser Gln Ser Leu Leu Asp Ser Asp Gly Asp Thr Tyr Leu
1               5                   10                  15

Asp

<210> SEQ ID NO 128
<211> LENGTH: 7
<212> TYPE: PRT
<213> ORGANISM: Homo sapiens

<400> SEQUENCE: 128

Thr Leu Ser Tyr Arg Ala Ser
1               5

<210> SEQ ID NO 129
<211> LENGTH: 14
<212> TYPE: PRT
<213> ORGANISM: Homo sapiens

<400> SEQUENCE: 129

Met Gln Arg Ile Glu Phe Pro Met Gln Arg Ile Glu Phe Pro
1               5                   10

<210> SEQ ID NO 130
<211> LENGTH: 7
<212> TYPE: PRT
<213> ORGANISM: Homo sapiens

<400> SEQUENCE: 130

Ser Gly Gly Tyr Tyr Trp Ser
1               5

<210> SEQ ID NO 131
<211> LENGTH: 16
<212> TYPE: PRT
<213> ORGANISM: Homo sapiens

<400> SEQUENCE: 131

Asp Ile Tyr Tyr Ser Gly Ser Thr Tyr Tyr Asn Pro Ser Leu Lys Ser
1               5                   10                  15

<210> SEQ ID NO 132
<211> LENGTH: 17
<212> TYPE: PRT
<213> ORGANISM: Homo sapiens

<400> SEQUENCE: 132

Asp Arg Ala Tyr Gly Asp Tyr Gly Asp Tyr Tyr Gly Met Asp
1               5                   10                  15

Val

<210> SEQ ID NO 133
<211> LENGTH: 11
<212> TYPE: PRT
<213> ORGANISM: Homo sapiens

<400> SEQUENCE: 133

Gln Ala Ser Gln Asp Ile Asn Asn Tyr Leu Asn
1               5                   10

<210> SEQ ID NO 134
<211> LENGTH: 7
<212> TYPE: PRT
<213> ORGANISM: Homo sapiens

<400> SEQUENCE: 134

Asp Ala Ser Asn Leu Glu Thr
1               5

<210> SEQ ID NO 135
<211> LENGTH: 9
<212> TYPE: PRT
<213> ORGANISM: Homo sapiens

<400> SEQUENCE: 135

Gln Gln Tyr Asp Asp Phe Pro Leu Thr
1               5

<210> SEQ ID NO 136
<211> LENGTH: 5
<212> TYPE: PRT
<213> ORGANISM: Homo sapiens

<400> SEQUENCE: 136

Ser Tyr Tyr Trp Ser
1               5

<210> SEQ ID NO 137
<211> LENGTH: 16
<212> TYPE: PRT
<213> ORGANISM: Homo sapiens

<400> SEQUENCE: 137

Tyr Ile Tyr Tyr Ser Gly Asn Thr Asn Tyr Asn Pro Ser Leu Lys Ser
1               5                   10                  15

<210> SEQ ID NO 138
<211> LENGTH: 10
<212> TYPE: PRT
<213> ORGANISM: Homo sapiens

<400> SEQUENCE: 138

Tyr Asn Trp Asn Asn Asp Leu Phe Asp Tyr
1               5                   10

<210> SEQ ID NO 139
<211> LENGTH: 11
<212> TYPE: PRT
<213> ORGANISM: Homo sapiens

<400> SEQUENCE: 139

Gln Ala Ser Gln Asp Ile Ser Asn Tyr Leu Asn
1               5                   10

<210> SEQ ID NO 140
<211> LENGTH: 7
<212> TYPE: PRT
<213> ORGANISM: Homo sapiens

<400> SEQUENCE: 140

Asp Ala Ser Asn Leu Glu Thr
1               5

<210> SEQ ID NO 141
<211> LENGTH: 9
<212> TYPE: PRT
<213> ORGANISM: Homo sapiens

<400> SEQUENCE: 141

Gln Gln Tyr Asp Asn Leu Pro Leu Thr
1               5

<210> SEQ ID NO 142
<211> LENGTH: 5
<212> TYPE: PRT
<213> ORGANISM: Homo sapiens

<400> SEQUENCE: 142

Ser Tyr Gly Met His
1               5

<210> SEQ ID NO 143
<211> LENGTH: 17
<212> TYPE: PRT
<213> ORGANISM: Homo sapiens

<400> SEQUENCE: 143

Val Ile Trp Cys Asp Gly Ser Asn Lys Tyr Tyr Ala Asp Ser Val Lys
1               5                   10                  15
Gly

<210> SEQ ID NO 144
<211> LENGTH: 17
<212> TYPE: PRT
<213> ORGANISM: Homo sapiens

<400> SEQUENCE: 144

Gly Gly Tyr Gly Ser Gly Ser Tyr Glu Asp Tyr Tyr Tyr Gly Met Asp
1               5                   10                  15
Val

<210> SEQ ID NO 145
<211> LENGTH: 11
<212> TYPE: PRT
<213> ORGANISM: Homo sapiens

<400> SEQUENCE: 145

Gln Ala Ser Gln Asp Ile Ser Lys Asp Leu Asn
1               5                   10

<210> SEQ ID NO 146
<211> LENGTH: 7
<212> TYPE: PRT
<213> ORGANISM: Homo sapiens

<400> SEQUENCE: 146

Asp Ala Ser Asn Leu Glu Thr
1               5

<210> SEQ ID NO 147
<211> LENGTH: 9
<212> TYPE: PRT
<213> ORGANISM: Homo sapiens

<400> SEQUENCE: 147

Gln Gln Tyr Asp Asn Leu Pro Leu Thr
1               5

<210> SEQ ID NO 148
<211> LENGTH: 5
<212> TYPE: PRT
<213> ORGANISM: Homo sapiens

<400> SEQUENCE: 148

Ser Tyr Gly Met His
1               5

<210> SEQ ID NO 149
<211> LENGTH: 17
<212> TYPE: PRT
<213> ORGANISM: Homo sapiens

<400> SEQUENCE: 149

Trp Met Asp Pro Asn Ser Gly Asn Thr Gly Tyr Ala Gln Lys Phe Gln
1               5                   10                  15

Gly

<210> SEQ ID NO 150
<211> LENGTH: 10
<212> TYPE: PRT
<213> ORGANISM: Homo sapiens

<400> SEQUENCE: 150

Thr Asp Tyr Phe Tyr Phe Gly Met Asp Val
1               5                   10

<210> SEQ ID NO 151
<211> LENGTH: 11
<212> TYPE: PRT
<213> ORGANISM: Homo sapiens

<400> SEQUENCE: 151

Gln Ala Ser Gln Asp Ile Ser Asn Tyr Leu Asn
1               5                   10

<210> SEQ ID NO 152
<211> LENGTH: 7
<212> TYPE: PRT
<213> ORGANISM: Homo sapiens

<400> SEQUENCE: 152

Asp Ala Ser Asn Leu Glu Ala
1               5

<210> SEQ ID NO 153
<211> LENGTH: 9
<212> TYPE: PRT
<213> ORGANISM: Homo sapiens

```
<400> SEQUENCE: 153

Gln Gln Tyr Asp Asn Leu Pro Leu Thr
1               5

<210> SEQ ID NO 154
<211> LENGTH: 5
<212> TYPE: PRT
<213> ORGANISM: Homo sapiens

<400> SEQUENCE: 154

Ser Tyr Gly Met His
1               5

<210> SEQ ID NO 155
<211> LENGTH: 17
<212> TYPE: PRT
<213> ORGANISM: Homo sapiens

<400> SEQUENCE: 155

Val Ile Trp Tyr Asp Gly Arg Asn Lys Tyr Tyr Ala Asp Ser Val Lys
1               5                   10                  15

Gly

<210> SEQ ID NO 156
<211> LENGTH: 16
<212> TYPE: PRT
<213> ORGANISM: Homo sapiens

<400> SEQUENCE: 156

Gly Gly Gly Ala Val Ala Asp Tyr Asn Tyr Tyr Tyr Gly Met Asp Val
1               5                   10                  15

<210> SEQ ID NO 157
<211> LENGTH: 11
<212> TYPE: PRT
<213> ORGANISM: Homo sapiens

<400> SEQUENCE: 157

Gln Ala Ser Gln Asp Ile Ser Lys Asp Leu Asn
1               5                   10

<210> SEQ ID NO 158
<211> LENGTH: 7
<212> TYPE: PRT
<213> ORGANISM: Homo sapiens

<400> SEQUENCE: 158

Asp Ala Ser Asn Leu Glu Thr
1               5

<210> SEQ ID NO 159
<211> LENGTH: 9
<212> TYPE: PRT
<213> ORGANISM: Homo sapiens

<400> SEQUENCE: 159

Gln Gln Tyr Asp Asp Leu Pro Ile Thr
1               5

<210> SEQ ID NO 160
<211> LENGTH: 5
<212> TYPE: PRT
<213> ORGANISM: Homo sapiens
```

<400> SEQUENCE: 160

Ser Tyr Asp Ile Ser
1               5

<210> SEQ ID NO 161
<211> LENGTH: 17
<212> TYPE: PRT
<213> ORGANISM: Homo sapiens

<400> SEQUENCE: 161

Trp Met Asn Pro Ser Ser Gly Tyr Thr Gly Tyr Ala Gln Asn Phe Gln
1               5                   10                  15

Gly

<210> SEQ ID NO 162
<211> LENGTH: 10
<212> TYPE: PRT
<213> ORGANISM: Homo sapiens

<400> SEQUENCE: 162

Thr Asp Tyr Tyr Tyr Tyr Gly Met Asp Val
1               5                   10

<210> SEQ ID NO 163
<211> LENGTH: 11
<212> TYPE: PRT
<213> ORGANISM: Homo sapiens

<400> SEQUENCE: 163

Gln Ala Ser Gln Asp Ile Ser Asn Tyr Leu Asn
1               5                   10

<210> SEQ ID NO 164
<211> LENGTH: 7
<212> TYPE: PRT
<213> ORGANISM: Homo sapiens

<400> SEQUENCE: 164

Asp Ala Ser Asn Leu Glu Thr
1               5

<210> SEQ ID NO 165
<211> LENGTH: 9
<212> TYPE: PRT
<213> ORGANISM: Homo sapiens

<400> SEQUENCE: 165

Gln Gln Tyr Asp Asn Phe Pro Leu Thr
1               5

<210> SEQ ID NO 166
<211> LENGTH: 5
<212> TYPE: PRT
<213> ORGANISM: Homo sapiens

<400> SEQUENCE: 166

Ser Tyr Tyr Trp Ser
1               5

<210> SEQ ID NO 167
<211> LENGTH: 16
<212> TYPE: PRT
<213> ORGANISM: Homo sapiens

<400> SEQUENCE: 167

Tyr Val Tyr Tyr Ser Gly Ser Thr Ser Tyr Asn Pro Ser Leu Lys Ser
1               5                   10                  15

<210> SEQ ID NO 168
<211> LENGTH: 10
<212> TYPE: PRT
<213> ORGANISM: Homo sapiens

<400> SEQUENCE: 168

Tyr Asn Trp Asn Asn Asp Leu Phe Asp Tyr
1               5                   10

<210> SEQ ID NO 169
<211> LENGTH: 11
<212> TYPE: PRT
<213> ORGANISM: Homo sapiens

<400> SEQUENCE: 169

Gly Gly Asn Asn Ile Gly Ser Lys Ser Val His
1               5                   10

<210> SEQ ID NO 170
<211> LENGTH: 7
<212> TYPE: PRT
<213> ORGANISM: Homo sapiens

<400> SEQUENCE: 170

Asp Asp Ser Asp Arg Pro Ser
1               5

<210> SEQ ID NO 171
<211> LENGTH: 11
<212> TYPE: PRT
<213> ORGANISM: Homo sapiens

<400> SEQUENCE: 171

Gln Val Leu Asp Ser Ser Ser Asp His Val Ile
1               5                   10

<210> SEQ ID NO 172
<211> LENGTH: 5
<212> TYPE: PRT
<213> ORGANISM: Homo sapiens

<400> SEQUENCE: 172

Asn Tyr Ala Met Ser
1               5

<210> SEQ ID NO 173
<211> LENGTH: 17
<212> TYPE: PRT
<213> ORGANISM: Homo sapiens

<400> SEQUENCE: 173

Ala Ile Ser Gly Gly Gly Gly Thr Thr Tyr Tyr Ala Asp Ser Val Glu
1               5                   10                  15

Gly

<210> SEQ ID NO 174
<211> LENGTH: 11
<212> TYPE: PRT
<213> ORGANISM: Homo sapiens -continued

<400> SEQUENCE: 174

Glu Phe Gly Glu Leu Glu Pro Arg Phe Asp Tyr
1               5                   10

<210> SEQ ID NO 175
<211> LENGTH: 11
<212> TYPE: PRT
<213> ORGANISM: Homo sapiens

<400> SEQUENCE: 175

Gly Gly Asn Asn Ile Gly Ser Glu Ser Val His
1               5                   10

<210> SEQ ID NO 176
<211> LENGTH: 7
<212> TYPE: PRT
<213> ORGANISM: Homo sapiens

<400> SEQUENCE: 176

Asp Asp Ser Asp Arg Pro Ser
1               5

<210> SEQ ID NO 177
<211> LENGTH: 11
<212> TYPE: PRT
<213> ORGANISM: Homo sapiens

<400> SEQUENCE: 177

Gln Val Trp Asp Ser Ser Asn Asp His Val Val
1               5                   10

<210> SEQ ID NO 178
<211> LENGTH: 7
<212> TYPE: PRT
<213> ORGANISM: Homo sapiens

<400> SEQUENCE: 178

Ser Ser Asn Tyr Tyr Trp Gly
1               5

<210> SEQ ID NO 179
<211> LENGTH: 16
<212> TYPE: PRT
<213> ORGANISM: Homo sapiens

<400> SEQUENCE: 179

Thr Ile Tyr Tyr Ser Gly Ser Thr Tyr Tyr Thr Pro Ser Leu Lys Ser
1               5                   10                  15

<210> SEQ ID NO 180
<211> LENGTH: 14
<212> TYPE: PRT
<213> ORGANISM: Homo sapiens

<400> SEQUENCE: 180

Glu Arg Ala Ile Ala Val Ala Ala Ile Val Phe Phe Asp Tyr
1               5                   10

<210> SEQ ID NO 181
<211> LENGTH: 11
<212> TYPE: PRT
<213> ORGANISM: Homo sapiens

<400> SEQUENCE: 181

```
Gly Gly Asn Asn Ile Gly Ser Lys Ser Val His
1               5                   10

<210> SEQ ID NO 182
<211> LENGTH: 7
<212> TYPE: PRT
<213> ORGANISM: Homo sapiens

<400> SEQUENCE: 182

Asp Asp Ser Asp Arg Pro Ser
1               5

<210> SEQ ID NO 183
<211> LENGTH: 11
<212> TYPE: PRT
<213> ORGANISM: Homo sapiens

<400> SEQUENCE: 183

Gln Val Trp Asp Ser Ser Ser Asp His Trp Val
1               5                   10

<210> SEQ ID NO 184
<211> LENGTH: 5
<212> TYPE: PRT
<213> ORGANISM: Homo sapiens

<400> SEQUENCE: 184

Ser Tyr Asp Ile Asn
1               5

<210> SEQ ID NO 185
<211> LENGTH: 17
<212> TYPE: PRT
<213> ORGANISM: Homo sapiens

<400> SEQUENCE: 185

Trp Met Asn Leu Asn Ser Asp Asn Thr Gly Tyr Ala Gln Lys Phe Gln
1               5                   10                  15

Gly

<210> SEQ ID NO 186
<211> LENGTH: 14
<212> TYPE: PRT
<213> ORGANISM: Homo sapiens

<400> SEQUENCE: 186

Ile Ala Ala Arg Arg Asp Tyr Asn Tyr Tyr Gly Met Asp Val
1               5                   10

<210> SEQ ID NO 187
<211> LENGTH: 12
<212> TYPE: PRT
<213> ORGANISM: Homo sapiens

<400> SEQUENCE: 187

Arg Ala Ser Gln Ser Val Ser Ser Ser Tyr Leu Ala
1               5                   10

<210> SEQ ID NO 188
<211> LENGTH: 7
<212> TYPE: PRT
<213> ORGANISM: Homo sapiens

<400> SEQUENCE: 188
```

```
Gly Ala Ser Gly Arg Ala Thr
1               5

<210> SEQ ID NO 189
<211> LENGTH: 8
<212> TYPE: PRT
<213> ORGANISM: Homo sapiens

<400> SEQUENCE: 189

Gln Gln Tyr Gly Ser Ser Phe Thr
1               5

<210> SEQ ID NO 190
<211> LENGTH: 5
<212> TYPE: PRT
<213> ORGANISM: Homo sapiens

<400> SEQUENCE: 190

Ser Tyr Gly Met His
1               5

<210> SEQ ID NO 191
<211> LENGTH: 17
<212> TYPE: PRT
<213> ORGANISM: Homo sapiens

<400> SEQUENCE: 191

Val Ile Leu Tyr Asp Gly Ser Asp Asn Tyr Tyr Ala Asp Ser Val Lys
1               5                   10                  15
Gly

<210> SEQ ID NO 192
<211> LENGTH: 16
<212> TYPE: PRT
<213> ORGANISM: Homo sapiens

<400> SEQUENCE: 192

Glu Gly Ile Ala Val Ala Gly Asp Tyr Tyr Tyr Tyr Gly Met Asp Val
1               5                   10                  15

<210> SEQ ID NO 193
<211> LENGTH: 14
<212> TYPE: PRT
<213> ORGANISM: Homo sapiens

<400> SEQUENCE: 193

Thr Gly Ser Ser Ser Asn Ile Gly Ala Asp Tyr Asp Val His
1               5                   10

<210> SEQ ID NO 194
<211> LENGTH: 7
<212> TYPE: PRT
<213> ORGANISM: Homo sapiens

<400> SEQUENCE: 194

Asp Tyr Ser Asn Arg Pro Ser
1               5

<210> SEQ ID NO 195
<211> LENGTH: 12
<212> TYPE: PRT
<213> ORGANISM: Homo sapiens

<400> SEQUENCE: 195
```

Gln Ser Tyr Asp Asn Ser Leu Ser Gly Tyr Val Val
1               5                   10

<210> SEQ ID NO 196
<211> LENGTH: 5
<212> TYPE: PRT
<213> ORGANISM: Homo sapiens

<400> SEQUENCE: 196

Ser Tyr Trp Ile Gly
1               5

<210> SEQ ID NO 197
<211> LENGTH: 17
<212> TYPE: PRT
<213> ORGANISM: Homo sapiens

<400> SEQUENCE: 197

Ile Ile Tyr Pro Gly Asp Ser Asp Thr Arg Tyr Ser Pro Ser Phe Gln
1               5                   10                  15

Gly

<210> SEQ ID NO 198
<211> LENGTH: 7
<212> TYPE: PRT
<213> ORGANISM: Homo sapiens

<400> SEQUENCE: 198

Gln Gly Glu Ser Phe Asp Tyr
1               5

<210> SEQ ID NO 199
<211> LENGTH: 14
<212> TYPE: PRT
<213> ORGANISM: Homo sapiens

<400> SEQUENCE: 199

Thr Gly Ser Ser Ser Asn Ile Gly Ala Gly Tyr Asp Val His
1               5                   10

<210> SEQ ID NO 200
<211> LENGTH: 7
<212> TYPE: PRT
<213> ORGANISM: Homo sapiens

<400> SEQUENCE: 200

Gly Asn Ser Asn Arg Pro Ser
1               5

<210> SEQ ID NO 201
<211> LENGTH: 10
<212> TYPE: PRT
<213> ORGANISM: Homo sapiens

<400> SEQUENCE: 201

Gln Ser Tyr Asp Ser Ser Leu Ser Val Ile
1               5                   10

<210> SEQ ID NO 202
<211> LENGTH: 5
<212> TYPE: PRT
<213> ORGANISM: Homo sapiens

<400> SEQUENCE: 202

Thr Tyr Trp Ile Gly
1               5

<210> SEQ ID NO 203
<211> LENGTH: 17
<212> TYPE: PRT
<213> ORGANISM: Homo sapiens

<400> SEQUENCE: 203

Ile Ile Tyr Pro Gly Asp Ser Asp Thr Arg Tyr Ser Pro Ser Phe Gln
1               5                   10                  15

Gly

<210> SEQ ID NO 204
<211> LENGTH: 7
<212> TYPE: PRT
<213> ORGANISM: Homo sapiens

<400> SEQUENCE: 204

Gln Gly Ile Ala Phe Asp Tyr
1               5

<210> SEQ ID NO 205
<211> LENGTH: 16
<212> TYPE: PRT
<213> ORGANISM: Homo sapiens

<400> SEQUENCE: 205

Lys Ser Gly Gln Ser Leu Leu His Ser Asp Gly Lys Thr Tyr Leu Tyr
1               5                   10                  15

<210> SEQ ID NO 206
<211> LENGTH: 7
<212> TYPE: PRT
<213> ORGANISM: Homo sapiens

<400> SEQUENCE: 206

Glu Val Ser Asn Arg Phe Ser
1               5

<210> SEQ ID NO 207
<211> LENGTH: 9
<212> TYPE: PRT
<213> ORGANISM: Homo sapiens

<400> SEQUENCE: 207

Met Gln Ser Ile Gln Leu Pro Trp Thr
1               5

<210> SEQ ID NO 208
<211> LENGTH: 5
<212> TYPE: PRT
<213> ORGANISM: Homo sapiens

<400> SEQUENCE: 208

Gly Tyr Gly Met His
1               5

<210> SEQ ID NO 209
<211> LENGTH: 17
<212> TYPE: PRT
<213> ORGANISM: Homo sapiens

<400> SEQUENCE: 209

Val Ile Ser Tyr Asp Gly Asn Asp Lys Tyr Tyr Ala Asp Ser Val Lys
1               5                   10                  15

Gly

<210> SEQ ID NO 210
<211> LENGTH: 5
<212> TYPE: PRT
<213> ORGANISM: Homo sapiens

<400> SEQUENCE: 210

Glu Leu Arg Val Leu
1               5

<210> SEQ ID NO 211
<211> LENGTH: 16
<212> TYPE: PRT
<213> ORGANISM: Homo sapiens

<400> SEQUENCE: 211

Lys Ser Gly Gln Ser Leu Leu His Asn Asp Gly Lys Thr Tyr Leu Tyr
1               5                   10                  15

<210> SEQ ID NO 212
<211> LENGTH: 7
<212> TYPE: PRT
<213> ORGANISM: Homo sapiens

<400> SEQUENCE: 212

Glu Val Ser Asn Arg Phe Ser
1               5

<210> SEQ ID NO 213
<211> LENGTH: 9
<212> TYPE: PRT
<213> ORGANISM: Homo sapiens

<400> SEQUENCE: 213

Met Gln Ser Ile Gln Leu Pro Trp Thr
1               5

<210> SEQ ID NO 214
<211> LENGTH: 5
<212> TYPE: PRT
<213> ORGANISM: Homo sapiens

<400> SEQUENCE: 214

Gly Tyr Gly Met His
1               5

<210> SEQ ID NO 215
<211> LENGTH: 17
<212> TYPE: PRT
<213> ORGANISM: Homo sapiens

<400> SEQUENCE: 215

Val Ile Ser Tyr Asp Gly Asn Asp Lys Tyr Tyr Ala Asp Ser Val Lys
1               5                   10                  15

Gly

<210> SEQ ID NO 216
<211> LENGTH: 5
<212> TYPE: PRT
<213> ORGANISM: Homo sapiens

<400> SEQUENCE: 216

Glu Leu Arg Val Leu
1               5

<210> SEQ ID NO 217
<211> LENGTH: 13
<212> TYPE: PRT
<213> ORGANISM: Homo sapiens

<400> SEQUENCE: 217

Ala Ala Ser Gly Phe Thr Phe Ser Arg Tyr Asp Met His
1               5                   10

<210> SEQ ID NO 218
<211> LENGTH: 12
<212> TYPE: PRT
<213> ORGANISM: Homo sapiens

<400> SEQUENCE: 218

Ile Phe Tyr Asp Gly Ser Asn Lys Tyr Tyr Ala Asp
1               5                   10

<210> SEQ ID NO 219
<211> LENGTH: 9
<212> TYPE: PRT
<213> ORGANISM: Homo sapiens

<400> SEQUENCE: 219

Ala Thr Leu Ala Ala Ala Phe Asp Tyr
1               5

<210> SEQ ID NO 220
<211> LENGTH: 5
<212> TYPE: PRT
<213> ORGANISM: Homo sapiens

<400> SEQUENCE: 220

Ser Tyr Gly Met His
1               5

<210> SEQ ID NO 221
<211> LENGTH: 17
<212> TYPE: PRT
<213> ORGANISM: Homo sapiens

<400> SEQUENCE: 221

Val Ile Ser Tyr Asp Gly Gly Asp Gln Tyr Tyr Ala Asp Ser Val Lys
1               5                   10                  15

Gly

<210> SEQ ID NO 222
<211> LENGTH: 5
<212> TYPE: PRT
<213> ORGANISM: Homo sapiens

<400> SEQUENCE: 222

Glu Leu Arg Val Leu
1               5

<210> SEQ ID NO 223
<211> LENGTH: 11
<212> TYPE: PRT
<213> ORGANISM: Homo sapiens

```
<400> SEQUENCE: 223

Gly Gly Asn Asn Ile Gly Ser Lys Ser Val His
1               5                   10

<210> SEQ ID NO 224
<211> LENGTH: 7
<212> TYPE: PRT
<213> ORGANISM: Homo sapiens

<400> SEQUENCE: 224

Asp Asp Ser Asp Arg Pro Ser
1               5

<210> SEQ ID NO 225
<211> LENGTH: 11
<212> TYPE: PRT
<213> ORGANISM: Homo sapiens

<400> SEQUENCE: 225

Gln Val Trp Asp Ser Ser Ser Asp His Val Val
1               5                   10

<210> SEQ ID NO 226
<211> LENGTH: 5
<212> TYPE: PRT
<213> ORGANISM: Homo sapiens

<400> SEQUENCE: 226

Arg Tyr Asp Met His
1               5

<210> SEQ ID NO 227
<211> LENGTH: 17
<212> TYPE: PRT
<213> ORGANISM: Homo sapiens

<400> SEQUENCE: 227

Ile Ile Phe Tyr Asp Gly Ser Asn Lys Tyr Tyr Ala Asp Pro Val Lys
1               5                   10                  15

Gly

<210> SEQ ID NO 228
<211> LENGTH: 7
<212> TYPE: PRT
<213> ORGANISM: Homo sapiens

<400> SEQUENCE: 228

Leu Ala Ala Ala Phe Asp Tyr
1               5

<210> SEQ ID NO 229
<211> LENGTH: 318
<212> TYPE: DNA
<213> ORGANISM: Homo sapiens

<400> SEQUENCE: 229
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
```

```
aaacacaaag tctacgcctg cgaagtcacc catcagggcc tgagctcgcc cgtcacaaag    300
agcttcaaca ggggagag                                                  318
```

<210> SEQ ID NO 230
<211> LENGTH: 107
<212> TYPE: PRT
<213> ORGANISM: Homo sapiens

<400> SEQUENCE: 230

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 231
<211> LENGTH: 318
<212> TYPE: DNA
<213> ORGANISM: Homo sapiens

<400> SEQUENCE: 231

```
ggtcagccca aggccaaccc cactgtcact ctgttcccgc cctcctctga ggagctccaa     60
gccaacaagg ccacactagt gtgtctgatc agtgacttct acccgggagc tgtgacagtg    120
gcctggaagg cagatggcag ccccgtcaag gcgggagtgg agaccaccaa accctccaaa    180
cagagcaaca acaagtacgc ggccagcagc tacctgagcc tgacgcccga gcagtggaag    240
tcccacagaa gctacagctg ccaggtcacg catgaaggga gcaccgtgga agacagtg     300 gccccctacag aatgttca                                                318
```

<210> SEQ ID NO 232
<211> LENGTH: 106
<212> TYPE: PRT
<213> ORGANISM: Homo sapiens

<400> SEQUENCE: 232

```
Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95
```

Glu Lys Thr Val Ala Pro Thr Glu Cys Ser
            100                 105

<210> SEQ ID NO 233
<211> LENGTH: 318
<212> TYPE: DNA
<213> ORGANISM: Homo sapiens

<400> SEQUENCE: 233

```
ggtcagccca aggctgcccc ctcggtcact ctgttcccgc cctcctctga ggagcttcaa    60
gccaacaagg ccacactggt gtgtctcata agtgacttct acccgggagc cgtgacagtg   120
gcctggaagg cagatagcag ccccgtcaag gcgggagtgg agaccaccac accctccaaa   180
caaagcaaca acaagtacgc ggccagcagc tatctgagcc tgacgcctga gcagtggaag   240
tcccacagaa gctacagctg ccaggtcacg catgaaggga gcaccgtgga agagacagtg   300
gcccctacag aatgttca                                                 318
```

<210> SEQ ID NO 234
<211> LENGTH: 106
<212> TYPE: PRT
<213> ORGANISM: Homo sapiens

<400> SEQUENCE: 234

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 235
<211> LENGTH: 318
<212> TYPE: DNA
<213> ORGANISM: Homo sapiens

<400> SEQUENCE: 235

```
ggtcagccca aggctgcccc ctcggtcact ctgttcccac cctcctctga ggagcttcaa    60
gccaacaagg ccacactggt gtgtctcata agtgacttct acccgggagc cgtgacagtg   120
gcctggaagg cagatagcag ccccgtcaag gcgggagtgg agaccaccac accctccaaa   180
caaagcaaca acaagtacgc ggccagcagc tacctgagcc tgacgcctga gcagtggaag   240
tcccacaaaa gctacagctg ccaggtcacg catgaaggga gcaccgtgga agagacagtg   300
gcccctacag aatgttca                                                 318
```

<210> SEQ ID NO 236
<211> LENGTH: 106
<212> TYPE: PRT
<213> ORGANISM: Homo sapiens

<400> SEQUENCE: 236

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
                100                 105

<210> SEQ ID NO 237
<211> LENGTH: 318
<212> TYPE: DNA
<213> ORGANISM: Homo sapiens

<400> SEQUENCE: 237
ggtcagccca aggctgcccc atcggtcact ctgttcccgc cctcctctga ggagcttcaa      60
gccaacaagg ccacactggt gtgcctgatc agtgacttct acccgggagc tgtgaaagtg     120
gcctggaagg cagatggcag ccccgtcaac acgggagtgg agaccaccac accctccaaa     180
cagagcaaca acaagtacgc ggccagcagc tacctgagcc tgacgcctga gcagtggaag     240
tcccacagaa gctacagctg ccaggtcacg catgaaggga gcaccgtgga agacagtg      300 gcccctgcag aatgtgca                                                   318

<210> SEQ ID NO 238
<211> LENGTH: 106
<212> TYPE: PRT
<213> ORGANISM: Homo sapiens

<400> SEQUENCE: 238

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ala
                100                 105

<210> SEQ ID NO 239
<211> LENGTH: 318
<212> TYPE: DNA
<213> ORGANISM: Homo sapiens

<400> SEQUENCE: 239

```
ggtcagccca aggctgcccc ctcggtcact ctgttcccac cctcctctga ggagcttcaa    60
gccaacaagg ccacactggt gtgtctcgta agtgacttct acccgggagc cgtgacagtg   120
gcctggaagg cagatggcag ccccgtcaag gtgggagtgg agaccaccaa accctccaaa   180
caaagcaaca caagtatgc ggccagcagc tacctgagcc tgacgcccga gcagtggaag   240
tcccacagaa gctacagctg ccgggtcacg catgaaggga gcaccgtgga agagacagtg   300
gcccctgcag aatgctct                                                 318
```

<210> SEQ ID NO 240
<211> LENGTH: 106
<212> TYPE: PRT
<213> ORGANISM: Homo sapiens

<400> SEQUENCE: 240

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105

<210> SEQ ID NO 241
<211> LENGTH: 978
<212> TYPE: DNA
<213> ORGANISM: Homo sapiens

<400> SEQUENCE: 241

```
gcctccacca agggcccatc ggtcttcccc ctggcgccct gctccaggag cacctccgag    60
agcacagcgg ccctgggctg cctggtcaag gactacttcc ccgaaccggt gacggtgtcg   120
tggaactcag cgctctgac cagcggcgtg cacaccttcc cagctgtcct acagtcctca   180
ggactctact ccctcagcag cgtggtgacc gtgccctcca gcaacttcgg cacccagacc   240
tacacctgca acgtagatca caagcccagc aacaccaagg tggacaagac agttgagcgc   300
aaatgttgtg tcgagtgccc accgtgccca gcaccacctg tggcaggacc gtcagtcttc   360
ctcttccccc caaaacccaa ggacaccctc atgatctccc ggacccctga ggtcacgtgc   420
gtggtggtgg acgtgagcca cgaagacccc gaggtccagt tcaactggta cgtggacggc   480
gtggaggtgc ataatgccaa gacaaagcca cgggaggagc agttcaacag cacgttccgt   540
gtggtcagcg tcctcaccgt tgtgcaccag gactggctga acggcaagga gtacaagtgc   600
aaggtctcca acaaaggcct cccagccccc atcgagaaaa ccatctccaa aaccaagggg   660
cagccccgag aaccacaggt gtacaccctg cccccatccc gggaggagat gaccaagaac   720
caggtcagcc tgacctgcct ggtcaaaggc ttctacccca gcgacatcgc cgtggagtgg   780
gagagcaatg ggcagccgga gaacaactac aagaccacac ctcccatgct ggactccgac   840
ggctccttct tcctctacag caagctcacc gtggacaaga gcaggtggca gcaggggaac   900
```

-continued

```
gtcttctcat gctccgtgat gcatgaggct ctgcacaacc actacacgca gaagagcctc    960
tccctgtctc cgggtaaa                                                  978
```

<210> SEQ ID NO 242
<211> LENGTH: 326
<212> TYPE: PRT
<213> ORGANISM: Homo sapiens
<400> SEQUENCE: 242

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 243
<211> LENGTH: 981
<212> TYPE: DNA

<213> ORGANISM: Homo sapiens

<400> SEQUENCE: 243

```
gccagcacca agggccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc cccatgccc atcatgccca gcacctgagt tcgagggggg accatcagtc      360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggcta accgtggaca gagcaggtg gcaggagggg      900
aatgtcttct catgctccgt gatgcatgag gctctgcaca accactacac acagaagagc     960
ctctcccctgt ctctgggtaa a                                              981
```

<210> SEQ ID NO 244
<211> LENGTH: 327
<212> TYPE: PRT
<213> ORGANISM: Homo sapiens

<400> SEQUENCE: 244

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
```

-continued

```
Asn Ser Thr Tyr Arg Val Val Ser Val Leu Thr Val Leu His Gln Asp
            180             185                 190

Trp Leu Asn Gly Lys Glu Tyr Lys Cys Lys Val Ser Asn Lys Gly Leu
        195             200             205

Pro Ser Ser Ile Glu Lys Thr Ile Ser Lys Ala Lys Gly Gln Pro Arg
        210             215             220

Glu Pro Gln Val Tyr Thr Leu Pro Pro Ser Gln Glu Glu Met Thr Lys
225             230             235             240

Asn Gln Val Ser Leu Thr Cys Leu Val Lys Gly Phe Tyr Pro Ser Asp
                245             250             255

Ile Ala Val Glu Trp Glu Ser Asn Gly Gln Pro Glu Asn Asn Tyr Lys
            260             265             270

Thr Thr Pro Pro Val Leu Asp Ser Asp Gly Ser Phe Phe Leu Tyr Ser
        275             280             285

Arg Leu Thr Val Asp Lys Ser Arg Trp Gln Gln Gly Asn Val Phe Ser
        290             295             300

Cys Ser Val Met His Glu Ala Leu His Asn His Tyr Thr Gln Lys Ser
305             310             315             320

Leu Ser Leu Ser Leu Gly Lys
                325
```